United States Patent
Takahashi et al.

(10) Patent No.: US 8,273,764 B2
(45) Date of Patent: Sep. 25, 2012

(54) FUSED HETEROCYCLIC COMPOUNDS AND USE THEREOF

(75) Inventors: Masaki Takahashi, Osaka (JP);
Mitsuhiko Iwakoshi, Toyonaka (JP);
Hiroshi Ikegami, Ikeda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/259,058

(22) PCT Filed: Apr. 20, 2010

(86) PCT No.: PCT/JP2010/057315
§ 371 (c)(1),
(2), (4) Date: Sep. 22, 2011

(87) PCT Pub. No.: WO2010/125985
PCT Pub. Date: Nov. 4, 2010

(65) Prior Publication Data
US 2012/0015975 A1    Jan. 19, 2012

(30) Foreign Application Priority Data
Apr. 28, 2009 (JP) .................................. 2009-108926

(51) Int. Cl.
*A01N 43/90* (2006.01)
*A01N 43/52* (2006.01)
*A01P 7/00* (2006.01)
*C07D 471/04* (2006.01)
*C07D 491/048* (2006.01)
*C07D 401/04* (2006.01)

(52) U.S. Cl. ..... 514/300; 514/338; 546/118; 546/273.1; 546/273.4

(58) Field of Classification Search .................. 546/113, 546/118, 273.1, 273.4; 514/303, 300, 338
See application file for complete search history.

(56) References Cited

OTHER PUBLICATIONS

Goker, H. et al. "Synthesis and Potent Antifungal Activity Against *Candida* Species of Some Novel 1H-Benzimidazoles", J. Heterocycl. Chem., 2009, vol. 46, pp. 936-948.
Hisano, T. et al. "Synthesis of Benzoxazoles, Benzothiazoles and Benzimidazoles and Evaluation of Their Antifungal, Insecticidal and Herbicidal Activities", Chem. Pharm. Bull., 1982, vol. 30, pp. 2996-3004.
International Search Report in PCT/JP2010/057315 dated Jul. 13, 2010.
Marzin, C. et al. "Dynamic Conformational and Exchange Processes in 2-(4'-Pyridyl)Benzazoles", Heterocycles, 1977, vol. 6, No. 7, pp. 911-927.
Online Chemical Abstract—CAPLUS, vol. 87, No. 151604, pp. 1 and 2, (1977).

*Primary Examiner* — Janet Andres
*Assistant Examiner* — Timothy R Rozof
(74) *Attorney, Agent, or Firm* — Foley & Lardner LLP

(57) ABSTRACT

A fused heterocyclic compound of formula (1): wherein, $A^1$ and $A^2$ represent a nitrogen atom or the like, $R^1$, $R^2$, $R^3$ and $R^4$ represent a halogen atom or the like, $R^2$ and $R^3$ represent a halogen atom or the like, $R^5$ represents a C1-C6 chain hydrocarbon group optionally substituted with one or more halogen atoms, or the like, $R^6$ and $R^7$ represent a C1-C4 chain hydrocarbon group substituted with one or more halogen atoms, or the like, and n represents 0 or 1, has an excellent noxious arthropod controlling effect.

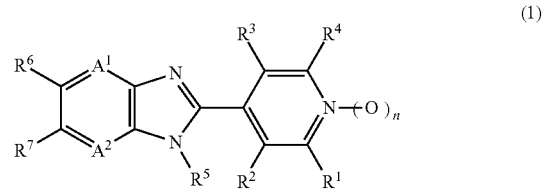

(1)

11 Claims, No Drawings

FUSED HETEROCYCLIC COMPOUNDS AND USE THEREOF

TECHNICAL FIELD

The present invention relates to a fused heterocyclic compound and its use for control of noxious arthropods

BACKGROUND ART

Various compounds have been investigated for the purpose of control of pests, and put into practical use.

Some kinds of substituted benzimidazole compounds are known in Farmaco, Edizione Scientifica (1987), 42(7), 475-90; Heterocycles (1977), 6(7), 911-27 and Chemical & Pharmaceutical Bulletin (1982), 30(8), 2996.

DISCLOSURE OF THE INVENTION

The present invention is to provide a compound having an excellent controlling effect on noxious arthropods.

The present inventors have intensively studied to solve the above-described problem and resultantly found that a fused heterocyclic compound of the following formula (1) has an excellent controlling effect on noxious arthropods, leading to completion of the present invention.

That is, the present invention provides the following.

[1] A fused heterocyclic compound of formula (1):

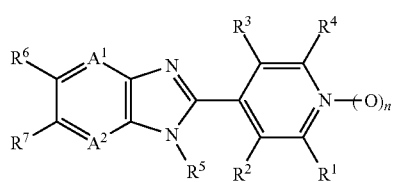

(1)

wherein, $A^1$ and $A^2$ are the same or different and represent a nitrogen atom or =CH—, m represents 0, 1 or 2, $R^1$, $R^2$, $R^3$ and $R^4$ are the same or different and represent a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y, —$OR^8$, —$NR^8R^9$, —$NR^8C(O)R^9$, —$S(O)_m$ $R^8$, —$SO_2Cl$, —$SO_2NR^8R^9$, —$CO_2R^{10}$, —$CONR^8R^9$, —$CONR^{10}NR^{11}R^{12}$, a cyano group, a nitro group, a halogen atom or a hydrogen atom, $R^5$ represents a C1-C4 chain hydrocarbon group optionally substituted with one or more halogen atoms, a cyclopropyl group optionally substituted with one or more halogen atoms, a cyclopropylmethyl group optionally substituted with one or more halogen atoms, —$OR^{13}$, —$NR^{13}R^{14}$ or a cyano group, $R^6$ and $R^7$ are the same or different and represent a C1-C4 chain hydrocarbon group substituted with one or more halogen atoms, —$OR^{15}$, —$S(O)_mR^{15}$, a halogen atom or a hydrogen atom (here, either $R^6$ or $R^7$ represents a C1-C4 chain hydrocarbon group substituted with one or more halogen atoms, —$OR^{15}$, —$S(O)_mR^{15}$.), alternatively $R^6$ and $R^7$ may be bonded to form a 5-membered ring or 6-membered ring substituted with one or more halogen atoms together with carbon atoms to which $R^6$ and $R^7$ are connected, $R^8$ and $R^9$ are the same or different and represent a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y, or a hydrogen atom (concerning —$S(O)_m$ $R^8$, m represents the same meaning as described above, but when m represents 1 or 2, $R^8$ does not represent a hydrogen atom.), $R^{10}$ represents a C1-C4 alkyl group optionally substituted with one or more halogen atoms, or a hydrogen atom, $R^{11}$ and $R^{12}$ are the same or different and represents a C1-C4 alkyl group optionally substituted with one or more halogen atoms, a C2-C5 alkoxycarbonyl group or a hydrogen atom, $R^{13}$ and $R^{14}$ are the same or different and represents a C1-C3 chain hydrocarbon group optionally substituted with one or more halogen atoms, a cyclopropyl group optionally substituted with one or more halogen atoms, or a hydrogen atom, $R^{15}$ represents a C1-C4 chain hydrocarbon group substituted with one or more halogen atoms, and n represents 0 or 1.

Group X: a group consisting of a C1-C4 alkoxy group optionally substituted with one or more halogen atoms, —$CO_2R^{16}$ (here, $R^{16}$ represents a C1-C4 alkyl group optionally substituted by a halogen.), a cyano group and a halogen atom.

Group Y: a group consisting of a C1-C4 alkyl group optionally substituted with one or more halogen atoms, a C1-C4 alkoxy group optionally substituted with one or more halogen atoms, a cyano group, a nitro group and a halogen atom (hereinafter, referred to as present active compound).

[1-2] A fused heterocyclic compound of formula (1):

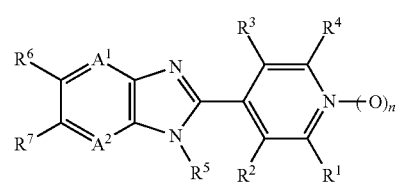

(1)

wherein, $A^1$ and $A^2$ are the same or different and represent a nitrogen atom or =CH—, m represents 0, 1 or 2, $R^1$, $R^2$, $R^3$ and $R^4$ are the same or different and represent a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y, —OR$^8$, —NR$^8$R$^9$, —NR$^8$C(O)R$^9$, —S(O)$_m$R$^8$, —CO$_2$R$^{10}$, —CONR$^8$R$^9$, —CONR$^{10}$NR$^{11}$R$^{12}$, a cyano group, a nitro group, a halogen atom or a hydrogen atom, R$^5$ represents a C1-C4 chain hydrocarbon group optionally substituted with one or more halogen atoms, a cyclopropyl group optionally substituted with one or more halogen atoms, a cyclopropylmethyl group optionally substituted with one or more halogen atoms, —OR$^{13}$, —NR$^{13}$R$^{14}$ or a cyano group, R$^6$ and R$^7$ are the same or different and represent a C1-C4 chain hydrocarbon group substituted with one or more halogen atoms, —OR$^{15}$, —S(O)$_m$R$^{15}$, a halogen atom or a hydrogen atom (here, either R$^6$ or R$^7$ represents a C1-C4 chain hydrocarbon group substituted with one or more halogen atoms, —OR$^{15}$, —S(O)$_m$R$^{15}$.), alternatively R$^6$ and R$^7$ may be bonded to form a 5-membered ring or 6-membered ring substituted with one or more halogen atoms together with carbon atoms to which R$^6$ and R$^7$ are connected, R$^8$ and R$^9$ are the same or different and represent a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y, or a hydrogen atom (concerning —S(O)$_m$R$^8$, m represents the same meaning as described above, but when m represents 1 or 2, R$^8$ does not represent a hydrogen atom.), R$^{10}$ represents a C1-C4 alkyl group optionally substituted with one or more halogen atoms, or a hydrogen atom, R$^{11}$ and R$^{12}$ are the same or different and represents a C1-C4 alkyl group optionally substituted with one or more halogen atoms, a C2-C5 alkoxycarbonyl group or a hydrogen atom, R$^{13}$ and R$^{14}$ are the same or different and represents a C1-C3 chain hydrocarbon group optionally substituted with one or more halogen atoms, a cyclopropyl group optionally substituted with one or more halogen atoms, or a hydrogen atom, R$^{15}$ represents a C1-C4 chain hydrocarbon group substituted with one or more halogen atoms, and n represents 0 or 1.

Group X: a group consisting of a C1-C4 alkoxy group optionally substituted with one or more halogen atoms, —CO$_2$R$^{16}$ (here, R$^{16}$ represents a C1-C4 alkyl group optionally substituted by a halogen.), a cyano group and a halogen atom.

Group Y: a group consisting of a C1-C4 alkyl group optionally substituted with one or more halogen atoms, a C1-C4 alkoxy group optionally substituted with one or more halogen atoms, a cyano group, a nitro group and a halogen atom

[2] The fused heterocyclic compound according to [1] or [1-2], wherein R$^6$ and R$^7$ are the same or different and are a C1-C4 chain hydrocarbon group substituted with one or more halogen atoms, —OR$^{15}$, —S(O)$_m$R$^{15}$, a halogen atom or a hydrogen atom (here, either R$^6$ or R$^7$ represents a C1-C4 chain hydrocarbon group substituted with one or more halogen atoms, —OR$^{15}$, —S(O)$_m$R$^{15}$.)

[3] The fused heterocyclic compound according to [1], [2] or [1-2], wherein R$^6$ is a C1-C4 chain hydrocarbon group substituted with one or more halogen atoms.

[4] The fused heterocyclic compound according to any one of [1] to [3] or [1-2], wherein R$^5$ is a methyl group, ethyl group, cyclopropyl group or cyclopropylmethyl group.

[5] The fused heterocyclic compound according to any one of [1] to [4] or [1-2], wherein R$^2$ and R$^4$ are hydrogen atoms.

[6] The fused heterocyclic compound according to any one of [1] to [5] or [1-2], wherein R$^2$ is a hydrogen atom or a halogen atom.

[6-2] The fused heterocyclic compound according to any one of [1] to [6], wherein A$^1$ is =CH— and A$^2$ is a nitrogen atom.

[6-3] The fused heterocyclic compound according to any one of [1] to [6], [1-2] or [6-2], wherein n is 0.

[7] The fused heterocyclic compound according to any one of [1] to [6], [1-2], [6-2] or [6-3], wherein R$^3$ is a C3-C6 alicyclic hydrocarbon group optionally substituted with one or more members selected from the group X, a phenyl group optionally substituted with one or more members selected from the group Y, a benzyl group optionally substituted with one or more members selected from the group Y, or a 5-membered heterocyclic group or 6-membered heterocyclic group optionally substituted with one or more members selected from the group Y.

[8] The fused heterocyclic compound according to any one of [1] to [6], [1-2], [6-2] or [6-3], wherein R$^3$ is a C1-C6 chain hydrocarbon group optionally substituted with one or more members selected from the group X, —OR$^8$, —NR$^8$R$^9$, —NR$^8$C(O)R$^9$, —S(O)$_m$R$^8$, —CO$_2$R$^{10}$, —CONR$^8$R$^9$, —CONR$^{10}$NR$^{11}$R$^{12}$, a cyano group, a nitro group, a halogen atom or a hydrogen atom, and R$^8$ and R$^9$ are the same or different and represent a C1-C6 chain hydrocarbon group optionally substituted with one or more members selected from the group X, or a hydrogen atom (here, R$^8$ is not a hydrogen atom when m in —S(O)$_m$R$^8$ represents 1 or 2.).

[9] The fused heterocyclic compound according to any one of [1] to [6], [1-2], [6-2] or [6-3], wherein R$^3$ is a C1-C6 chain hydrocarbon group optionally substituted with one or more members selected from the group X, —OR$^8$, —NR$^8$R$^9$, —S(O)$_m$R$^8$, a halogen atom or a hydrogen atom, and R$^8$ and R$^9$ are the same or different and represent a C1-C6 chain hydrocarbon group optionally substituted with one or more members selected from the group X, or a hydrogen atom (here, R$^8$ is not a hydrogen atom when m in —S(O)$_m$R$^8$ represents 1 or 2.)

[9-2] The fused heterocyclic compound according to any one of [1] to [6], [1-2], [6-2] or [6-3], wherein R$^3$ is —OR$^8$ and R$^8$ is a C1-C3 chain hydrocarbon group optionally substituted with one or more halogen atoms.

[9-3] The fused heterocyclic compound according to any one of [1] to [6], [1-2], [6-2] or [6-3], wherein R$^3$ is —S(O)$_m$R$^8$ and R$^8$ is a C1-C3 chain hydrocarbon group provided that R$^8$ is not a hydrogen atom when m represents 1 or 2.

[10] A noxious arthropod controlling composition which comprises the fused heterocyclic compound as described in any one of [1] to [9], [1-2], [6-2], [6-3], [9-2] or [9-3], and an inert carrier.

[11] A method of controlling a noxious arthropod which comprises applying an effective amount of the fused heterocyclic compound as described in any one of [1] to [9], [1-2], [6-2], [6-3], [9-2] or [9-3] to a noxious arthropod or to a habitat of a noxious arthropod (hereinafter, referred to as composition of the present invention).

[12] Use of the fused heterocyclic compound as described in any one of [1] to [9], [1-2], [6-2], [6-3], [9-2] or [9-3] for controlling a noxious arthropod.

MODE OF CARRYING OUT THE INVENTION

The substituents used in descriptions of the instant specification will be explained with examples listed below. In the present invention, "halogen atom" means a fluorine atom, chlorine atom, bromine atom and iodine atom.

In the instant specification, the description of a part "C2-C5" of "C2-C5 alkoxycarbonyl group" oe the like means that the number of carbon atoms constituting the whole alkoxycarbonyl group is in the range of 2 to 5.

Examples of "C1-C6 chain hydrocarbon group optionally substituted with one or more members selected from the group X" represented by $R^1$, $R^2$, $R^3$ or $R^4$ include a C1-C6 alkyl group optionally substituted with one or more members selected from the group X such as a methyl group, ethyl group, propyl group, isopropyl group, butyl group, isobutyl group, sec-butyl group, tert-butyl group, pentyl group, hexyl group, methoxymethyl group, ethoxymethyl group, propoxymethyl group, isopropoxymethyl group, 2-methoxyethyl group, 2-ethoxyethyl group, 2-propoxyethyl group, 2-isopropoxyethyl group, methoxycarbonylmethyl group, ethoxycarbonylmethyl group, 2-methoxycarbonylethyl group, 2-ethoxycarbonylethyl group, cyanomethyl group, dicyanomethyl group, 1-cyanoethyl group, 1,1-dicyanoethyl group, 2-cyanoethyl group, trifluoromethyl group, 2,2,2-trifluoroethyl group and pentafluoroethyl group; a C2-C6 alkenyl group optionally substituted with one or more members selected from the group X such as a vinyl group, 1-propenyl group, 2-propenyl group, 1-methylvinyl group, 2-methyl-1-propenyl group, 1-butenyl group, 2-butenyl group, 3-butenyl group, 1-pentenyl group, 1-hexenyl group, 1,1-difluoroallyl group, and pentafluoroallyl group; and a C2-C6 alkynyl group optionally substituted with one or more members selected from the group X such as an ethynyl group, propargyl group, 2-butynyl group, 3-butynyl group, 1-pentynyl group, 1-hexynyl group and 4,4,4-trifluoro-2-butynyl group.

Examples of "C3-C6 alicyclic hydrocarbon group optionally substituted with one or more members selected from the group X" represented by $R^1$, $R^2$, $R^3$ or $R^4$ include a cyclopropyl group, cyclobutyl group, cyclopentyl group and cyclohexyl group.

Examples of "phenyl group optionally substituted with one or more members selected from the group Y" represented by $R^1$, $R^2$, $R^3$ or $R^4$ include a phenyl group, 2-chlorophenyl group, 3-chlorophenyl group, 4-chlorophenyl group, 2-methylphenyl group, 3-methylphenyl group, 4-methylphenyl group, 2-methoxyphenyl group, 3-methoxyphenyl group, 4-methoxyphenyl group, 2-(trifluoromethyl)phenyl group, 3-(trifluoromethyl)phenyl group, 4-(trifluoromethyl)phenyl group, 2-nitrophenyl group, 3-nitrophenyl group, 4-nitrophenyl group, 2-cyanophenyl group, 3-cyanophenyl group and 4-cyanophenyl group.

Examples of "benzyl group optionally substituted with one or more members selected from the group Y" represented by $R^1$, $R^2$, $R^3$, $R^4$, $R^8$ or $R^9$ include a benzyl group, 2-chlorobenzyl group, 3-chlorobenzyl group, 4-chlorobenzyl group, 2-methylbenzyl group, 3-methylbenzyl group, 4-methylbenzyl group, 2-methoxybenzyl group, 3-methoxybenzyl group and 4-methoxybenzyl group.

"Heterocyclic group" in "5-membered heterocyclic group or 6-membered heterocyclic group optionally substituted with one or more members selected from the group Y" represented by $R^1$, $R^2$, $R^3$ or $R^4$ means a residual group of a heterocyclic compound, and examples of "5-membered heterocyclic group or 6-membered heterocyclic group optionally substituted with one or more members selected from the group Y" include a 5-membered saturated heterocyclic group such as a pyrrolidin-1-yl group and tetrahydrofuran-2-yl group; a 6-membered saturated heterocyclic group such as a piperidyl group, morpholyl group, thiomorpholyl group and 4-methylpiperazin-1-yl group; a 5-membered aromatic heterocyclic group such as a pyrazol-1-yl group, 3-chloropyrazol-1-yl group, 3-bromopyrazol-1-yl group, 3-nitropyrazol-1-yl group, 3-methylpyrazol-1-yl group, 3-(trifluoromethyl)pyrazol-1-yl group, 4-methylpyrazol-1-yl group, 4-chloropyrazol-1-yl group, 4-bromopyrazol-1-yl group, 4-cyanopyrazol-1-yl group, imidazol-1-yl group, 4-(trifluoromethylimidazol)-1-yl group, pyrrol-1-yl group, 1,2,4-triazol-1-yl group, 3-chloro-1,2,4-triazol-1-yl group, 1,2,3,4-tetrazol-1-yl group, 1,2,3,5-tetrazol-1-yl group, 2-thienyl group and 3-thienyl group; and a 6-membered aromatic heterocyclic group such as a 2-pyridyl group, 3-pyridyl group and 4-pyridyl group.

Examples of "C1-C4 chain hydrocarbon group optionally substituted with one or more halogen atoms" represented by $R^5$ include a C1-C4 alkyl group optionally substituted with one or more halogen atoms such as a methyl group, ethyl group, propyl group, isopropyl group, butyl group, isobutyl group, sec-butyl group, tert-butyl group, trifluoromethyl group, 2,2,2-trifluoroethyl group and pentafluoroethyl group; a C2-C4 alkenyl group optionally substituted with one or more halogen atoms such as a vinyl group, allyl group, and 3,3-difluoroallyl group; and a C2-C4 alkynyl group optionally substituted with one or more halogen atoms such as a propargyl group, and 4,4,4-trifluoro-2-butynyl group.

Examples of "C1-C4 chain hydrocarbon group substituted with one or more halogen atoms" represented by $R^6$ or $R^7$ include a fluoromethyl group, difluoromethyl group, trifluoromethyl group, 2,2,2-trifluoroethyl group, pentafluoroethyl group, heptafluoropropyl group, 1,1,1,3,3,3-hexafluoroisopropyl group, heptafluoroisopropyl group, nonafluorobutyl group, nonafluoroisobutyl group, nonafluoro-sec-butyl group and nonafluoro-tert-butyl group.

Examples of "5-membered ring or 6-membered ring substituted with one or more halogen atoms" obtained by bonding of $R^6$ and $R^7$, together with carbon atoms to which $R^6$ and $R^7$ are connected, include rings of the following formulae (a) to (j) (here, $A^6$ represents a carbon atom to which $R^6$ is connected, and $A^7$ represents a carbon atom to which $R^7$ is connected).

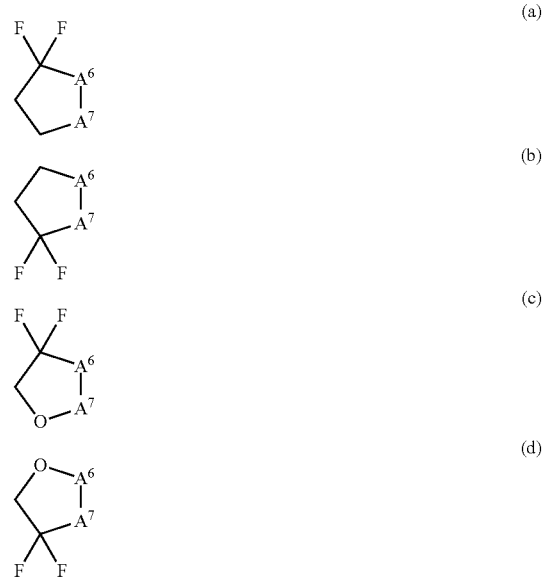

(e)
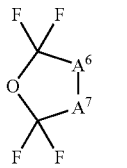

(f)
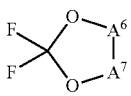

(g)
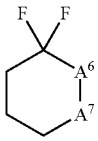

(h)
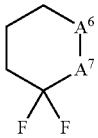

(i)
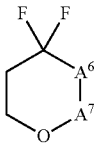

(j)
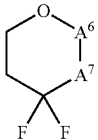

Examples of "C1-C6 chain hydrocarbon group optionally substituted with one or more members selected from the group X" represented by $R^8$ or $R^9$ include a C1-C6 alkyl group optionally substituted with one or more members selected from the group X such as a methyl group, ethyl group, propyl group, isopropyl group, butyl group, isobutyl group, sec-butyl group, tert-butyl group, 1-methylbutyl group, 1-methylbutyl group, 2-methylbutyl group, 3-methylbutyl group, 1-ethylpropyl group, 1,2-dimethylpropyl group, 2,2-dimethylpropyl group, pentyl group, 1,2-dimethylbutyl group, 2,2-dimethylbutyl group, 1-methylpentyl group, 2-methylpentyl group, 3-methylpentyl group, 4-methylpentyl group, hexyl group, fluoromethyl group, difluoromethyl group, trifluoromethyl group, 2-fluoroethyl group, 2,2-difluoroethyl group, 2,2,2-trifluoroethyl group, pentafluoroethyl group and 1-methyl-2,2,2-trifluoroethyl group; a C3-C6 alkenyl group optionally substituted with one or more members selected from the group X such as a 2-propenyl group, 3,3-dichloro-2-propenyl group, 3,3-difluoro-2-propenyl group, 1-methyl-2-propenyl group, 2-methyl-2-propenyl group, 2-butenyl group, 3-butenyl group, 1-methyl-2-butenyl group, and 1-methyl-3-butenyl group; and a C3-C6 alkynyl group optionally substituted with one or more members selected from the group X such as a propargyl group, 1-methyl-2-propynyl group, 2-butynyl group, 3-butynyl group, 1-methyl-2-butynyl group and 1-methyl-3-butynyl group.

Examples of "C3-C6 alicyclic hydrocarbon group optionally substituted with one or more members selected from the group X" represented by $R^8$ or $R^9$ include a cyclopropyl group, cyclobutyl group, cyclopentyl group, cyclohexyl group and 2-cyclohexenyl group.

Examples of "phenyl group optionally substituted with one or more members selected from the group Y" represented by $R^8$ and $R^9$ include a 2-chlorophenyl group, 3-chlorophenyl group, 4-chlorophenyl group, 2-methylphenyl group, 3-methylphenyl group, 4-methylphenyl group, 2-methoxyphenyl group, 3-methoxyphenyl group, 4-methoxyphenyl group, 2-(trifluoromethyl)phenyl group, 3-(trifluoromethyl)phenyl group, 4-(trifluoromethyl)phenyl group, 2-cyanophenyl group, 3-cyanophenyl group, 4-cyanophenyl group, 2-nitrophenyl group, 3-nitrophenyl group and 4-nitrophenyl group.

Examples of "5-membered heterocyclic group or 6-membered heterocyclic group optionally substituted with one or more members selected from the group Y" represented by $R^8$ or $R^9$ include a 5-membered aromatic heterocyclic group such as a 2-thienyl group and 3-thienyl group; and a 6-membered aromatic heterocyclic group such as a 2-pyridyl group, 3-pyridyl group, 4-pyridyl group, 2-pyrimidinyl group and 4-pyrimidinyl group.

Examples of "C1-C4 alkyl group optionally substituted with one or more halogen atoms" represented by $R^{10}$ include a methyl group, ethyl group, propyl group, isopropyl group, butyl group, isobutyl group, sec-butyl group and tert-butyl group, trifluoromethyl group and pentafluoroethyl group.

Examples of "C1-C4 alkyl group optionally substituted with one or more halogen atoms" represented by $R^{11}$ or $R^{12}$ include a methyl group, ethyl group, propyl group, isopropyl group, butyl group, isobutyl group, sec-butyl group, tert-butyl group, trifluoromethyl group, 2,2,2-trifluoroethyl group and pentafluoroethyl group.

Examples of "C2-C5 alkoxycarbonyl group" represented by $R^{11}$ or $R^{12}$ include a methoxycarbonyl group, ethoxycarbonyl group, propoxycarbonyl group, isopropoxycarbonyl group, butoxycarbonyl group, isobutoxycarbonyl group, sec-butoxycarbonyl group and tert-butoxycarbonyl group.

Examples of "C1-C3 chain hydrocarbon group optionally substituted with one or more halogen atoms" represented by $R^{13}$ or $R^{14}$ include a C1-C3 alkyl group optionally substituted with one or more halogen atoms such as a methyl group, ethyl group, propyl group, isopropyl group, fluoromethyl group, difluoromethyl group, trifluoromethyl group, 2,2,2-trifluoroethyl group and pentafluoroethyl group; a C2-C3 alkenyl group optionally substituted with one or more halogen atoms such as a vinyl group, 2-propenyl group, 3,3-difluoro-2-propenyl group and 3,3-dichloro-2-propenyl group; and a C2-C3 alkynyl group optionally substituted with one or more halogen atoms such as an ethynyl group, and propargyl group.

Examples of "C1-C4 chain hydrocarbon group substituted with one or more halogen atoms" represented by $R^{15}$ include a C1-C4 alkyl group substituted with one or more halogen atoms such as a fluoromethyl group, difluoromethyl group, trifluoromethyl group, 2,2,2-trifluoroethyl group, pentafluoroethyl group, heptafluoropropyl group, 1,1,1,3,3,3-hexafluoroisopropyl group, heptafluoroisopropyl group, nonafluorobutyl group, nonafluoroisobutyl group, nonafluoro-sec-butyl group and nonafluoro-tert-butyl group; a C2-C4 alkenyl group substituted with one or more halogen atoms such as a 3,3-difluoroallyl group and pentafluoroallyl group; and a C2-C4 alkynyl group substituted with one or more halogen atoms such as a 4,4,4-trifluoro-2-butynyl group.

Examples of "C1-C4 alkyl group optionally substituted with one or more halogen atoms" represented by $R^{16}$ include a methyl group, ethyl group, propyl group, isopropyl group, butyl group, isobutyl group, sec-butyl group, tert-butyl group, trifluoromethyl group, 2,2,2-trifluoroethyl group and pentafluoroethyl group and the like.

Examples of the present active compound include the following.

The present active compound of formula (1) in which $R^1$ and $R^4$ represent hydrogen atoms;

The present active compound of formula (1) in which $R^2$ represents a hydrogen atom or halogen atom;

The present active compound of formula (1) in which $R^3$ represents a C3-C6 alicyclic hydrocarbon group optionally substituted with one or more members selected from the group X, a phenyl group optionally substituted with one or more members selected from the group Y, a benzyl group optionally substituted with one or more members selected from the group Y or a 5-membered heterocyclic group or 6-membered heterocyclic group optionally substituted with one or more members selected from the group Y;

The present active compound of formula (1) in which $R^3$ represents a C1-C6 chain hydrocarbon group optionally substituted with one or more members selected from the group X, —$OR^8$, —$NR^8R^9$, —$NR^8C(O)R^9$, —$S(O)_mR^8$, —$CO_2R^{10}$, —$CONR^8R^9$, —$CONR^{10}NR^{11}R^{12}$, a cyano group, a nitro group, a halogen atom or a hydrogen atom, and $R^8$ and $R^9$ are the same or different and represent a C1-C6 chain hydrocarbon group optionally substituted with one or more members selected from the group X, or a hydrogen atom (here, when m in —$S(O)_mR^8$ represents 1 or 2, $R^8$ does not represent a hydrogen atom.);

The present active compound of formula (1) in which $R^3$ represents a C1-C6 chain hydrocarbon group optionally substituted with one or more members selected from the group X, —$OR^8$, —$NR^8R^9$, —$S(O)_mR^8$, a halogen atom or a hydrogen atom and $R^8$ and $R^9$ are the same or different and represent a C1-C6 chain hydrocarbon group optionally substituted with one or more members selected from the group X, or a hydrogen atom (here, when m in —$S(O)_mR^8$ represents 1 or 2, $R^8$ does not represent a hydrogen atom.);

The present active compound of formula (1) in which $R^6$ and $R^7$ are the same or different and represent a C1-C4 chain hydrocarbon group substituted with one or more halogen atoms, —$OR^{15}$, —$S(O)_mR^{15}$, a halogen atom or a hydrogen atom (here, either $R^6$ or $R^7$ represents a C1-C4 chain hydrocarbon group substituted with one or more halogen atoms, —$OR^{15}$, —$S(O)_mR^{15}$.), and $R^{15}$ represents a C1-C4 chain hydrocarbon group substituted with one or more halogen atoms;

The present active compound of formula (1) in which $R^6$ represents a C1-C4 chain hydrocarbon group substituted with one or more halogen atoms, or —$OR^{15}$, and $R^{15}$ represents a C1-C4 chain hydrocarbon group substituted with one or more halogen atoms;

The present active compound of formula (1) in which $R^7$ represents a C1-C4 chain hydrocarbon group substituted with one or more halogen atoms, or —$OR^{15}$, and $R^{15}$ represents a C1-C4 chain hydrocarbon group substituted with one or more halogen atoms;

The present active compound of formula (1) in which $R^6$ represents a C1-C4 chain hydrocarbon group substituted with one or more halogen atoms;

The present active compound of formula (1) in which $R^6$ represents a fluoromethyl group;

The present active compound of formula (1) in which $R^6$ represents a difluoromethyl group;

The present active compound of formula (1) in which $R^6$ represents a trifluoromethyl group;

The present active compound of formula (1) in which $R^6$ represents —$OR^{15}$ and $R^{15}$ represents a C1-C4 alkyl group substituted with one or more halogen atoms;

The present active compound of formula (1) in which $R^7$ represents —$OR^{15}$ and $R^{15}$ represents a C1-C4 alkyl group substituted with one or more halogen atoms;

The present active compound of formula (1) in which $R^6$ represents —$OR^{15}$ and $R^{15}$ represents a fluoromethyl group, difluoromethyl group or trifluoromethyl group;

The present active compound of formula (1) in which $R^6$ represents a C1-C4 chain hydrocarbon group substituted with one or more halogen atoms and $R^7$ represents a hydrogen atom or halogen atom;

The present active compound of formula (1) in which $R^6$ represents —$OR^{15}$, $R^{15}$ represents a C1-C4 chain hydrocarbon group substituted with one or more halogen atoms and $R^7$ represents a hydrogen atom or halogen atom;

The present active compound of formula (1) in which $R^6$ represents a hydrogen atom or halogen atom and $R^7$ represents a C1-C4 chain hydrocarbon group substituted with one or more halogen atoms;

The present active compound of formula (1) in which $R^6$ represents a hydrogen atom or halogen atom, $R^7$ represents —$OR^{15}$ and $R^{15}$ represents a C1-C4 chain hydrocarbon group substituted with one or more halogen atoms;

The present active compound of formula (1) in which $R^6$ represents a fluoromethyl group, difluoromethyl group or trifluoromethyl group and $R^7$ represents a hydrogen atom or halogen atom;

The present active compound of formula (1) in which $R^6$ represents a fluoromethyl group, difluoromethyl group or trifluoromethyl group and $R^7$ represents a hydrogen atom;

The present active compound of formula (1) in which $R^6$ represents a —$OR^{15}$, $R^{15}$ represents a fluoromethyl group, difluoromethyl group or trifluoromethyl group and $R^7$ represents a hydrogen atom or halogen atom;

The present active compound of formula (1) in which $R^6$ represents —$OR^{15}$, $R^{15}$ represents a fluoromethyl group, difluoromethyl group or trifluoromethyl group and $R^7$ represents a hydrogen atom;

The present active compound of formula (1) in which $R^6$ represents a hydrogen atom or halogen atom and $R^7$ represents a fluoromethyl group, difluoromethyl group or trifluoromethyl group;

The present active compound of formula (1) in which $R^6$ represents a hydrogen atom and $R^7$ represents a fluoromethyl group, difluoromethyl group or trifluoromethyl group;

The present active compound of formula (1) in which $R^6$ represents a hydrogen atom or halogen atom, $R^7$ represents —$OR^{15}$ and $R^{15}$ represents a fluoromethyl group, difluoromethyl group or trifluoromethyl group;

The present active compound of formula (1) in which $R^6$ represents a hydrogen atom, $R^7$ represents —$OR^{15}$ and $R^{15}$ represents a fluoromethyl group, difluoromethyl group or trifluoromethyl group;

The present active compound of formula (1) in which $A^1$ represents a nitrogen atom and $A^2$ represents =CH—;

The present active compound of formula (1) in which $A^1$ represents =CH— and $A^2$ represents a nitrogen atom;

The present active compound of formula (1) in which $A^1$ and $A^2$ represent =CH—;

The present active compound of formula (1) in which n represents 0;

The present active compound of formula (1) in which $R^3$ represents —$OR^8$ and $R^8$ represents a C1-C3 alkyl group optionally substituted with one or more halogen atoms;

The present active compound of formula (1) in which $R^3$ represents —$OR^8$ and $R^8$ represents a methyl group, ethyl group, propyl group, isopropyl group, fluoromethyl group, difluoromethyl group, trifluoromethyl group, 2-fluoroethyl group, 2,2-difluoroethyl group, 2,2,2-trifluoroethyl group or pentafluoroethyl group;

The present active compound of formula (1) in which $R^3$ represents —$OR^8$ and $R^8$ represents a methyl group, ethyl group, propyl group, isopropyl group, 2-fluoroethyl group, 2,2-difluoroethyl group or 2,2,2-trifluoroethyl group;

The present active compound of formula (1) in which $R^1$, $R^2$ and $R^4$ represent a hydrogen atom, $R^3$ represents —$OR^8$ and $R^8$ represents a C1-C3 alkyl group optionally substituted with one or more halogen atoms;

The present active compound of formula (1) in which $R^1$, $R^2$ and $R^4$ represent hydrogen atoms, $R^3$ represents —$OR^8$ and $R^8$ represents a methyl group, ethyl group, propyl group, isopropyl group, fluoromethyl group, difluoromethyl group, trifluoromethyl group, 2-fluoroethyl group, 2,2-difluoroethyl group, 2,2,2-trifluoroethyl group or pentafluoroethyl group;

The present active compound of formula (1) in which $R^1$, $R^2$ and $R^4$ represent hydrogen atoms, $R^3$ represents —$OR^8$ and $R^8$ represents a methyl group, ethyl group, propyl group, isopropyl group, 2-fluoroethyl group, 2,2-difluoroethyl group or 2,2,2-trifluoroethyl group;

The present active compound of formula (1) in which $R^3$ represents —$S(O)_m R^8$ and $R^8$ represents a C1-C3 alkyl group;

The present active compound of formula (1) in which $R^3$ represents —$S(O)_m R^8$ and $R^8$ represents a methyl group or ethyl group;

The present active compound of formula (1) in which $R^1$, $R^2$ and $R^4$ represent hydrogen atoms, $R^3$ represents —$S(O)_m R^8$ and $R^8$ represents a C1-C3 alkyl group;

The present active compound of formula (1) in which $R^1$, $R^2$ and $R^4$ represent hydrogen atoms, $R^3$ represents —$S(O)_m R^8$ and $R^8$ represents a methyl group or ethyl group.

Next, the method of producing the present active compound will be described.

The present active compound can be produced, for example, by the following (Production Method 1) to (Production Method 12) and (Production Method 21) to (Production Method 36).

(Production Method 1)

Among the present active compounds, a compound (4) in which n is 0 can be produced by reacting a compound (2) and a compound (3) in the presence of a base.

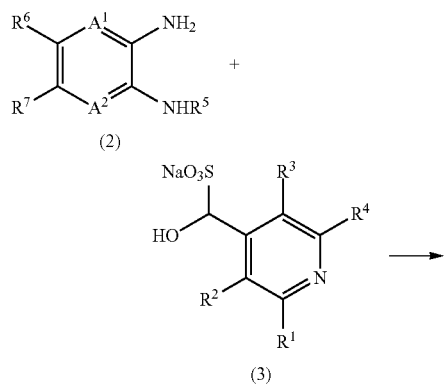

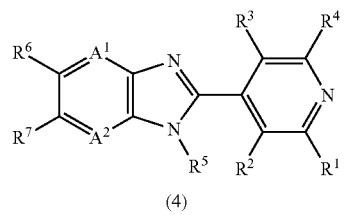

[wherein, $R^1$, $R^2$, $R^3$, $R^4$, $R^5$, $R^6$, $R^7$, $A^1$ and $A^2$ represent the same meaning as described above.]

The reaction is carried out usually in the presence of a solvent.

Examples of the solvent to be used in the reaction include ethers such as tetrahydrofuran (hereinafter, referred to as THF in some cases), ethylene glycol dimethyl ether, 1,4-dioxane and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile and the like, acid amides such as N,N-dimethylformamide (hereinafter, referred to as DMF in some cases) and the like, sulfoxides such as dimethyl sulfoxide (hereinafter, referred to as DMSO in some cases) and the like, nitrogen-containing aromatic compounds such as pyridine, quinoline and the like, and mixtures thereof.

The compound (3) is used usually in a proportion of 1 to 3 mol with respect to 1 mol of the compound (2).

The reaction temperature of the reaction is usually in the range of 30 to 200° C., and the reaction time thereof is usually in the range of 0.1 to 24 hours.

After completion of the reaction, the compound (4) can be isolated by subjecting post treatment operations such as water being poured into the reaction mixture, the mixture being extracted with an organic solvent, then the organic layer being dried and concentrated. The isolated compound (4) can also be further purified by chromatography, recrystallization and the like.

(Production Method 2)

Among the present active compounds, a compound (4) in which n is 0 can be produced by reacting a compound (2) and a compound (5).

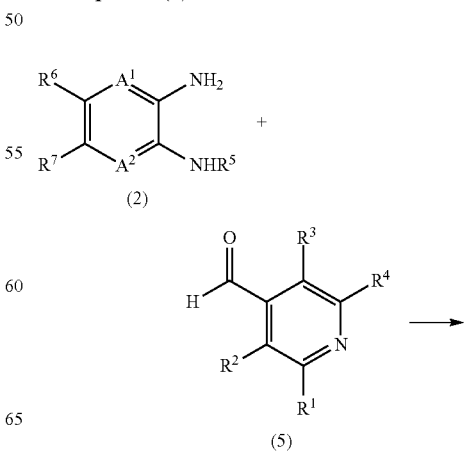

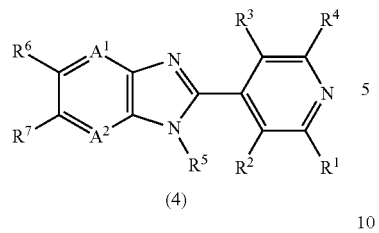

(4)

[wherein, $R^1$, $R^2$, $R^3$, $R^4$, $R^5$, $R^6$, $R^7$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile and the like, acid amides such as DMF and the like, sulfoxides such as dimethyl sulfoxide and the like, nitrogen-containing aromatic compounds such as pyridine, quinoline and the like, and mixtures thereof.

The reaction can also be carried out with addition of a base if necessary.

The base to be used in the reaction includes hydrogen carbonates such as sodium hydrogen carbonate, potassium hydrogen carbonate and the like, carbonates such as sodium carbonate, potassium carbonate and the like, sulfites such as sodium sulfite, potassium sulfite and the like, hydrogen sulfates such as sodium hydrogen sulfate, potassium hydrogen sulfate and the like, and mixtures thereof.

The compound (5) is used usually in a proportion of 1 to 3 mol with respect to 1 mol of the compound (2). In the case of addition of a base, the base is used usually in a proportion of 1 to 5 mol with respect to 1 mol of the compound (2).

The reaction temperature of the reaction is usually in the range of 30 to 200° C., and the reaction time thereof is usually in the range of 0.1 to 24 hours.

After completion of the reaction, the compound (4) can be isolated by subjecting post treatment operations such as water being poured into the reaction mixture, the mixture being extracted with an organic solvent, then the organic layer being dried and concentrated. The isolated compound (4) can also be further purified by chromatography, recrystallization and the like.

(Production Method 3)

Among the compounds, a compound (4) in which n is 0 can be produced by reacting a compound (2) and a compound (6) in the presence of a dehydrocondensing agent.

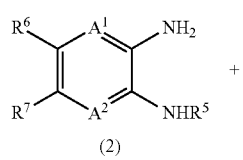

(2)

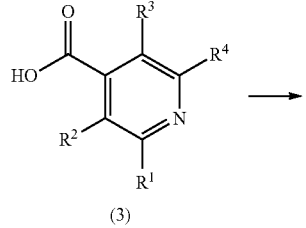

(3)

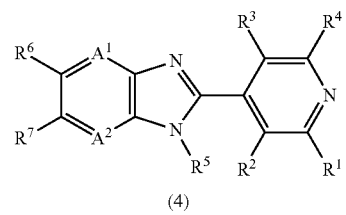

(4)

[wherein, $R^1$, $R^2$, $R^3$, $R^4$, $R^5$, $R^6$, $R^7$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile and the like, acid amides such as DMF and the like, sulfoxides such as DMSO and the like, nitrogen-containing aromatic compounds such as pyridine, quinoline and the like, and mixtures thereof.

The dehydrocondensing agent to be used in the reaction includes carbodiimides such as 1-ethyl-3-(3-dimethylaminopropyl)carbodiimide hydrochloride (hereinafter, referred to as WSC in some cases), 1,3-dicyclohexylcarbodiimide and the like.

The reaction may be performed in the presence of 1-hydroxybenzotriazole.

When the compound (6) is used usually in a proportion of 1 to 3 mol with respect to 1 mol of the compound (2), the dehydrocondensing agent is used usually in a proportion of 1 to 5 mol, 1-hydroxybenzotriazole is used usually in a proportion of 0.01 to 0.1 mol.

The reaction temperature of the reaction is usually in the range of 30 to 200° C., and the reaction time thereof is usually in the range of 0.1 to 24 hours.

After completion of the reaction, the compound (4) can be isolated by subjecting post treatment operations such as water being poured into the reaction mixture, the mixture being extracted with an organic solvent, then the organic layer being dried and concentrated. The isolated compound (4) can also be further purified by chromatography, recrystallization and the like.

(Production Method 4)

Among the compounds, a compound (4) in which n is 0 can be produced by reacting a compound (7) in the presence of a dehydrating agent.

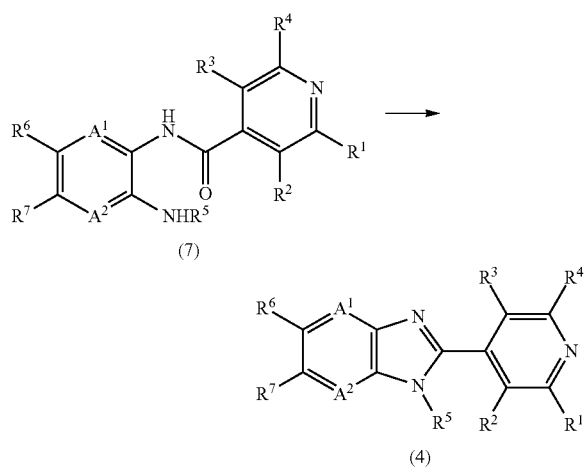

(7)

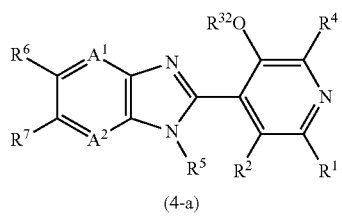

(4)

[wherein, $R^1$, $R^2$, $R^3$, $R^4$, $R^5$, $R^6$, $R^7$, $A^1$ and $A^2$ represent the same meaning as described above.]

The reaction is carried out usually in the presence of a solvent, and it may also be permissible to use a dehydrating agent in solvent quantity.

Examples of the solvent to be used in the reaction include ethers such as THF, ethylene glycol dimethyl ether, 1,4-dioxane and the like, aliphatic hydrocarbons such as hexane, heptane, octane and the like, aromatic hydrocarbons such as toluene, xylene and the like, halogenated hydrocarbons chlorobenzene and the like, esters such as ethyl acetate, butyl acetate and the like, nitriles such as acetonitrile and the like, acid amides such as DMF and the like, sulfoxides such as DMSO and the like, and mixtures thereof.

The dehydrating agent to be used in the reaction includes sulfonic acids such as p-toluenesulfonic acid and the like, phosphorus oxy chloride, acetic anhydride, trifluoroacetic anhydride and the like.

The dehydrating agent is used usually in a proportion of 0.1 to excess amount with respect to 1 mol of the compound (7).

The reaction temperature of the reaction is usually in the range of 30 to 200° C., and the reaction time thereof is usually in the range of 0.1 to 24 hours.

After completion of the reaction, the compound (4) can be isolated by subjecting post treatment operations such as the reaction mixture being extracted with an organic solvent, the organic layer being dried and concentrated. The isolated compound (4) can also be further purified by chromatography, recrystallization and the like.

(Production Method 5)

Among the compounds (4), a compound (4-a) can be produced by reacting a compound (8) and a compound (9) in the presence of a base.

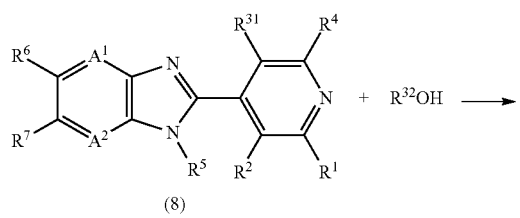

(4-a)

[wherein, $R^1$, $R^2$, $R^4$, $R^5$, $R^6$, $R^7$, $A^1$ and $A^2$ represent the same meaning as described above, $R^{31}$ represents a chlorine atom or a fluorine atom, and $R^{32}$ represents a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y.]

The reaction is carried out usually in the presence of a solvent, and it may also be permissible to use the compound (9) in solvent quantity.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, and mixtures thereof.

Examples of the base to be used in the reaction include alkali metal hydrides such as sodium hydride and the like.

The compound (9) is used usually in a proportion of 1 to excess amount and the base is used usually in a proportion of 1 to 10 mol with respect to 1 mol of the compound (8).

The reaction temperature of the reaction is usually in the range of 0 to 150° C., and the reaction time thereof is usually in the range of 0.1 to 24 hours.

After completion of the reaction, the compound (4-a) can be isolated by subjecting post treatment operations such as the reaction mixture being extracted with an organic solvent, the organic layer being dried and concentrated. The isolated compound (4-a) can also be further purified by chromatography, recrystallization and the like.

(Production Method 6)

Among the compounds (4), a compound (4-b) can be produced by reacting a compound (8) and a compound (10) in the presence of a base.

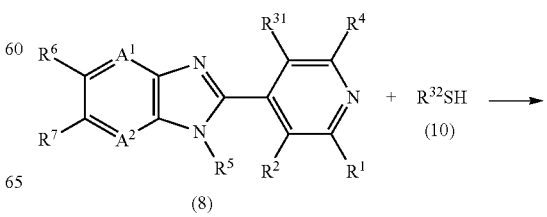

-continued

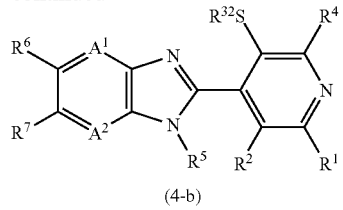

(4-b)

[wherein, $R^1$, $R^2$, $R^4$, $R^5$, $R^6$, $R^7$, $R^{31}$, $R^{32}$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, and mixtures thereof.

Examples of the base to be used in the reaction include alkali metal hydrides such as sodium hydride and the like.

The compound (10) is used usually in a proportion of 1 to 10 mol and the base is used usually in a proportion of 1 to 10 mol with respect to 1 mol of the compound (8).

The reaction temperature of the reaction is usually in the range of 0 to 150° C., and the reaction time thereof is usually in the range of 0.5 to 24 hours.

After completion of the reaction, the compound (4-b) can be isolated by subjecting post treatment operations such as the reaction mixture being extracted with an organic solvent, the organic layer being dried and concentrated. The isolated compound (4-b) can also be further purified by chromatography, recrystallization and the like.

(Production Method 7)

Among the compounds (4), a compound (4-c) can be produced by reacting the compound (4-b) in the presence of an oxidation agent.

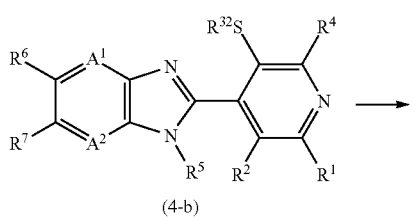

(4-b)

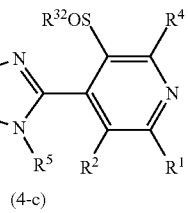

(4-c)

[wherein, $R^1$, $R^2$, $R^4$, $R^5$, $R^6$, $R^7$, $R^{32}$, $A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like, alcohols such as methanol, ethanol and the like, acetic acid, water and mixtures thereof.

Examples of the oxidation agent to be used in the reaction include sodium periodate.

The oxidation agent is used usually in a proportion of 1 to 3 mol with respect to 1 mol of the compound (4-b).

The reaction temperature of the reaction is usually in the range of −20 to 80° C., and the reaction time thereof is usually in the range of 0.1 to 12 hours.

After completion of the reaction, the compound (4-c) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (4-c) can also be further purified by chromatography, recrystallization and the like.

(Production Method 8)

Among the compounds (4), a compound (4-d) can be produced by reacting the compound (4-b) in the presence of an oxidation agent.

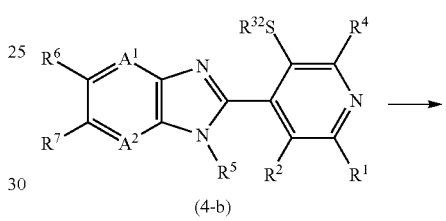

(4-b)

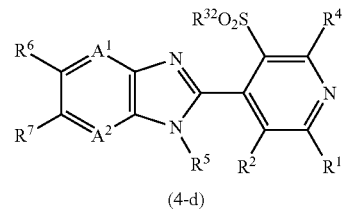

(4-d)

[wherein, $R^1$, $R^2$, $R^4$, $R^5$, $R^6$, $R^7$, $R^{32}$, $A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like, acetic acid, water and mixtures thereof.

Examples of the oxidation agent to be used in the reaction include carboxylic acid peroxides such as 3-chloroperbenzoic acid and the like.

The oxidation agent is used usually in a proportion of 2 to 4 mol with respect to 1 mol of the compound (4-b).

The reaction temperature of the reaction is usually in the range of −20 to 30° C., and the reaction time thereof is usually in the range of 0.1 to 12 hours.

After completion of the reaction, the compound (4-d) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (4-d) can also be further purified by chromatography, recrystallization and the like.

(Production Method 9)

Among the compounds (4), a compound (4-e) can be produced by reacting a compound (11) with an acid anhydride represented by (12) or an acid chloride represented by (13).

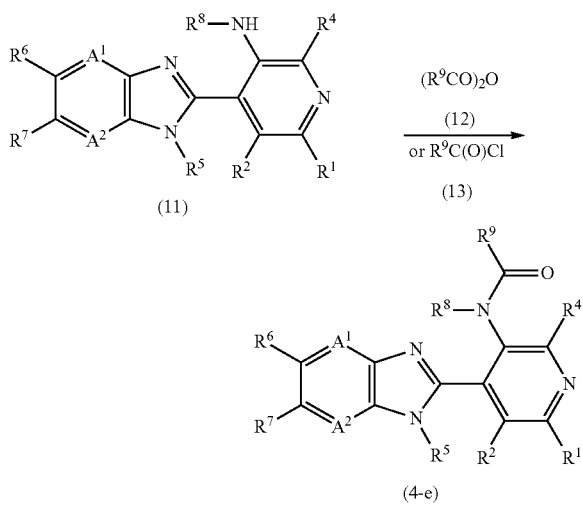

[wherein, $R^1$, $R^2$, $R^4$, $R^5$, $R^6$, $R^7$, $R^8$, $R^9$, $A^1$ and $A^2$ represent the same meaning as described above.]

The reaction is carried out usually in the presence of a solvent, and it may also be permissible to use the compound (12) in solvent quantity.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, nitrogen-containing aromatic compounds such as pyridine, quinoline and the like, and mixtures thereof.

The reaction can also be carried out with addition of a base if necessary.

Examples of the base to be used in the reaction include alkali metal hydrides such as sodium hydride and the like, carbonates such as potassium carbonate and the like, tertiary amines such as triethylamine, diisopropylethylamine and the like, and nitrogen-containing aromatic compounds such as pyridine, 4-dimethylaminopyridine and the like.

The compound (12) or the compound (13) is used usually in a proportion of 1 to 10 mol and the base is used usually in a proportion of 1 to 10 mol with respect to 1 mol of the compound (11).

The reaction temperature of the reaction is usually in the range of 0 to 120° C., and the reaction time thereof is usually in the range of 0.1 to 24 hours.

After completion of the reaction, the compound (4-e) can be isolated by subjecting post treatment operations such as the reaction mixture being extracted with an organic solvent, the organic layer being dried and concentrated. The isolated compound (4-e) can also be further purified by chromatography, recrystallization and the like.

(Production Method 10)

Among the compounds (4), a compound (4-f) can be produced by reacting a compound (14) with a boronic acid compound represented by (15) or a tin compound represented by (16) in the presence of a palladium compound.

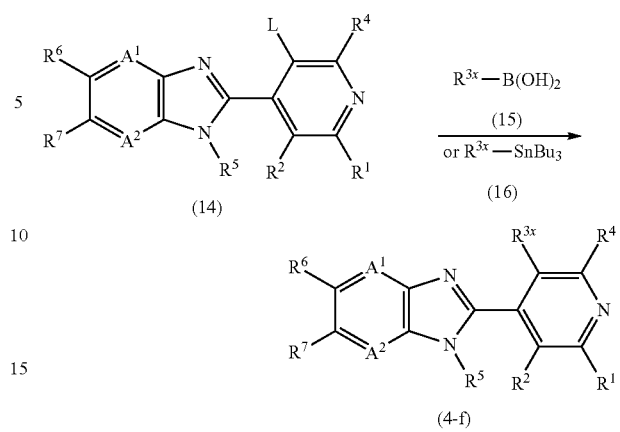

[wherein, $R^1$, $R^2$, $R^4$, $R^5$, $R^6$, $R^7$, $A^1$ and $A^2$ represent the same meaning as described above, L represents a bromine or iodine atom, $R^{3x}$ represents a phenyl group optionally substituted with one or more members selected from the group Y, a 5-membered aromatic heterocyclic group or a 6-membered aromatic heterocyclic group optionally substituted with one or more members selected from the group Y (here, limited to aromatic heterocyclic groups bonding to a pyridine ring on its carbon atom).]

The reaction is carried out usually in the presence of a solvent.

Examples of the solvent to be used in the reaction include ethers such as THF, ethylene glycol dimethyl ether, 1,4-dioxane and the like, alcohols such as methanol, ethanol and the like, aliphatic hydrocarbons such as hexane, heptane, octane and the like, aromatic hydrocarbons such as toluene, xylene and the like, acid amides such as DMF and the like, water and mixtures thereof, and the like.

The palladium compound to be used in the reaction includes palladium acetate, tetrakistriphenylphosphinepalladium, {1,1'-bis(diphenylphosphino)ferrocene}dichloropalladium methylene chloride complex, and bis(triphenylphosphine)palladium dichloride, and the like.

The compound (15) or the compound (16) is used usually in a proportion of 0.5 to 5 mol and the palladium compound is used usually in a proportion of 0.001 to 0.1 mol with respect to 1 mol of the compound (14).

The reaction can also be carried out in the presence of a base (inorganic salts such as sodium acetate, potassium acetate, potassium carbonate, tripotassium phosphate, sodium hydrogen carbonate and the like are mentioned) and/or a phase transfer catalyst (quaternary ammonium salts such as tetrabutyl ammonium bromide, benzyl triethyl ammonium bromide and the like are mentioned), if necessary.

The reaction temperature of the reaction is usually in the range of 50 to 120° C., and the reaction time thereof is usually in the range of 0.5 to 24 hours.

After completion of the reaction, the compound (4-f) can be isolated by subjecting post treatment operations such as the reaction mixture being extracted with an organic solvent, the organic layer being dried and concentrated. The isolated compound (4-f) can also be further purified by chromatography, recrystallization and the like.

(Production Method 11)

Among the compounds (4), a compound (4-g) can be produced by reacting a compound (8) and a compound (17) in the presence of a base.

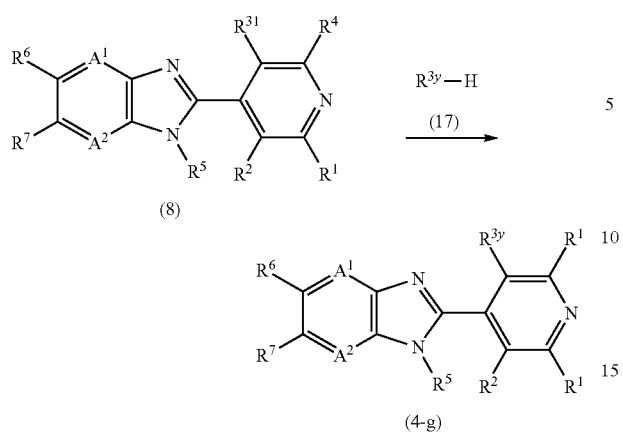

(8)

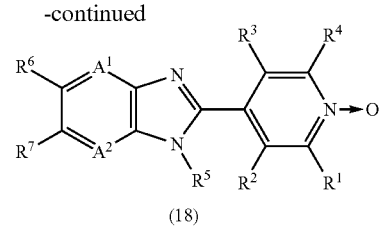

(4-g)

[wherein, $R^1$, $R^2$, $R^4$, $R^5$, $R^6$, $R^7$, $R^{31}$, $A^1$ and $A^2$ represent the same meaning as described above, $R^{3y}$ represents a 5-membered heterocyclic group or a 6-membered heterocyclic group optionally substituted with one or more members selected from the group Y (here, limited to heterocyclic groups bonding to a pyridine ring on its nitrogen atom).]

The reaction is carried out usually in the presence of a solvent.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, and mixtures thereof.

Examples of the base to be used in the reaction include alkali metal hydrides such as sodium hydride and the like, carbonates such as potassium carbonate and the like.

The compound (17) is used usually in a proportion of 1 to 10 mol and the base is used usually in the range of 1 to 10 mol with respect to 1 mol of the compound (8).

The reaction temperature of the reaction is usually in the range of 0 to 100° C., and the reaction time thereof is usually in the range of 0.1 to 24 hours.

After completion of the reaction, the compound (4-g) can be isolated by subjecting post treatment operations such as the reaction mixture being extracted with an organic solvent, the organic layer being dried and concentrated. The isolated compound (4-g) can also be further purified by chromatography, recrystallization and the like.

(Production Method 12)

Among the compounds, a compound (18) in which n is 1 can be produced by reacting a compound (4) in the presence of an oxidation agent.

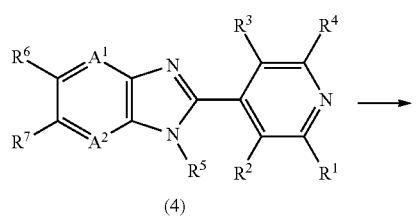

(4)

(18)

[wherein, $R^1$, $R^2$, $R^3$, $R^4$, $R^5$, $R^6$, $R^7$, $A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like, acetic acid, water and mixtures thereof.

Examples of the oxidation agent to be used in the reaction include carboxylic acid peroxides such as 3-chloroperbenzoic acid and the like, and hydrogen peroxide water and the like.

The oxidation agent is used usually in a proportion of 1 to 3 mol with respect to 1 mol of the compound (4).

The reaction temperature of the reaction is usually in the range of 40 to 100° C., and the reaction time thereof is usually in the range of 0.1 to 24 hours.

After completion of the reaction, the compound (18) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (18) can also be further purified by chromatography, recrystallization and the like.

(Production Method 21)

Among the compounds (4), the compound (4-h) can be produced by reacting a compound (21) and a compound (10) in the presence of a base.

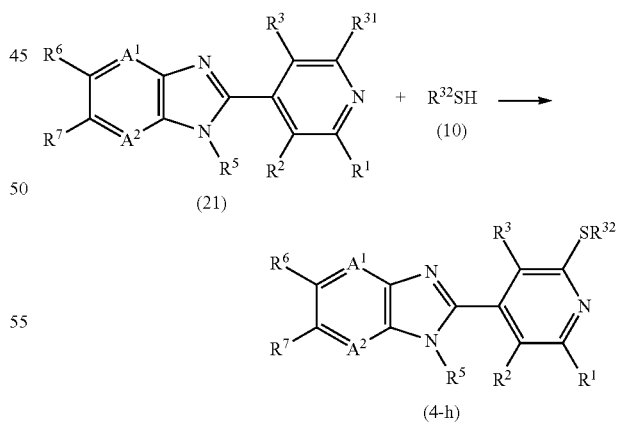

[wherein, $R^1$, $R^2$, $R^3$, $R^5$, $R^6$, $R^7$, $R^{31}$, $R^{32}$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, and mixtures thereof.

Examples of the base to be used in the reaction include alkali metal hydrides such as sodium hydride and the like, etc.

The compound (10) is used usually in a proportion of 1 to 10 mol and the base is used usually in a proportion of 1 to 10 mol with respect to 1 mol of the compound (21).

The reaction temperature of the reaction is usually in the range of 0 to 100° C., and the reaction time is usually in the range of 0.1 to 24 hours.

After completion of the reaction, the compound (4-h) can be isolated by subjecting post treatment operations such as the reaction mixture being extracted with an organic solvent, the organic layer being dried and concentrated. The isolated compound (4-h) can also be further purified by chromatography, recrystallization and the like.

(Production Method 22)

Among the compounds (4), the compound (4-j) can be produced by reacting the compound (4-h) and an oxidation agent.

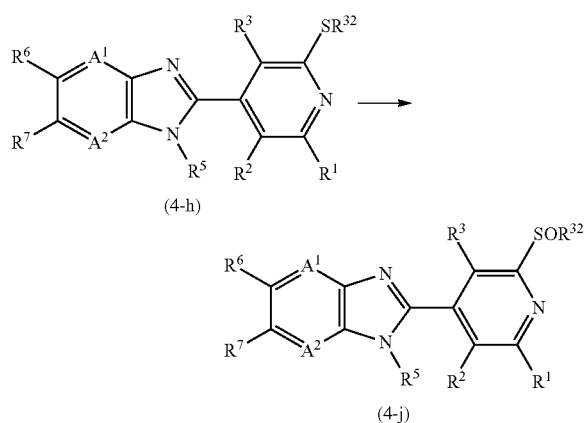

[wherein, $R^1$, $R^2$, $R^3$, $R^5$, $R^6$, $R^7$, $R^{32}$, $A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like, alcohols such as methanol, ethanol and the like, ethers such as THF, ethylene glycol dimethyl ether, 1,4-dioxane and the like; acetic acid, water, and mixtures thereof.

Examples of the oxidation agent to be used in the reaction include sodium periodate.

The oxidation agent is used usually in a proportion of 1 to 3 mol with respect to 1 mol of the compound (4-h).

The reaction temperature of the reaction is usually in the range of −20 to 80° C., and the reaction time is usually in the range of 0.1 to 12 hours.

After completion of the reaction, the compound (4-j) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (4-j) can also be further purified by chromatography, recrystallization and the like.

(Production Method 23)

Among the compounds (4), the compound (4-k) can be produced by reacting the compound (4-h) and an oxidation agent.

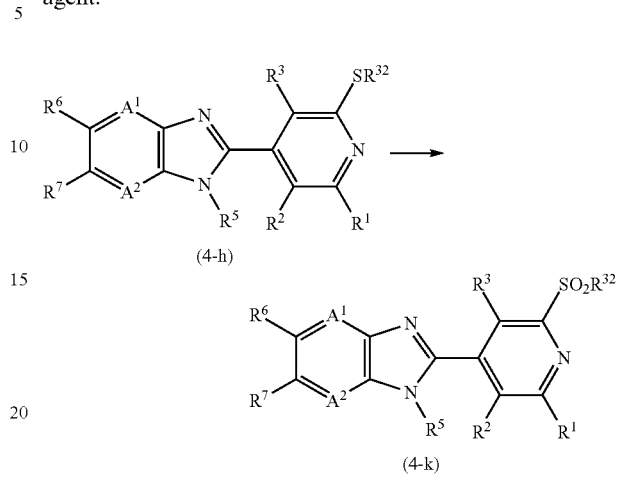

[wherein, $R^1$, $R^2$, $R^3$, $R^5$, $R^6$, $R^7$, $R^{32}$, $A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like; acetic acid, water, and mixtures thereof.

Examples of the oxidation agent to be used in the reaction include carboxylic acid peroxides such as 3-chloroperbenzoic acid and the like.

The oxidation agent is used usually in a proportion of 2 to 4 mol with respect to 1 mol of the compound (4-h).

The reaction temperature of the reaction is usually in the range of −20 to 30° C., and the reaction time is usually in the range of 0.1 to 12 hours.

After completion of the reaction, the compound (4-k) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (4-k) can also be further purified by chromatography, recrystallization and the like.

(Production Method 24)

Among the compounds (4), the compound (4-k) can be produced, for example, by reacting the compound (4-j) and an oxidation agent.

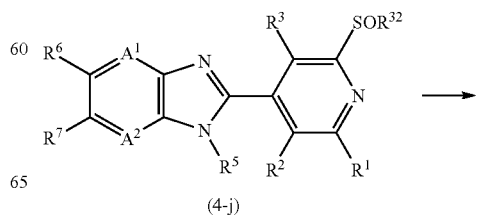

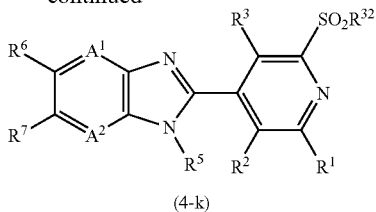

(4-k)

[wherein, $R^1, R^2, R^4, R^5, R^6, R^7, R^{32}, A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like; acetic acid, water, and mixtures thereof.

Examples of the oxidation agent to be used in the reaction include carboxylic acid peroxides such as 3-chloroperbenzoic acid and the like.

The oxidation agent is used usually in a proportion of 1 to 3 mol with respect to 1 mol of the compound (4-j).

The reaction temperature of the reaction is usually in the range of −20 to 30° C., and the reaction time is usually in the range of 0.1 to 12 hours.

After completion of the reaction, the compound (4-k) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (4-k) can also be further purified by chromatography, recrystallization and the like.

(Production Method 25)

Among the compounds (4), the compound (4-p) can be produced by reacting the compound (8) and a cyanide.

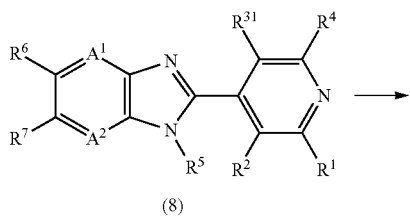

(8)

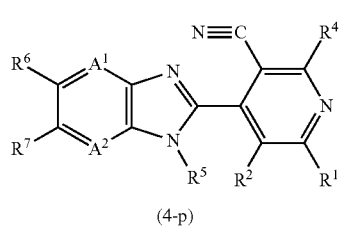

(4-p)

[wherein, $R^1, R^2, R^4, R^5, R^6, R^7, R^{31}, A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, acid amides such as DMF, 1-methyl-2-pyrrolidinone and the like, sulfoxides such as DMSO and the like, and mixtures thereof.

Examples of the cyanide to be used in the reaction include sodium cyanide and potassium cyanide.

The reaction is carried out, if necessary, in the presence of crown ethers such as 15-crown-5, 18-crown-6 and the like.

The cyanide is used usually in a proportion of 1 to 3 mol and the catalyst is used usually in a proportion of 0.01 to 0.5 mol with respect to 1 mol of the compound (8).

The reaction temperature of the reaction is usually in the range of 0 to 200° C., and the reaction time is usually in the range of 0.1 to 12 hours.

After completion of the reaction, the compound (4-p) can be isolated by subjecting post treatment operations such as the reaction mixture being extracted with an organic solvent, the organic layer being dried and concentrated. The isolated compound (4-p) can also be further purified by chromatography, recrystallization and the like.

(Production Method 26)

Among the compounds (4), the compound (4-q) can be produced by subjecting the compound (4-p) to a hydrolysis reaction in the presence of a base.

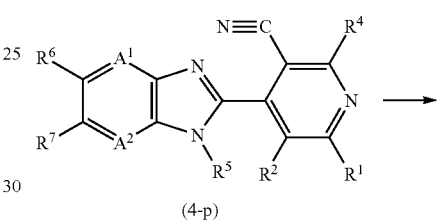

(4-p)

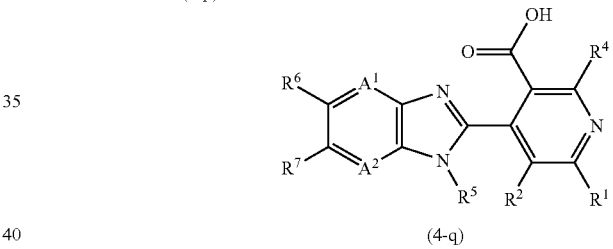

(4-q)

[wherein, $R^1, R^2, R^4, R^5, R^6, R^7, A^1$ and $A^2$ represent the same meaning as described above.]

The reaction is carried out usually in the presence of a solvent.

Examples of the solvent to be used in the reaction include alcohols such as methanol, ethanol and the like; water, and mixtures thereof.

Examples of the base to be used in the reaction include hydroxides of alkali metals or alkaline earth metals such as sodium hydroxide, potassium hydroxide, barium hydroxide and the like.

The base is used usually in a proportion of 1 to 3 mol with respect to 1 mol of the compound (4-p).

The reaction temperature of the reaction is usually in the range of 0 to 150° C., and the reaction time is usually in the range of 0.1 to 24 hours.

After completion of the reaction, the compound (4-q) can be isolated by subjecting post treatment operations such as neutralized with an acid of the reaction mixture, being filtration to obtain a solid or neutralized with an acid of the reaction mixture, being extraction of the mixture with an organic solvent, then the organic layer being dried and concentrated. The isolated compound (4-q) can also be further purified by chromatography, recrystallization and the like.

(Production Method 27)

Among the compounds (4), the compound (4-r) can be produced by reacting the compound (4-p) with hydrogen peroxide in the presence of a base.

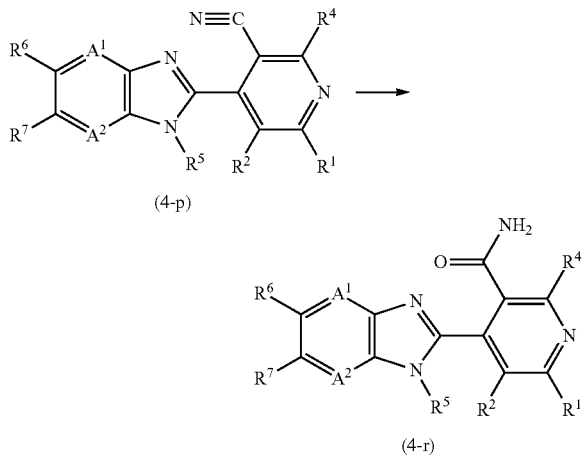

[wherein, $R^1, R^2, R^4, R^5, R^6, R^7, A^1$ and $A^2$ represent the same meaning as described above.]

The reaction is carried out usually in the presence of a solvent.

Examples of the solvent to be used in the reaction include sulfoxides such as DMSO and the like; water, and mixtures thereof.

Examples of the base to be used in the reaction include hydroxides of alkali metals or alkaline earth metals such as sodium hydroxide, potassium hydroxide, calcium hydroxide and the like, and carbonates such as sodium carbonate, potassium carbonate and the like.

Hydrogen peroxide is used usually in a proportion of 1 to 5 mol and the base is used usually in a proportion of 1 to 5 mol with respect to 1 mol of the compound (4-p).

The reaction temperature of the reaction is usually in the range of 0 to 100° C., and the reaction time is usually in the range of 0.1 to 24 hours.

After completion of the reaction, the compound (4-r) can be isolated by subjecting post treatment operations such as the reaction mixture being extracted with an organic solvent, the organic layer being dried and concentrated. The isolated compound (4-r) can also be further purified by chromatography, recrystallization and the like.

(Production Method 28)

Among the compounds (4), the compound (4-s) can be produced by reacting a compound (22) and a compound (23).

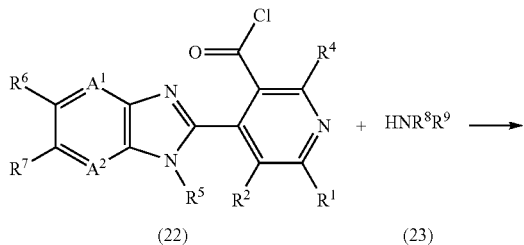

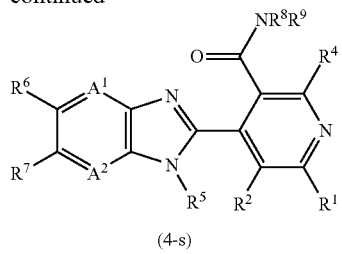

[wherein, $R^1, R^2, R^4, R^5, R^6, R^7, R^8, R^9, A^1$ and $A^2$ represent the same meaning as described above.]

The reaction is carried out usually in the presence of a base, and carried out usually in the presence of a solvent.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, nitrogen-containing aromatic compounds such as pyridine, quinoline and the like; water, and mixtures thereof.

Examples of the base to be used in the reaction include carbonates such as potassium carbonate and the like, tertiary amines such as triethylamine, diisopropylethylamine and the like, and nitrogen-containing aromatic compounds such as pyridine, 4-dimethylaminopyridine and the like.

The compound (23) is used usually in a proportion of 1 mol to excess quantity and the base is used usually in a proportion of 1 mol to excess quantity with respect to 1 mol of the compound (22). In the case of excessive use of the compound (23), the reaction can also be carried out without using the above-described base. When tertiary amines such as triethylamine, diisopropylethylamine and the like or liquid nitrogen-containing aromatic compounds such as pyridine and the like are used in excess amount as the base, the reaction can also be carried out without using the above-described solvent.

The reaction temperature of the reaction is usually in the range of 0 to 100° C., and the reaction time is usually in the range of 0.1 to 24 hours.

After completion of the reaction, the compound (4-s) can be isolated by subjecting post treatment operations such as the reaction mixture being extracted with an organic solvent, the organic layer being dried and concentrated. The isolated compound (4-s) can also be further purified by chromatography, recrystallization and the like.

(Production Method 29)

Among the compounds (4), the compound (4-s) can be produced by reacting the compound (4-q), a compound (23) and a condensing agent.

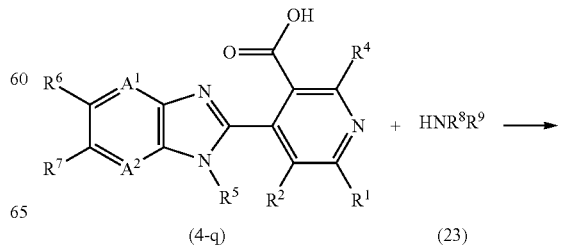

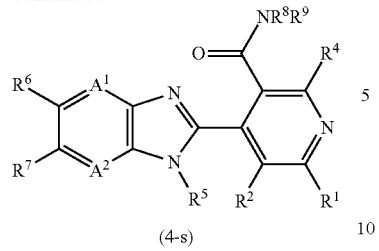

(4-s)

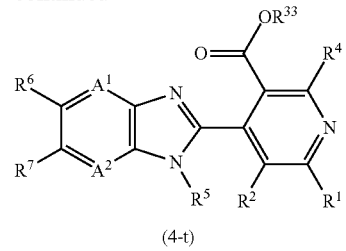

(4-t)

[wherein, $R^1$, $R^2$, $R^4$, $R^5$, $R^6$, $R^7$, $R^8$, $R^9$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aliphatic hydrocarbons such as hexane, heptane, octane and the like, aromatic hydrocarbons such as toluene, xylene and the like, halogenated hydrocarbons such as chlorobenzene and the like, esters such as ethyl acetate, butyl acetate and the like, nitriles such as acetonitrile and the like, acid amides such as DMF and the like, sulfoxides such as DMSO and the like, nitrogen-containing aromatic compounds such as pyridine, quinoline and the like, and mixtures thereof.

The condensing agent to be used in the reaction include carbodiimides such as WSC, 1,3-dicyclohexylcarbodiimide and the like.

The reaction is carried out, if necessary, in the presence of 1-hydroxybenzotriazole.

The compound (23) is used usually in a proportion of 1 to 3 mol, the condensing agent is used usually in a proportion of 1 to 5 mol and 1-hydroxybenzotriazole is used usually in a proportion of 0.01 to 0.1 mol with respect to 1 mol of the compound (4-q).

The reaction temperature of the reaction is usually in the range of 0 to 100° C., and the reaction time is usually in the range of 0.1 to 24 hours.

After completion of the reaction, the compound (4-q) can be isolated by subjecting post treatment operations such as the reaction mixture being extracted with an organic solvent, the organic layer being dried and concentrated. The isolated compound (4-s) can also be further purified by chromatography, recrystallization and the like.

(Production Method 30)

Among the compounds (4), the compound (4-t) can be produced by reacting the compound (4-q) and a compound (24) in the presence of an acid.

[wherein, $R^1$, $R^2$, $R^4$, $R^5$, $R^6$, $R^7$, $A^1$ and $A^2$ represents the same meaning as described above, and $R^{33}$ represents a C1-C4 alkyl group optionally substituted with one or more halogen atoms.]

The reaction is carried out in the presence of a solvent or in the absence of a solvent.

Examples of the solvent to be used in the reaction include ethers such as 1,4-dioxane and the like, aliphatic hydrocarbons such as hexane, heptane, octane and the like, aromatic hydrocarbons such as toluene, xylene and the like, halogenated hydrocarbons such as chlorobenzene and the like, and mixtures thereof.

Examples of the acid to be used in the reaction include mineral acids such as hydrochloric acid, sulfuric acid and the like, and organic acids such as p-toluenesulfonic acid and the like.

The compound (24) is used usually in a proportion of 1 mol to excess quantity and the acid is used usually 0.01 mol to 1 mol with respect to 1 mol of the compound (4-q).

In the case of excessive use of the compound (24), the reaction can also be carried out without using the above-described solvent.

The reaction temperature of the reaction is usually in the range of 0 to 200° C., and the reaction time is usually in the range of 0.1 to 24 hours.

After completion of the reaction, the compound (4-t) can be isolated by subjecting post treatment operations such as the reaction mixture being extracted with an organic solvent, the organic layer being dried and concentrated. The isolated compound (4-t) can also be further purified by chromatography, recrystallization and the like.

(Production Method 31)

Among the compounds (4), the compound (4-u) can be produced by reacting a compound (8) with a sulfurizing agent such as sodium hydrosulfide and the like.

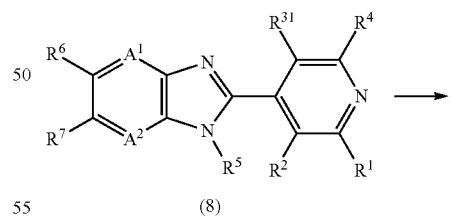

(8)

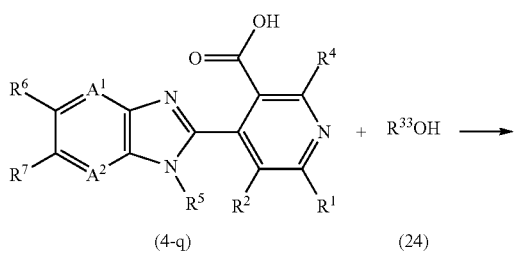

(4-q)    (24)

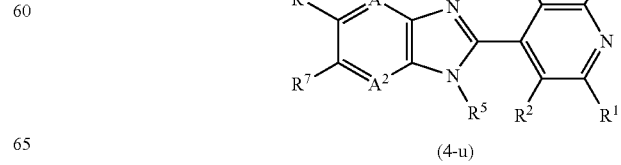

(4-u)

[wherein, $R^1$, $R^2$, $R^4$, $R^5$, $R^6$, $R^7$, $R^{31}$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, nitrogen-containing aromatic compounds such as pyridine, quinoline and the like; water, and mixtures thereof.

The sulfurizing agent such as sodium hydrosulfide and the like is used usually in a proportion of 1 mol to 3 mol with respect to 1 mol of the compound (8).

The reaction temperature of the reaction is usually in the range of 0 to 150° C., and the reaction time is usually in the range of 0.1 to 24 hours.

After completion of the reaction, the compound (4-u) can be isolated by subjecting post treatment operations such as neutralized with an acid of the reaction mixture, being filtration to obtain a solid or neutralized with an acid of the reaction mixture, being extraction of the mixture with an organic solvent, then the organic layer being dried and concentrated. The isolated compound (4-u) can also be further purified by chromatography, recrystallization and the like.

(Production Method 32)

Among the compounds (4), the compound (4-w) can be produced by reacting the compound (4-u) and a compound (25) in the presence of a base.

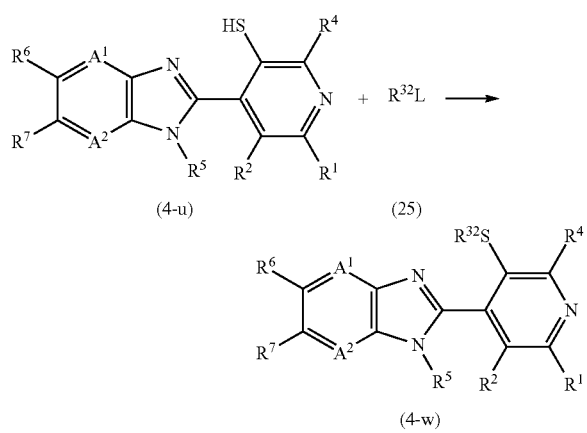

[wherein, $R^1$, $R^2$, $R^4$, $R^5$, $R^6$, $R^7$, $R^{32}$, $A^1$ and $A^2$ represent the same meaning as described above.]

The reaction is carried out usually in the presence of a solvent.

Examples of the solvent to be used in the reaction include ethers such as THF, ethylene glycol dimethyl ether, 1,4-dioxane and the like, aromatic hydrocarbons such as toluene, xylene and the like, nitriles such as acetonitrile and the like, acid amides such as DMF and the like, sulfoxides such as DMSO and the like, and mixtures thereof.

Examples of the base to be used in the reaction include hydrides of alkali metals or alkaline earth metals such as sodium hydride, potassium hydride, calcium hydride and the like, inorganic bases such as sodium carbonate, potassium carbonate and the like, or organic bases such as triethylamine, and the like.

The base is used usually in a proportion of 1 to 3 mol with respect to 1 mol of the compound (4-u).

The reaction temperature of the reaction is usually in the range of 0 to 100° C., and the reaction time is usually in the range of 0.1 to 24 hours.

After completion of the reaction, the compound (4-w) can be isolated by subjecting post treatment operations such as the reaction mixture being extracted with an organic solvent, the organic layer being dried and concentrated. The isolated compound (4-w) can also be further purified by chromatography, recrystallization and the like.

(Production Method 33)

Among the compounds (4), the compound (4-w) can be produced by reacting the compound (4-u) with an oxidation agent such as potassium nitrate and the like and a chlorinating agent such as trimethylsilyl chloride and the like.

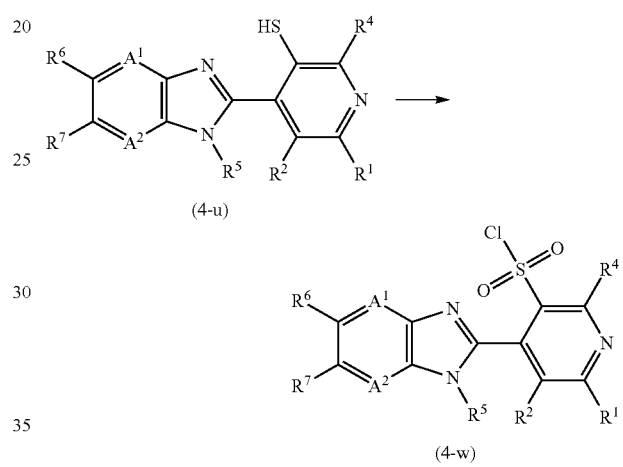

[wherein, $R^1$, $R^2$, $R^4$, $R^5$, $R^6$, $R^7$, $A^1$ and $A^2$ represent the same meaning as described above.]

The reaction is carried out usually in the presence of a solvent.

Examples of the solvent to be used in the reaction include halogenated hydrocarbons such as methylene chloride, chloroform and the like, aromatic halides such as chlorobenzene and the like, aromatic hydrocarbons such as toluene, xylene and the like, and mixtures thereof.

The oxidation agent such as potassium nitrate and the like is used usually in a proportion of 1 to 5 mol and the chlorinating agent such as trimethylsilyl chloride and the like is used usually in a proportion of 1 to 5 mol with respect to 1 mol of the compound (4-u).

The reaction temperature of the reaction is usually in the range of 0 to 150° C., and the reaction time is usually in the range of 0.1 to 24 hours.

After completion of the reaction, the compound (4-w) can be isolated by subjecting post treatment operations such as the reaction mixture being extracted with an organic solvent, the organic layer being dried and concentrated. The isolated compound (4-w) can also be further purified by recrystallization and the like.

(Production Method 34)

Among the compounds (4), the compound (4-y) can be produced by reacting the compound (4-w) and a compound (23).

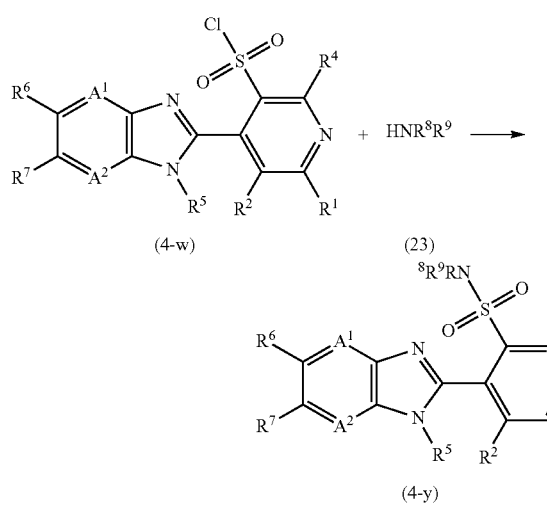

(4-w)           (23)

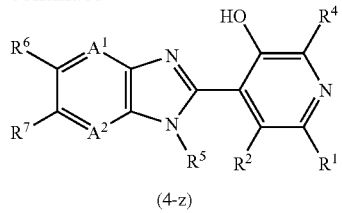

(4-y)

[wherein, $R^1$, $R^2$, $R^4$, $R^5$, $R^6$, $R^7$, $R^8$, $R^9$, $A^1$ and $A^2$ represent the same meaning as described above.]

The reaction is carried out usually in the presence of a solvent, and usually carried out in the presence of a base.

Examples of the solvent to be used in the reaction include ethers such as THF, ethylene glycol dimethyl ether, 1,4-dioxane and the like, aromatic hydrocarbons such as toluene, xylene and the like, and mixtures thereof.

Examples of the base to be used in the reaction include inorganic bases such as sodium carbonate, potassium carbonate and the like or organic bases such as triethylamine, diisopropylethylamine and the like, nitrogen-containing aromatic compounds such as pyridine, quinoline and the like.

The compound (23) is used usually in a proportion of 1 mol to excess quantity and the base is used usually in a proportion of 1 mol to excess quantity with respect to 1 mol of the compound (4-w).

In the case of excessive use of the compound (23), the reaction can also be carried out without using the above-described base.

The reaction temperature of the reaction is usually in the range of 0 to 100° C., and the reaction time is usually in the range of 0.1 to 24 hours.

After completion of the reaction, the compound (4-y) can be isolated by subjecting post treatment operations such as the reaction mixture being extracted with an organic solvent, the organic layer being dried and concentrated. The isolated compound (4-y) can also be further purified by chromatography, recrystallization and the like.

(Production Method 35)

Among the compounds (4), the compound (4-z) can be produced by reacting the compound (26) and hydrogen in the presence of a transition metal catalyst.

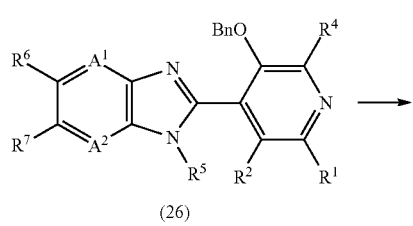

(26)

(4-z)

The reaction is carried out usually under a hydrogen atmosphere and in the presence of a solvent.

Examples of the solvent to be used in the reaction include aliphatic hydrocarbons such as hexane, heptane, octane and the like, alcohols such as methanol, ethanol and the like, esters such as ethyl acetate, butyl acetate and the like, and mixtures thereof.

Examples of the transition metal catalyst to be used in the reaction include palladium catalysts such as palladium charcoal and the like.

The transition metal catalyst is used usually in a proportion of 0.01 mol to 0.1 mol with respect to 1 mol of the compound (26).

The reaction temperature of the reaction is usually in the range of 0 to 100° C., and the reaction time is usually in the range of 0.1 to 24 hours.

After completion of the reaction, the compound (4-z) can be isolated by subjecting post treatment operations such as the reaction mixture being filtrated to remove the transition metal catalyst, the filtrate being extracted with an organic solvent, the organic layer being dried and concentrated. The isolated compound (4-z) can also be further purified by chromatography, recrystallization and the like.

(Production Method 36)

Among the compounds (4), the compound (4-d) can be produced by reacting the compound (4-c) and an oxidation agent.

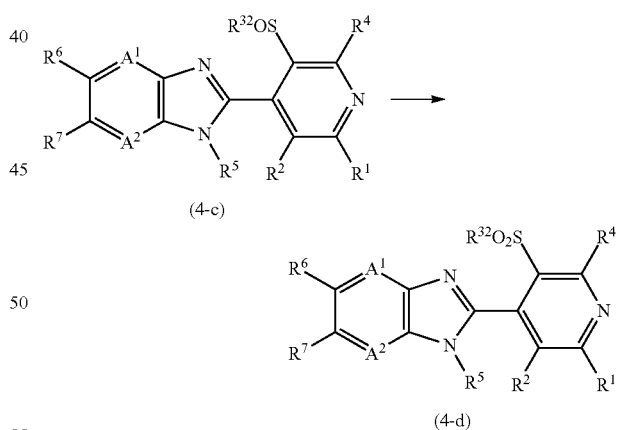

(4-c)

(4-d)

[wherein, $R^1$, $R^2$, $R^4$, $R^5$, $R^6$, $R^7$, $R^{32}$, $A^1$ and $A^2$ represent the same meaning as described above.]

The reaction is carried out usually in the presence of a solvent.

Examples of the solvent to be used in the reaction include aliphatic halogenated hydrocarbons such as dichloromethane, chloroform and the like; acetic acid, water, and mixtures thereof.

Examples of the oxidation agent to be used in the reaction include carboxylic acid peroxides such as 3-chloroperbenzoic acid and the like.

The oxidation agent is used usually in a proportion of 1 to 3 mol with respect to 1 mol of the compound (4-c).

The reaction temperature of the reaction is usually in the range of −20 to 30° C., and the reaction time is usually in the range of 0.1 to 12 hours.

After completion of the reaction, the compound (4-d) can be isolated by subjecting post treatment operations such as the reaction mixture being extracted with an organic solvent, the organic layer being washed with an aqueous solution of a reducing agent (for example, sodium sulfite, sodium thiosulfate) and an aqueous solution of a base (for example, sodium hydrogen carbonate) if necessary, then being dried and concentrated. The isolated compound (4-d) can also be further purified by chromatography, recrystallization and the like.

Some intermediates used for production of the present active compound are commercially available, disclosed in known literatures and the like, or can be produced by methods known to those skilled in the art.

The intermediate according to the present invention can be produced, for example, by the following method.

(Intermediate Production Method 1)

A compound (2) can be produced by a method shown in the following scheme.

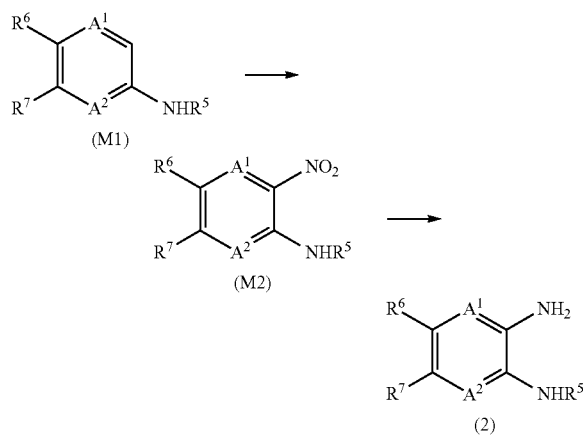

[wherein, $R^5$, $R^6$, $R^7$, $A^1$ and $A^2$ represent the same meaning as described above.]

(Process M1-1)

A compound (M2) can be produced by reacting a compound (M1) in the presence of a nitrating agent.

The reaction is carried out usually in the presence of a solvent.

Examples of the solvent to be used in the reaction include aliphatic halogenated hydrocarbons such as chloroform and the like, acetic acid, concentrated sulfuric acid, concentrated nitric acid, water and mixtures thereof.

Examples of the nitrating agent to be used in the reaction include concentrated nitric acid and the like.

The nitrating agent is used usually in a proportion of 1 to 3 mol with respect to 1 mol of the compound (M1).

The reaction temperature of the reaction is usually in the range of −10 to 100° C., and the reaction time thereof is usually in the range of 0.1 to 24 hours.

After completion of the reaction, the compound (M2) can be isolated by subjecting post treatment operations such as the reaction mixture being poured into water, the mixture being extracted with an organic solvent, then the organic layer being dried and concentrated. The isolated compound (M2) can also be further purified by chromatography, recrystallization and the like.

(Process M1-2)

A compound (2) can be produced by reacting the compound (M2) and hydrogen in the presence of a hydrogenation catalyst.

The reaction is carried out usually under a hydrogen atmosphere of 1 to 100 atm, usually in the presence of a solvent.

Examples of the solvent to be used in the reaction include ethers such as THF, 1,4-dioxane and the like, esters such as ethyl acetate, butyl acetate and the like, alcohols such as methanol, ethanol and the like, water and mixtures thereof.

Examples of the hydrogenation catalyst to be used in the reaction include transition metal compounds such as palladium charcoal, palladium hydroxide, raney nickel, platinum oxide and the like.

Hydrogen is used usually in a proportion of 3 mol and the hydrogenation catalyst is used usually in a proportion of 0.001 to 0.5 mol with respect to 1 mol of the compound (M1).

The reaction can also be carried out with addition of an acid (base or the like), if necessary.

The reaction temperature of the reaction is usually in the range of −20 to 100° C., and the reaction time thereof is usually in the range of 0.1 to 24 hours.

After completion of the reaction, the compound (2) can be isolated by subjecting post treatment operations such as the reaction mixture being filtrated to remove the transition metal catalyst, the filtrate being extracted with an organic solvent, the organic layer being dried and concentrated. The isolated compound (2) can also be further purified by chromatography, recrystallization and the like.

Next, specific examples of the present active compound are shown below.

Compound of formula (1-A):

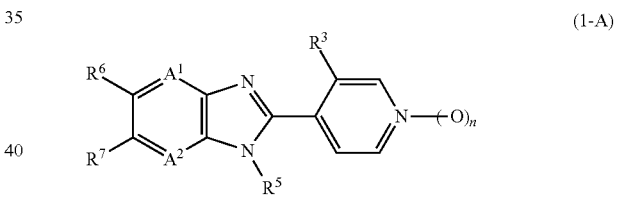

In the above-described formula (1-A), $R^3$, $R^5$, $R^6$, $R^7$, $A^1$, $A^2$ and n are combined as described in (Table 1) to (Table 48).

TABLE 1

| $R^3$ | $R^5$ | $R^6$ | $R^7$ | $A^1$ | $A^2$ | n |
|---|---|---|---|---|---|---|
| H | Me | $CF_3$ | H | =C(H)— | =C(H)— | 0 |
| F | Me | $CF_3$ | H | =C(H)— | =C(H)— | 0 |
| Cl | Me | $CF_3$ | H | =C(H)— | =C(H)— | 0 |
| Br | Me | $CF_3$ | H | =C(H)— | =C(H)— | 0 |
| I | Me | $CF_3$ | H | =C(H)— | =C(H)— | 0 |
| Me | Me | $CF_3$ | H | =C(H)— | =C(H)— | 0 |
| Et | Me | $CF_3$ | H | =C(H)— | =C(H)— | 0 |
| Pr | Me | $CF_3$ | H | =C(H)— | =C(H)— | 0 |
| iPr | Me | $CF_3$ | H | =C(H)— | =C(H)— | 0 |
| tBu | Me | $CF_3$ | H | =C(H)— | =C(H)— | 0 |
| CH≡C | Me | $CF_3$ | H | =C(H)— | =C(H)— | 0 |
| $CH_2$=CH | Me | $CF_3$ | H | =C(H)— | =C(H)— | 0 |
| $CF_3$ | Me | $CF_3$ | H | =C(H)— | =C(H)— | 0 |
| $CF_3CF_2$ | Me | $CF_3$ | H | =C(H)— | =C(H)— | 0 |
| MeO | Me | $CF_3$ | H | =C(H)— | =C(H)— | 0 |
| EtO | Me | $CF_3$ | H | =C(H)— | =C(H)— | 0 |
| PrO | Me | $CF_3$ | H | =C(H)— | =C(H)— | 0 |
| iPrO | Me | $CF_3$ | H | =C(H)— | =C(H)— | 0 |
| tBuO | Me | $CF_3$ | H | =C(H)— | =C(H)— | 0 |
| $CF_3CH_2O$ | Me | $CF_3$ | H | =C(H)— | =C(H)— | 0 |
| $CHF_2CH_2O$ | Me | $CF_3$ | H | =C(H)— | =C(H)— | 0 |

TABLE 1-continued

| R³ | R⁵ | R⁶ | R⁷ | A¹ | A² | n |
|---|---|---|---|---|---|---|
| CH₂FCH₂O | Me | CF₃ | H | =C(H)— | =C(H)— | 0 |
| MeOCH₂O | Me | CF₃ | H | =C(H)— | =C(H)— | 0 |
| EtOCH₂O | Me | CF₃ | H | =C(H)— | =C(H)— | 0 |

TABLE 2

| R³ | R⁵ | R⁶ | R⁷ | A¹ | A² | n |
|---|---|---|---|---|---|---|
| MeOCH₂CH₂O | Me | CF₃ | H | =C(H)— | =C(H)— | 0 |
| EtOCH₂CH₂O | Me | CF₃ | H | =C(H)— | =C(H)— | 0 |
| MeS | Me | CF₃ | H | =C(H)— | =C(H)— | 0 |
| MeSO | Me | CF₃ | H | =C(H)— | =C(H)— | 0 |
| MeSO₂ | Me | CF₃ | H | =C(H)— | =C(H)— | 0 |
| EtS | Me | CF₃ | H | =C(H)— | =C(H)— | 0 |
| EtSO | Me | CF₃ | H | =C(H)— | =C(H)— | 0 |
| EtSO₂ | Me | CF₃ | H | =C(H)— | =C(H)— | 0 |
| PrS | Me | CF₃ | H | =C(H)— | =C(H)— | 0 |
| PrSO | Me | CF₃ | H | =C(H)— | =C(H)— | 0 |
| PrSO₂ | Me | CF₃ | H | =C(H)— | =C(H)— | 0 |
| iPrS | Me | CF₃ | H | =C(H)— | =C(H)— | 0 |
| iPrSO | Me | CF₃ | H | =C(H)— | =C(H)— | 0 |
| iPrSO₂ | Me | CF₃ | H | =C(H)— | =C(H)— | 0 |
| CF₃CH₂S | Me | CF₃ | H | =C(H)— | =C(H)— | 0 |
| CF₃CH₂SO | Me | CF₃ | H | =C(H)— | =C(H)— | 0 |
| CF₃CH₂SO₂ | Me | CF₃ | H | =C(H)— | =C(H)— | 0 |
| Ph | Me | CF₃ | H | =C(H)— | =C(H)— | 0 |
| 2-Py | Me | CF₃ | H | =C(H)— | =C(H)— | 0 |
| 3-Py | Me | CF₃ | H | =C(H)— | =C(H)— | 0 |
| 4-Py | Me | CF₃ | H | =C(H)— | =C(H)— | 0 |
| 1-Tz | Me | CF₃ | H | =C(H)— | =C(H)— | 0 |
| 1-Pz | Me | CF₃ | H | =C(H)— | =C(H)— | 0 |
| H | Me | CF₃ | H | =C(H)— | =C(H)— | 1 |

TABLE 3

| R³ | R⁵ | R⁶ | R⁷ | A¹ | A² | n |
|---|---|---|---|---|---|---|
| F | Me | CF₃ | H | =C(H)— | =C(H)— | 1 |
| Cl | Me | CF₃ | H | =C(H)— | =C(H)— | 1 |
| MeO | Me | CF₃ | H | =C(H)— | =C(H)— | 1 |
| EtO | Me | CF₃ | H | =C(H)— | =C(H)— | 1 |
| CF₃CH₂O | Me | CF₃ | H | =C(H)— | =C(H)— | 1 |
| CHF₂CH₂O | Me | CF₃ | H | =C(H)— | =C(H)— | 1 |
| CH₂FCH₂O | Me | CF₃ | H | =C(H)— | =C(H)— | 1 |
| MeS | Me | CF₃ | H | =C(H)— | =C(H)— | 1 |
| MeSO | Me | CF₃ | H | =C(H)— | =C(H)— | 1 |
| MeSO₂ | Me | CF₃ | H | =C(H)— | =C(H)— | 1 |
| EtS | Me | CF₃ | H | =C(H)— | =C(H)— | 1 |
| EtSO | Me | CF₃ | H | =C(H)— | =C(H)— | 1 |
| EtSO₂ | Me | CF₃ | H | =C(H)— | =C(H)— | 1 |
| H | Me | C₂F₅ | H | =C(H)— | =C(H)— | 0 |
| F | Me | C₂F₅ | H | =C(H)— | =C(H)— | 0 |
| Cl | Me | C₂F₅ | H | =C(H)— | =C(H)— | 0 |
| Br | Me | C₂F₅ | H | =C(H)— | =C(H)— | 0 |
| I | Me | C₂F₅ | H | =C(H)— | =C(H)— | 0 |
| Me | Me | C₂F₅ | H | =C(H)— | =C(H)— | 0 |
| Et | Me | C₂F₅ | H | =C(H)— | =C(H)— | 0 |
| Pr | Me | C₂F₅ | H | =C(H)— | =C(H)— | 0 |
| iPr | Me | C₂F₅ | H | =C(H)— | =C(H)— | 0 |
| tBu | Me | C₂F₅ | H | =C(H)— | =C(H)— | 0 |
| CH≡C | Me | C₂F₅ | H | =C(H)— | =C(H)— | 0 |

TABLE 4

| R³ | R⁵ | R⁶ | R⁷ | A¹ | A² | n |
|---|---|---|---|---|---|---|
| CH₂=CH | Me | C₂F₅ | H | =C(H)— | =C(H)— | 0 |
| CF₃ | Me | C₂F₅ | H | =C(H)— | =C(H)— | 0 |
| CF₃CF₂ | Me | C₂F₅ | H | =C(H)— | =C(H)— | 0 |
| MeO | Me | C₂F₅ | H | =C(H)— | =C(H)— | 0 |
| EtO | Me | C₂F₅ | H | =C(H)— | =C(H)— | 0 |

TABLE 4-continued

| R³ | R⁵ | R⁶ | R⁷ | A¹ | A² | n |
|---|---|---|---|---|---|---|
| PrO | Me | C₂F₅ | H | =C(H)— | =C(H)— | 0 |
| iPrO | Me | C₂F₅ | H | =C(H)— | =C(H)— | 0 |
| tBuO | Me | C₂F₅ | H | =C(H)— | =C(H)— | 0 |
| CF₃CH₂O | Me | C₂F₅ | H | =C(H)— | =C(H)— | 0 |
| CHF₂CH₂O | Me | C₂F₅ | H | =C(H)— | =C(H)— | 0 |
| CH₂FCH₂O | Me | C₂F₅ | H | =C(H)— | =C(H)— | 0 |
| MeOCH₂O | Me | C₂F₅ | H | =C(H)— | =C(H)— | 0 |
| EtOCH₂O | Me | C₂F₅ | H | =C(H)— | =C(H)— | 0 |
| MeOCH₂CH₂O | Me | C₂F₅ | H | =C(H)— | =C(H)— | 0 |
| EtOCH₂CH₂O | Me | C₂F₅ | H | =C(H)— | =C(H)— | 0 |
| MeS | Me | C₂F₅ | H | =C(H)— | =C(H)— | 0 |
| MeSO | Me | C₂F₅ | H | =C(H)— | =C(H)— | 0 |
| MeSO₂ | Me | C₂F₅ | H | =C(H)— | =C(H)— | 0 |
| EtS | Me | C₂F₅ | H | =C(H)— | =C(H)— | 0 |
| EtSO | Me | C₂F₅ | H | =C(H)— | =C(H)— | 0 |
| EtSO₂ | Me | C₂F₅ | H | =C(H)— | =C(H)— | 0 |
| PrS | Me | C₂F₅ | H | =C(H)— | =C(H)— | 0 |
| PrSO | Me | C₂F₅ | H | =C(H)— | =C(H)— | 0 |
| PrSO₂ | Me | C₂F₅ | H | =C(H)— | =C(H)— | 0 |

TABLE 5

| R³ | R⁵ | R⁶ | R⁷ | A¹ | A² | n |
|---|---|---|---|---|---|---|
| iPrS | Me | C₂F₅ | H | =C(H)— | =C(H)— | 0 |
| iPrSO | Me | C₂F₅ | H | =C(H)— | =C(H)— | 0 |
| iPrSO₂ | Me | C₂F₅ | H | =C(H)— | =C(H)— | 0 |
| CF₃CH₂S | Me | C₂F₅ | H | =C(H)— | =C(H)— | 0 |
| CF₃CH₂SO | Me | C₂F₅ | H | =C(H)— | =C(H)— | 0 |
| CF₃CH₂SO₂ | Me | C₂F₅ | H | =C(H)— | =C(H)— | 0 |
| Ph | Me | C₂F₅ | H | =C(H)— | =C(H)— | 0 |
| 2-Py | Me | C₂F₅ | H | =C(H)— | =C(H)— | 0 |
| 3-Py | Me | C₂F₅ | H | =C(H)— | =C(H)— | 0 |
| 4-Py | Me | C₂F₅ | H | =C(H)— | =C(H)— | 0 |
| 1-Tz | Me | C₂F₅ | H | =C(H)— | =C(H)— | 0 |
| 1-Pz | Me | C₂F₅ | H | =C(H)— | =C(H)— | 0 |
| H | Me | OCF₃ | H | =C(H)— | =C(H)— | 0 |
| F | Me | OCF₃ | H | =C(H)— | =C(H)— | 0 |
| Cl | Me | OCF₃ | H | =C(H)— | =C(H)— | 0 |
| Br | Me | OCF₃ | H | =C(H)— | =C(H)— | 0 |
| I | Me | OCF₃ | H | =C(H)— | =C(H)— | 0 |
| Me | Me | OCF₃ | H | =C(H)— | =C(H)— | 0 |
| Et | Me | OCF₃ | H | =C(H)— | =C(H)— | 0 |
| Pr | Me | OCF₃ | H | =C(H)— | =C(H)— | 0 |
| iPr | Me | OCF₃ | H | =C(H)— | =C(H)— | 0 |
| tBu | Me | OCF₃ | H | =C(H)— | =C(H)— | 0 |
| CH≡C | Me | OCF₃ | H | =C(H)— | =C(H)— | 0 |
| CH₂=CH | Me | OCF₃ | H | =C(H)— | =C(H)— | 0 |

TABLE 6

| R³ | R⁵ | R⁶ | R⁷ | A¹ | A² | n |
|---|---|---|---|---|---|---|
| CF₃ | Me | OCF₃ | H | =C(H)— | =C(H)— | 0 |
| CF₃CF₂ | Me | OCF₃ | H | =C(H)— | =C(H)— | 0 |
| MeO | Me | OCF₃ | H | =C(H)— | =C(H)— | 0 |
| EtO | Me | OCF₃ | H | =C(H)— | =C(H)— | 0 |
| PrO | Me | OCF₃ | H | =C(H)— | =C(H)— | 0 |
| iPrO | Me | OCF₃ | H | =C(H)— | =C(H)— | 0 |
| tBuO | Me | OCF₃ | H | =C(H)— | =C(H)— | 0 |
| CF₃CH₂O | Me | OCF₃ | H | =C(H)— | =C(H)— | 0 |
| CHF₂CH₂O | Me | OCF₃ | H | =C(H)— | =C(H)— | 0 |
| CH₂FCH₂O | Me | OCF₃ | H | =C(H)— | =C(H)— | 0 |
| MeOCH₂ | Me | OCF₃ | H | =C(H)— | =C(H)— | 0 |
| EtOCH₂ | Me | OCF₃ | H | =C(H)— | =C(H)— | 0 |
| MeOCH₂CH₂O | Me | OCF₃ | H | =C(H)— | =C(H)— | 0 |
| EtOCH₂CH₂O | Me | OCF₃ | H | =C(H)— | =C(H)— | 0 |
| MeS | Me | OCF₃ | H | =C(H)— | =C(H)— | 0 |
| MeSO | Me | OCF₃ | H | =C(H)— | =C(H)— | 0 |
| MeSO₂ | Me | OCF₃ | H | =C(H)— | =C(H)— | 0 |
| EtS | Me | OCF₃ | H | =C(H)— | =C(H)— | 0 |
| EtSO | Me | OCF₃ | H | =C(H)— | =C(H)— | 0 |
| EtSO₂ | Me | OCF₃ | H | =C(H)— | =C(H)— | 0 |

TABLE 6-continued

| R³ | R⁵ | R⁶ | R⁷ | A¹ | A² | n |
|---|---|---|---|---|---|---|
| PrS | Me | OCF₃ | H | =C(H)— | =C(H)— | 0 |
| PrSO | Me | OCF₃ | H | =C(H)— | =C(H)— | 0 |
| PrSO₂ | Me | OCF₃ | H | =C(H)— | =C(H)— | 0 |
| iPrS | Me | OCF₃ | H | =C(H)— | =C(H)— | 0 |

TABLE 7

| R³ | R⁵ | R⁶ | R⁷ | A¹ | A² | n |
|---|---|---|---|---|---|---|
| iPrSO | Me | OCF₃ | H | =C(H)— | =C(H)— | 0 |
| iPrSO₂ | Me | OCF₃ | H | =C(H)— | =C(H)— | 0 |
| CF₃CH₂S | Me | OCF₃ | H | =C(H)— | =C(H)— | 0 |
| CF₃CH₂SO | Me | OCF₃ | H | =C(H)— | =C(H)— | 0 |
| CF₃CH₂SO₂ | Me | OCF₃ | H | =C(H)— | =C(H)— | 0 |
| Ph | Me | OCF₃ | H | =C(H)— | =C(H)— | 0 |
| 2-Py | Me | OCF₃ | H | =C(H)— | =C(H)— | 0 |
| 3-Py | Me | OCF₃ | H | =C(H)— | =C(H)— | 0 |
| 4-Py | Me | OCF₃ | H | =C(H)— | =C(H)— | 0 |
| 1-Tz | Me | OCF₃ | H | =C(H)— | =C(H)— | 0 |
| 1-Pz | Me | OCF₃ | H | =C(H)— | =C(H)— | 0 |
| H | Me | —CF₂OCF₂— | | =C(H)— | =C(H)— | 0 |
| F | Me | —CF₂OCF₂— | | =C(H)— | =C(H)— | 0 |
| Cl | Me | —CF₂OCF₂— | | =C(H)— | =C(H)— | 0 |
| Br | Me | —CF₂OCF₂— | | =C(H)— | =C(H)— | 0 |
| I | Me | —CF₂OCF₂— | | =C(H)— | =C(H)— | 0 |
| Me | Me | —CF₂OCF₂— | | =C(H)— | =C(H)— | 0 |
| Et | Me | —CF₂OCF₂— | | =C(H)— | =C(H)— | 0 |
| Pr | Me | —CF₂OCF₂— | | =C(H)— | =C(H)— | 0 |
| iPr | Me | —CF₂OCF₂— | | =C(H)— | =C(H)— | 0 |
| tBu | Me | —CF₂OCF₂— | | =C(H)— | =C(H)— | 0 |
| CH≡C | Me | —CF₂OCF₂— | | =C(H)— | =C(H)— | 0 |
| CH₂=CH | Me | —CF₂OCF₂— | | =C(H)— | =C(H)— | 0 |
| CF₃ | Me | —CF₂OCF₂— | | =C(H)— | =C(H)— | 0 |

TABLE 8

| R³ | R⁵ | R⁶ | R⁷ | A¹ | A² | n |
|---|---|---|---|---|---|---|
| CF₃CF₂ | Me | —CF₂OCF₂— | | =C(H)— | =C(H)— | 0 |
| MeO | Me | —CF₂OCF₂— | | =C(H)— | =C(H)— | 0 |
| EtO | Me | —CF₂OCF₂— | | =C(H)— | =C(H)— | 0 |
| PrO | Me | —CF₂OCF₂— | | =C(H)— | =C(H)— | 0 |
| iPrO | Me | —CF₂OCF₂— | | =C(H)— | =C(H)— | 0 |
| tBuO | Me | —CF₂OCF₂— | | =C(H)— | =C(H)— | 0 |
| CF₃CH₂O | Me | —CF₂OCF₂— | | =C(H)— | =C(H)— | 0 |
| CHF₂CH₂O | Me | —CF₂OCF₂— | | =C(H)— | =C(H)— | 0 |
| CH₂FCH₂O | Me | —CF₂OCF₂— | | =C(H)— | =C(H)— | 0 |
| MeOCH₂O | Me | —CF₂OCF₂— | | =C(H)— | =C(H)— | 0 |
| EtOCH₂O | Me | —CF₂OCF₂— | | =C(H)— | =C(H)— | 0 |
| MeOCH₂CH₂O | Me | —CF₂OCF₂— | | =C(H)— | =C(H)— | 0 |
| EtOCH₂CH₂O | Me | —CF₂OCF₂— | | =C(H)— | =C(H)— | 0 |
| MeS | Me | —CF₂OCF₂— | | =C(H)— | =C(H)— | 0 |
| MeSO | Me | —CF₂OCF₂— | | =C(H)— | =C(H)— | 0 |
| MeSO₂ | Me | —CF₂OCF₂— | | =C(H)— | =C(H)— | 0 |
| EtS | Me | —CF₂OCF₂— | | =C(H)— | =C(H)— | 0 |
| EtSO | Me | —CF₂OCF₂— | | =C(H)— | =C(H)— | 0 |
| EtSO₂ | Me | —CF₂OCF₂— | | =C(H)— | =C(H)— | 0 |
| PrS | Me | —CF₂OCF₂— | | =C(H)— | =C(H)— | 0 |
| PrSO | Me | —CF₂OCF₂— | | =C(H)— | =C(H)— | 0 |
| PrSO₂ | Me | —CF₂OCF₂— | | =C(H)— | =C(H)— | 0 |
| iPrS | Me | —CF₂OCF₂— | | =C(H)— | =C(H)— | 0 |
| iPrSO | Me | —CF₂OCF₂— | | =C(H)— | =C(H)— | 0 |

TABLE 9

| R³ | R⁵ | R⁶ | R⁷ | A¹ | A² | n |
|---|---|---|---|---|---|---|
| iPrSO₂ | Me | —CF₂OCF₂— | | =C(H)— | =C(H)— | 0 |
| CF₃CH₂S | Me | —CF₂OCF₂— | | =C(H)— | =C(H)— | 0 |
| CF₃CH₂SO | Me | —CF₂OCF₂— | | =C(H)— | =C(H)— | 0 |
| CF₃CH₂SO₂ | Me | —CF₂OCF₂— | | =C(H)— | =C(H)— | 0 |
| Ph | Me | —CF₂OCF₂— | | =C(H)— | =C(H)— | 0 |
| 2-Py | Me | —CF₂OCF₂— | | =C(H)— | =C(H)— | 0 |
| 3-Py | Me | —CF₂OCF₂— | | =C(H)— | =C(H)— | 0 |
| 4-Py | Me | —CF₂OCF₂— | | =C(H)— | =C(H)— | 0 |
| 1-Tz | Me | —CF₂OCF₂— | | =C(H)— | =C(H)— | 0 |
| 1-Pz | Me | —CF₂OCF₂— | | =C(H)— | =C(H)— | 0 |
| H | Me | H | CF₃ | =C(H)— | =C(H)— | 0 |
| F | Me | H | CF₃ | =C(H)— | =C(H)— | 0 |
| Cl | Me | H | CF₃ | =C(H)— | =C(H)— | 0 |
| Br | Me | H | CF₃ | =C(H)— | =C(H)— | 0 |
| I | Me | H | CF₃ | =C(H)— | =C(H)— | 0 |
| Me | Me | H | CF₃ | =C(H)— | =C(H)— | 0 |
| Et | Me | H | CF₃ | =C(H)— | =C(H)— | 0 |
| Pr | Me | H | CF₃ | =C(H)— | =C(H)— | 0 |
| iPr | Me | H | CF₃ | =C(H)— | =C(H)— | 0 |
| tBu | Me | H | CF₃ | =C(H)— | =C(H)— | 0 |
| CH≡C | Me | H | CF₃ | =C(H)— | =C(H)— | 0 |
| CH₂=CH | Me | H | CF₃ | =C(H)— | =C(H)— | 0 |
| CF₃ | Me | H | CF₃ | =C(H)— | =C(H)— | 0 |
| CF₃CF₂ | Me | H | CF₃ | =C(H)— | =C(H)— | 0 |

TABLE 10

| R³ | R⁵ | R⁶ | R⁷ | A¹ | A² | n |
|---|---|---|---|---|---|---|
| MeO | Me | H | CF₃ | =C(H)— | =C(H)— | 0 |
| EtO | Me | H | CF₃ | =C(H)— | =C(H)— | 0 |
| PrO | Me | H | CF₃ | =C(H)— | =C(H)— | 0 |
| iPrO | Me | H | CF₃ | =C(H)— | =C(H)— | 0 |
| tBuO | Me | H | CF₃ | =C(H)— | =C(H)— | 0 |
| CF₃CH₂O | Me | H | CF₃ | =C(H)— | =C(H)— | 0 |
| CHF₂CH₂O | Me | H | CF₃ | =C(H)— | =C(H)— | 0 |
| CH₂FCH₂O | Me | H | CF₃ | =C(H)— | =C(H)— | 0 |
| MeOCH₂O | Me | H | CF₃ | =C(H)— | =C(H)— | 0 |
| EtOCH₂O | Me | H | CF₃ | =C(H)— | =C(H)— | 0 |
| MeOCH₂CH₂O | Me | H | CF₃ | =C(H)— | =C(H)— | 0 |
| EtOCH₂CH₂O | Me | H | CF₃ | =C(H)— | =C(H)— | 0 |
| MeS | Me | H | CF₃ | =C(H)— | =C(H)— | 0 |
| MeSO | Me | H | CF₃ | =C(H)— | =C(H)— | 0 |
| MeSO₂ | Me | H | CF₃ | =C(H)— | =C(H)— | 0 |
| EtS | Me | H | CF₃ | =C(H)— | =C(H)— | 0 |
| EtSO | Me | H | CF₃ | =C(H)— | =C(H)— | 0 |
| EtSO₂ | Me | H | CF₃ | =C(H)— | =C(H)— | 0 |
| PrS | Me | H | CF₃ | =C(H)— | =C(H)— | 0 |
| PrSO | Me | H | CF₃ | =C(H)— | =C(H)— | 0 |
| PrSO₂ | Me | H | CF₃ | =C(H)— | =C(H)— | 0 |
| iPrS | Me | H | CF₃ | =C(H)— | =C(H)— | 0 |
| iPrSO | Me | H | CF₃ | =C(H)— | =C(H)— | 0 |
| iPrSO₂ | Me | H | CF₃ | =C(H)— | =C(H)— | 0 |

TABLE 11

| R³ | R⁵ | R⁶ | R⁷ | A¹ | A² | n |
|---|---|---|---|---|---|---|
| CF₃CH₂S | Me | H | CF₃ | =C(H)— | =C(H)— | 0 |
| CF₃CH₂SO | Me | H | CF₃ | =C(H)— | =C(H)— | 0 |
| CF₃CH₂SO₂ | Me | H | CF₃ | =C(H)— | =C(H)— | 0 |
| Ph | Me | H | CF₃ | =C(H)— | =C(H)— | 0 |
| 2-Py | Me | H | CF₃ | =C(H)— | =C(H)— | 0 |
| 3-Py | Me | H | CF₃ | =C(H)— | =C(H)— | 0 |
| 4-Py | Me | H | CF₃ | =C(H)— | =C(H)— | 0 |
| 1-Tz | Me | H | CF₃ | =C(H)— | =C(H)— | 0 |
| 1-Pz | Me | H | CF₃ | =C(H)— | =C(H)— | 0 |
| H | Et | CF₃ | H | =C(H)— | =C(H)— | 0 |
| F | Et | CF₃ | H | =C(H)— | =C(H)— | 0 |
| Cl | Et | CF₃ | H | =C(H)— | =C(H)— | 0 |
| Br | Et | CF₃ | H | =C(H)— | =C(H)— | 0 |
| I | Et | CF₃ | H | =C(H)— | =C(H)— | 0 |
| Me | Et | CF₃ | H | =C(H)— | =C(H)— | 0 |
| Et | Et | CF₃ | H | =C(H)— | =C(H)— | 0 |
| Pr | Et | CF₃ | H | =C(H)— | =C(H)— | 0 |
| iPr | Et | CF₃ | H | =C(H)— | =C(H)— | 0 |
| tBu | Et | CF₃ | H | =C(H)— | =C(H)— | 0 |

TABLE 11-continued

| R³ | R⁵ | R⁶ | R⁷ | A¹ | A² | n |
|---|---|---|---|---|---|---|
| CH≡C | Et | CF₃ | H | =C(H)— | =C(H)— | 0 |
| CH₂=CH | Et | CF₃ | H | =C(H)— | =C(H)— | 0 |
| CF₃ | Et | CF₃ | H | =C(H)— | =C(H)— | 0 |
| CF₃CF₂ | Et | CF₃ | H | =C(H)— | =C(H)— | 0 |
| MeO | Et | CF₃ | H | =C(H)— | =C(H)— | 0 |

TABLE 12

| R³ | R⁵ | R⁶ | R⁷ | A¹ | A² | n |
|---|---|---|---|---|---|---|
| EtO | Et | CF₃ | H | =C(H)— | =C(H)— | 0 |
| PrO | Et | CF₃ | H | =C(H)— | =C(H)— | 0 |
| iPrO | Et | CF₃ | H | =C(H)— | =C(H)— | 0 |
| tBuO | Et | CF₃ | H | =C(H)— | =C(H)— | 0 |
| CF₃CH₂O | Et | CF₃ | H | =C(H)— | =C(H)— | 0 |
| CHF₂CH₂O | Et | CF₃ | H | =C(H)— | =C(H)— | 0 |
| CH₂FCH₂O | Et | CF₃ | H | =C(H)— | =C(H)— | 0 |
| MeOCH₂O | Et | CF₃ | H | =C(H)— | =C(H)— | 0 |
| EtOCH₂O | Et | CF₃ | H | =C(H)— | =C(H)— | 0 |
| MeOCH₂CH₂O | Et | CF₃ | H | =C(H)— | =C(H)— | 0 |
| EtOCH₂CH₂O | Et | CF₃ | H | =C(H)— | =C(H)— | 0 |
| MeS | Et | CF₃ | H | =C(H)— | =C(H)— | 0 |
| MeSO | Et | CF₃ | H | =C(H)— | =C(H)— | 0 |
| MeSO₂ | Et | CF₃ | H | =C(H)— | =C(H)— | 0 |
| EtS | Et | CF₃ | H | =C(H)— | =C(H)— | 0 |
| EtSO | Et | CF₃ | H | =C(H)— | =C(H)— | 0 |
| EtSO₂ | Et | CF₃ | H | =C(H)— | =C(H)— | 0 |
| PrS | Et | CF₃ | H | =C(H)— | =C(H)— | 0 |
| PrSO | Et | CF₃ | H | =C(H)— | =C(H)— | 0 |
| PrSO₂ | Et | CF₃ | H | =C(H)— | =C(H)— | 0 |
| iPrS | Et | CF₃ | H | =C(H)— | =C(H)— | 0 |
| iPrSO | Et | CF₃ | H | =C(H)— | =C(H)— | 0 |
| iPrSO₂ | Et | CF₃ | H | =C(H)— | =C(H)— | 0 |
| CF₃CH₂S | Et | CF₃ | H | =C(H)— | =C(H)— | 0 |

TABLE 13

| R³ | R⁵ | R⁶ | R⁷ | A¹ | A² | n |
|---|---|---|---|---|---|---|
| CF₃CH₂SO | Et | CF₃ | H | =C(H)— | =C(H)— | 0 |
| CF₃CH₂SO₂ | Et | CF₃ | H | =C(H)— | =C(H)— | 0 |
| Ph | Et | CF₃ | H | =C(H)— | =C(H)— | 0 |
| 2-Py | Et | CF₃ | H | =C(H)— | =C(H)— | 0 |
| 3-Py | Et | CF₃ | H | =C(H)— | =C(H)— | 0 |
| 4-Py | Et | CF₃ | H | =C(H)— | =C(H)— | 0 |
| 1-Tz | Et | CF₃ | H | =C(H)— | =C(H)— | 0 |
| 1-Pz | Et | CF₃ | H | =C(H)— | =C(H)— | 0 |
| H | CyPr | CF₃ | H | =C(H)— | =C(H)— | 0 |
| F | CyPr | CF₃ | H | =C(H)— | =C(H)— | 0 |
| Cl | CyPr | CF₃ | H | =C(H)— | =C(H)— | 0 |
| Br | CyPr | CF₃ | H | =C(H)— | =C(H)— | 0 |
| I | CyPr | CF₃ | H | =C(H)— | =C(H)— | 0 |
| Me | CyPr | CF₃ | H | =C(H)— | =C(H)— | 0 |
| Et | CyPr | CF₃ | H | =C(H)— | =C(H)— | 0 |
| Pr | CyPr | CF₃ | H | =C(H)— | =C(H)— | 0 |
| iPr | CyPr | CF₃ | H | =C(H)— | =C(H)— | 0 |
| tBu | CyPr | CF₃ | H | =C(H)— | =C(H)— | 0 |
| CH≡C | CyPr | CF₃ | H | =C(H)— | =C(H)— | 0 |
| CH₂=CH | CyPr | CF₃ | H | =C(H)— | =C(H)— | 0 |
| CF₃ | CyPr | CF₃ | H | =C(H)— | =C(H)— | 0 |
| CF₃CF₂ | CyPr | CF₃ | H | =C(H)— | =C(H)— | 0 |
| MeO | CyPr | CF₃ | H | =C(H)— | =C(H)— | 0 |
| EtO | CyPr | CF₃ | H | =C(H)— | =C(H)— | 0 |

TABLE 14

| R³ | R⁵ | R⁶ | R⁷ | A¹ | A² | n |
|---|---|---|---|---|---|---|
| PrO | CyPr | CF₃ | H | =C(H)— | =C(H)— | 0 |
| iPrO | CyPr | CF₃ | H | =C(H)— | =C(H)— | 0 |
| tBuO | CyPr | CF₃ | H | =C(H)— | =C(H)— | 0 |

TABLE 14-continued

| R³ | R⁵ | R⁶ | R⁷ | A¹ | A² | n |
|---|---|---|---|---|---|---|
| CF₃CH₂O | CyPr | CF₃ | H | =C(H)— | =C(H)— | 0 |
| CHF₂CH₂O | CyPr | CF₃ | H | =C(H)— | =C(H)— | 0 |
| CH₂FCH₂O | CyPr | CF₃ | H | =C(H)— | =C(H)— | 0 |
| MeOCH₂O | CyPr | CF₃ | H | =C(H)— | =C(H)— | 0 |
| EtOCH₂O | CyPr | CF₃ | H | =C(H)— | =C(H)— | 0 |
| MeOCH₂CH₂O | CyPr | CF₃ | H | =C(H)— | =C(H)— | 0 |
| EtOCH₂CH₂O | CyPr | CF₃ | H | =C(H)— | =C(H)— | 0 |
| MeS | CyPr | CF₃ | H | =C(H)— | =C(H)— | 0 |
| MeSO | CyPr | CF₃ | H | =C(H)— | =C(H)— | 0 |
| MeSO₂ | CyPr | CF₃ | H | =C(H)— | =C(H)— | 0 |
| EtS | CyPr | CF₃ | H | =C(H)— | =C(H)— | 0 |
| EtSO | CyPr | CF₃ | H | =C(H)— | =C(H)— | 0 |
| EtSO₂ | CyPr | CF₃ | H | =C(H)— | =C(H)— | 0 |
| PrS | CyPr | CF₃ | H | =C(H)— | =C(H)— | 0 |
| PrSO | CyPr | CF₃ | H | =C(H)— | =C(H)— | 0 |
| PrSO₂ | CyPr | CF₃ | H | =C(H)— | =C(H)— | 0 |
| iPrS | CyPr | CF₃ | H | =C(H)— | =C(H)— | 0 |
| iPrSO | CyPr | CF₃ | H | =C(H)— | =C(H)— | 0 |
| iPrSO₂ | CyPr | CF₃ | H | =C(H)— | =C(H)— | 0 |
| CF₃CH₂S | CyPr | CF₃ | H | =C(H)— | =C(H)— | 0 |
| CF₃CH₂SO | CyPr | CF₃ | H | =C(H)— | =C(H)— | 0 |

TABLE 15

| R³ | R⁵ | R⁶ | R⁷ | A¹ | A² | n |
|---|---|---|---|---|---|---|
| CF₃CH₂SO₂ | CyPr | CF₃ | H | =C(H)— | =C(H)— | 0 |
| Ph | CyPr | CF₃ | H | =C(H)— | =C(H)— | 0 |
| 2-Py | CyPr | CF₃ | H | =C(H)— | =C(H)— | 0 |
| 3-Py | CyPr | CF₃ | H | =C(H)— | =C(H)— | 0 |
| 4-Py | CyPr | CF₃ | H | =C(H)— | =C(H)— | 0 |
| 1-Tz | CyPr | CF₃ | H | =C(H)— | =C(H)— | 0 |
| 1-Pz | CyPr | CF₃ | H | =C(H)— | =C(H)— | 0 |
| H | Me | CF₃ | H | =C(H)— | =N— | 0 |
| F | Me | CF₃ | H | =C(H)— | =N— | 0 |
| Cl | Me | CF₃ | H | =C(H)— | =N— | 0 |
| Br | Me | CF₃ | H | =C(H)— | =N— | 0 |
| I | Me | CF₃ | H | =C(H)— | =N— | 0 |
| Me | Me | CF₃ | H | =C(H)— | =N— | 0 |
| Et | Me | CF₃ | H | =C(H)— | =N— | 0 |
| Pr | Me | CF₃ | H | =C(H)— | =N— | 0 |
| iPr | Me | CF₃ | H | =C(H)— | =N— | 0 |
| tBu | Me | CF₃ | H | =C(H)— | =N— | 0 |
| CH≡C | Me | CF₃ | H | =C(H)— | =N— | 0 |
| CH₂=CH | Me | CF₃ | H | =C(H)— | =N— | 0 |
| CF₃ | Me | CF₃ | H | =C(H)— | =N— | 0 |
| CF₃CF₂ | Me | CF₃ | H | =C(H)— | =N— | 0 |
| MeO | Me | CF₃ | H | =C(H)— | =N— | 0 |
| EtO | Me | CF₃ | H | =C(H)— | =N— | 0 |
| PrO | Me | CF₃ | H | =C(H)— | =N— | 0 |

TABLE 16

| R³ | R⁵ | R⁶ | R⁷ | A¹ | A² | n |
|---|---|---|---|---|---|---|
| iPrO | Me | CF₃ | H | =C(H)— | =N— | 0 |
| tBuO | Me | CF₃ | H | =C(H)— | =N— | 0 |
| CF₃CH₂O | Me | CF₃ | H | =C(H)— | =N— | 0 |
| CHF₂CH₂O | Me | CF₃ | H | =C(H)— | =N— | 0 |
| CH₂FCH₂O | Me | CF₃ | H | =C(H)— | =N— | 0 |
| MeOCH₂O | Me | CF₃ | H | =C(H)— | =N— | 0 |
| EtOCH₂O | Me | CF₃ | H | =C(H)— | =N— | 0 |
| MeOCH₂CH₂O | Me | CF₃ | H | =C(H)— | =N— | 0 |
| EtOCH₂CH₂O | Me | CF₃ | H | =C(H)— | =N— | 0 |
| MeS | Me | CF₃ | H | =C(H)— | =N— | 0 |
| MeSO | Me | CF₃ | H | =C(H)— | =N— | 0 |
| MeSO₂ | Me | CF₃ | H | =C(H)— | =N— | 0 |
| EtS | Me | CF₃ | H | =C(H)— | =N— | 0 |
| EtSO | Me | CF₃ | H | =C(H)— | =N— | 0 |
| EtSO₂ | Me | CF₃ | H | =C(H)— | =N— | 0 |
| PrS | Me | CF₃ | H | =C(H)— | =N— | 0 |
| PrSO | Me | CF₃ | H | =C(H)— | =N— | 0 |
| PrSO₂ | Me | CF₃ | H | =C(H)— | =N— | 0 |

TABLE 16-continued

| R³ | R⁵ | R⁶ | R⁷ | A¹ | A² | n |
|---|---|---|---|---|---|---|
| iPrS | Me | CF₃ | H | =C(H)— | =N— | 0 |
| iPrSO | Me | CF₃ | H | =C(H)— | =N— | 0 |
| iPrSO₂ | Me | CF₃ | H | =C(H)— | =N— | 0 |
| CF₃CH₂S | Me | CF₃ | H | =C(H)— | =N— | 0 |
| CF₃CH₂SO | Me | CF₃ | H | =C(H)— | =N— | 0 |
| CF₃CH₂SO₂ | Me | CF₃ | H | =C(H)— | =N— | 0 |

TABLE 17

| R³ | R⁵ | R⁶ | R⁷ | A¹ | A² | n |
|---|---|---|---|---|---|---|
| Ph | Me | CF₃ | H | =C(H)— | =N— | 0 |
| 2-Py | Me | CF₃ | H | =C(H)— | =N— | 0 |
| 3-Py | Me | CF₃ | H | =C(H)— | =N— | 0 |
| 4-Py | Me | CF₃ | H | =C(H)— | =N— | 0 |
| 1-Tz | Me | CF₃ | H | =C(H)— | =N— | 0 |
| 1-Pz | Me | CF₃ | H | =C(H)— | =N— | 0 |
| H | Me | CF₃ | H | =C(H)— | =N— | 1 |
| F | Me | CF₃ | H | =C(H)— | =N— | 1 |
| Cl | Me | CF₃ | H | =C(H)— | =N— | 1 |
| MeO | Me | CF₃ | H | =C(H)— | =N— | 1 |
| EtO | Me | CF₃ | H | =C(H)— | =N— | 1 |
| CF₃CH₂O | Me | CF₃ | H | =C(H)— | =N— | 1 |
| CHF₂CH₂O | Me | CF₃ | H | =C(H)— | =N— | 1 |
| CH₂FCH₂O | Me | CF₃ | H | =C(H)— | =N— | 1 |
| MeS | Me | CF₃ | H | =C(H)— | =N— | 1 |
| MeSO | Me | CF₃ | H | =C(H)— | =N— | 1 |
| MeSO₂ | Me | CF₃ | H | =C(H)— | =N— | 1 |
| EtS | Me | CF₃ | H | =C(H)— | =N— | 1 |
| EtSO | Me | CF₃ | H | =C(H)— | =N— | 1 |
| EtSO₂ | Me | CF₃ | H | =C(H)— | =N— | 1 |
| H | Me | C₂F₅ | H | =C(H)— | =N— | 0 |
| F | Me | C₂F₅ | H | =C(H)— | =N— | 0 |
| Cl | Me | C₂F₅ | H | =C(H)— | =N— | 0 |
| Br | Me | C₂F₅ | H | =C(H)— | =N— | 0 |

TABLE 18

| R³ | R⁵ | R⁶ | R⁷ | A¹ | A² | n |
|---|---|---|---|---|---|---|
| I | Me | C₂F₅ | H | =C(H)— | =N— | 0 |
| Me | Me | C₂F₅ | H | =C(H)— | =N— | 0 |
| Et | Me | C₂F₅ | H | =C(H)— | =N— | 0 |
| Pr | Me | C₂F₅ | H | =C(H)— | =N— | 0 |
| iPr | Me | C₂F₅ | H | =C(H)— | =N— | 0 |
| tBu | Me | C₂F₅ | H | =C(H)— | =N— | 0 |
| CH≡C | Me | C₂F₅ | H | =C(H)— | =N— | 0 |
| CH₂=CH | Me | C₂F₅ | H | =C(H)— | =N— | 0 |
| CF₃ | Me | C₂F₅ | H | =C(H)— | =N— | 0 |
| CF₃CF₂ | Me | C₂F₅ | H | =C(H)— | =N— | 0 |
| MeO | Me | C₂F₅ | H | =C(H)— | =N— | 0 |
| EtO | Me | C₂F₅ | H | =C(H)— | =N— | 0 |
| PrO | Me | C₂F₅ | H | =C(H)— | =N— | 0 |
| iPrO | Me | C₂F₅ | H | =C(H)— | =N— | 0 |
| tBuO | Me | C₂F₅ | H | =C(H)— | =N— | 0 |
| CF₃CH₂O | Me | C₂F₅ | H | =C(H)— | =N— | 0 |
| CHF₂CH₂O | Me | C₂F₅ | H | =C(H)— | =N— | 0 |
| CH₂FCH₂O | Me | C₂F₅ | H | =C(H)— | =N— | 0 |
| MeOCH₂O | Me | C₂F₅ | H | =C(H)— | =N— | 0 |
| EtOCH₂O | Me | C₂F₅ | H | =C(H)— | =N— | 0 |
| MeOCH₂CH₂O | Me | C₂F₅ | H | =C(H)— | =N— | 0 |
| EtOCH₂CH₂O | Me | C₂F₅ | H | =C(H)— | =N— | 0 |
| MeS | Me | C₂F₅ | H | =C(H)— | =N— | 0 |
| MeSO | Me | C₂F₅ | H | =C(H)— | =N— | 0 |

TABLE 19

| R³ | R⁵ | R⁶ | R⁷ | A¹ | A² | n |
|---|---|---|---|---|---|---|
| MeSO₂ | Me | C₂F₅ | H | =C(H)— | =N— | 0 |
| EtS | Me | C₂F₅ | H | =C(H)— | =N— | 0 |

TABLE 19-continued

| R³ | R⁵ | R⁶ | R⁷ | A¹ | A² | n |
|---|---|---|---|---|---|---|
| EtSO | Me | C₂F₅ | H | =C(H)— | =N— | 0 |
| EtSO₂ | Me | C₂F₅ | H | =C(H)— | =N— | 0 |
| PrS | Me | C₂F₅ | H | =C(H)— | =N— | 0 |
| PrSO | Me | C₂F₅ | H | =C(H)— | =N— | 0 |
| PrSO₂ | Me | C₂F₅ | H | =C(H)— | =N— | 0 |
| iPrS | Me | C₂F₅ | H | =C(H)— | =N— | 0 |
| iPrSO | Me | C₂F₅ | H | =C(H)— | =N— | 0 |
| iPrSO₂ | Me | C₂F₅ | H | =C(H)— | =N— | 0 |
| CF₃CH₂S | Me | C₂F₅ | H | =C(H)— | =N— | 0 |
| CF₃CH₂SO | Me | C₂F₅ | H | =C(H)— | =N— | 0 |
| CF₃CH₂SO₂ | Me | C₂F₅ | H | =C(H)— | =N— | 0 |
| Ph | Me | C₂F₅ | H | =C(H)— | =N— | 0 |
| 2-Py | Me | C₂F₅ | H | =C(H)— | =N— | 0 |
| 3-Py | Me | C₂F₅ | H | =C(H)— | =N— | 0 |
| 4-Py | Me | C₂F₅ | H | =C(H)— | =N— | 0 |
| 1-Tz | Me | C₂F₅ | H | =C(H)— | =N— | 0 |
| 1-Pz | Me | C₂F₅ | H | =C(H)— | =N— | 0 |
| H | Me | H | CF₃ | =C(H)— | =N— | 0 |
| F | Me | H | CF₃ | =C(H)— | =N— | 0 |
| Cl | Me | H | CF₃ | =C(H)— | =N— | 0 |
| Br | Me | H | CF₃ | =C(H)— | =N— | 0 |
| I | Me | H | CF₃ | =C(H)— | =N— | 0 |

TABLE 20

| R³ | R⁵ | R⁶ | R⁷ | A¹ | A² | n |
|---|---|---|---|---|---|---|
| Me | Me | H | CF₃ | =C(H)— | =N— | 0 |
| Et | Me | H | CF₃ | =C(H)— | =N— | 0 |
| Pr | Me | H | CF₃ | =C(H)— | =N— | 0 |
| iPr | Me | H | CF₃ | =C(H)— | =N— | 0 |
| tBu | Me | H | CF₃ | =C(H)— | =N— | 0 |
| CH≡C | Me | H | CF₃ | =C(H)— | =N— | 0 |
| CH₂=CH | Me | H | CF₃ | =C(H)— | =N— | 0 |
| CF₃ | Me | H | CF₃ | =C(H)— | =N— | 0 |
| CF₃CF₂ | Me | H | CF₃ | =C(H)— | =N— | 0 |
| MeO | Me | H | CF₃ | =C(H)— | =N— | 0 |
| EtO | Me | H | CF₃ | =C(H)— | =N— | 0 |
| PrO | Me | H | CF₃ | =C(H)— | =N— | 0 |
| iPrO | Me | H | CF₃ | =C(H)— | =N— | 0 |
| tBuO | Me | H | CF₃ | =C(H)— | =N— | 0 |
| CF₃CH₂O | Me | H | CF₃ | =C(H)— | =N— | 0 |
| CHF₂CH₂O | Me | H | CF₃ | =C(H)— | =N— | 0 |
| CH₂FCH₂O | Me | H | CF₃ | =C(H)— | =N— | 0 |
| MeOCH₂O | Me | H | CF₃ | =C(H)— | =N— | 0 |
| EtOCH₂O | Me | H | CF₃ | =C(H)— | =N— | 0 |
| MeOCH₂CH₂O | Me | H | CF₃ | =C(H)— | =N— | 0 |
| EtOCH₂CH₂O | Me | H | CF₃ | =C(H)— | =N— | 0 |
| MeS | Me | H | CF₃ | =C(H)— | =N— | 0 |
| MeSO | Me | H | CF₃ | =C(H)— | =N— | 0 |
| MeSO₂ | Me | H | CF₃ | =C(H)— | =N— | 0 |

TABLE 21

| R³ | R⁵ | R⁶ | R⁷ | A¹ | A² | n |
|---|---|---|---|---|---|---|
| EtS | Me | H | CF₃ | =C(H)— | =N— | 0 |
| EtSO | Me | H | CF₃ | =C(H)— | =N— | 0 |
| EtSO₂ | Me | H | CF₃ | =C(H)— | =N— | 0 |
| PrS | Me | H | CF₃ | =C(H)— | =N— | 0 |
| PrSO | Me | H | CF₃ | =C(H)— | =N— | 0 |
| PrSO₂ | Me | H | CF₃ | =C(H)— | =N— | 0 |
| iPrS | Me | H | CF₃ | =C(H)— | =N— | 0 |
| iPrSO | Me | H | CF₃ | =C(H)— | =N— | 0 |
| iPrSO₂ | Me | H | CF₃ | =C(H)— | =N— | 0 |
| CF₃CH₂S | Me | H | CF₃ | =C(H)— | =N— | 0 |
| CF₃CH₂SO | Me | H | CF₃ | =C(H)— | =N— | 0 |
| CF₃CH₂SO₂ | Me | H | CF₃ | =C(H)— | =N— | 0 |
| Ph | Me | H | CF₃ | =C(H)— | =N— | 0 |
| 2-Py | Me | H | CF₃ | =C(H)— | =N— | 0 |
| 3-Py | Me | H | CF₃ | =C(H)— | =N— | 0 |
| 4-Py | Me | H | CF₃ | =C(H)— | =N— | 0 |
| 1-Tz | Me | H | CF₃ | =C(H)— | =N— | 0 |

TABLE 21-continued

| R³ | R⁵ | R⁶ | R⁷ | A¹ | A² | n |
|---|---|---|---|---|---|---|
| 1-Pz | Me | H | CF₃ | =C(H)— | =N— | 0 |
| H | Et | CF₃ | H | =C(H)— | =N— | 0 |
| F | Et | CF₃ | H | =C(H)— | =N— | 0 |
| Cl | Et | CF₃ | H | =C(H)— | =N— | 0 |
| Br | Et | CF₃ | H | =C(H)— | =N— | 0 |
| I | Et | CF₃ | H | =C(H)— | =N— | 0 |
| Me | Et | CF₃ | H | =C(H)— | =N— | 0 |

TABLE 22

| R³ | R⁵ | R⁶ | R⁷ | A¹ | A² | n |
|---|---|---|---|---|---|---|
| Et | Et | CF₃ | H | =C(H)— | =N— | 0 |
| Pr | Et | CF₃ | H | =C(H)— | =N— | 0 |
| iPr | Et | CF₃ | H | =C(H)— | =N— | 0 |
| tBu | Et | CF₃ | H | =C(H)— | =N— | 0 |
| CH≡C | Et | CF₃ | H | =C(H)— | =N— | 0 |
| CH₂=CH | Et | CF₃ | H | =C(H)— | =N— | 0 |
| CF₃ | Et | CF₃ | H | =C(H)— | =N— | 0 |
| CF₃CF₂ | Et | CF₃ | H | =C(H)— | =N— | 0 |
| MeO | Et | CF₃ | H | =C(H)— | =N— | 0 |
| EtO | Et | CF₃ | H | =C(H)— | =N— | 0 |
| PrO | Et | CF₃ | H | =C(H)— | =N— | 0 |
| iPrO | Et | CF₃ | H | =C(H)— | =N— | 0 |
| tBuO | Et | CF₃ | H | =C(H)— | =N— | 0 |
| CF₃CH₂O | Et | CF₃ | H | =C(H)— | =N— | 0 |
| CHF₂CH₂O | Et | CF₃ | H | =C(H)— | =N— | 0 |
| CH₂FCH₂O | Et | CF₃ | H | =C(H)— | =N— | 0 |
| MeOCH₂O | Et | CF₃ | H | =C(H)— | =N— | 0 |
| EtOCH₂O | Et | CF₃ | H | =C(H)— | =N— | 0 |
| MeOCH₂CH₂O | Et | CF₃ | H | =C(H)— | =N— | 0 |
| EtOCH₂CH₂O | Et | CF₃ | H | =C(H)— | =N— | 0 |
| MeS | Et | CF₃ | H | =C(H)— | =N— | 0 |
| MeSO | Et | CF₃ | H | =C(H)— | =N— | 0 |
| MeSO₂ | Et | CF₃ | H | =C(H)— | =N— | 0 |
| EtS | Et | CF₃ | H | =C(H)— | =N— | 0 |

TABLE 23

| R³ | R⁵ | R⁶ | R⁷ | A¹ | A² | n |
|---|---|---|---|---|---|---|
| EtSO | Et | CF₃ | H | =C(H)— | =N— | 0 |
| EtSO₂ | Et | CF₃ | H | =C(H)— | =N— | 0 |
| PrS | Et | CF₃ | H | =C(H)— | =N— | 0 |
| PrSO | Et | CF₃ | H | =C(H)— | =N— | 0 |
| PrSO₂ | Et | CF₃ | H | =C(H)— | =N— | 0 |
| iPrS | Et | CF₃ | H | =C(H)— | =N— | 0 |
| iPrSO | Et | CF₃ | H | =C(H)— | =N— | 0 |
| iPrSO₂ | Et | CF₃ | H | =C(H)— | =N— | 0 |
| CF₃CH₂S | Et | CF₃ | H | =C(H)— | =N— | 0 |
| CF₃CH₂SO | Et | CF₃ | H | =C(H)— | =N— | 0 |
| CF₃CH₂SO₂ | Et | CF₃ | H | =C(H)— | =N— | 0 |
| Ph | Et | CF₃ | H | =C(H)— | =N— | 0 |
| 2-Py | Et | CF₃ | H | =C(H)— | =N— | 0 |
| 3-Py | Et | CF₃ | H | =C(H)— | =N— | 0 |
| 4-Py | Et | CF₃ | H | =C(H)— | =N— | 0 |
| 1-Tz | Et | CF₃ | H | =C(H)— | =N— | 0 |
| 1-Pz | Et | CF₃ | H | =C(H)— | =N— | 0 |
| H | CyPr | CF₃ | H | =C(H)— | =N— | 0 |
| F | CyPr | CF₃ | H | =C(H)— | =N— | 0 |
| Cl | CyPr | CF₃ | H | =C(H)— | =N— | 0 |
| Br | CyPr | CF₃ | H | =C(H)— | =N— | 0 |
| I | CyPr | CF₃ | H | =C(H)— | =N— | 0 |
| Me | CyPr | CF₃ | H | =C(H)— | =N— | 0 |
| Et | CyPr | CF₃ | H | =C(H)— | =N— | 0 |

TABLE 24

| R³ | R⁵ | R⁶ | R⁷ | A¹ | A² | n |
|---|---|---|---|---|---|---|
| Pr | CyPr | CF₃ | H | =C(H)— | =N— | 0 |
| iPr | CyPr | CF₃ | H | =C(H)— | =N— | 0 |
| tBu | CyPr | CF₃ | H | =C(H)— | =N— | 0 |
| CH≡C | CyPr | CF₃ | H | =C(H)— | =N— | 0 |
| CH₂=CH | CyPr | CF₃ | H | =C(H)— | =N— | 0 |
| CF₃ | CyPr | CF₃ | H | =C(H)— | =N— | 0 |
| CF₃CF₂ | CyPr | CF₃ | H | =C(H)— | =N— | 0 |
| MeO | CyPr | CF₃ | H | =C(H)— | =N— | 0 |
| EtO | CyPr | CF₃ | H | =C(H)— | =N— | 0 |
| PrO | CyPr | CF₃ | H | =C(H)— | =N— | 0 |
| iPrO | CyPr | CF₃ | H | =C(H)— | =N— | 0 |
| tBuO | CyPr | CF₃ | H | =C(H)— | =N— | 0 |
| CF₃CH₂O | CyPr | CF₃ | H | =C(H)— | =N— | 0 |
| CHF₂CH₂O | CyPr | CF₃ | H | =C(H)— | =N— | 0 |
| CH₂FCH₂O | CyPr | CF₃ | H | =C(H)— | =N— | 0 |
| MeOCH₂O | CyPr | CF₃ | H | =C(H)— | =N— | 0 |
| EtOCH₂O | CyPr | CF₃ | H | =C(H)— | =N— | 0 |
| MeOCH₂CH₂O | CyPr | CF₃ | H | =C(H)— | =N— | 0 |
| EtOCH₂CH₂O | CyPr | CF₃ | H | =C(H)— | =N— | 0 |
| MeS | CyPr | CF₃ | H | =C(H)— | =N— | 0 |
| MeSO | CyPr | CF₃ | H | =C(H)— | =N— | 0 |
| MeSO₂ | CyPr | CF₃ | H | =C(H)— | =N— | 0 |
| EtS | CyPr | CF₃ | H | =C(H)— | =N— | 0 |
| EtSO | CyPr | CF₃ | H | =C(H)— | =N— | 0 |

TABLE 25

| R³ | R⁵ | R⁶ | R⁷ | A¹ | A² | n |
|---|---|---|---|---|---|---|
| EtSO₂ | CyPr | CF₃ | H | =C(H)— | =N— | 0 |
| PrS | CyPr | CF₃ | H | =C(H)— | =N— | 0 |
| PrSO | CyPr | CF₃ | H | =C(H)— | =N— | 0 |
| PrSO₂ | CyPr | CF₃ | H | =C(H)— | =N— | 0 |
| iPrS | CyPr | CF₃ | H | =C(H)— | =N— | 0 |
| iPrSO | CyPr | CF₃ | H | =C(H)— | =N— | 0 |
| iPrSO₂ | CyPr | CF₃ | H | =C(H)— | =N— | 0 |
| CF₃CH₂S | CyPr | CF₃ | H | =C(H)— | =N— | 0 |
| CF₃CH₂SO | CyPr | CF₃ | H | =C(H)— | =N— | 0 |
| CF₃CH₂SO₂ | CyPr | CF₃ | H | =C(H)— | =N— | 0 |
| Ph | CyPr | CF₃ | H | =C(H)— | =N— | 0 |
| 2-Py | CyPr | CF₃ | H | =C(H)— | =N— | 0 |
| 3-Py | CyPr | CF₃ | H | =C(H)— | =N— | 0 |
| 4-Py | CyPr | CF₃ | H | =C(H)— | =N— | 0 |
| 1-Tz | CyPr | CF₃ | H | =C(H)— | =N— | 0 |
| 1-Pz | CyPr | CF₃ | H | =C(H)— | =N— | 0 |
| H | Me | CF₃ | H | =N— | =C(H)— | 0 |
| F | Me | CF₃ | H | =N— | =C(H)— | 0 |
| Cl | Me | CF₃ | H | =N— | =C(H)— | 0 |
| Br | Me | CF₃ | H | =N— | =C(H)— | 0 |
| I | Me | CF₃ | H | =N— | =C(H)— | 0 |
| Me | Me | CF₃ | H | =N— | =C(H)— | 0 |
| Et | Me | CF₃ | H | =N— | =C(H)— | 0 |
| Pr | Me | CF₃ | H | =N— | =C(H)— | 0 |

TABLE 26

| R³ | R⁵ | R⁶ | R⁷ | A¹ | A² | n |
|---|---|---|---|---|---|---|
| iPr | Me | CF₃ | H | =N— | =C(H)— | 0 |
| tBu | Me | CF₃ | H | =N— | =C(H)— | 0 |
| CH≡C | Me | CF₃ | H | =N— | =C(H)— | 0 |
| CH₂=CH | Me | CF₃ | H | =N— | =C(H)— | 0 |
| CF₃ | Me | CF₃ | H | =N— | =C(H)— | 0 |
| CF₃CF₂ | Me | CF₃ | H | =N— | =C(H)— | 0 |
| MeO | Me | CF₃ | H | =N— | =C(H)— | 0 |
| EtO | Me | CF₃ | H | =N— | =C(H)— | 0 |
| PrO | Me | CF₃ | H | =N— | =C(H)— | 0 |
| iPrO | Me | CF₃ | H | =N— | =C(H)— | 0 |
| tBuO | Me | CF₃ | H | =N— | =C(H)— | 0 |
| CF₃CH₂O | Me | CF₃ | H | =N— | =C(H)— | 0 |
| CHF₂CH₂O | Me | CF₃ | H | =N— | =C(H)— | 0 |
| CH₂FCH₂O | Me | CF₃ | H | =N— | =C(H)— | 0 |
| MeOCH₂O | Me | CF₃ | H | =N— | =C(H)— | 0 |
| EtOCH₂O | Me | CF₃ | H | =N— | =C(H)— | 0 |
| MeOCH₂CH₂O | Me | CF₃ | H | =N— | =C(H)— | 0 |

TABLE 26-continued

| R³ | R⁵ | R⁶ | R⁷ | A¹ | A² | n |
|---|---|---|---|---|---|---|
|  | Me | CF₃ | H | =N— | =C(H)— | 0 |
| EtOCH₂CH₂O | Me | CF₃ | H | =N— | =C(H)— | 0 |
|  | Me | CF₃ | H | =N— | =C(H)— | 0 |
| MeS | Me | CF₃ | H | =N— | =C(H)— | 0 |
| MeSO | Me | CF₃ | H | =N— | =C(H)— | 0 |
| MeSO₂ | Me | CF₃ | H | =N— | =C(H)— | 0 |
| EtS | Me | CF₃ | H | =N— | =C(H)— | 0 |
| EtSO | Me | CF₃ | H | =N— | =C(H)— | 0 |
| EtSO₂ | Me | CF₃ | H | =N— | =C(H)— | 0 |

TABLE 27

| R³ | R⁵ | R⁶ | R⁷ | A¹ | A² | n |
|---|---|---|---|---|---|---|
| PrS | Me | CF₃ | H | =N— | =C(H)— | 0 |
| PrSO | Me | CF₃ | H | =N— | =C(H)— | 0 |
| PrSO₂ | Me | CF₃ | H | =N— | =C(H)— | 0 |
| iPrS | Me | CF₃ | H | =N— | =C(H)— | 0 |
| iPrSO | Me | CF₃ | H | =N— | =C(H)— | 0 |
| iPrSO₂ | Me | CF₃ | H | =N— | =C(H)— | 0 |
| CF₃CH₂S | Me | CF₃ | H | =N— | =C(H)— | 0 |
| CF₃CH₂SO | Me | CF₃ | H | =N— | =C(H)— | 0 |
| CF₃CH₂SO₂ | Me | CF₃ | H | =N— | =C(H)— | 0 |
| Ph | Me | CF₃ | H | =N— | =C(H)— | 0 |
| 2-Py | Me | CF₃ | H | =N— | =C(H)— | 0 |
| 3-Py | Me | CF₃ | H | =N— | =C(H)— | 0 |
| 4-Py | Me | CF₃ | H | =N— | =C(H)— | 0 |
| 1-Tz | Me | CF₃ | H | =N— | =C(H)— | 0 |
| 1-Pz | Me | CF₃ | H | =N— | =C(H)— | 0 |
| H | Me | CF₃ | H | =N— | =C(H)— | 1 |
| F | Me | CF₃ | H | =N— | =C(H)— | 1 |
| Cl | Me | CF₃ | H | =N— | =C(H)— | 1 |
| MeO | Me | CF₃ | H | =N— | =C(H)— | 1 |
| EtO | Me | CF₃ | H | =N— | =C(H)— | 1 |
| CF₃CH₂O | Me | CF₃ | H | =N— | =C(H)— | 1 |
| CHF₂CH₂O | Me | CF₃ | H | =N— | =C(H)— | 1 |
| CH₂FCH₂O | Me | CF₃ | H | =N— | =C(H)— | 1 |
| MeS | Me | CF₃ | H | =N— | =C(H)— | 1 |

TABLE 28

| R³ | R⁵ | R⁶ | R⁷ | A¹ | A² | n |
|---|---|---|---|---|---|---|
| MeSO | Me | CF₃ | H | =N— | =C(H)— | 1 |
| MeSO₂ | Me | CF₃ | H | =N— | =C(H)— | 1 |
| EtS | Me | CF₃ | H | =N— | =C(H)— | 1 |
| EtSO | Me | CF₃ | H | =N— | =C(H)— | 1 |
| EtSO₂ | Me | CF₃ | H | =N— | =C(H)— | 1 |
| H | Me | C₂F₅ | H | =N— | =C(H)— | 0 |
| F | Me | C₂F₅ | H | =N— | =C(H)— | 0 |
| Cl | Me | C₂F₅ | H | =N— | =C(H)— | 0 |
| Br | Me | C₂F₅ | H | =N— | =C(H)— | 0 |
| I | Me | C₂F₅ | H | =N— | =C(H)— | 0 |
| Me | Me | C₂F₅ | H | =N— | =C(H)— | 0 |
| Et | Me | C₂F₅ | H | =N— | =C(H)— | 0 |
| Pr | Me | C₂F₅ | H | =N— | =C(H)— | 0 |
| iPr | Me | C₂F₅ | H | =N— | =C(H)— | 0 |
| tBu | Me | C₂F₅ | H | =N— | =C(H)— | 0 |
| CH≡C | Me | C₂F₅ | H | =N— | =C(H)— | 0 |
| CH₂=CH | Me | C₂F₅ | H | =N— | =C(H)— | 0 |
| CF₃ | Me | C₂F₅ | H | =N— | =C(H)— | 0 |
| CF₃CF₂ | Me | C₂F₅ | H | =N— | =C(H)— | 0 |
| MeO | Me | C₂F₅ | H | =N— | =C(H)— | 0 |
| EtO | Me | C₂F₅ | H | =N— | =C(H)— | 0 |
| PrO | Me | C₂F₅ | H | =N— | =C(H)— | 0 |
| iPrO | Me | C₂F₅ | H | =N— | =C(H)— | 0 |
| tBuO | Me | C₂F₅ | H | =N— | =C(H)— | 0 |

TABLE 29

| R³ | R⁵ | R⁶ | R⁷ | A¹ | A² | n |
|---|---|---|---|---|---|---|
| CF₃CH₂O | Me | C₂F₅ | H | =N— | =C(H)— | 0 |
| CHF₂CH₂O | Me | C₂F₅ | H | =N— | =C(H)— | 0 |
| CH₂FCH₂O | Me | C₂F₅ | H | =N— | =C(H)— | 0 |
| MeOCH₂O | Me | C₂F₅ | H | =N— | =C(H)— | 0 |
| EtOCH₂O | Me | C₂F₅ | H | =N— | =C(H)— | 0 |
| MeOCH₂CH₂O | Me | C₂F₅ | H | =N— | =C(H)— | 0 |
| EtOCH₂CH₂O | Me | C₂F₅ | H | =N— | =C(H)— | 0 |
| MeS | Me | C₂F₅ | H | =N— | =C(H)— | 0 |
| MeSO | Me | C₂F₅ | H | =N— | =C(H)— | 0 |
| MeSO₂ | Me | C₂F₅ | H | =N— | =C(H)— | 0 |
| EtS | Me | C₂F₅ | H | =N— | =C(H)— | 0 |
| EtSO | Me | C₂F₅ | H | =N— | =C(H)— | 0 |
| EtSO₂ | Me | C₂F₅ | H | =N— | =C(H)— | 0 |
| PrS | Me | C₂F₅ | H | =N— | =C(H)— | 0 |
| PrSO | Me | C₂F₅ | H | =N— | =C(H)— | 0 |
| PrSO₂ | Me | C₂F₅ | H | =N— | =C(H)— | 0 |
| iPrS | Me | C₂F₅ | H | =N— | =C(H)— | 0 |
| iPrSO | Me | C₂F₅ | H | =N— | =C(H)— | 0 |
| iPrSO₂ | Me | C₂F₅ | H | =N— | =C(H)— | 0 |
| CF₃CH₂S | Me | C₂F₅ | H | =N— | =C(H)— | 0 |
| CF₃CH₂SO | Me | C₂F₅ | H | =N— | =C(H)— | 0 |
| CF₃CH₂SO₂ | Me | C₂F₅ | H | =N— | =C(H)— | 0 |
| Ph | Me | C₂F₅ | H | =N— | =C(H)— | 0 |
| 2-Py | Me | C₂F₅ | H | =N— | =C(H)— | 0 |

TABLE 30

| R³ | R⁵ | R⁶ | R⁷ | A¹ | A² | n |
|---|---|---|---|---|---|---|
| 3-Py | Me | C₂F₅ | H | =N— | =C(H)— | 0 |
| 4-Py | Me | C₂F₅ | H | =N— | =C(H)— | 0 |
| 1-Tz | Me | C₂F₅ | H | =N— | =C(H)— | 0 |
| 1-Pz | Me | C₂F₅ | H | =N— | =C(H)— | 0 |
| H | Me | H | CF₃ | =N— | =C(H)— | 0 |
| F | Me | H | CF₃ | =N— | =C(H)— | 0 |
| Cl | Me | H | CF₃ | =N— | =C(H)— | 0 |
| Br | Me | H | CF₃ | =N— | =C(H)— | 0 |
| I | Me | H | CF₃ | =N— | =C(H)— | 0 |
| Me | Me | H | CF₃ | =N— | =C(H)— | 0 |
| Et | Me | H | CF₃ | =N— | =C(H)— | 0 |
| Pr | Me | H | CF₃ | =N— | =C(H)— | 0 |
| iPr | Me | H | CF₃ | =N— | =C(H)— | 0 |
| tBu | Me | H | CF₃ | =N— | =C(H)— | 0 |
| CH≡C | Me | H | CF₃ | =N— | =C(H)— | 0 |
| CH₂=CH | Me | H | CF₃ | =N— | =C(H)— | 0 |
| CF₃ | Me | H | CF₃ | =N— | =C(H)— | 0 |
| CF₃CF₂ | Me | H | CF₃ | =N— | =C(H)— | 0 |
| MeO | Me | H | CF₃ | =N— | =C(H)— | 0 |
| EtO | Me | H | CF₃ | =N— | =C(H)— | 0 |
| PrO | Me | H | CF₃ | =N— | =C(H)— | 0 |
| iPrO | Me | H | CF₃ | =N— | =C(H)— | 0 |
| tBuO | Me | H | CF₃ | =N— | =C(H)— | 0 |
| CF₃CH₂O | Me | H | CF₃ | =N— | =C(H)— | 0 |

TABLE 31

| R³ | R⁵ | R⁶ | R⁷ | A¹ | A² | n |
|---|---|---|---|---|---|---|
| CHF₂CH₂O | Me | H | CF₃ | =N— | =C(H)— | 0 |
| CH₂FCH₂O | Me | H | CF₃ | =N— | =C(H)— | 0 |
| MeOCH₂O | Me | H | CF₃ | =N— | =C(H)— | 0 |
| EtOCH₂O | Me | H | CF₃ | =N— | =C(H)— | 0 |
| MeOCH₂CH₂O | Me | H | CF₃ | =N— | =C(H)— | 0 |
| EtOCH₂CH₂O | Me | H | CF₃ | =N— | =C(H)— | 0 |
| MeS | Me | H | CF₃ | =N— | =C(H)— | 0 |
| MeSO | Me | H | CF₃ | =N— | =C(H)— | 0 |
| MeSO₂ | Me | H | CF₃ | =N— | =C(H)— | 0 |
| EtS | Me | H | CF₃ | =N— | =C(H)— | 0 |
| EtSO | Me | H | CF₃ | =N— | =C(H)— | 0 |
| EtSO₂ | Me | H | CF₃ | =N— | =C(H)— | 0 |
| PrS | Me | H | CF₃ | =N— | =C(H)— | 0 |
| PrSO | Me | H | CF₃ | =N— | =C(H)— | 0 |
| PrSO₂ | Me | H | CF₃ | =N— | =C(H)— | 0 |

TABLE 31-continued

| R³ | R⁵ | R⁶ | R⁷ | A¹ | A² | n |
|---|---|---|---|---|---|---|
| iPrS | Me | H | CF₃ | =N— | =C(H)— | 0 |
| iPrSO | Me | H | CF₃ | =N— | =C(H)— | 0 |
| iPrSO₂ | Me | H | CF₃ | =N— | =C(H)— | 0 |
| CF₃CH₂S | Me | H | CF₃ | =N— | =C(H)— | 0 |
| CF₃CH₂SO | Me | H | CF₃ | =N— | =C(H)— | 0 |
| CF₃CH₂SO₂ | Me | H | CF₃ | =N— | =C(H)— | 0 |
| Ph | Me | H | CF₃ | =N— | =C(H)— | 0 |
| 2-Py | Me | H | CF₃ | =N— | =C(H)— | 0 |
| 3-Py | Me | H | CF₃ | =N— | =C(H)— | 0 |

TABLE 32

| R³ | R⁵ | R⁶ | R⁷ | A¹ | A² | n |
|---|---|---|---|---|---|---|
| 4-Py | Me | H | CF₃ | =N— | =C(H)— | 0 |
| 1-Tz | Me | H | CF₃ | =N— | =C(H)— | 0 |
| 1-Pz | Me | H | CF₃ | =N— | =C(H)— | 0 |
| H | Et | CF₃ | H | =N— | =C(H)— | 0 |
| F | Et | CF₃ | H | =N— | =C(H)— | 0 |
| Cl | Et | CF₃ | H | =N— | =C(H)— | 0 |
| Br | Et | CF₃ | H | =N— | =C(H)— | 0 |
| I | Et | CF₃ | H | =N— | =C(H)— | 0 |
| Me | Et | CF₃ | H | =N— | =C(H)— | 0 |
| Et | Et | CF₃ | H | =N— | =C(H)— | 0 |
| Pr | Et | CF₃ | H | =N— | =C(H)— | 0 |
| iPr | Et | CF₃ | H | =N— | =C(H)— | 0 |
| tBu | Et | CF₃ | H | =N— | =C(H)— | 0 |
| CH≡C | Et | CF₃ | H | =N— | =C(H)— | 0 |
| CH₂=CH | Et | CF₃ | H | =N— | =C(H)— | 0 |
| CF₃ | Et | CF₃ | H | =N— | =C(H)— | 0 |
| CF₃CF₂ | Et | CF₃ | H | =N— | =C(H)— | 0 |
| MeO | Et | CF₃ | H | =N— | =C(H)— | 0 |
| EtO | Et | CF₃ | H | =N— | =C(H)— | 0 |
| PrO | Et | CF₃ | H | =N— | =C(H)— | 0 |
| iPrO | Et | CF₃ | H | =N— | =C(H)— | 0 |
| tBuO | Et | CF₃ | H | =N— | =C(H)— | 0 |
| CF₃CH₂O | Et | CF₃ | H | =N— | =C(H)— | 0 |
| CHF₂CH₂O | Et | CF₃ | H | =N— | =C(H)— | 0 |

TABLE 33

| R³ | R⁵ | R⁶ | R⁷ | A¹ | A² | n |
|---|---|---|---|---|---|---|
| CH₂FCH₂O | Et | CF₃ | H | =N— | =C(H)— | 0 |
| MeOCH₂O | Et | CF₃ | H | =N— | =C(H)— | 0 |
| EtOCH₂O | Et | CF₃ | H | =N— | =C(H)— | 0 |
| MeOCH₂CH₂O | Et | CF₃ | H | =N— | =C(H)— | 0 |
| EtOCH₂CH₂O | Et | CF₃ | H | =N— | =C(H)— | 0 |
| MeS | Et | CF₃ | H | =N— | =C(H)— | 0 |
| MeSO | Et | CF₃ | H | =N— | =C(H)— | 0 |
| MeSO₂ | Et | CF₃ | H | =N— | =C(H)— | 0 |
| EtS | Et | CF₃ | H | =N— | =C(H)— | 0 |
| EtSO | Et | CF₃ | H | =N— | =C(H)— | 0 |
| EtSO₂ | Et | CF₃ | H | =N— | =C(H)— | 0 |
| PrS | Et | CF₃ | H | =N— | =C(H)— | 0 |
| PrSO | Et | CF₃ | H | =N— | =C(H)— | 0 |
| PrSO₂ | Et | CF₃ | H | =N— | =C(H)— | 0 |
| iPrS | Et | CF₃ | H | =N— | =C(H)— | 0 |
| iPrSO | Et | CF₃ | H | =N— | =C(H)— | 0 |
| iPrSO₂ | Et | CF₃ | H | =N— | =C(H)— | 0 |
| CF₃CH₂S | Et | CF₃ | H | =N— | =C(H)— | 0 |
| CF₃CH₂SO | Et | CF₃ | H | =N— | =C(H)— | 0 |
| CF₃CH₂SO₂ | Et | CF₃ | H | =N— | =C(H)— | 0 |
| Ph | Et | CF₃ | H | =N— | =C(H)— | 0 |
| 2-Py | Et | CF₃ | H | =N— | =C(H)— | 0 |
| 3-Py | Et | CF₃ | H | =N— | =C(H)— | 0 |
| 4-Py | Et | CF₃ | H | =N— | =C(H)— | 0 |

TABLE 34

| R³ | R⁵ | R⁶ | R⁷ | A¹ | A² | n |
|---|---|---|---|---|---|---|
| 1-Tz | Et | CF₃ | H | =N— | =C(H)— | 0 |
| 1-Pz | Et | CF₃ | H | =N— | =C(H)— | 0 |
| H | CyPr | CF₃ | H | =N— | =C(H)— | 0 |
| F | CyPr | CF₃ | H | =N— | =C(H)— | 0 |
| Cl | CyPr | CF₃ | H | =N— | =C(H)— | 0 |
| Br | CyPr | CF₃ | H | =N— | =C(H)— | 0 |
| I | CyPr | CF₃ | H | =N— | =C(H)— | 0 |
| Me | CyPr | CF₃ | H | =N— | =C(H)— | 0 |
| Et | CyPr | CF₃ | H | =N— | =C(H)— | 0 |
| Pr | CyPr | CF₃ | H | =N— | =C(H)— | 0 |
| iPr | CyPr | CF₃ | H | =N— | =C(H)— | 0 |
| tBu | CyPr | CF₃ | H | =N— | =C(H)— | 0 |
| CH≡C | CyPr | CF₃ | H | =N— | =C(H)— | 0 |
| CH₂=CH | CyPr | CF₃ | H | =N— | =C(H)— | 0 |
| CF₃ | CyPr | CF₃ | H | =N— | =C(H)— | 0 |
| CF₃CF₂ | CyPr | CF₃ | H | =N— | =C(H)— | 0 |
| MeO | CyPr | CF₃ | H | =N— | =C(H)— | 0 |
| EtO | CyPr | CF₃ | H | =N— | =C(H)— | 0 |
| PrO | CyPr | CF₃ | H | =N— | =C(H)— | 0 |
| iPrO | CyPr | CF₃ | H | =N— | =C(H)— | 0 |
| tBuO | CyPr | CF₃ | H | =N— | =C(H)— | 0 |
| CF₃CH₂O | CyPr | CF₃ | H | =N— | =C(H)— | 0 |
| CHF₂CH₂O | CyPr | CF₃ | H | =N— | =C(H)— | 0 |
| CH₂FCH₂O | CyPr | CF₃ | H | =N— | =C(H)— | 0 |

TABLE 35

| R³ | R⁵ | R⁶ | R⁷ | A¹ | A² | n |
|---|---|---|---|---|---|---|
| MeOCH₂O | CyPr | CF₃ | H | =N— | =C(H)— | 0 |
| EtOCH₂O | CyPr | CF₃ | H | =N— | =C(H)— | 0 |
| MeOCH₂CH₂O | CyPr | CF₃ | H | =N— | =C(H)— | 0 |
| EtOCH₂CH₂O | CyPr | CF₃ | H | =N— | =C(H)— | 0 |
| MeS | CyPr | CF₃ | H | =N— | =C(H)— | 0 |
| MeSO | CyPr | CF₃ | H | =N— | =C(H)— | 0 |
| MeSO₂ | CyPr | CF₃ | H | =N— | =C(H)— | 0 |
| EtS | CyPr | CF₃ | H | =N— | =C(H)— | 0 |
| EtSO | CyPr | CF₃ | H | =N— | =C(H)— | 0 |
| EtSO₂ | CyPr | CF₃ | H | =N— | =C(H)— | 0 |
| PrS | CyPr | CF₃ | H | =N— | =C(H)— | 0 |
| PrSO | CyPr | CF₃ | H | =N— | =C(H)— | 0 |
| PrSO₂ | CyPr | CF₃ | H | =N— | =C(H)— | 0 |
| iPrS | CyPr | CF₃ | H | =N— | =C(H)— | 0 |
| iPrSO | CyPr | CF₃ | H | =N— | =C(H)— | 0 |
| iPrSO₂ | CyPr | CF₃ | H | =N— | =C(H)— | 0 |
| CF₃CH₂S | CyPr | CF₃ | H | =N— | =C(H)— | 0 |
| CF₃CH₂SO | CyPr | CF₃ | H | =N— | =C(H)— | 0 |
| CF₃CH₂SO₂ | CyPr | CF₃ | H | =N— | =C(H)— | 0 |
| Ph | CyPr | CF₃ | H | =N— | =C(H)— | 0 |
| 2-Py | CyPr | CF₃ | H | =N— | =C(H)— | 0 |
| 3-Py | CyPr | CF₃ | H | =N— | =C(H)— | 0 |
| 4-Py | CyPr | CF₃ | H | =N— | =C(H)— | 0 |
| 1-Tz | CyPr | CF₃ | H | =N— | =C(H)— | 0 |

TABLE 36

| R³ | R⁵ | R⁶ | R⁷ | A¹ | A² | n |
|---|---|---|---|---|---|---|
| 1-Pz | CyPr | CF₃ | H | =N— | =C(H)— | 0 |

TABLE 37

| R³ | R⁵ | R⁶ | R⁷ | A¹ | A² | n |
|---|---|---|---|---|---|---|
| HO | Me | CF₃ | H | =C(H)— | =C(H)— | 0 |
| iPrCH₂O | Me | CF₃ | H | =C(H)— | =C(H)— | 0 |
| tBuCH₂O | Me | CF₃ | H | =C(H)— | =C(H)— | 0 |
| HS | Me | CF₃ | H | =C(H)— | =C(H)— | 0 |
| tBuS | Me | CF₃ | H | =C(H)— | =C(H)— | 0 |
| tBuSO | Me | CF₃ | H | =C(H)— | =C(H)— | 0 |
| tBuSO₂ | Me | CF₃ | H | =C(H)— | =C(H)— | 0 |

TABLE 37-continued

| $R^3$ | $R^5$ | $R^6$ | $R^7$ | $A^1$ | $A^2$ | n |
|---|---|---|---|---|---|---|
| CF$_3$S | Me | CF$_3$ | H | =C(H)— | =C(H)— | 0 |
| CF$_3$SO | Me | CF$_3$ | H | =C(H)— | =C(H)— | 0 |
| CF$_3$SO$_2$ | Me | CF$_3$ | H | =C(H)— | =C(H)— | 0 |
| CHF$_2$CH$_2$S | Me | CF$_3$ | H | =C(H)— | =C(H)— | 0 |
| CHF$_2$CH$_2$SO | Me | CF$_3$ | H | =C(H)— | =C(H)— | 0 |
| CHF$_2$CH$_2$SO$_2$ | Me | CF$_3$ | H | =C(H)— | =C(H)— | 0 |
| NC | Me | CF$_3$ | H | =C(H)— | =C(H)— | 0 |
| HO(CO) | Me | CF$_3$ | H | =C(H)— | =C(H)— | 0 |
| MeO(CO) | Me | CF$_3$ | H | =C(H)— | =C(H)— | 0 |
| EtO(CO) | Me | CF$_3$ | H | =C(H)— | =C(H)— | 0 |
| H$_2$N(CO) | Me | CF$_3$ | H | =C(H)— | =C(H)— | 0 |
| MeHN(CO) | Me | CF$_3$ | H | =C(H)— | =C(H)— | 0 |
| EtHN(CO) | Me | CF$_3$ | H | =C(H)— | =C(H)— | 0 |
| Me$_2$N(CO) | Me | CF$_3$ | H | =C(H)— | =C(H)— | 0 |
| Et$_2$N(CO) | Me | CF$_3$ | H | =C(H)— | =C(H)— | 0 |
| (MeO)MeN(CO) | Me | CF$_3$ | H | =C(H)— | =C(H)— | 0 |
| MeOCH$_2$ | Me | CF$_3$ | H | =C(H)— | =C(H)— | 0 |

TABLE 38

| $R^3$ | $R^5$ | $R^6$ | $R^7$ | $A^1$ | $A^2$ | n |
|---|---|---|---|---|---|---|
| HO | Me | C$_2$F$_5$ | H | =C(H)— | =C(H)— | 0 |
| iPrCH$_2$O | Me | C$_2$F$_5$ | H | =C(H)— | =C(H)— | 0 |
| tBuCH$_2$O | Me | C$_2$F$_5$ | H | =C(H)— | =C(H)— | 0 |
| HS | Me | C$_2$F$_5$ | H | =C(H)— | =C(H)— | 0 |
| tBuS | Me | C$_2$F$_5$ | H | =C(H)— | =C(H)— | 0 |
| tBuSO | Me | C$_2$F$_5$ | H | =C(H)— | =C(H)— | 0 |
| tBuSO$_2$ | Me | C$_2$F$_5$ | H | =C(H)— | =C(H)— | 0 |
| CF$_3$S | Me | C$_2$F$_5$ | H | =C(H)— | =C(H)— | 0 |
| CF$_3$SO | Me | C$_2$F$_5$ | H | =C(H)— | =C(H)— | 0 |
| CF$_3$SO$_2$ | Me | C$_2$F$_5$ | H | =C(H)— | =C(H)— | 0 |
| CHF$_2$CH$_2$S | Me | C$_2$F$_5$ | H | =C(H)— | =C(H)— | 0 |
| CHF$_2$CH$_2$SO | Me | C$_2$F$_5$ | H | =C(H)— | =C(H)— | 0 |
| CHF$_2$CH$_2$SO$_2$ | Me | C$_2$F$_5$ | H | =C(H)— | =C(H)— | 0 |
| NC | Me | C$_2$F$_5$ | H | =C(H)— | =C(H)— | 0 |
| HO(CO) | Me | C$_2$F$_5$ | H | =C(H)— | =C(H)— | 0 |
| MeO(CO) | Me | C$_2$F$_5$ | H | =C(H)— | =C(H)— | 0 |
| EtO(CO) | Me | C$_2$F$_5$ | H | =C(H)— | =C(H)— | 0 |
| H$_2$N(CO) | Me | C$_2$F$_5$ | H | =C(H)— | =C(H)— | 0 |
| MeHN(CO) | Me | C$_2$F$_5$ | H | =C(H)— | =C(H)— | 0 |
| EtHN(CO) | Me | C$_2$F$_5$ | H | =C(H)— | =C(H)— | 0 |
| Me$_2$N(CO) | Me | C$_2$F$_5$ | H | =C(H)— | =C(H)— | 0 |
| Et$_2$N(CO) | Me | C$_2$F$_5$ | H | =C(H)— | =C(H)— | 0 |
| (MeO)MeN(CO) | Me | C$_2$F$_5$ | H | =C(H)— | =C(H)— | 0 |
| MeOCH$_2$ | Me | C$_2$F$_5$ | H | =C(H)— | =C(H)— | 0 |

TABLE 39

| $R^3$ | $R^5$ | $R^6$ | $R^7$ | $A^1$ | $A^2$ | n |
|---|---|---|---|---|---|---|
| HO | Me | OCF$_3$ | H | =C(H)— | =C(H)— | 0 |
| iPrCH$_2$O | Me | OCF$_3$ | H | =C(H)— | =C(H)— | 0 |
| tBuCH$_2$O | Me | OCF$_3$ | H | =C(H)— | =C(H)— | 0 |
| HS | Me | OCF$_3$ | H | =C(H)— | =C(H)— | 0 |
| tBuS | Me | OCF$_3$ | H | =C(H)— | =C(H)— | 0 |
| tBuSO | Me | OCF$_3$ | H | =C(H)— | =C(H)— | 0 |
| tBuSO$_2$ | Me | OCF$_3$ | H | =C(H)— | =C(H)— | 0 |
| CF$_3$S | Me | OCF$_3$ | H | =C(H)— | =C(H)— | 0 |
| CF$_3$SO | Me | OCF$_3$ | H | =C(H)— | =C(H)— | 0 |
| CF$_3$SO$_2$ | Me | OCF$_3$ | H | =C(H)— | =C(H)— | 0 |
| CHF$_2$CH$_2$S | Me | OCF$_3$ | H | =C(H)— | =C(H)— | 0 |
| CHF$_2$CH$_2$SO | Me | OCF$_3$ | H | =C(H)— | =C(H)— | 0 |
| CHF$_2$CH$_2$SO$_2$ | Me | OCF$_3$ | H | =C(H)— | =C(H)— | 0 |
| NC | Me | OCF$_3$ | H | =C(H)— | =C(H)— | 0 |
| HO(CO) | Me | OCF$_3$ | H | =C(H)— | =C(H)— | 0 |
| MeO(CO) | Me | OCF$_3$ | H | =C(H)— | =C(H)— | 0 |
| EtO(CO) | Me | OCF$_3$ | H | =C(H)— | =C(H)— | 0 |
| H$_2$N(CO) | Me | OCF$_3$ | H | =C(H)— | =C(H)— | 0 |
| MeHN(CO) | Me | OCF$_3$ | H | =C(H)— | =C(H)— | 0 |
| EtHN(CO) | Me | OCF$_3$ | H | =C(H)— | =C(H)— | 0 |
| Me$_2$N(CO) | Me | OCF$_3$ | H | =C(H)— | =C(H)— | 0 |
| Et$_2$N(CO) | Me | OCF$_3$ | H | =C(H)— | =C(H)— | 0 |

TABLE 39-continued

| $R^3$ | $R^5$ | $R^6$ | $R^7$ | $A^1$ | $A^2$ | n |
|---|---|---|---|---|---|---|
| (MeO)MeN(CO) | Me | OCF$_3$ | H | =C(H)— | =C(H)— | 0 |
| MeOCH$_2$ | Me | OCF$_3$ | H | =C(H)— | =C(H)— | 0 |

TABLE 40

| $R^3$ | $R^5$ | $R^6$ | $R^7$ | $A^1$ | $A^2$ | n |
|---|---|---|---|---|---|---|
| HO | Me | —CF$_2$OCF$_2$— | | =C(H)— | =C(H)— | 0 |
| iPrCH$_2$O | Me | —CF$_2$OCF$_2$— | | =C(H)— | =C(H)— | 0 |
| tBuCH$_2$O | Me | —CF$_2$OCF$_2$— | | =C(H)— | =C(H)— | 0 |
| HS | Me | —CF$_2$OCF$_2$— | | =C(H)— | =C(H)— | 0 |
| tBuS | Me | —CF$_2$OCF$_2$— | | =C(H)— | =C(H)— | 0 |
| tBuSO | Me | —CF$_2$OCF$_2$— | | =C(H)— | =C(H)— | 0 |
| tBuSO$_2$ | Me | —CF$_2$OCF$_2$— | | =C(H)— | =C(H)— | 0 |
| CF$_3$S | Me | —CF$_2$OCF$_2$— | | =C(H)— | =C(H)— | 0 |
| CF$_3$SO | Me | —CF$_2$OCF$_2$— | | =C(H)— | =C(H)— | 0 |
| CF$_3$SO$_2$ | Me | —CF$_2$OCF$_2$— | | =C(H)— | =C(H)— | 0 |
| CHF$_2$CH$_2$S | Me | —CF$_2$OCF$_2$— | | =C(H)— | =C(H)— | 0 |
| CHF$_2$CH$_2$SO | Me | —CF$_2$OCF$_2$— | | =C(H)— | =C(H)— | 0 |
| CHF$_2$CH$_2$SO$_2$ | Me | —CF$_2$OCF$_2$— | | =C(H)— | =C(H)— | 0 |
| NC | Me | —CF$_2$OCF$_2$— | | =C(H)— | =C(H)— | 0 |
| HO (CO) | Me | —CF$_2$OCF$_2$— | | =C(H)— | =C(H)— | 0 |
| MeO (CO) | Me | —CF$_2$OCF$_2$— | | =C(H)— | =C(H)— | 0 |
| EtO (CO) | Me | —CF$_2$OCF$_2$— | | =C(H)— | =C(H)— | 0 |
| H$_2$N (CO) | Me | —CF$_2$OCF$_2$— | | =C(H)— | =C(H)— | 0 |
| MeHN (CO) | Me | —CF$_2$OCF$_2$— | | =C(H)— | =C(H)— | 0 |
| EtHN (CO) | Me | —CF$_2$OCF$_2$— | | =C(H)— | =C(H)— | 0 |
| Me$_2$N (CO) | Me | —CF$_2$OCF$_2$— | | =C(H)— | =C(H)— | 0 |
| Et$_2$N (CO) | Me | —CF$_2$OCF$_2$— | | =C(H)— | =C(H)— | 0 |
| (MeO)MeN (CO) | Me | —CF$_2$OCF$_2$— | | =C(H)— | =C(H)— | 0 |
| MeOCH$_2$ | Me | —CF$_2$OCF$_2$— | | =C(H)— | =C(H)— | 0 |

TABLE 41

| $R^3$ | $R^5$ | $R^6$ | $R^7$ | $A^1$ | $A^2$ | n |
|---|---|---|---|---|---|---|
| HO | Me | H | CF$_3$ | =C(H)— | =C(H)— | 0 |
| iPrCH$_2$O | Me | H | CF$_3$ | =C(H)— | =C(H)— | 0 |
| tBuCH$_2$O | Me | H | CF$_3$ | =C(H)— | =C(H)— | 0 |
| HS | Me | H | CF$_3$ | =C(H)— | =C(H)— | 0 |
| tBuS | Me | H | CF$_3$ | =C(H)— | =C(H)— | 0 |
| tBuSO | Me | H | CF$_3$ | =C(H)— | =C(H)— | 0 |
| tBuSO$_2$ | Me | H | CF$_3$ | =C(H)— | =C(H)— | 0 |
| CF$_3$S | Me | H | CF$_3$ | =C(H)— | =C(H)— | 0 |
| CF$_3$SO | Me | H | CF$_3$ | =C(H)— | =C(H)— | 0 |
| CF$_3$SO$_2$ | Me | H | CF$_3$ | =C(H)— | =C(H)— | 0 |
| CHF$_2$CH$_2$S | Me | H | CF$_3$ | =C(H)— | =C(H)— | 0 |
| CHF$_2$CH$_2$SO | Me | H | CF$_3$ | =C(H)— | =C(H)— | 0 |
| CHF$_2$CH$_2$SO$_2$ | Me | H | CF$_3$ | =C(H)— | =C(H)— | 0 |
| NC | Me | H | CF$_3$ | =C(H)— | =C(H)— | 0 |
| HO(CO) | Me | H | CF$_3$ | =C(H)— | =C(H)— | 0 |
| MeO(CO) | Me | H | CF$_3$ | =C(H)— | =C(H)— | 0 |
| EtO(CO) | Me | H | CF$_3$ | =C(H)— | =C(H)— | 0 |
| H$_2$N(CO) | Me | H | CF$_3$ | =C(H)— | =C(H)— | 0 |
| MeHN(CO) | Me | H | CF$_3$ | =C(H)— | =C(H)— | 0 |
| EtHN(CO) | Me | H | CF$_3$ | =C(H)— | =C(H)— | 0 |
| Me$_2$N(CO) | Me | H | CF$_3$ | =C(H)— | =C(H)— | 0 |
| Et$_2$N(CO) | Me | H | CF$_3$ | =C(H)— | =C(H)— | 0 |
| (MeO)MeN(CO) | Me | H | CF$_3$ | =C(H)— | =C(H)— | 0 |
| MeOCH$_2$ | Me | H | CF$_3$ | =C(H)— | =C(H)— | 0 |

TABLE 42

| $R^3$ | $R^5$ | $R^6$ | $R^7$ | $A^1$ | $A^2$ | n |
|---|---|---|---|---|---|---|
| HO | Et | CF$_3$ | H | =C(H)— | =C(H)— | 0 |
| iPrCH$_2$O | Et | CF$_3$ | H | =C(H)— | =C(H)— | 0 |
| tBuCH$_2$O | Et | CF$_3$ | H | =C(H)— | =C(H)— | 0 |
| HS | Et | CF$_3$ | H | =C(H)— | =C(H)— | 0 |
| tBuS | Et | CF$_3$ | H | =C(H)— | =C(H)— | 0 |
| tBuSO | Et | CF$_3$ | H | =C(H)— | =C(H)— | 0 |

TABLE 42-continued

| R³ | R⁵ | R⁶ | R⁷ | A¹ | A² | n |
|---|---|---|---|---|---|---|
| tBuSO₂ | Et | CF₃ | H | =C(H)— | =C(H)— | 0 |
| CF₃S | Et | CF₃ | H | =C(H)— | =C(H)— | 0 |
| CF₃SO | Et | CF₃ | H | =C(H)— | =C(H)— | 0 |
| CF₃SO₂ | Et | CF₃ | H | =C(H)— | =C(H)— | 0 |
| CHF₂CH₂S | Et | CF₃ | H | =C(H)— | =C(H)— | 0 |
| CHF₂CH₂SO | Et | CF₃ | H | =C(H)— | =C(H)— | 0 |
| CHF₂CH₂SO₂ | Et | CF₃ | H | =C(H)— | =C(H)— | 0 |
| NC | Et | CF₃ | H | =C(H)— | =C(H)— | 0 |
| HO(CO) | Et | CF₃ | H | =C(H)— | =C(H)— | 0 |
| MeO(CO) | Et | CF₃ | H | =C(H)— | =C(H)— | 0 |
| EtO(CO) | Et | CF₃ | H | =C(H)— | =C(H)— | 0 |
| H₂N(CO) | Et | CF₃ | H | =C(H)— | =C(H)— | 0 |
| MeHN(CO) | Et | CF₃ | H | =C(H)— | =C(H)— | 0 |
| EtHN(CO) | Et | CF₃ | H | =C(H)— | =C(H)— | 0 |
| Me₂N(CO) | Et | CF₃ | H | =C(H)— | =C(H)— | 0 |
| Et₂N(CO) | Et | CF₃ | H | =C(H)— | =C(H)— | 0 |
| (MeO)MeN(CO) | Et | CF₃ | H | =C(H)— | =C(H)— | 0 |
| MeOCH₂ | Et | CF₃ | H | =C(H)— | =C(H)— | 0 |

TABLE 43

| R³ | R⁵ | R⁶ | R⁷ | A¹ | A² | n |
|---|---|---|---|---|---|---|
| HO | CyPr | CF₃ | H | =C(H)— | =C(H)— | 0 |
| iPrCH₂O | CyPr | CF₃ | H | =C(H)— | =C(H)— | 0 |
| tBuCH₂O | CyPr | CF₃ | H | =C(H)— | =C(H)— | 0 |
| HS | CyPr | CF₃ | H | =C(H)— | =C(H)— | 0 |
| tBuS | CyPr | CF₃ | H | =C(H)— | =C(H)— | 0 |
| tBuSO | CyPr | CF₃ | H | =C(H)— | =C(H)— | 0 |
| tBuSO₂ | CyPr | CF₃ | H | =C(H)— | =C(H)— | 0 |
| CF₃S | CyPr | CF₃ | H | =C(H)— | =C(H)— | 0 |
| CF₃SO | CyPr | CF₃ | H | =C(H)— | =C(H)— | 0 |
| CF₃SO₂ | CyPr | CF₃ | H | =C(H)— | =C(H)— | 0 |
| CHF₂CH₂S | CyPr | CF₃ | H | =C(H)— | =C(H)— | 0 |
| CHF₂CH₂SO | CyPr | CF₃ | H | =C(H)— | =C(H)— | 0 |
| CHF₂CH₂SO₂ | CyPr | CF₃ | H | =C(H)— | =C(H)— | 0 |
| NC | CyPr | CF₃ | H | =C(H)— | =C(H)— | 0 |
| HO(CO) | CyPr | CF₃ | H | =C(H)— | =C(H)— | 0 |
| MeO(CO) | CyPrCy | CF₃ | H | =C(H)— | =C(H)— | 0 |
| EtO(CO) | Pr | CF₃ | H | =C(H)— | =C(H)— | 0 |
| H₂N(CO) | CyPr | CF₃ | H | =C(H)— | =C(H)— | 0 |
| MeHN(CO) | CyPr | CF₃ | H | =C(H)— | =C(H)— | 0 |
| EtHN(CO) | CyPr | CF₃ | H | =C(H)— | =C(H)— | 0 |
| Me₂N(CO) | CyPr | CF₃ | H | =C(H)— | =C(H)— | 0 |
| Et₂N(CO) | CyPr | CF₃ | H | =C(H)— | =C(H)— | 0 |
| (MeO)MeN(CO) | CyPrCy | CF₃ | H | =C(H)— | =C(H)— | 0 |
| MeOCH₂ | Pr | CF₃ | H | =C(H)— | =C(H)— | 0 |

TABLE 44

| R³ | R⁵ | R⁶ | R⁷ | A¹ | A² | n |
|---|---|---|---|---|---|---|
| HO | Me | CF₃ | H | =C(H)— | =N— | 0 |
| iPrCH₂O | Me | CF₃ | H | =C(H)— | =N— | 0 |
| tBuCH₂O | Me | CF₃ | H | =C(H)— | =N— | 0 |
| HS | Me | CF₃ | H | =C(H)— | =N— | 0 |
| tBuS | Me | CF₃ | H | =C(H)— | =N— | 0 |
| tBuSO | Me | CF₃ | H | =C(H)— | =N— | 0 |
| tBuSO₂ | Me | CF₃ | H | =C(H)— | =N— | 0 |
| CF₃S | Me | CF₃ | H | =C(H)— | =N— | 0 |
| CF₃SO | Me | CF₃ | H | =C(H)— | =N— | 0 |
| CF₃SO₂ | Me | CF₃ | H | =C(H)— | =N— | 0 |
| CHF₂CH₂S | Me | CF₃ | H | =C(H)— | =N— | 0 |
| CHF₂CH₂SO | Me | CF₃ | H | =C(H)— | =N— | 0 |
| CHF₂CH₂SO₂ | Me | CF₃ | H | =C(H)— | =N— | 0 |
| NC | Me | CF₃ | H | =C(H)— | =N— | 0 |
| HO(CO) | Me | CF₃ | H | =C(H)— | =N— | 0 |
| MeO(CO) | Me | CF₃ | H | =C(H)— | =N— | 0 |
| EtO(CO) | Me | CF₃ | H | =C(H)— | =N— | 0 |
| H₂N(CO) | Me | CF₃ | H | =C(H)— | =N— | 0 |
| MeHN(CO) | Me | CF₃ | H | =C(H)— | =N— | 0 |
| EtHN(CO) | Me | CF₃ | H | =C(H)— | =N— | 0 |
| Me₂N(CO) | Me | CF₃ | H | =C(H)— | =N— | 0 |
| Et₂N(CO) | Me | CF₃ | H | =C(H)— | =N— | 0 |
| (MeO)MeN(CO) | Me | CF₃ | H | =C(H)— | =N— | 0 |
| MeOCH₂ | Me | CF₃ | H | =C(H)— | =N— | 0 |

TABLE 45

| R³ | R⁵ | R⁶ | R⁷ | A¹ | A² | n |
|---|---|---|---|---|---|---|
| HO | Me | C₂F₅ | H | =C(H)— | =N— | 0 |
| iPrCH₂O | Me | C₂F₅ | H | =C(H)— | =N— | 0 |
| tBuCH₂O | Me | C₂F₅ | H | =C(H)— | =N— | 0 |
| HS | Me | C₂F₅ | H | =C(H)— | =N— | 0 |
| tBuS | Me | C₂F₅ | H | =C(H)— | =N— | 0 |
| tBuSO | Me | C₂F₅ | H | =C(H)— | =N— | 0 |
| tBuSO₂ | Me | C₂F₅ | H | =C(H)— | =N— | 0 |
| CF₃S | Me | C₂F₅ | H | =C(H)— | =N— | 0 |
| CF₃SO | Me | C₂F₅ | H | =C(H)— | =N— | 0 |
| CF₃SO₂ | Me | C₂F₅ | H | =C(H)— | =N— | 0 |
| CHF₂CH₂S | Me | C₂F₅ | H | =C(H)— | =N— | 0 |
| CHF₂CH₂SO | Me | C₂F₅ | H | =C(H)— | =N— | 0 |
| CHF₂CH₂SO₂ | Me | C₂F₅ | H | =C(H)— | =N— | 0 |
| NC | Me | C₂F₅ | H | =C(H)— | =N— | 0 |
| HO(CO) | Me | C₂F₅ | H | =C(H)— | =N— | 0 |
| MeO(CO) | Me | C₂F₅ | H | =C(H)— | =N— | 0 |
| EtO(CO) | Me | C₂F₅ | H | =C(H)— | =N— | 0 |
| H₂N(CO) | Me | C₂F₅ | H | =C(H)— | =N— | 0 |
| MeHN(CO) | Me | C₂F₅ | H | =C(H)— | =N— | 0 |
| EtHN(CO) | Me | C₂F₅ | H | =C(H)— | =N— | 0 |
| Me₂N(CO) | Me | C₂F₅ | H | =C(H)— | =N— | 0 |
| Et₂N(CO) | Me | C₂F₅ | H | =C(H)— | =N— | 0 |
| (MeO)MeN(CO) | Me | C₂F₅ | H | =C(H)— | =N— | 0 |
| MeOCH₂ | Me | C₂F₅ | H | =C(H)— | =N— | 0 |

TABLE 46

| R³ | R⁵ | R⁶ | R⁷ | A¹ | A² | n |
|---|---|---|---|---|---|---|
| HO | Me | H | CF₃ | =C(H)— | =N— | 0 |
| iPrCH₂O | Me | H | CF₃ | =C(H)— | =N— | 0 |
| tBuCH₂O | Me | H | CF₃ | =C(H)— | =N— | 0 |
| HS | Me | H | CF₃ | =C(H)— | =N— | 0 |
| tBuS | Me | H | CF₃ | =C(H)— | =N— | 0 |
| tBuSO | Me | H | CF₃ | =C(H)— | =N— | 0 |
| tBuSO₂ | Me | H | CF₃ | =C(H)— | =N— | 0 |
| CF₃S | Me | H | CF₃ | =C(H)— | =N— | 0 |
| CF₃SO | Me | H | CF₃ | =C(H)— | =N— | 0 |
| CF₃SO₂ | Me | H | CF₃ | =C(H)— | =N— | 0 |
| CHF₂CH₂S | Me | H | CF₃ | =C(H)— | =N— | 0 |
| CHF₂CH₂SO | Me | H | CF₃ | =C(H)— | =N— | 0 |
| CHF₂CH₂SO₂ | Me | H | CF₃ | =C(H)— | =N— | 0 |
| NC | Me | H | CF₃ | =C(H)— | =N— | 0 |
| HO(CO) | Me | H | CF₃ | =C(H)— | =N— | 0 |
| MeO(CO) | Me | H | CF₃ | =C(H)— | =N— | 0 |
| EtO(CO) | Me | H | CF₃ | =C(H)— | =N— | 0 |
| H₂N(CO) | Me | H | CF₃ | =C(H)— | =N— | 0 |
| MeHN(CO) | Me | H | CF₃ | =C(H)— | =N— | 0 |
| EtHN(CO) | Me | H | CF₃ | =C(H)— | =N— | 0 |
| Me₂N(CO) | Me | H | CF₃ | =C(H)— | =N— | 0 |
| Et₂N(CO) | Me | H | CF₃ | =C(H)— | =N— | 0 |
| (MeO)MeN(CO) | Me | H | CF₃ | =C(H)— | =N— | 0 |
| MeOCH₂ | Me | H | CF₃ | =C(H)— | =N— | 0 |

TABLE 47

| R³ | R⁵ | R⁶ | R⁷ | A¹ | A² | n |
|---|---|---|---|---|---|---|
| HO | Et | CF₃ | H | =C(H)— | =N— | 0 |
| iPrCH₂O | Et | CF₃ | H | =C(H)— | =N— | 0 |
| tBuCH₂O | Et | CF₃ | H | =C(H)— | =N— | 0 |
| HS | Et | CF₃ | H | =C(H)— | =N— | 0 |
| tBuS | Et | CF₃ | H | =C(H)— | =N— | 0 |

TABLE 47-continued

| $R^3$ | $R^5$ | $R^6$ | $R^7$ | $A^1$ | $A^2$ | n |
|---|---|---|---|---|---|---|
| tBuSO | Et | $CF_3$ | H | =C(H)— | =N— | 0 |
| tBuSO$_2$ | Et | $CF_3$ | H | =C(H)— | =N— | 0 |
| $CF_3S$ | Et | $CF_3$ | H | =C(H)— | =N— | 0 |
| $CF_3SO$ | Et | $CF_3$ | H | =C(H)— | =N— | 0 |
| $CF_3SO_2$ | Et | $CF_3$ | H | =C(H)— | =N— | 0 |
| $CHF_2CH_2S$ | Et | $CF_3$ | H | =C(H)— | =N— | 0 |
| $CHF_2CH_2SO$ | Et | $CF_3$ | H | =C(H)— | =N— | 0 |
| $CHF_2CH_2SO_2$ | Et | $CF_3$ | H | =C(H)— | =N— | 0 |
| NC | Et | $CF_3$ | H | =C(H)— | =N— | 0 |
| HO(CO) | Et | $CF_3$ | H | =C(H)— | =N— | 0 |
| MeO(CO) | Et | $CF_3$ | H | =C(H)— | =N— | 0 |
| EtO(CO) | Et | $CF_3$ | H | =C(H)— | =N— | 0 |
| $H_2N(CO)$ | Et | $CF_3$ | H | =C(H)— | =N— | 0 |
| MeHN(CO) | Et | $CF_3$ | H | =C(H)— | =N— | 0 |
| EtHN(CO) | Et | $CF_3$ | H | =C(H)— | =N— | 0 |
| $Me_2N(CO)$ | Et | $CF_3$ | H | =C(H)— | =N— | 0 |
| $Et_2N(CO)$ | Et | $CF_3$ | H | =C(H)— | =N— | 0 |
| (MeO)MeN(CO) | Et | $CF_3$ | H | =C(H)— | =N— | 0 |
| $MeOCH_2$ | Et | $CF_3$ | H | =C(H)— | =N— | 0 |

TABLE 48

| $R^3$ | $R^5$ | $R^6$ | $R^7$ | $A^1$ | $A^2$ | n |
|---|---|---|---|---|---|---|
| HO | CyPr | $CF_3$ | H | =C(H)— | =N— | 0 |
| $iPrCH_2O$ | CyPr | $CF_3$ | H | =C(H)— | =N— | 0 |
| $tBuCH_2O$ | CyPr | $CF_3$ | H | =C(H)— | =N— | 0 |
| HS | CyPr | $CF_3$ | H | =C(H)— | =N— | 0 |
| tBuS | CyPr | $CF_3$ | H | =C(H)— | =N— | 0 |
| tBuSO | CyPr | $CF_3$ | H | =C(H)— | =N— | 0 |
| tBuSO$_2$ | CyPr | $CF_3$ | H | =C(H)— | =N— | 0 |
| $CF_3S$ | CyPr | $CF_3$ | H | =C(H)— | =N— | 0 |
| $CF_3SO$ | CyPr | $CF_3$ | H | =C(H)— | =N— | 0 |
| $CF_3SO_2$ | CyPr | $CF_3$ | H | =C(H)— | =N— | 0 |
| $CHF_2CH_2S$ | CyPr | $CF_3$ | H | =C(H)— | =N— | 0 |
| $CHF_2CH_2SO$ | CyPr | $CF_3$ | H | =C(H)— | =N— | 0 |
| $CHF_2CH_2SO_2$ | CyPr | $CF_3$ | H | =C(H)— | =N— | 0 |
| NC | CyPr | $CF_3$ | H | =C(H)— | =N— | 0 |
| HO(CO) | CyPr | $CF_3$ | H | =C(H)— | =N— | 0 |
| MeO(CO) | CyPr | $CF_3$ | H | =C(H)— | =N— | 0 |
| EtO(CO) | CyPr | $CF_3$ | H | =C(H)— | =N— | 0 |
| $H_2N(CO)$ | CyPr | $CF_3$ | H | =C(H)— | =N— | 0 |
| MeHN(CO) | CyPr | $CF_3$ | H | =C(H)— | =N— | 0 |
| EtHN(CO) | CyPr | $CF_3$ | H | =C(H)— | =N— | 0 |
| $Me_2N(CO)$ | CyPr | $CF_3$ | H | =C(H)— | =N— | 0 |
| $Et_2N(CO)$ | CyPr | $CF_3$ | H | =C(H)— | =N— | 0 |
| (MeO)MeN(CO) | CyPr | $CF_3$ | H | =C(H)— | =N— | 0 |
| $MeOCH_2$ | CyPr | $CF_3$ | H | =C(H)— | =N— | 0 |

In the above-described Tables 1 to 48, Me represents a methyl group, Et represents an ethyl group, Pr represents a propyl group, iPr represents an isopropyl group, tBu represents a tert-butyl group, Ph represents a phenyl group, 2-Py represents a 2-pyridyl group, 3-Py represents a 3-pyridyl group, 4-Py represents a 4-pyridyl group, 1-Tz represents a 1,2,4-triazol-1-yl group, 1-Pz represents a pyrazol-1-yl group, and CyPr represents a cyclopropyl group.

The composition of the present invention contains the present active compound and an inert carrier. Generally, the composition of the present invention is a formulation obtained by mixing the present active compound and an inert carrier such as a solid carrier, a liquid carrier and a gaseous carrier, and further adding a surfactant and other adjuvant for formulation, if necessary. The formulation includes, for example, an emulsion, an oil solution, a powder, a granule, a wettable powder, a flowable formulation, a microcapsule, an aerosol, a smoking agent, a poison bait, and a resin formulation. In the composition of the present invention, the present active compound is usually contained in an amount of 0.01% to 95% by weight.

The solid carrier used for formulation includes, for example, a fine power and a granule of clays (e.g., kaolin clay, diatomite, bentonite, Fubasami clay, and acid clay), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, urea, and ammonium chloride).

The liquid carrier includes, for example, water, alcohols (e.g., methanol, ethanol, isopropyl alcohol, butanol, hexanol, benzyl alcohol, ethylene glycol, propylene glycol, phenoxyethanol), ketones (e.g., acetone, methyl ethyl ketone, cyclohexanone), aromatic hydrocarbons (e.g., toluene, xylene, ethylbenzene, dodecylbenzene, phenylxylylethane, methylnaphthalene), aliphatic hydrocarbons (e.g., hexane, cyclohexane, kerosine, light oil), esters (e.g., ethyl acetate, butyl acetate, isopropyl mylistate, ethyl oleate, diisopropyl adipate, diisobutyl adipate, propyleneglycol monomethyl ether acetate), nitriles (e.g., acetonitrile, isobutyronitrile), ethers (e.g., diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol), acid amides (e.g., N,N-dimethylformamide, N,N-dimethylacetamide), halogenated hydrocarbons (e.g., dichloromethane, trichloroethane, tetrachlorocarbon), sulfoxides (e.g., dimethylsulfoxide), propylene carbonate, and vegetable oils (e.g., soy bean oil, cotton seed oil).

The gaseous carrier includes, for example, fluorocarbons, butane gas, liquefied petroleum gas (LPG), dimethylether, and carbon dioxide.

The surfactant includes, for example, nonionic surfactant, such as polyoxyethylene alkyl ether, polyoxyethylene alkylaryl ether, polyethyleneglycol fatty acid ester; and anionic surfactant, such as alkylsulfonic acid salts, alkylbenzenesulfonic acid salts, and alkylsurfic acid salts.

The other adjuvant for formulation includes, for example, binders, dispersants, colorants and stabilizers, and specifically for example, casein, gelatin, polysaccharides (e.g., starch, gum arabic, cellulose derivatives, alginic acid), lignin derivatives, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol).

The method for controlling noxious arthropod of the present invention is applying an effective amount of the present active compound to a noxious arthropod directly and/or habitats of a noxious arthropod (e.g., plant, soil, indoor, and in-body of animals). The present active compound is usually used as the composition of the present invention for the method for controlling a noxious arthropod of the present invention.

When the composition of the present invention is used for a control of a noxious arthropod in agriculture, the application amount is usually 1 to 10,000 g as the present active compound per 10,000 m$^2$. When the composition of the present invention is a formulation of emulsions, wettable powders or flowables, they are usually applied after a dilution with water to have an active ingredient concentration of 0.01 to 10,000 ppm. When the composition of the present invention is a formulation of granules or powders, they are usually applied as such.

These formulations and the dilute aqueous solution of the formulation may be sprayed directly to the plant to be protected from a noxious arthropod, and may be applied to the soil to control the a noxious arthropod living in a soil.

Furthermore, the resin formulations of sheets or strip form can be applied by a method such as winding around plants, stretching in the vicinity of plants and laying on the soil surface at the plant bottom.

When the composition of the present invention is used for a control of a noxious arthropod in indoor, the application amount is usually 0.01 to 1,000 mg as the present active compound per 1 m$^2$ in case of application for plane surface, and 0.01 to 500 mg as the present active compound per 1 m$^3$ in case of application for space. When the composition of the present invention is a formulation of emulsions, wettable powders or flowables, they are usually applied after a dilution with water to have an active ingredient concentration of 0.1 to 1,000 ppm. When the composition of the present invention is a formulation of oil solutions, aerosols, smoking agents and poison baits, they are usually applied as such.

The composition of the present invention can be a admixture with or together with other insecticides, acaricides, nematocides, fungicides, plant growth regulators, herbicides, and synergists.

Examples of active ingredients of the insecticide, the acaricide, the nematocide, the fungicide, the plant growth regulator, the herbicide, and the synergist are shown below.

Active Ingredients of the Insecticides:

(1) Organic Phosphorus Compounds:

Acephate, Aluminum phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos (DDVP), dimethoate, dimethylvinphos, disulfoton, EPN, ethion, ethoprophos, etrimfos, fenthion: MPP, fenitrothion: MEP, fosthiazate, formothion, hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, cadusafos;

(2) Carbamate Compounds:

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, aldicarb;

(3) Pyrethroid Compounds:

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl(EZ)-(1RS,3RS; 1RS,3SR)-2,2-dimethyl-3-prop-1-enylcyclopropanecarboxylate, and 2,3,5,6-tetrafluoro-4-(methoxymethyl)benzyl(1RS,3RS; 1RS,3SR)-2,2-dimethyl-3-(2-methyl-1-propenyl)cyclopropanecarboxylate;

(4) Nereistoxin Compounds:

Cartap, bensultap, thiocyclam, monosultap, bisultap;

(5) Neonicotinoid Compounds:

Imidacloprid, nitenpyram, acetamiprid, thiamethoxam, thiacloprid, dinotefuran, clothianidin;

(6) Benzoylurea Compounds:

Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron;

(7) Phenylpyrazole Compounds:

Acetoprole, ethiprole, fipronil, vaniliprole, pyriprole, pyrafluprole;

(8) Bt Toxins:

Live spores derived from and crystal toxins produced from *Bacillus thuringiesis* and a mixture thereof;

(9) Hydrazine Compounds:

Chromafenozide, halofenozide, methoxyfenozide, tebufenozide;

(10) Organic Chlorine Compounds:

Aldrin, dieldrin, dienochlor, endosulfan, methoxychlor;

(11) Other Insecticidal Active Ingredients:

Machine oil, nicotine-sulfate; avermectin-B, bromopropylate, buprofezin, chlorphenapyr, cyantraniliprole, cyromazine, D-D (1,3-Dichloropropene, emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, any compound represented by the following formula (K):

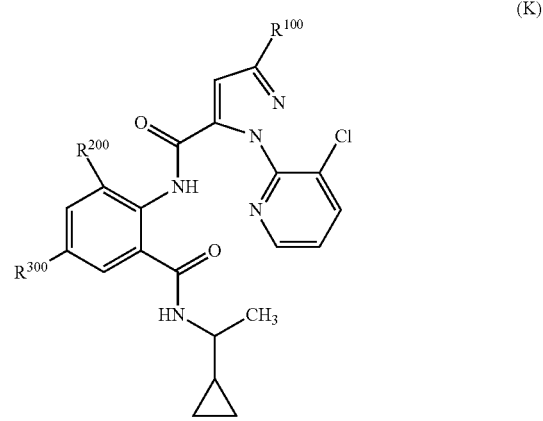

(K)

wherein

R$^{100}$ represents chlorine, bromine or a trifluoromethyl group,

R$^{200}$ represents chlorine, bromine or a methyl group,

R$^{300}$ represents chlorine, bromine or a cyano group and, any compound represented by the following formula (L):

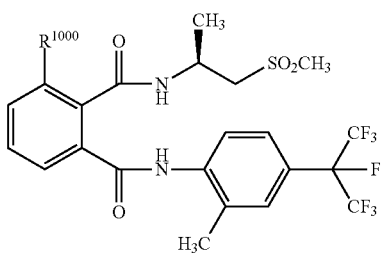

(L)

wherein
R$^{1000}$ represents chlorine, bromine or iodide.

Active Ingredients of the Acardides:

Acequinocyl, amitraz, benzoximate, bifenaate, bromopropylate, chinomethionat, chlorobenzilate, CPCBS (chlorfenson), clofentezine, cyflumetofen, dicofol, etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, cyenopyrafen.

Active Ingredients of the Nematocides:

DCIP, fosthiazate, levamisol, methylsothiocyanate, morantel tartarate, imicyafos.

Active Ingredients of the Fungicides:

Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl;

Procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb); cyazofamid; mandipropamid; boscalid; penthiopyrad; metrafenone; fluopiran; bixafen; cyflufenamid; proquinazid; isotianil, tiadinil.

Active Ingredients of the Herbicides:

(1) Phenoxyfatty Acid Herbicidal Compounds
2,4-PA, MCP, MCPB, phenothiol, mecoprop, fluoroxypyr, triclopyr, clomeprop, and naproanilide.

(2) Benzoic Acid Herbicidal Compounds
2,3,6-TBA, dicamba, clopyralid, picloram, aminopyralid, quinclorac, and quinmerac.

(3) Urea Herbicidal Compounds
diuron, linuron, chlortoluron, isoproturon, fluometuron, isouron, tebuthiuron, methabenzthiazuron, cumyluron, daimuron, and methyl-daimuron.

(4) Triazine Herbicidal Compounds
atrazine, ametoryn, cyanazine, simazine, propazine, simetryn, dimethametryn, prometryn, metribuzin, indaziflam, and triaziflam.

(5) Bipyridinium Herbicidal Compounds
paraquat, and diquat.

(6) Hydroxybenzonitrile Herbicidal Compounds
bromoxynil and ioxynil.

(7) Dinitroaniline Herbicidal Compounds
pendimethalin, prodiamine, and trifluralin.

(8) Organic Phosphorus Herbicidal Compounds
amiprofos-methyl, butamifos, bensulide, piperophos, anilofos, glyphosate, glufosinate, and bialaphos.

(9) Carbamate Herbicidal Compounds
di-allate, tri-allate, EPIC, butylate, benthiocarb, esprocarb, molinate, dimepiperate, swep, chlorpropham, phenmedipham, phenisopham, pyributicarb, and asulam;

(10) Acid Amide Herbicidal Compounds
propanil, propyzamide, bromobutide, and etobenzanid.

(11) Chloroacetanilide Herbicidal Compounds
acetochlor, alachlor, butachlor, dimethenamid, propachlor, metazachlor, metolachlor, pretilachlor, thenylchlor, and pethoxamid.

(12) Diphenylether Herbicidal Compounds
acifluorfen-sodium, bifenox, oxyfluorfen, lactofen, fomesafen, chlomethoxynil, and aclonifen.

(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, and saflufenacil.

(14) Pyrazole Herbicidal Compounds
benzofenap, pyrazolate, pyrazoxyfen, topramezone, and pyrasulfotole.

(15) Triketone Herbicidal Compounds
isoxaflutole, benzobicyclon, sulcotrione, mesotrione, tembotrione, and tefuryltrione.

(16) Aryloxyphenoxypropionic Acid Herbicidal Compounds
clodinafop-propargyl, cyhalofop-butyl, diclofop-methyl, fenoxaprop-ethyl, fluazifop-butyl, haloxyfop-methyl, and quizalofop-ethyl and metamifol.

(17) Trioneoxime Herbicidal Compounds
alloxydim-sodium, sethoxydim, butroxydim, clethodim, cloproxydim, cycloxydim, tepraloxydim, tralkoxydim, and profoxydim.

(18) Sulfonylurea Herbicidal Compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds
imazamethabenz-methyl, imazamethapyr, imazamox, imazapyr, imazaquin, and imazethapyr.

(20) Sulfonamide Herbicidal Compounds
flumetsulam, metosulam, diclosulam, florasulam, cloransulam-methyl, penoxsulam, and pyroxsulam.

(21) Pyrimidinyloxybenzoic Acid Herbicidal Compounds
pyrithiobac-sodium, bispyribac-sodium, pyriminobac-methyl, pyribenzoxim, pyriftalid, and pyrimisulfan.

(22) Other Herbicidal Compounds
Bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of the Synergists:

Piperonyl butoxide, sesamex, sulfoxide, N-(2-ethylhexyl)-8,9,10-trinorborn-5-ene-2,3-dicarboxyimide (MGK 264), N-declyimidazole, WARF-antiresistant, TBPT, TPP, IBP, PSCP, methyl iodide (CH3I), t-phenylbutenone, diethylmaleate, DMC, FDMC, ETP, and ETN.

Noxious arthropod against which the present active compound has an activity include, for example, noxious insects and noxious acarines. Specific examples of these noxious arthropods include the following.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae).

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai.*), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tuberworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*).

Thysanoptera:

*Thrips* (Thripidae) such as yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*).

Diptera:

Culices such as common mosquito (*Culex pipiens pallens*), *Culex tritaeniorhynchus*, and *Culex quinquefasciatus*; *Aedes* spp. such as yellow fever mosquito (*Aedes aegypti*), and Asian tiger mosquito (*Aedes albopictus*); *Anopheles* spp. such as *Anopheles sinensis*; chironomids (Chironomidae); house flies (Muscidae) such as *Musca domestica*, and *Muscina stabulans*; blow flies (Calliphoridae); flesh flies (Sarcophagidae); little house flies (Fanniidae); anthomyiid flies (Anthomyiidae) such as seedcorn fly (*Delia platura*), and onion fly (*Delia antiqua*); leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Mediterranean fruit fly (*Ceratitis capitata*); Drosophilidae; humpbacked flies (Phoridae) such as *Megaselia spiracularis*; moth flies (Psychodidae) such as *Clogmia albipunctata*; Simuliidae; Tabanidae such as horsefly (*Tabanus trigonus*); stable flies.

Coleoptera:

Corn root worms (*Diabrotica* spp.) such as Western corn root worm (*Diabrotica virgifera virgifera*), and Sourthern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado potato beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as Twenty-eight-spotted ladybird (*Epilachna vigintioctopunctata*); bark beetles (Scolytidae) such as powder-post beetle (*Lyctus brunneus*), and pine shoot beetle (*Tomicus piniperda*); false powder-post beetles (Bostrychidae); spider beetles (Ptinidae); longhorn beetles (Cerambycidae) such as white-spotted longicorn beetle (*Anoplophora malasiaca*); click beetles (*Agriotes* spp.); *Paederus fuscipens*.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae.

Hymenoptera:

Ants (Formicidae) such as pharaoh ant (*Monomorium pharaosis*), negro ant (*Formica fusca japonica*), black house ant (*Ochetellus glaber*), *Pristomyrmex pungens, Pheidole noda*, leaf-cutting ant (*Acromyrmex* spp.), and fire ant (*Solenopsis* spp.); hornets (Vespidae); bethylid wasps (Betylidae); sawflies (Tenthredinidae) such as cabbage sawfly (*Athalia rosae*), and *Athalia japonica*.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*);

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis, Haemaphysalis flava, Dermacentor taiwanicus, Ixodes ovatus, Ixodes persulcatus*, black legged tick (*Ixodes scapularis*), *Boophilus microplus*, and *Rhipicephalus sanguineus*; acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssmus*; cheyletide mites (Cheyletidae) such as *Cheyletus eruditus, Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*).

In the controlling method of the present invention, hemiptera noxious insects are mentioned as a noxious arthropod showing a high effect of the compound of the present invention.

The composition of the present invention could be used in farmlands on which "crops" shown below are cultivated.

"Crops"

Agricultural crops: corn, rice, wheat, barley, rye, oat, sorghum, cotton, soybean, peanut, sarrazin, sugar beet, rapeseed, sunflower, sugar cane, tobacco;

Vegetables: Solanaceae vegetables (eggplant, tomato, green pepper, hot pepper, and potato), Cucurbitaceae vegetables (cucumber, pumpkin, zucchini, watermelon, and melon), Cruciferae vegetables (Japanese radish, turnip, horseradish, kohlrabi, Chinese cabbage, cabbage, brown mustard, broccoli, and cauliflower), Compositae vegetables (burdock, garland chrysanthemum, artichoke, and lettuce), Liliaceae vegetables (Welsh onion, onion, garlic, and asparagus), Umbelliferae vegetables (carrot, parsley, celery, and parsnip), Chenopodiaceae vegetables (spinach, and Swiss chard), Labiatae vegetables (Japanese basil, mint, and basil), strawberry, sweat potato, yam, aroid;

Fruit trees: pomaceous fruits (apple, common pear, Japanese pear, Chinese quince, and quince), stone fleshy fruits (peach, plum, nectarine, Japanese plum, cherry, apricot, and prune), citrus plants (Satsuma mandarin, orange, lemon, lime, and grapefruit), nuts (chestnut, walnut, hazel nut, almond, pistachio, cashew nut, and *macadamia* nut), berry fruits (blueberry, cranberry, blackberry, and raspberry), grape, persimmon, olive, loquat, banana, coffee, date, coconut palm, and oil palm;

Trees other fruit trees: tea, mulberry, flowering trees (azalea, japonica, hydrangea, sasanqua, Illicium anisatum, cherry tree, tulip poplar, crepe myetle, and orange osmanthus), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, and horse-chestnut), sweet viburnum, *Podocarpus macrophyllus*, Japanese cedar, Japanese cypress, croton, spindle tree, Chainese howthorn.

Lawn: zoysia (Japanese lawn grass, mascarene grass), Bermuda grass (*Cynodon dactylon*), bent grass (creeping bent grass, *Agrostis stolonifera, Agrostis tenuis*), bluegrass (Kentucky bluegrass, rough bluegrass), fescue (tall fescue, chewing fescue, creeping fescue), ryegrass (darnel, perennial ryegrass), cocksfoot, timothy grass;

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, verbena, cymbidium, begonia), biofuel plants (*Jatropha, curcas*, safflower, *Camelina alyssum*, switchgrass, miscanthus, reed canary grass, *Arundo donax*, kenaf, cassaya, willow, algae), foliage plant.

The "crops" include genetically modified crops.

EXAMPLES

The present invention will be described further in detail below by production examples, preparation examples and test examples, but the present invention is not limited to these examples.

Production Example 1

A mixture of 0.59 g of 1,1,3,3-tetrafluoro-N-methyl-1,3-dihydroisobenzofuran-5,6-diamine, 0.63 g of sodium hydroxy-pyridin-4-yl-methanesulfonate and 5 ml of DMF was stirred for 1 hour while heating at 120° C. After cooling down to room temperature, a saturated sodium hydrogen carbonate aqueous solution was poured, and the mixture was extracted three times with ethyl acetate. The combined organic layers were dried over magnesium sulfate, then, concentrated under reduced pressure. The residue was subjected to silica gel column chromatography to obtain 0.71 g of 5,5,7,7-tetrafluoro-1-methyl-2-(pyridin-4-yl)-5,7-dihydro-1H-furo[3',4':4,5]benzo[1,2-d]imidazole (hereinafter, referred to as present active compound 1).

Present active compound 1

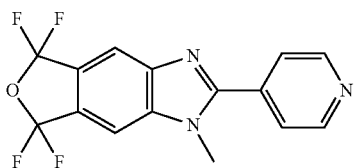

¹H-NMR (CDCl₃) δ: δ8.90-8.87 (m, 2H), 8.08 (s, 1H), 7.74-7.70 (m, 3H), 4.03 (s, 3H)

Production Example 2

1-methyl-2-(pyridin-4-yl)-6-trifluoromethyl-1H-benzimidazole (hereinafter, referred to as present active compound 2) was obtained according to the method described in Production Example 1, using N2-methyl-4-trifluoromethylbenzene-1,2-diamine instead of 1,1,3,3-tetrafluoro-N-methyl-1,3-dihydroisobenzofuran-5,6-diamine.

Present active compound 2

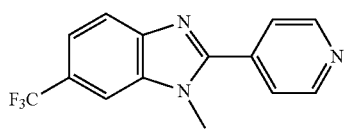

¹H-NMR (CDCl₃) δ: 8.85 (dd, J=4.4, 1.5 Hz, 2H), 7.93 (d, J=8.5 Hz, 1H), 7.75-7.71 (m, 3H), 7.61 (dd, J=8.7, 1.3 Hz, 1H), 3.99 (s, 3H)

Production Example 3

1-methyl-2-(pyridin-4-yl)-5-trifluoromethyl-1H-benzimidazole (hereinafter, referred to as present active compound 3) was obtained according to the method described in Production Example 1, using N1-methyl-4-trifluoromethylbenzene-1,2-diamine instead of 1,1,3,3-tetrafluoro-N-methyl-1,3-dihydroisobenzofuran-5,6-diamine.

Present active compound 3

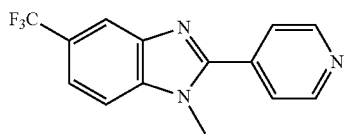

¹H-NMR (CDCl₃) δ: 8.86-8.84 (m, 2H), 8.14-8.13 (m, 1H), 7.74-7.71 (m, 2H), 7.66-7.62 (m, 1H), 7.53 (d, J=8.0 Hz, 1H), 3.98 (s, 3H)

Production Example 4

A mixture of 1.90 g of N1-methyl-4-trifluoromethylbenzene-1,2-diamine, 1.49 g of 3-fluoropyridine-4-carbaldehyde, 3.12 g of sodium bisulfite and 20 ml of DMF was stirred for 1.5 hours while heating at 80° C., then, was stirred for 2 hours while heating at 120° C. After cooling down to room temperature, a saturated ammonium chloride aqueous solution was poured, and the mixture was extracted three times with ethyl acetate. The combined organic layers were dried over magnesium sulfate, then, concentrated under reduced pressure. The residue was subjected to silica gel column chromatography to obtain 1.83 g of 2-(3-fluoropyridin-4-yl)-1-methyl-5-trifluoromethyl-1H-benzimidazole (hereinafter, referred to as present active compound 4).

Present active compound 4

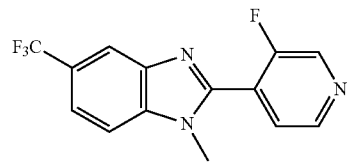

¹H-NMR (CDCl₃) δ: 8.73-8.71 (m, 1H), 8.68-8.65 (m, 1H), 8.15 (d, J=0.7 Hz, 1H), 7.72 (t, J=5.4 Hz, 1H), 7.65 (dd, J=8.7, 0.7 Hz, 1H), 7.56 (d, J=8.7 Hz, 1H), 3.85 (d, J=2.9 Hz, 3H)

Production Example 5

2-(3-chloropyridin-4-yl)-1-methyl-5-trifluoromethyl-1H-benzimidazole (hereinafter, referred to as present active compound 5) was obtained according to the method described in Production Example 4, using 3-chloropyridine-4-carbaldehyde instead of 3-fluoropyridine-4-carbaldehyde.

Present active compound 5

¹H-NMR (CDCl₃) δ: 8.83 (s, 1H), 8.72 (dd, J=4.8, 0.5 Hz, 1H), 8.15-8.13 (m, 1H), 7.66 (dd, J=8.6, 1.6 Hz, 1H), 7.57-7.53 (m, 2H), 3.77 (s, 3H)

Production Example 6

A mixture of 0.38 g of N1-methyl-4-trifluoromethylbenzene-1,2-diamine, 0.33 g of 3-methylisonicotinic acid, 0.46 g of WSC and 10 ml of pyridine was stirred for 5 hours while heating at 120° C. After cooling down to room temperature, water was poured, and the mixture was extracted three times with ethyl acetate. The combined organic layers were dried over magnesium sulfate, then, concentrated under reduced pressure. To the residue were added a mixture of 0.57 g of p-toluenesulfonic acid monohydrate and 10 ml of toluene, and the mixture was stirred for 1 hour while heating at 80° C., and stirred for 2 hours while heating at 120° C. After cooling down to room temperature, a saturated sodium hydrogen carbonate aqueous solution was poured, and the mixture was extracted three times with ethyl acetate. The combined organic layers were dried over magnesium sulfate, then, concentrated under reduced pressure. The residue was subjected to silica gel column chromatography to obtain 0.48 g of 1-methyl-2-(3-methylpyridin-4-yl)-5-trifluoromethyl-1H-benzimidazole (hereinafter, referred to as present active compound 6).

Present active compound 6

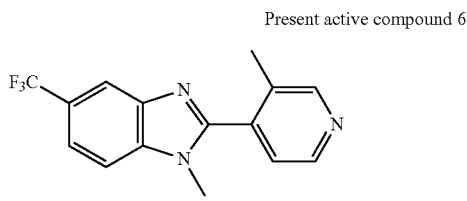

¹H-NMR(CDCl₃) δ: 8.70 (d, J=0.7 Hz, 1H), 8.64 (d, J=5.1 Hz, 1H), 8.13-8.12 (m, 1H), 7.66-7.62 (m, 1H), 7.54-7.51 (m, 1H), 7.33 (d, J=4.6 Hz, 1H), 3.72 (s, 3H), 2.33 (s, 3H)

Production Example 7

2-(3-ethylpyridin-4-yl)-1-methyl-5-trifluoromethyl-1H-benzimidazole (hereinafter, referred to as present active compound 7) (0.47 g) was obtained according to the method described in Production Example 6, using 3-ethylisonicotinic acid instead of 3-methylisonicotinic acid.

Present active compound 7

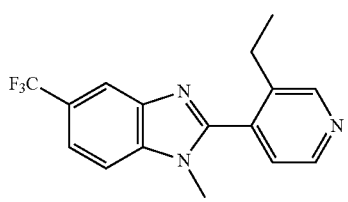

¹H-NMR (CDCl₃) δ: 8.73 (s, 1H), 8.64 (d, J=4.8 Hz, 1H), 8.13-8.12 (m, 1H), 7.66-7.62 (m, 1H), 7.52 (d, J=8.5 Hz, 1H), 7.29 (d, J=5.1 Hz, 1H), 3.70 (s, 3H), 2.69 (q, J=7.6 Hz, 2H), 1.13 (t, J=7.6 Hz, 3H)

Production Example 8

To a mixture of 0.30 g of 2-(3-fluoropyridin-4-yl)-1-methyl-5-trifluoromethyl-1H-benzimidazole and 10 ml of DMF was added 0.16 g of sodium methoxide under ice cool, then, the mixture was heated up to room temperature and stirred for 1.5 hours. A saturated ammonium chloride aqueous solution was poured, and the mixture was extracted three times with ethyl acetate. The combined organic layers were dried over magnesium sulfate, then, concentrated under reduced pressure. The residue was subjected to silica gel column chromatography to obtain 0.28 g of 2-(3-methoxypyridin-4-yl)-1-methyl-5-trifluoromethyl-1H-benzimidazole (hereinafter, referred to as present active compound 8).

Present active compound 8

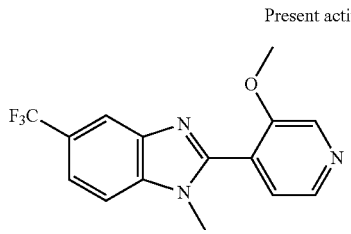

¹H-NMR (CDCl₃) δ: 8.53 (s, 1.0H), 8.48 (d, J=4.8 Hz, 1.0H), 8.11 (s, 1.0H), 7.61 (d, J=8.7 Hz, 1.0H), 7.53 (d, J=4.6 Hz, 1.0H), 7.51 (d, J=8.9 Hz, 1.0H), 3.98 (s, 3.0H), 3.73 (s, 3.0H)

Production Example 9

2-(3-ethoxypyridin-4-yl)-1-methyl-5-trifluoromethyl-1H-benzimidazole (hereinafter, referred to as present active compound 9) was obtained according to the method described in Production Example 8, using sodium ethoxide instead of sodium methoxide.

Present active compound 9

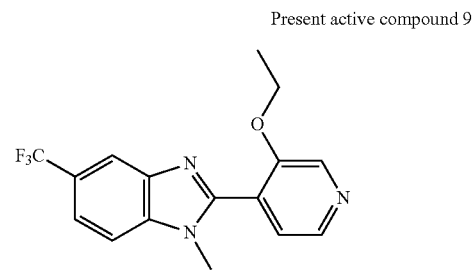

¹H-NMR (CDCl₃) δ: 8.50 (s, 1H), 8.45 (d, J=4.6 Hz, 1H), 8.12-8.11 (m, 1H), 7.62 (dd, J=8.5, 1.5 Hz, 1H), 7.54 (d, J=4.6 Hz, 1H), 7.52 (d, J=8.5 Hz, 1H), 4.24 (q, J=7.0 Hz, 2H), 3.75 (s, 3H), 1.37 (t, J=7.0 Hz, 3H)

Production Example 10

To a mixture of 0.36 g of 1-propanol and 6 ml of DMF was added 0.24 g of 60% sodium hydride (oily) under ice cool, and the mixture was stirred for 10 minutes. 2-(3-fluoropyridin-4-yl)-1-methyl-5-trifluoromethyl-1H-benzimidazole (0.35 g) was added, then, the mixture was heated up to room temperature and further stirred for 1 hour. A saturated ammonium chloride aqueous solution was poured, and the mixture was extracted three times with ethyl acetate. The combined organic layers were dried over magnesium sulfate, then, concentrated under reduced pressure. The residue was subjected to silica gel column chromatography to obtain 0.36 g of 1-methyl-2-(3-propoxypyridin-4-yl)-5-trifluoromethyl-1H-benzimidazole (hereinafter, referred to as present active compound 10).

Present active compound 10

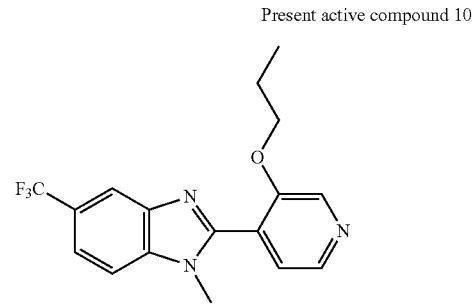

¹H-NMR (CDCl₃) δ: 8.51 (s, 1H), 8.45 (d, J=4.7, 1H), 8.11 (d, J=0.7 Hz, 1H), 7.62 (d, J=8.7 Hz, 1H), 7.54 (d, J=4.7 Hz, 1H), 7.52 (d, J=8.7 Hz, 1H), 4.11 (t, J=6.6 Hz, 2H), 3.74 (d, J=0.7 Hz, 3H), 1.80-1.69 (m, 2H), 0.91 (t, J=7.2 Hz, 3H)

Production Example 11

2-(3-isopropoxypyridin-4-yl)-1-methyl-5-trifluoromethyl-1H-benzimidazole (hereinafter, referred to as present active compound 11) was obtained according to the method described in Production Example 10, using 2-propanol instead of 1-propanol.

Present active compound 11

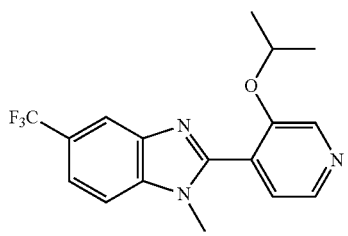

¹H-NMR (CDCl₃) δ: 8.51 (s, 1H), 8.43 (dd, J=4.8, 1.6 Hz, 1H), 8.12 (s, 1H), 7.62 (d, J=8.5 Hz, 1H), 7.55 (dd, J=4.8, 1.3 Hz, 1H), 7.52 (d, J=8.5 Hz, 1H), 4.72-4.64 (m, 1H), 3.75 (d, J=2.0 Hz, 3H), 1.29 (dd, J=6.1, 1.7 Hz, 6H)

Production Example 12

2-(3-tert-butoxypyridin-4-yl)-1-methyl-5-trifluoromethyl-1H-benzimidazole (hereinafter, referred to as present active compound 12) was obtained according to the method described in Production Example 10, using tert-butyl alcohol instead of 1-propanol.

Present active compound 12

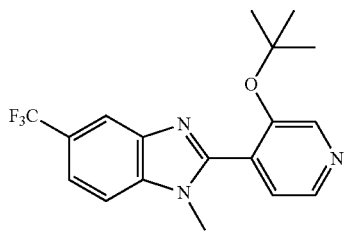

¹H-NMR (CDCl₃) δ: 8.58 (s, 1H), 8.54 (d, J=4.9 Hz, 1H), 8.13-8.10 (m, 1H), 7.64-7.59 (m, 2H), 7.53 (d, J=8.5 Hz, 1H), 3.77 (s, 3H), 1.12 (s, J=4.8, 1.6 Hz, 9H)

Production Example 13

1-methyl-2-[3-(2,2,2-trifluoroethoxy)-pyridin-4-yl]-5-trifluoromethyl-1H-benzimidazole (hereinafter, referred to as present active compound 13) was obtained according to the method described in Production Example 10, using 2,2,2-trifluoroethanol instead of 1-propanol.

Present active compound 13

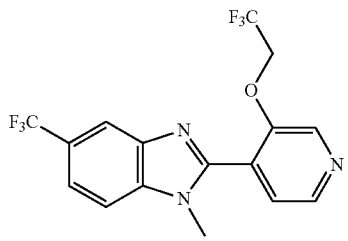

¹H-NMR (CDCl₃) δ: 8.59 (d, J=4.6 Hz, 1H), 8.55 (s, 1H), 8.12 (s, 1H), 7.66-7.60 (m, 2H), 7.54 (d, J=8.5 Hz, 1H), 4.47 (q, J=7.9 Hz, 2H), 3.76 (s, 3H)

Production Example 14

2-[3-(2,2-difluoroethoxy)-pyridin-4-yl]-1-methyl-5-trifluoromethyl-1H-benzimidazole (hereinafter, referred to as present active compound 14) was obtained according to the method described in Production Example 10, using 2,2-difluoroethanol instead of 1-propanol.

Present active compound 14

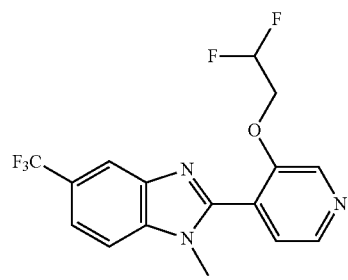

¹H-NMR (CDCl₃) δ: 8.56 (d, J=4.6 Hz, 1H), 8.52 (s, 1H), 8.13-8.11 (m, 1H), 7.66-7.62 (m, 1H), 7.60 (d, J=4.6 Hz, 1H), 7.54 (d, J=8.0 Hz, 1H), 5.97 (tt, J=54.7, 3.9 Hz, 1H), 4.37 (td, J=13.0, 3.9 Hz, 2H), 3.75 (s, 3H)

Production Example 15

2-[3-(2-fluoroethoxy)-pyridin-4-yl]-1-methyl-5-trifluoromethyl-1H-benzimidazole (hereinafter, referred to as present active compound 15) was obtained according to the method described in Production Example 10, using 2-fluoroethanol instead of 1-propanol.

Present active compound 15

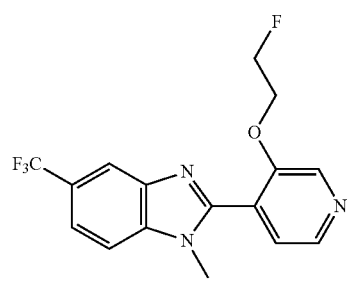

¹H-NMR (CDCl₃) δ: 8.52 (s, 1H), 8.50 (s, 1H), 8.13-8.10 (m, 1H), 7.63 (dd, J=8.5, 1.4 Hz, 1H), 7.60 (d, J=4.8 Hz, 1H), 7.53 (d, J=8.5 Hz, 1H), 4.75-4.60 (m, 2H), 4.44-4.33 (m, 2H), 3.76 (s, 3H)

Production Example 16

2-(3-benzyloxypyridin-4-yl)-1-methyl-5-trifluoromethyl-1H-benzimidazole (hereinafter, referred to as present active compound 16) was obtained according to the method described in Production Example 10, using benzyl alcohol instead of 1-propanol.

Present active compound 16

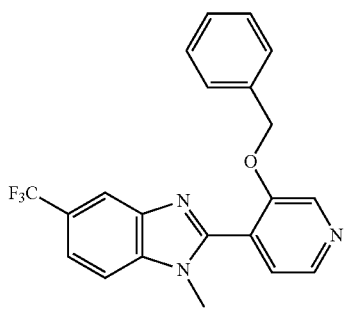

¹H-NMR (CDCl₃) δ: 8.58 (s, 1H), 8.47 (d, J=4.6 Hz, 1H), 8.12 (d, J=0.7 Hz, 1H), 7.60 (dd, J=8.5, 1.5 Hz, 1H), 7.57 (d, J=4.6 Hz, 1H), 7.46 (d, J=8.5 Hz, 1H), 7.32-7.22 (m, 5H), 5.21 (s, 2H), 3.69 (s, 3H)

Production Example 17

1-methyl-2-(3-methylthiopyridin-4-yl)-5-trifluoromethyl-1H-benzimidazole (hereinafter, referred to as present active compound 17) was obtained according to the method described in Production Example 8, using methyl mercaptan sodium salt instead of sodium methoxide.

Present active compound 17

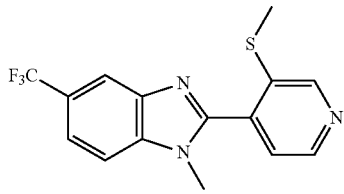

¹H-NMR (CDCl₃) δ: 8.70 (s, 1H), 8.60 (d, J=4.8 Hz, 1H), 8.15-8.13 (m, 1H), 7.64 (dd, J=8.5, 1.7 Hz, 1H), 8.53 (d, J=8.5 Hz, 1H), 8.38 (d, J=4.8 Hz, 1H), 3.74 (s, 3H), 2.47 (s, 3H)

Production Example 18

To a mixture of 0.49 g of 1-methyl-2-(3-methylthiopyridine-4-yl)-5-trifluoromethyl-1H-benzimidazole, 5 ml of methanol and 10 ml of water was added 0.65 g of sodium periodate under ice cool, then, the mixture was stirred for 1 hour at 40° C. After cooling down to room temperature, a saturated sodium hydrogen carbonate aqueous solution and a saturated sodium thiosulfate aqueous solution were poured, and the mixture was extracted three times with chloroform. The combined organic layers were dried over magnesium sulfate, then, concentrated under reduced pressure. The residue was subjected to silica gel column chromatography to obtain 0.48 g of 2-(3-methanesulfinylpyridin-4-yl)-1-methyl-5-trifluoromethyl-1H-benzimidazole (hereinafter, referred to as present active compound 18).

Present active compound 18

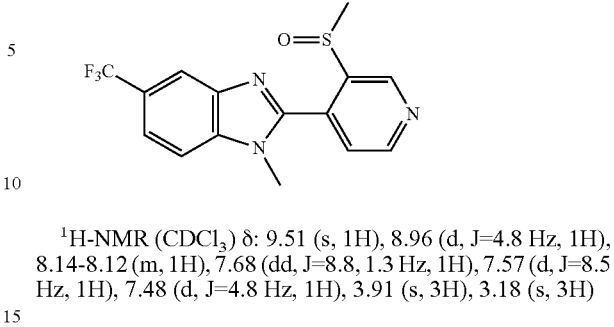

¹H-NMR (CDCl₃) δ: 9.51 (s, 1H), 8.96 (d, J=4.8 Hz, 1H), 8.14-8.12 (m, 1H), 7.68 (dd, J=8.8, 1.3 Hz, 1H), 7.57 (d, J=8.5 Hz, 1H), 7.48 (d, J=4.8 Hz, 1H), 3.91 (s, 3H), 3.18 (s, 3H)

Production Example 19

To a mixture of 0.60 g of 1-methyl-2-(3-methylthiopyridin-4-yl)-5-trifluoromethyl-1H-benzimidazole and 9 ml of chloroform was added 1.40 g of 69% m-chloroperbenzoic acid under ice cool, then, the mixture was stirred for 2 hours at room temperature. Thereafter, a saturated sodium hydrogen carbonate aqueous solution and a saturated sodium thiosulfate aqueous solution were poured, and the mixture was extracted three times with chloroform. The combined organic layers were dried over magnesium sulfate, then, concentrated under reduced pressure. The residue was subjected to silica gel column chromatography to obtain 0.52 g of 2-(3-methanesulfonylpyridin-4-yl)-1-methyl-5-trifluoromethyl-1H-benzimidazole (hereinafter, referred to as present active compound 19).

Present active compound 19

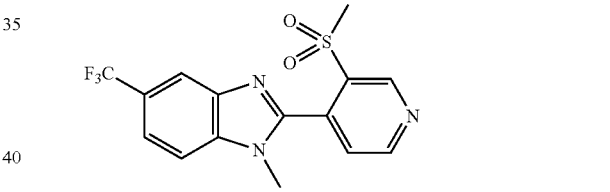

¹H-NMR (CDCl₃) δ: 9.45 (s, 1H), 9.09 (d, J=4.8 Hz, 1H), 8.08 (s, 1H), 7.66 (d, J=8.2 Hz, 1H), 7.55 (d, J=8.2 Hz, 1H), 7.51 (d, J=4.8 Hz, 1H), 3.68 (s, 3H), 3.34 (s, 3H)

Production Example 20

2-(3-ethylthiopyridin-4-yl)-1-methyl-5-trifluoromethyl-1H-benzimidazole (hereinafter, referred to as present active compound 20) was obtained according to the method described in Production Example 8, using ethyl mercaptan sodium salt instead of sodium methoxide.

Present active compound 20

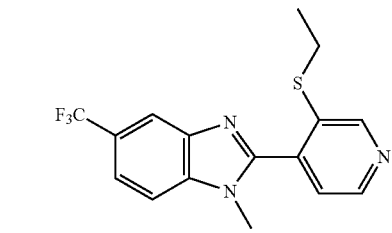

¹H-NMR (CDCl₃) δ: 8.76 (s, 1H), 8.62 (d, J=5.1 Hz, 1H), 8.14-8.12 (m, 1H), 7.65-7.62 (m, 1H), 7.53 (dd, J=8.7, 0.5 Hz, 1H), 7.41 (d, J=4.8 Hz, 1H), 3.72 (d, J=0.5 Hz, 3H), 2.87 (q, J=7.2 Hz, 2H), 1.23 (t, J=7.2 Hz, 3H)

Production Example 21

2-(3-ethanesulfinylpyridin-4-yl)-1-methyl-5-trifluoromethyl-1H-benzimidazole (hereinafter, referred to as present active compound 21) was obtained according to the method described in Production Example 18, using 2-(3-ethylthiopyridin-4-yl)-1-methyl-5-trifluoromethyl-1H-benzimidazole instead of 1-methyl-2-(3-methylthiopyridin-4-yl)-5-trifluoromethyl-1H-benzimidazole.

Present active compound 21

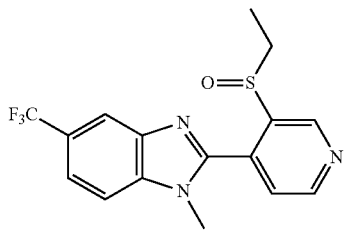

¹H-NMR (CDCl₃) δ: 9.40 (s, 1H), 8.95 (d, J=5.1 Hz, 1H), 8.12-8.10 (m, 1H), 7.68 (dd, J=8.8, 1.3 Hz, 1H), 7.57 (d, J=8.8 Hz, 1H), 7.49 (d, J=5.1 Hz, 1H), 3.89 (s, 3H), 3.56-3.46 (m, 1H), 3.21-3.10 (m, 1H), 1.39 (t, J=7.4 Hz, 3H)

Production Example 22

2-(3-ethanesulfonylpyridin-4-yl)-1-methyl-5-trifluoromethyl-1H-benzimidazole (hereinafter, referred to as present active compound 22) was obtained according to the method described in Production Example 19, using 2-(3-ethylthiopyridin-4-yl)-1-methyl-5-trifluoromethyl-1H-benzimidazole instead of 1-methyl-2-(3-methylthiopyridin-4-yl)-5-trifluoromethyl-1H-benzimidazole.

Present active compound 22

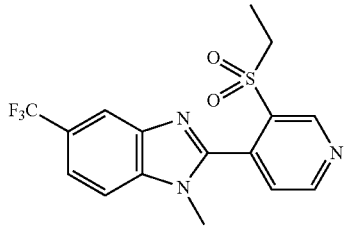

¹H-NMR (CDCl₃) δ: 9.38 (s, 1H), 9.08 (d, J=4.9 Hz, 1H), 8.09-8.06 (m, 1H), 7.66 (dd, J=8.4, 1.3 Hz, 1H), 7.54 (d, J=8.4 Hz, 1H), 7.51 (dd, J=4.9, 0.7 Hz, 1H), 3.67 (s, 3H), 3.45 (q, J=7.4 Hz, 2H), 1.29 (t, J=7.4 Hz, 3H)

Production Example 23

2-(3-isopropylthiopyridin-4-yl)-1-methyl-5-trifluoromethyl-1H-benzimidazole (hereinafter, referred to as present active compound 23) was obtained according to the method described in Production Example 10, using 2-propanethiol instead of 1-propanol.

Present active compound 23

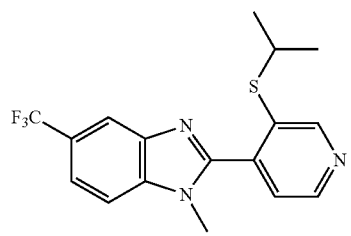

¹H-NMR (CDCl₃) δ: 8.83 (s, 1H), 8.66 (d, J=4.8 Hz, 1H), 8.14-8.11 (m, 1H), 7.64 (dd, J=8.4, 1.3 Hz, 1H), 7.53 (d, J=8.4 Hz, 1H), 7.45 (d, J=4.8 Hz, 1H), 3.70 (s, 3H), 3.31 (sep, J=6.7 Hz, 1H), 1.17 (d, J=6.7 Hz, 6H)

Production Example 24

To a mixture of 0.42 g of 1-methyl-2-(pyridin-4-yl)-5-trifluoromethyl-1H-benzimidazole and 8 ml of chloroform was added 0.52 g of 69% m-chloroperbenzoic acid, then, the mixture was stirred for 2 hours while heating at 60° C. After cooling down to room temperature, to the reaction mixture was added a saturated sodium hydrogen carbonate aqueous solution, and the mixture was extracted three times with ethyl acetate. The organic layer was dried over anhydrous magnesium sulfate, then, concentrated under reduced pressure. The residue was subjected to silica gel column chromatography to obtain 0.36 g of 1-methyl-2-(1-oxypyridin-4-yl)-5-trifluoromethyl-1H-benzimidazole (hereinafter, referred to as present active compound 24).

Present active compound 24

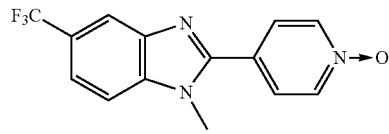

¹H-NMR (CDCl₃) δ: 8.35 (dd, J=5.3, 1.9 Hz, 2H), 8.11 (s, 1H), 7.80-7.77 (m, 2H), 7.64 (dd, J=8.5, 1.4 Hz, 1H), 7.52 (d, J=8.5 Hz, 1H), 4.00 (s, 3H)

Production Example 25

2-(3-fluoro-1-oxypyridin-4-yl)-1-methyl-5-trifluoromethyl-1H-benzimidazole (hereinafter, referred to as present active compound 25) was obtained according to the method described in Production Example 24, using 2-(3-fluoropyridin-4-yl)-1-methyl-5-trifluoromethyl-1H-benzimidazole instead of 1-methyl-2-(pyridin-4-yl)-5-trifluoromethyl-1H-benzimidazole.

Present active compound 25

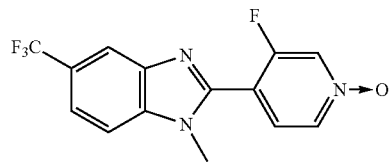

$^1$H-NMR (CDCl$_3$) δ: 8.31 (dd, J=5.4, 1.6 Hz, 1H), 8.22-8.19 (m, 1H), 8.13-8.11 (m, 1H), 7.72 (dd, J=8.3, 6.9 Hz, 1H), 7.67-7.63 (m, 1H), 7.55 (d, J=8.7 Hz, 1H), 3.86 (d, J=2.7 Hz, 3H)

Production Example 26

2-(2-fluoropyridin-4-yl)-1-methyl-5-trifluoromethyl-1H-benzimidazole (hereinafter, referred to as present active compound 26) was obtained according to the method described in Production Example 4, using 2-fluoropyridine-4-carbaldehyde instead of 3-fluoropyridine-4-carbaldehyde.

Present active compound 26

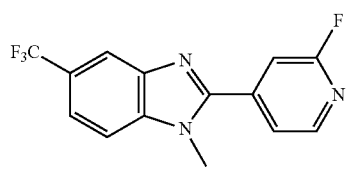

$^1$H-NMR (CDCl$_3$) δ: 8.45 (dd, J=5.1, 0.7 Hz, 1H), 8.14 (d, J=0.7 Hz, 1H), 7.67-7.63 (m, 2H), 7.54 (d, J=8.5 Hz, 1H), 7.40-7.38 (m, 1H), 4.00 (s, 3H)

Production Example 27

2-(2-chloropyridin-4-yl)-1-methyl-5-trifluoromethyl-1H-benzimidazole (hereinafter, referred to as present active compound 27) was obtained according to the method described in Production Example 4, using 2-chloropyridine-4-carbaldehyde instead of 3-fluoropyridine-4-carbaldehyde.

Present active compound 27

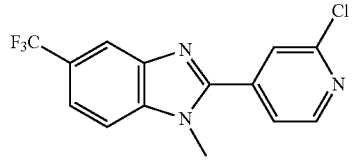

$^1$H-NMR (CDCl$_3$) δ: 8.61 (dd, J=5.1, 0.7 Hz, 1H), 8.13 (t, J=0.7 Hz, 1H), 7.79 (dd, J=1.5, 0.7 Hz, 1H), 7.66 (dd, J=5.1, 1.5 Hz, 1H), 7.64 (d, J=1.0 Hz, 1H), 7.54 (d, J=8.5 Hz, 1H), 3.99 (s, 3H)

Production Example 28

1-cyclopropyl-2-(3-fluoropyridin-4-yl)-5-trifluoromethyl-1H-benzimidazole (hereinafter, referred to as present active compound 28) was obtained according to the method described in Production Example 6, using N-1-cyclopropyl-4-trifluoromethylbenzene-1,2-diamine instead of N-1-methyl-4-trifluoromethylbenzene-1,2-diamine and using 3-fluoroisonicotinic acid instead of 3-methylisonicotinic acid.

Present active compound 28

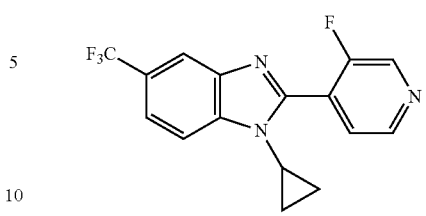

$^1$H-NMR (CDCl$_3$) δ: 8.70 (d, J=2.0 Hz, 1H), 8.64 (dd, J=4.9, 1.0 Hz, 1H), 8.12-8.11 (m, 1H), 7.76-7.70 (m, 2H), 7.63 (dd, J=8.7, 1.3 Hz, 1H), 3.67-3.59 (m, 1H), 1.13-1.06 (m, 2H), 0.74-0.67 (m, 2H)

Production Example 29

1-cyclopropyl-2-(3-methylthiopyridine-4-yl)-5-trifluoromethyl-1H-benzimidazole (hereinafter, referred to as present active compound 29) was obtained according to the method described in Production Example 4, using 1-cyclopropyl-2-(3-fluoropyridin-4-yl)-5-trifluoromethyl-1H-benzimidazole instead of 2-(3-fluoropyridin-4-yl)-1-methyl-5-trifluoromethyl-1H-benzimidazole and using methyl mercaptan sodium salt instead of sodium methoxide.

Present active compound 29

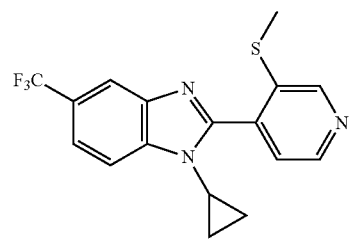

$^1$H-NMR (CDCl$_3$) δ: 8.70 (s, 1H), 8.59 (dd, J=4.8, 0.5 Hz, 1H), 8.13-8.10 (m, 1H), 7.73 (d, J=8.5 Hz, 1H), 7.64-7.60 (m, 1H), 7.40 (d, J=4.8 Hz, 1H), 3.57-3.50 (m, 1H), 2.49 (s, 3H), 1.03-0.96 (m, 2H), 0.76-0.70 (m, 2H)

Production Example 30

1-cyclopropyl-2-(3-methanesulfinylpyridin-4-yl)-5-trifluoromethyl-1H-benzimidazole (hereinafter, referred to as present active compound 30) was obtained according to the method described in Production Example 18, using 1-cyclopropyl-2-(3-methylthiopyridin-4-yl)-5-trifluoromethyl-1H-benzimidazole instead of 1-methyl-2-(3-methylthiopyridin-4-yl)-5-trifluoromethyl-1H-benzimidazole.

Present active compound 30

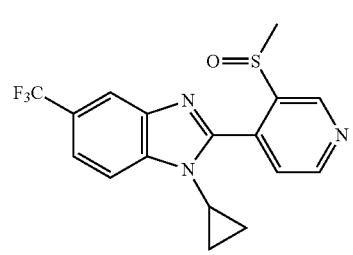

¹H-NMR (CDCl₃) δ: 9.52 (s, 1H), 8.94 (d, J=5.1 Hz, 1H), 8.09 (d, J=0.7 Hz, 1H), 7.76 (d, J=8.7 Hz, 1H), 7.72 (d, J=5.1 Hz, 1H), 7.66 (dd, J=8.6, 1.6 Hz, 1H), 3.63-3.57 (m, 1H), 3.21 (s, 3H), 1.34-1.23 (m, 1H), 1.14-1.05 (m, 1H), 1.01-0.93 (m, 1H), 0.67-0.59 (m, 1H)

Production Example 31

1-cyclopropyl-2-(3-methanesulfonylpyridin-4-yl)-5-trifluoromethyl-1H-benzimidazole (hereinafter, referred to as present active compound 31) was obtained according to the method described in Production Example 19, using 1-cyclopropyl-2-(3-methylthiopyridin-4-yl)-5-trifluoromethyl-1H-benzimidazole instead of 1-methyl-2-(3-methylthiopyridin-4-yl)-5-trifluoromethyl-1H-benzimidazole.

Present active compound 31

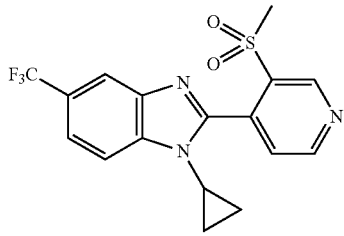

¹H-NMR (CDCl₃) δ: 9.45 (s, 1H), 9.06 (d, J=4.8 Hz, 1H), 8.06-8.04 (m, 1H), 7.75 (d, J=8.7 Hz, 1H), 7.66-7.62 (m, 1H), 7.56 (d, J=4.8 Hz, 1H), 3.50 (s, 3H), 3.43-3.37 (m, 1H), 0.97-0.93 (m, 4H)

Production Example 32

1-cyclopropyl-2-(3-ethylthiopyridin-4-yl)-5-trifluoromethyl-1H-benzimidazole (hereinafter, referred to as present active compound 32) was obtained according to the method described in Production Example 4, using 1-cyclopropyl-2-(3-fluoropyridin-4-yl)-5-trifluoromethyl-1H-benzimidazole instead of 2-(3-fluoropyridin-4-yl)-1-methyl-5-trifluoromethyl-1H-benzimidazole and using ethyl mercaptan sodium salt instead of sodium methoxide.

Present active compound 32

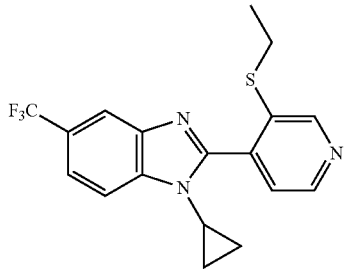

¹H-NMR (CDCl₃) δ: 8.77 (s, 1H), 8.61 (d, J=4.8 Hz, 1H), 8.12-8.09 (m, 1H), 7.73 (d, J=8.7 Hz, 1H), 7.62 (dd, J=8.7, 1.6 Hz, 1H), 7.42 (d, J=4.8 Hz, 1H), 3.58-3.52 (m, 1H), 2.90 (q, J=7.4 Hz, 2H), 1.23 (t, J=7.4 Hz, 3H), 0.98 (dd, J=12.8, 7.0 Hz, 2H), 0.74-0.67 (m, 2H)

Production Example 33

1-cyclopropyl-2-(3-ethanesulfinylpyridin-4-yl)-5-trifluoromethyl-1H-benzimidazole (hereinafter, referred to as present active compound 33) was obtained according to the method described in Production Example 18, using 1-cyclopropyl-2-(3-ethylthiopyridin-4-yl)-5-trifluoromethyl-1H-benzimidazole instead of 1-methyl-2-(3-methylthiopyridin-4-yl)-5-trifluoromethyl-1H-benzimidazole.

Present active compound 33

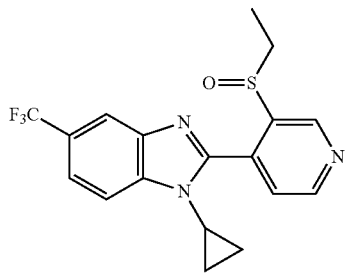

¹H-NMR (CDCl₃) δ: 9.41 (s, 1H), 8.93 (d, J=5.1 Hz, 1H), 8.08 (d, J=0.7 Hz, 1H), 7.77-7.74 (m, 1H), 7.71 (d, J=5.1 Hz, 1H), 7.68-7.64 (m, 1H), 3.64-3.53 (m, 2H), 3.24-3.14 (m, 1H), 1.43 (t, J=7.4 Hz, 3H), 1.32-1.23 (m, 1H), 1.13-1.05 (m, 1H), 0.97-0.89 (m, 1H), 0.67-0.60 (m, 1H)

Production Example 34

1-cyclopropyl-2-(3-ethanesulfonylpyridin-4-yl)-5-trifluoromethyl-1H-benzimidazole (hereinafter, referred to as present active compound 34) was obtained according to the method described in Production Example 19, using 1-cyclopropyl-2-(3-ethylthiopyridin-4-yl)-5-trifluoromethyl-1H-benzimidazole instead of 1-methyl-2-(3-methylthiopyridin-4-yl)-5-trifluoromethyl-1H-benzimidazole.

Present active compound 34

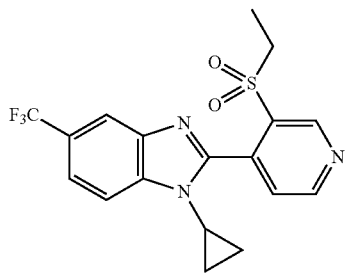

¹H-NMR (CDCl₃) δ: 9.38 (s, 1H), 9.05 (d, J=4.8 Hz, 1H), 8.05-8.03 (m, 1H), 7.74 (dd, J=8.5, 0.5 Hz, 1H), 7.65-7.62 (m, 1H), 7.56 (d, J=4.8 Hz, 1H), 3.65 (q, J=7.4 Hz, 2H), 3.43-3.36 (m, 1H), 1.33 (t, J=7.4 Hz, 3H), 0.97-0.92 (m, 4H)

Production Example 35

3-methyl-2-(pyridin-4-yl)-6-trifluoromethyl-3H-imidazo[4,5-b]pyridine (hereinafter, referred to as present active compound 35) was obtained according to the method described in Production Example 1, using N2-methyl-5-trifluoromethylpyridine-2,3-diamine instead of 1,1,3,3-tetrafluoro-N-methyl-1,3-dihydroisobenzofuran-5,6-diamine.

Present active compound 35

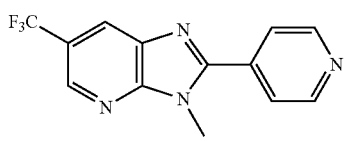

¹H-NMR (CDCl₃) δ: 8.88 (dd, J=4.5, 1.7 Hz, 2H), 8.75 (d, J=1.9 Hz, 1H), 8.35 (d, J=1.9 Hz, 1H), 7.79 (dd, J=4.5, 1.7 Hz, 2H), 4.09 (s, 3H)

Production Example 36

A mixture of 5.51 g of N2-methyl-5-trifluoromethylpyridine-2,3-diamine, 6.10 g of 3-fluoroisonicotinic acid, 8.28 g of WSC and 58 ml of pyridine was stirred for 3 hours while heating at 120° C. After cooling down to room temperature, water was poured, and the mixture was extracted three times with ethyl acetate. The combined organic layers were dried over magnesium sulfate, then, concentrated under reduced pressure. The residue was subjected to silica gel column chromatography to obtain 6.77 g of 2-(3-fluoropyridin-4-yl)-3-methyl-6-trifluoromethyl-3H-imidazo[4,5-b]pyridine (hereinafter, referred to as present active compound 36).

Present active compound 36

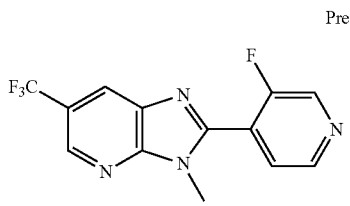

¹H-NMR (CDCl₃) δ: 8.77 (s, 1H), 8.76 (s, 1H), 8.69 (d, J=4.8 Hz, 1H), 8.37 (s, 1H), 7.72-7.71 (m, 1H), 3.94 (d, J=2.7 Hz, 3H)

Production Example 37

2-(3-chloropyridin-4-yl)-3-methyl-6-trifluoromethyl-3H-imidazo[4,5-b]pyridine (hereinafter, referred to as present active compound 37) was obtained according to the method described in Production Example 36, using 3-chloroisonicotinic acid instead of 3-fluoroisonicotinic acid.

Present active compound 37

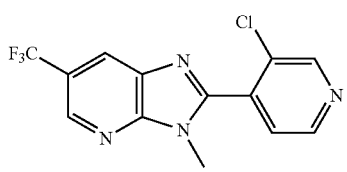

¹H-NMR (CDCl₃) δ: 8.86 (s, 1H), 8.78-8.76 (m, 1H), 8.74 (d, J=4.9 Hz, 1H), 8.37 (t, J=1.0 Hz, 1H), 7.54 (dd, J=4.9, 0.7 Hz, 1H), 3.85 (s, 3H)

Production Example 38

2-(3-methoxypyridin-4-yl)-3-methyl-6-trifluoromethyl-3H-imidazo[4,5-b]pyridine (hereinafter, referred to as present active compound 38) was obtained according to the method described in Production Example 8, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole.

Present active compound 38

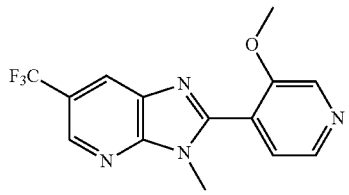

¹H-NMR (CDCl₃) δ: 8.73 (d, J=1.9 Hz, 1H), 8.56 (s, 1H), 8.50 (d, J=4.7 Hz, 1H), 8.33 (d, J=1.9 Hz, 1H), 7.53 (d, J=4.7 Hz, 1H), 4.40 (s, 3H), 3.82 (s, 3H)

Production Example 39

2-(3-ethoxypyridin-4-yl)-3-methyl-6-trifluoromethyl-3H-imidazo[4,5-b]pyridine (hereinafter, referred to as present active compound 39) was obtained according to the method described in Production Example 8, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using sodium ethoxide instead of sodium methoxide.

Present active compound 39

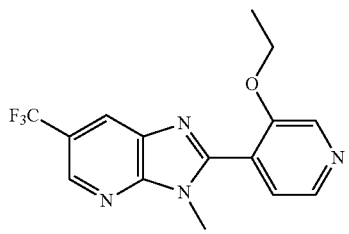

¹H-NMR (CDCl₃) δ: 8.73 (d, J=1.3 Hz, 1H), 8.57 (s, 1H), 8.47 (d, J=4.8 Hz, 1H), 8.33 (d, J=1.3 Hz, 1H), 7.54 (d, J=4.8 Hz, 1H), 4.27 (q, J=7.0 Hz, 2H), 3.84 (s, 3H), 1.38 (t, J=7.0 Hz, 3H)

Production Example 40

3-methyl-2-(3-propoxypyridin-4-yl)-6-trifluoromethyl-3H-imidazo[4,5-b]pyridine (hereinafter, referred to as present active compound 40) was obtained according to the method described in Production Example 10, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole.

Present active compound 40

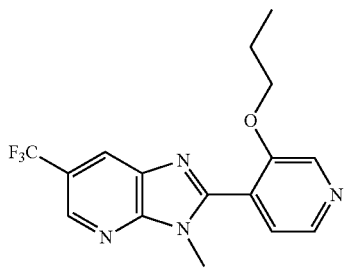

¹H-NMR (CDCl₃) δ: 8.74-8.72 (m, 1H), 8.54 (s, 1H), 8.47 (d, J=4.8 Hz, 1H), 8.34-8.32 (m, 1H), 7.53 (d, J=4.8 Hz, 1H), 4.14 (t, J=6.8 Hz, 2H), 3.83 (s, 3H), 1.81-1.71 (m, 2H), 0.92 (t, J=7.4 Hz, 3H)

Production Example 41

2-(3-isopropoxypyridin-4-yl)-3-methyl-6-trifluoromethyl-3H-imidazo[4,5-b]pyridine (hereinafter, referred to as present active compound 41) was obtained according to the method described in Production Example 10, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using 2-propanol instead of 1-propanol.

Present active compound 41

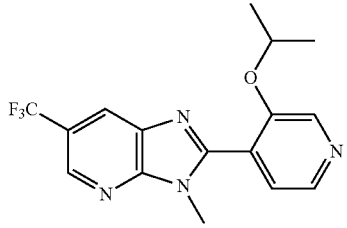

¹H-NMR (CDCl₃) δ: 8.74-8.72 (m, 1H), 8.53 (s, 1H), 8.44 (d, J=4.6 Hz, 1H), 8.34-8.32 (m, 1H), 7.54 (d, J=4.8 Hz, 1H), 4.78-4.72 (m, 1H), 3.84 (s, 3H), 1.32 (s, 3H), 1.31 (s, 3H)

Production Example 42

2-(3-tert-butoxypyridin-4-yl)-3-methyl-6-trifluoromethyl-3H-imidazo[4,5-b]pyridine (hereinafter, referred to as present active compound 42) was obtained according to the method described in Production Example 10, using 2-(3-fluoropyridin-4-yl)-3-methyl-6-trifluoromethyl-3H-imidazo[4,5-b]pyridine instead of 2-(3-fluoropyridine-4-yl)-1-methyl-5-trifluoromethyl-1H-benzimidazole and using tert-butyl alcohol instead of 1-propanol.

Present active compound 42

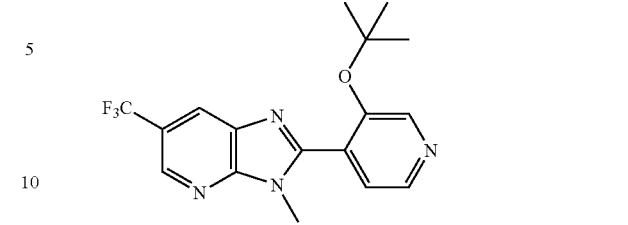

¹H-NMR (CDCl₃) δ: 8.75-8.72 (m, 1H), 8.61 (s, 1H), 8.56 (d, J=4.8 Hz, 1H), 8.35-8.32 (m, 1H), 7.60 (d, J=4.8 Hz, 1H), 3.87 (s, 3H), 1.15 (s, 9H)

Production Example 43

3-methyl-2-[3-(2,2,2-trifluoroethoxy)-pyridin-4-yl]-6-trifluoromethyl-3H-imidazo[4,5-b]pyridine (hereinafter, referred to as present active compound 43) was obtained according to the method described in Production Example 10, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using 2,2,2-trifluoroethanol instead of 1-propanol.

Present active compound 43

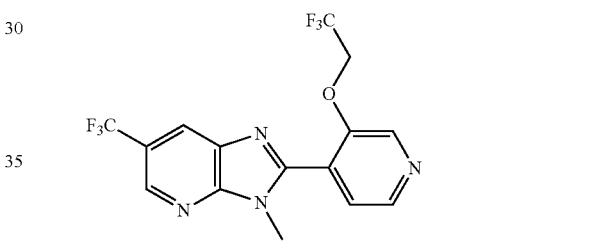

¹H-NMR (CDCl₃) δ: 8.76 (d, J=1.9 Hz, 1H), 8.62 (d, J=4.8 Hz, 1H), 8.57 (s, 1H), 8.35 (d, J=1.9 Hz, 1H), 7.61 (d, J=4.8 Hz, 1H), 4.52 (q, J=7.9 Hz, 2H), 3.85 (s, 3H)

Production Example 44

2-[3-(2,2-difluoroethoxy)-pyridin-4-yl]-3-methyl-6-trifluoromethyl-3H-imidazo[4,5-b]pyridine (hereinafter, referred to as present active compound 44) was obtained according to the method described in Production Example 10, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using 2,2-difluoroethanol instead of 1-propanol.

Present active compound 44

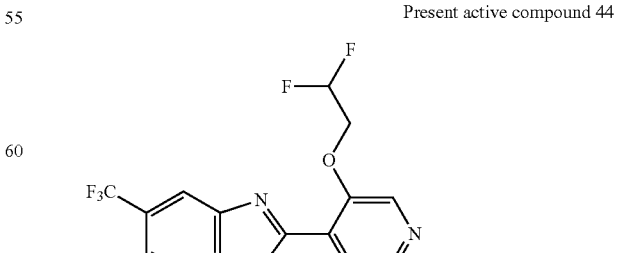

$^1$H-NMR (CDCl$_3$) δ: 8.76-8.74 (m, 1H), 8.58 (d, J=4.6 Hz, 1H), 8.55 (s, 1H), 8.34-8.33 (m, 1H), 7.58 (d, J=4.9 Hz, 1H), 5.98 (tt, J=54.6, 3.8 Hz, 1H), 4.38 (td, J=12.9, 3.8 Hz, 2H), 3.84 (s, 3H)

Production Example 45

2-[3-(2-fluoroethoxy)-pyridin-4-yl]-3-methyl-6-trifluoromethyl-3H-imidazo[4,5-b]pyridine (hereinafter, referred to as present active compound 45) was obtained according to the method described in Production Example 10, using 2-(3-fluoropyridin-4-yl)-3-methyl-6-trifluoromethyl-3H-imidazo [4,5-b]pyridine instead of 2-(3-fluoropyridin-4-yl)-1-methyl-5-trifluoromethyl-1H-benzimidazole and using 2-fluoroethanol instead of 1-propanol.

Present active compound 45

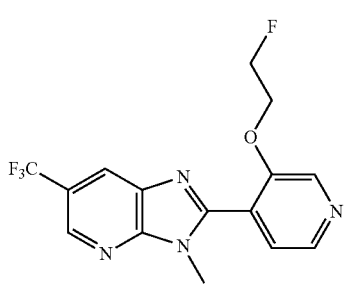

$^1$H-NMR (CDCl$_3$) δ: 8.76-8.73 (m, 1H), 8.54 (t, J=4.8 Hz, 2H), 8.34-8.32 (m, 1H), 7.58 (dd, J=4.8, 0.6 Hz, 1H), 4.76-4.73 (m, 1H), 4.64-4.61 (m, 1H), 4.47-4.44 (m, 1H), 4.41-4.37 (m, 1H), 3.86 (s, 3H)

Production Example 46

2-[3-(2-methoxyethoxy)-pyridin-4-yl]-3-methyl-6-trifluoromethyl-3H-imidazo[4,5-b]pyridine (hereinafter, referred to as present active compound 46) was obtained according to the method described in Production Example 10, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using 2-methoxyethanol instead of 1-propanol.

Present active compound 46

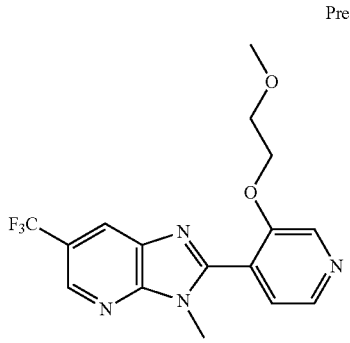

$^1$H-NMR (CDCl$_3$) δ: 8.74-8.72 (m, 1H), 8.56 (s, 1H), 8.49 (d, J=4.3 Hz, 1H), 8.34-8.32 (m, 1H), 7.56 (d, J=4.8 Hz, 1H), 4.33-4.29 (m, 2H), 3.87 (s, 3H), 3.67-3.64 (m, 2H), 3.32 (s, 3H)

Production Example 47

2-[3-(2-ethoxyethoxy)-pyridin-4-yl]-3-methyl-6-trifluoromethyl-3H-imidazo[4,5-b]pyridine (hereinafter, referred to as present active compound 47) was obtained according to the method described in Production Example 10, using 2-(3-fluoropyridin-4-yl)-3-methyl-6-trifluoromethyl-3H-imidazo [4,5-b]pyridine instead of 2-(3-fluoropyridin-4-yl)-1-methyl-5-trifluoromethyl-1H-benzimidazole and using 2-ethoxyethanol instead of 1-propanol.

Present active compound 47

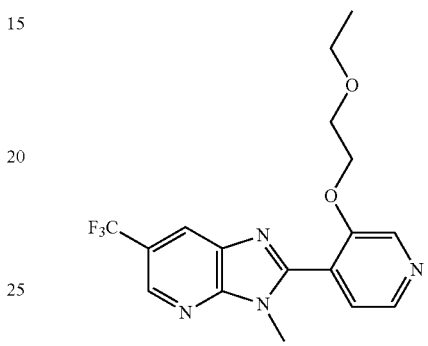

$^1$H-NMR (CDCl$_3$) δ: 8.74-8.72 (m, 1H), 8.56 (s, 1H), 8.49 (d, J=4.8 Hz, 1H), 8.33-8.31 (m, 1H), 7.56 (d, J=4.6 Hz, 1H), 4.34-4.29 (m, 2H), 3.88 (s, 3H), 3.71-3.66 (m, 2H), 3.45 (q, J=7.0 Hz, 2H), 1.14 (t, J=7.0 Hz, 3H)

Production Example 48

3-methyl-2-(3-methylthiopyridin-4-yl)-6-trifluoromethyl-3H-imidazo[4,5-b]pyridine (hereinafter, referred to as present active compound 48) was obtained according to the method described in Production Example 8, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using methyl mercaptan sodium salt instead of sodium methoxide.

Present active compound 48

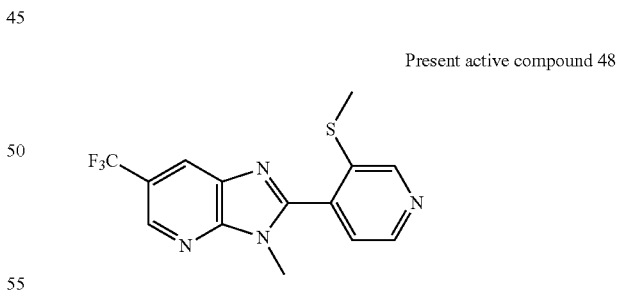

$^1$H-NMR (CDCl$_3$) δ: 8.75 (d, J=1.4, 1H), 8.73 (s, 1H), 8.62 (d, J=4.9, 1H), 8.36 (d, J=1.4, 1H), 7.37 (d, J=4.9, 1H), 3.82 (s, 3H), 2.51 (s, 3H)

Production Example 49

2-(3-methanesulfinylpyridin-4-yl)-3-methyl-6-trifluoromethyl-3H-imidazo[4,5-b]pyridine (hereinafter, referred to as present active compound 49) was obtained according to the method described in Production Example 18, using 3-methyl-2-(3-methylthiopyridin-4-yl)-6-trifluoromethyl-3H- imidazo[4,5-b]pyridine instead of 1-methyl-2-(3-methylthiopyridin-4-yl)-5-trifluoromethyl-1H-benzimidazole.

Present active compound 49

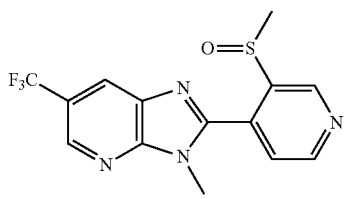

$^1$H-NMR (CDCl$_3$) δ: 9.55 (s, 1H), 9.00 (d, J=4.9 Hz, 1H), 8.80-8.79 (m, 1H), 8.38-8.37 (m, 1H), 7.55 (d, J=4.9 Hz, 1H), 4.02 (s, 3H), 3.20 (s, 3H)

Production Example 50

2-(3-methanesulfonylpyridin-4-yl)-3-methyl-6-trifluoromethyl-3H-imidazo[4,5-b]pyridine (hereinafter, referred to as present active compound 50) was obtained according to the method described in Production Example 19, using 3-methyl-2-(3-methylthiopyridin-4-yl)-6-trifluoromethyl-3H-imidazo[4,5-b]pyridine instead of 1-methyl-2-(3-methylthiopyridin-4-yl)-5-trifluoromethyl-1H-benzimidazole.

Present active compound 50

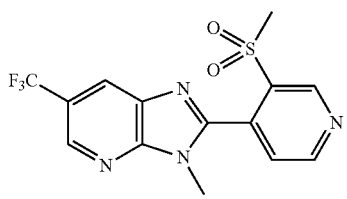

$^1$H-NMR (CDCl$_3$) δ: 9.47 (s, 1H), 9.12 (d, J=4.8 Hz, 1H), 8.79-8.77 (m, 1H), 8.32-8.31 (m, 1H), 7.52 (d, J=4.8 Hz, 1H), 3.77 (s, 3H), 3.36 (s, 3H)

Production Example 51

2-(3-ethylthiopyridin-4-yl)-3-methyl-6-trifluoromethyl-3H-imidazo[4,5-b]pyridine (hereinafter, referred to as present active compound 51) was obtained according to the method described in Production Example 8, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using ethyl mercaptan sodium salt instead of sodium methoxide.

Present active compound 51

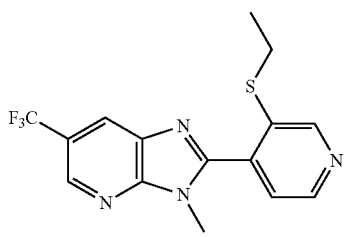

$^1$H-NMR (CDCl$_3$) δ: 8.79 (s, 1H), 8.76-8.75 (m, 1H), 8.65 (d, J=4.9 Hz, 1H), 8.35 (d, J=2.0 Hz, 1H), 7.40 (dd, J=4.9, 0.7 Hz, 1H), 3.81 (s, 3H), 2.92 (q, J=7.4 Hz, 2H), 1.26 (t, J=7.4 Hz, 3H)

Production Example 52

2-(3-ethanesulfinylpyridin-4-yl)-3-methyl-6-trifluoromethyl-3H-imidazo[4,5-b]pyridine (hereinafter, referred to as present active compound 52) was obtained according to the method described in Production Example 18, using 2-(3-ethylthiopyridin-4-yl)-3-methyl-6-trifluoromethyl-3H-imidazo[4,5-b]pyridine instead of 1-methyl-2-(3-methylthiopyridin-4-yl)-5-trifluoromethyl-1H-benzimidazole.

Present active compound 52

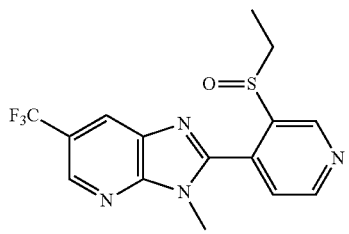

$^1$H-NMR (CDCl$_3$) δ: 9.43 (s, 1H), 8.98 (dd, J=5.1, 0.7 Hz, 1H), 8.81-8.78 (m, 1H), 8.37-8.34 (m, 1H), 7.55 (d, J=5.1 Hz, 1H), 4.00 (s, 3H), 3.58-3.48 (m, 1H), 3.24-3.13 (m, 1H), 1.42 (t, J=7.5 Hz, 3H)

Production Example 53

2-(3-ethanesulfonylpyridin-4-yl)-3-methyl-6-trifluoromethyl-3H-imidazo[4,5-b]pyridine (hereinafter, referred to as present active compound 53) was obtained according to the method described in Production Example 19, using 2-(3-ethylthiopyridin-4-yl)-3-methyl-6-trifluoromethyl-3H-imidazo[4,5-b]pyridine instead of 1-methyl-2-(3-methylthiopyridin-4-yl)-5-trifluoromethyl-1H-benzimidazole.

Present active compound 53

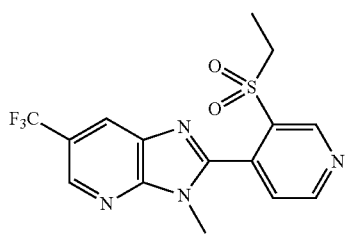

$^1$H-NMR (CDCl$_3$) δ: 9.40 (s, 1H), 9.11 (d, J=4.9 Hz, 1H), 8.79-8.76 (m, 1H), 8.32-8.30 (m, 1H), 7.52 (dd, J=4.9, 0.7 Hz, 1H), 3.76 (s, 3H), 3.47 (q, J=7.4 Hz, 2H), 1.32 (t, J=7.4 Hz, 3H)

Production Example 54

3-methyl-2-[3-(2,2,2-trifluoroethylthio)pyridin-4-yl]-6-trifluoromethyl-3H-imidazo[4,5-b]pyridine (hereinafter, referred to as present active compound 54) was obtained according to the method described in Production Example 10, using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole and using 2,2,2-trifluoroethanethiol instead of 1-propanol.

Present active compound 54

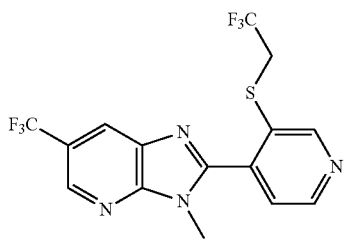

¹H-NMR (CDCl₃) δ: 9.01 (s, 1H), 8.80 (d, J=5.0 Hz, 1H), 8.79-8.77 (m, 1H), 8.38-8.36 (m, 1H), 7.46 (d, J=5.0 Hz, 1H), 3.80 (s, 3H), 3.42 (q, J=9.5 Hz, 2H)

Production Example 55

3-methyl-2-(1-oxypyridin-4-yl)-6-trifluoromethyl-3H-imidazo[4,5-b]pyridine (hereinafter, referred to as present active compound 55) was obtained according to the method described in Production Example 24, using 3-methyl-2-(pyridin-4-yl)-6-trifluoromethyl-3H-imidazo[4,5-b]pyridine instead of 1-methyl-2-(pyridin-4-yl)-5-trifluoromethyl-1H-benzimidazole.

Present active compound 55

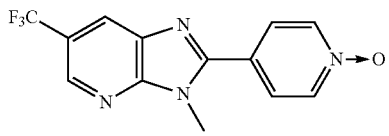

¹H-NMR (CDCl₃) δ: 8.74 (s, 1H), 8.37 (d, J=6.5 Hz, 2H), 8.33 (s, 1H), 7.88 (d, J=6.5 Hz, 2H), 4.12 (s, 3H)

Production Example 56

2-(3-fluoro1-oxypyridin-4-yl)-3-methyl-6-trifluoromethyl-3H-imidazo[4,5-b]pyridine (hereinafter, referred to as present active compound 56) was obtained according to the method described in Production Example 24, using 2-(3-fluoropyridin-4-yl)-3-methyl-6-trifluoromethyl-3H-imidazo[4,5-b]pyridine instead of 1-methyl-2-(pyridin-4-yl)-5-trifluoromethyl-1H-benzimidazole.

Present active compound 56

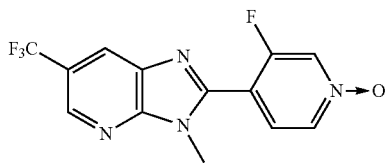

¹H-NMR (CDCl₃) δ: 8.77 (d, J=1.2 Hz, 1H), 8.35 (d, J=2.0 Hz, 1H), 8.33 (dd, J=5.6, 1.7 Hz, 1H), 8.24-8.20 (m, 1H), 7.73 (dd, J=8.5, 6.8 Hz, 1H), 3.96 (d, J=3.2 Hz, 3H)

Production Example 101

To a mixture of 0.20 g of the present active compound 36, 20.08 g of propanethiol and 1 ml of DMF was added 0.08 g of 60% sodium hydride (oily) under water cool, and the mixture was stirred for 3 hours at room temperature. Thereafter, a saturated ammonium chloride aqueous solution was poured into the reaction mixture, and the mixture was extracted with t-butyl methyl ether.

The organic layer was washed sequentially with a saturated ammonium chloride aqueous solution and a saturated sodium chloride aqueous solution, dried over sodium sulfate, then, concentrated under reduced pressure. The resultant solid was washed with hexane, to obtain 0.17 g of a compound of formula (101):

(101)

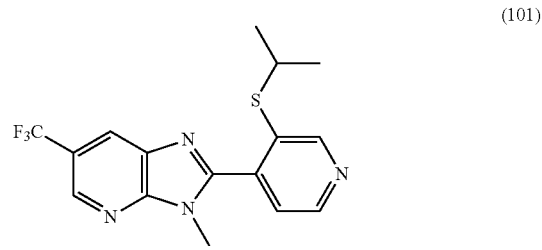

(hereinafter, referred to as present active compound 101).

Present Active Compound 101

¹H-NMR (CDCl₃) δ: 8.85 (m, 1H), 8.75 (m, 1H), 8.68 (d, J=4.9 Hz, 1H), 8.34 (m, 1H), 7.43 (dd, J=4.9, 0.7 Hz, 1H), 3.79 (s, 3H), 3.40-3.33 (m, 1H), 1.20 (d, J=6.8 Hz, 6H).

Production Example 102

A compound (0.19 g) of formula (102):

(102)

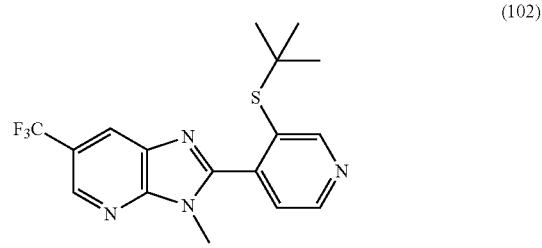

(hereinafter, referred to as present active compound 102) was obtained according to the method described in Production Example 101, using 0.09 g of 2-methyl-2-propanethiol instead of 2-propanethiol.

Present Active Compound 102

¹H-NMR (CDCl₃) δ: 8.97 (m, 1H), 8.81 (d, J=4.9 Hz, 1H), 8.75 (m, 1H), 8.34 (m, 1H), 7.55 (dd, J=4.9, 0.7 Hz), 3.76 (s, 3H), 1.13 (s, 9H).

Production Example 103

A compound (0.22 g) of formula (103):

(103)

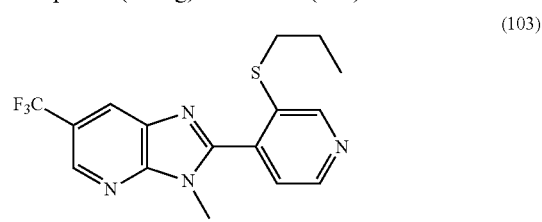

(hereinafter, referred to as present active compound 103) was obtained according to the method described in Production Example 101, using 0.08 g of 1-propanethiol instead of 2-propanethiol.

Present Active Compound 103

¹H-NMR (CDCl₃) δ: 8.79 (m, 1H), 8.75 (m, 1H), 8.64 (d, J=4.9 Hz, 1H), 8.35 (m, 1H), 7.39 (dd, J=4.9, 0.7 Hz), 3.81 (s, 3H), 2.86 (t, J=7.3 Hz, 2H), 1.63-1.56 (m, 2H), 0.94 (t, J=7.3 Hz, 3H).

Production Example 104

To a mixture of 0.20 g of the present active compound 36, 0.09 g of 2-(methylthio)ethanol and 1 ml of DMF was added 0.04 g of 60% sodium hydride (oily) under ice cool, and the mixture was stirred for 4 hours under ice cool. Thereafter, a saturated ammonium chloride aqueous solution was poured into the reaction mixture, and the mixture was extracted with t-butyl methyl ether. The organic layer was washed sequentially with a saturated ammonium chloride aqueous solution and a saturated sodium chloride aqueous solution, dried over sodium sulfate, then, concentrated under reduced pressure. The resultant solid was washed with hexane, to obtain 0.22 g of a compound of formula (104):

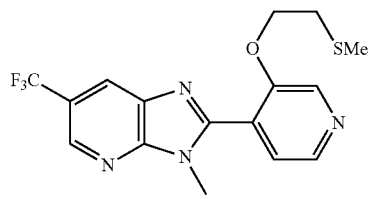

(104)

(hereinafter, referred to as present active compound 104).

Present Active Compound 104

¹H-NMR (CDCl₃) δ: 8.73 (m, 1H), 8.55 (s, 1H), 8.50 (d, J=4.9 Hz, 1H), 8.32 (m, 1H), 7.54 (d, J=4.6 Hz, 1H), 4.34 (t, J=6.5 Hz, 2H), 3.87 (s, H), 2.79 (t, J=6.6 Hz, 2H), 2.01 (s, 3H).

Production Example 105

A compound (0.23 g) of formula (105):

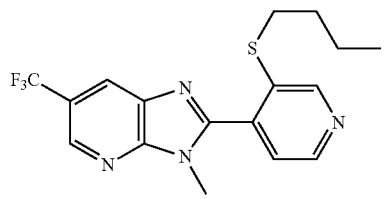

(105)

(hereinafter, referred to as present active compound 105) was obtained according to the method described in Production Example 101, using 0.09 g of 1-butanethiol instead of 2-propanethiol.

Present Active Compound 105)

¹H-NMR (CDCl₃) δ: 8.78 (s, 1H), 8.75 (m, H), 8.64 (d, J=4.8 Hz, 1H), 8.35 (m, 1H), 7.39 (d, J=4.8 Hz, 1H), 3.81 (s, 3H), 2.89 (t, J=7.5 Hz, 2H), 1.57-1.51 (m, 2H), 1.39-1.30 (m, 2H), 0.85 (t, J=7.4 Hz, 3H).

Production Example 106

To a mixture of 0.18 g of 3-methoxyisonicotinic acid and 2 ml of pyridine were added 0.32 g of WSC and 0.20 g of N2-methyl-5-trifluoromethylpyridine-2,3-diamine sequentially, and the mixture was refluxed with heat for 6 hours. Thereafter, to this mixture was added 0.20 g of WSC, and the mixture was refluxed with heat for 4 hours. The reaction mixture was allowed to cool to room temperature, then, water was poured and the mixture was extracted with t-butyl methyl ether. The organic layer was washed sequentially with water, a saturated sodium hydrogen carbonate aqueous solution and a saturated sodium chloride aqueous solution, dried over sodium sulfate, then, concentrated under reduced pressure. The residue was subjected to silica gel preparative thin layer chromatography to obtain 0.15 g of a compound of formula (106):

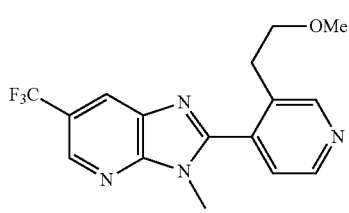

(106)

(hereinafter, referred to as present active compound 106).

Present Active Compound 106

¹H-NMR (CDCl₃) δ: 8.90 (s, 1H), 8.79 (d, J=5.1 Hz, 1H), 8.75 (m, 1H), 8.34 (m, 1H), 7.38 (d, J=5.6 Hz, 1H), 4.55 (s, 2H), 3.80 (s, 3H), 3.22 (s, 3H).

Production Example 107

To a mixture of 0.20 g of the present active compound 4, 0.09 g of 2-methyl-2-propanethiol and 1 ml of DMF was added 0.04 g of 60% sodium hydride (oily) under ice cool, and the mixture was stirred for 2 hours under ice cool. Thereafter, the mixture was heated up to room temperature and stirred for 1 hour. Into the reaction mixture was poured water under ice cool and the mixture was extracted with t-butyl methyl ether. The organic layer was washed sequentially with water and a saturated sodium chloride aqueous solution, dried over sodium sulfate, then, concentrated under reduced pressure. The resultant solid was washed with hexane to obtain 0.19 g of a compound of formula (107):

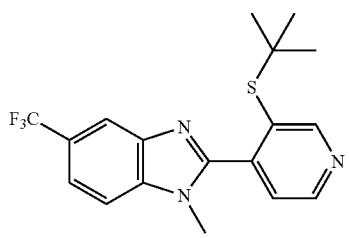

(107)

(hereinafter, referred to as present active compound 107).

Present Active Compound 107

¹H-NMR (CDCl₃) δ: 8.94 (m, 1H), 8.78 (d, J=4.9 Hz, 1H), 8.12 (m, 1H), 7.64 (dd, J=8.5, 1.5 Hz, 1H), 7.58 (dd, J=4.9, 0.7 Hz, 1H), 7.53 (d, J=8.3 Hz), 3.67 (s, 3H), 1.11 (s, 9H).

Production Example 108

A compound (0.15 g) of formula (108):

(108)

(hereinafter, referred to as present active compound 108) was obtained according to the method described in Production Example 107, using 0.09 g of 1-butanethiol instead of 2-methyl-2-propanethiol.

Present Active Compound 108

$^1$H-NMR (CDCl$_3$) δ: 8.76 (s, 1H), 8.61 (d, J=4.9 Hz, 1H), 8.13 (m, 1H), 7.64 (dd, J=8.4, 1.3 Hz, 1H), 7.53 (d, J=8.3 Hz, 1H), 7.40 (dd, J=4.9, 0.7 Hz, 1H), 3.72 (s, 3H), 2.84 (t, J=7.4 Hz, 2H), 1.55-1.49 (m, 2H), 1.37-1.28 (m, 2H), 0.84 (t, 3H).

Production Example 109

To a mixture of 1.00 g of N2-methyl-5-trifluoromethylpyridine-2,3-diamine, 0.78 g of 2-fluoroisonicotinic acid and 5 ml of pyridine was added 1.50 g of WSC, and the mixture was refluxed with heat for 2 hours. The reaction mixture was cooled down to room temperature, then, water was poured. The generated crystal was filtrated, then, washed with water, and dried under reduced pressure to obtain 1.44 g of a compound of formula (109):

(109)

(hereinafter, referred to as present active compound 109).

Present Active Compound 109

$^1$H-NMR (CDCl$_3$) δ: 8.77-8.76 (m, 1H), 8.49-8.48 (m, 1H), 8.37-8.36 (1H, m), 7.72-7.70 (m, 1H), 7.47-7.46 (m, 1H), 4.11 (s, 3H).

Production Example 110

To a mixture of 0.70 g of the present active compound 109 and 2 ml of THF was added 0.18 g of methyl mercaptan sodium salt under ice cool, and the mixture was stirred for 1 hour at room temperature. To the reaction mixture was added 0.08 g of methyl mercaptan sodium salt, and the mixture was stirred for 5 hours, thereafter, 2 ml of DMF was added, and the mixture was stirred for 1 hour, and water was poured under ice cool. The generated crystal was filtrated, then, washed with water and dried under reduced pressure, to obtain 0.61 g of a compound of formula (110):

(110)

(hereinafter, referred to as present active compound 110).

Present Active Compound 110

$^1$H-NMR (CDCl$_3$) δ: 8.74 (d, J=1.2 Hz, 1H), 8.66 (dd, J=5.1, 0.6 Hz, 1H), 8.34 (d, J=1.2 Hz, 1H), 7.65 (dd, J=1.5, 0.7 Hz, 1H), 7.42 (dd, J=5.1, 1.5 Hz, 1H), 4.06 (s, 3H), 2.65 (s, 3H).

Production Example 111

A compound (0.17 g) of formula (111):

(111)

(hereinafter, referred to as present active compound 111) was obtained according to the method described in Production Example 104, using 0.09 g of 2,2-dimethyl-1-propanol instead of 2-(methylthio)ethanol.

Present Active Compound 111

$^1$H-NMR (CDCl$_3$) δ: 8.73 (d, J=1.5 Hz, 1H), 8.53 (s, 1H), 8.47 (d, J=4.9 Hz, 1H), 8.33 (d, J=1.5 Hz, 1H), 7.49 (d, J=4.9 Hz, 1H), 3.83 (s, 3H), 3.81 (s, 2H), 0.85 (s, 9H).

Production Example 112

A compound (0.21 g) of formula (112):

(112)

(hereinafter, referred to as present active compound 112) was obtained according to the method described in Production Example 104, using 0.07 g of 2-methyl-1-propanol instead of 2-(methylthio)ethanol.

Present Active Compound 112

$^1$H-NMR (CDCl$_3$) δ: 8.73 (d, J=1.5 Hz, 1H), 8.53 (s, 1H), 8.47 (d, J=4.9 Hz, 1H), 8.33 (d, J=2.0 Hz, 1H), 7.51 (d, J=4.9 Hz, 1H), 3.94 (d, J=6.6 Hz, 2H), 3.83 (s, 3H), 2.05-1.95 (m, 1H), 0.88 (d, J=6.8 Hz, 6H).

Production Example 113

To a mixture of 0.20 g of the present active compound 110, 3 ml of methanol, 1 ml of water and 0.4 ml of THF was added 0.16 g of sodium periodate, and the mixture was stirred for 8 hours at about 60° C. Thereafter, the reaction mixture was allowed to cool to room temperature, and water was poured under ice cool. The deposited crystal was filtrated, washed with water, then, dissolved in chloroform and washed sequentially with a saturated sodium thiosulfate aqueous solution, a saturated sodium hydrogen carbonate aqueous solution and saline, dried over sodium sulfate, then, concentrated under reduced pressure. The generated solid was washed with t-butyl methyl ether, to obtain 0.17 g of a compound of formula (113):

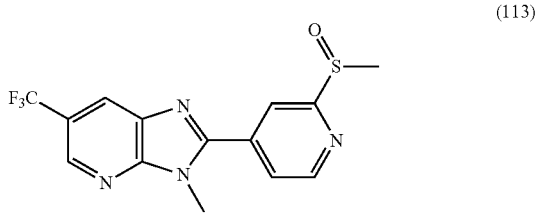

(113)

(hereinafter, referred to as present active compound 113).
Present Active Compound 113
$^1$H-NMR (CDCl$_3$) δ: 8.87 (dd, J=4.9, 0.7 Hz, 1H), 8.77 (d, J=1.5 Hz, 1H), 8.49 (dd, J=1.7, 0.7 Hz, 1H), 8.37 (d, J=1.5 Hz, 1H), 7.99 (dd, J=4.9, 1.7 Hz, 1H), 4.16 (3H,$), 2.95 (3H, s).

Production Example 114

The present active compound 110 (0.20 g) was dissolved in 2 ml of chloroform, and 0.39 g of 65% m-chloroperbenzoic acid was added under ice cool, and the mixture was stirred for 4 hours at room temperature. The reaction mixture was diluted with chloroform, then, washed sequentially with a saturated sodium hydrogen carbonate aqueous solution, a saturated sodium thiosulfate aqueous solution and saline, dried over sodium sulfate, then, concentrated under reduced pressure. The resultant solid was washed with hexane, to obtain 0.18 g of a compound of formula (114):

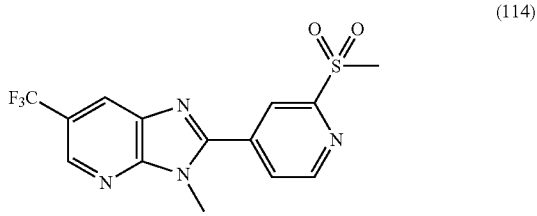

(114)

(hereinafter, referred to as present active compound 114).
Present Active Compound 114
$^1$H-NMR (CDCl$_3$) δ: 8.98 (dd, J=4.9, 0.7 Hz, 1H), 8.79 (d, J=1.2 Hz, 1H), 8.58 (dd, J=1.5, 0.7 Hz, 1H), 8.39 (d, J=1.5 Hz, 1H), 8.14 (dd, J=5.0, 1.6 Hz, 1H), 4.15 (s, 3H), 3.33 (s, 3H).

Production Example 115

The present active compound 36 (5.0 g) was dissolved in 20 ml of DMF, and 3.38 g of 70% sodium hydrosulfide was added, and the mixture was stirred for 5 hours about 80° C. The reaction mixture was allowed to cool to room temperature, then, poured into ice water, and concentrated hydrochloric acid was added until pH reached about 3. The deposited crystal was filtrated, then, washed with water and dried under reduced pressure, to obtain 5.2 g of a compound of formula (115):

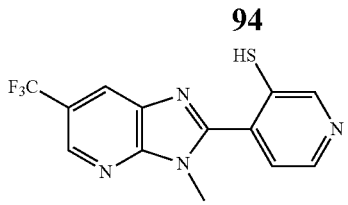

(115)

(hereinafter, referred to as present active compound 115).
Present Active Compound 115
$^1$H-NMR (CDCl$_3$) δ: 8.79-8.77 (m, 2H), 8.59 (d, J=4.9 Hz, 1H), 8.38 (d, J=2.0 Hz, 1H), 7.39 (d, J=5.0, 1H), 4.37 (brs, 1H), 3.91 (s, 3H).

Production Example 116

To a mixture of 0.40 g of the present active compound 115, 0.52 g of potassium nitrate and 8 ml of chloroform was added 0.70 g of trimethylsilyl chloride, and the mixture was refluxed with heat for 5 hours. The reaction mixture was allowed to cool to room temperature, diluted with chloroform. The solid was filtrated, and the filtrate was concentrated under reduced pressure, to obtain 0.36 g of a compound of formula (116):

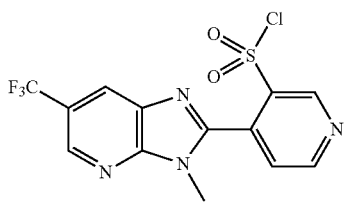

(116)

(hereinafter, referred to as present active compound 116).
Present Active Compound 116
$^1$H-NMR (CDCl$_3$) δ: 9.54 (s, 1H), 9.18 (d, J=4.9 Hz, 1H), 8.79 (m, 1H), 8.38 (m, 1H), 7.60 (d, J=4.9, 1H), 3.76 (s, 3H).

Production Example 117

The present active compound 116 (0.15 g) was suspended in 2 ml of THF, and 0.1 g of a 40% methylamine aqueous solution was added, and the mixture was stirred for 2 hours at room temperature. The reaction mixture was concentrated under reduced pressure, and the resultant residue was subjected to silica gel column chromatography, to obtain 95 mg of a compound of formula (117):

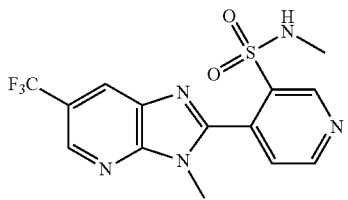

(117)

(hereinafter, referred to as present active compound 117).
Present Active Compound 117
$^1$H-NMR (CDCl$_3$) δ: 9.39 (d, J=0.5 Hz, 1H), 9.07 (d, J=4.9 Hz, 1H), 8.79 (m, 1H), 8.33 (m, 1H), 7.52 (dd, J=4.9, 0.7 Hz, 1H), 6.29 (brq, J=5.0 Hz, 1H), 3.87 (s, 3H), 2.81 (d, J=5.4 Hz, 3H).

Production Example 118

To a mixture of 4.5 g of the present active compound 36, 0.40 g of 18-crown-6-ether and 25 ml of THF was added 0.89 g of sodium cyanide, and the mixture was refluxed with heat for 1 hour. The reaction mixture was allowed to cool to room temperature, then, cold water was poured under ice cool. The generated crystal was filtrated, dissolved in ethyl acetate, then, silica gel and activated carbon were added, and filtration was performed. The filtrate was concentrated under reduced pressure, to obtain 3.49 g of a compound of formula (118):

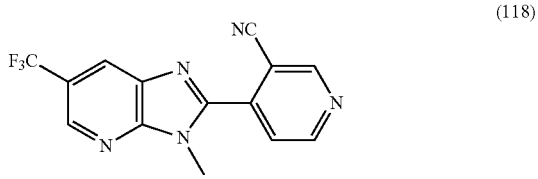

(hereinafter, referred to as present active compound 118).
Present Active Compound 118
$^1$H-NMR (CDCl$_3$) δ: 9.16 (s, 1H), 9.05 (d, J=5.1 Hz, 1H), 8.81 (m, 1H), 8.44 (m, 1H), 7.73 (dd, J=5.1, 0.7 Hz, 1H), 4.01 (s, 3H).

Production Example 119

The present active compound 118 (2.46 g) was suspended in 30 ml of ethanol, and 15 ml of a 2N sodium hydroxide aqueous solution was added, and the mixture was refluxed with heat for 5 hours. The reaction mixture was allowed to cool to room temperature, then, concentrated under reduced pressure. The residue was dissolved in water, washed with toluene, and concentrated hydrochloric acid was added until pH reached about 2. The generated crystal was filtrated, then, washed with water, and dried under reduced pressure, to obtain 2.35 g of a compound of formula (119):

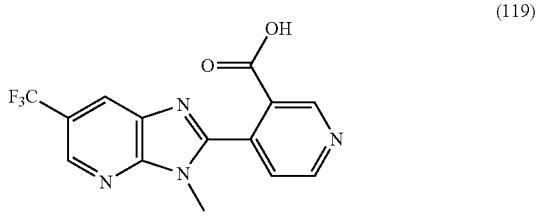

(hereinafter, referred to as present active compound 119).
Present Active Compound 119
$^1$H-NMR (DMSO-D$_6$) δ: 13.66 (brs, 1H), 9.25 (d, J=0.5 Hz, 1H), 9.01 (d, J=4.8 Hz, 1H), 8.83 (d, J=1.4 Hz, 1H), 8.59 (d, J=1.4 Hz, 1H), 7.77 (dd, J=5.0, 0.6 Hz, 1H), 3.65 (s, 3H).

Production Example 120

A compound (0.88 g) of formula (120):

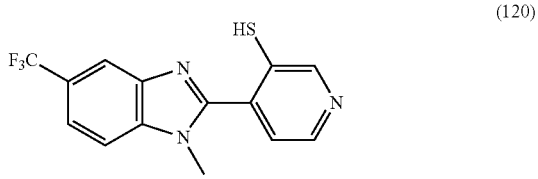

(hereinafter, referred to as present active compound 120) was obtained according to the method described in Production Example 115, using 1.0 g of the present active compound 4 instead of the present active compound 36.

Present Active Compound 120
$^1$H-NMR (CDCl$_3$) δ: 8.76 (d, J=0.5 Hz, 1H), 8.57 (d, J=4.9 Hz, 1H), 8.15 (m, 1H), 7.66 (dd, J=8.5, 1.2 Hz, 1H), 7.55 (d, J=8.5 Hz, 1H), 7.36 (dd, J=4.9, 0.5 Hz, 1H), 3.81 (s, 3H).

Production Example 121

The present active compound 115 (0.15 g) was suspended in 1 ml of THF, and 0.05 g of 60% sodium hydride (oily) was added under ice cool, and the mixture was stirred for 10 minutes. To the mixture was added 0.63 g of S-(trifluoromethyl)dibenzothiophenium trifluoromethane sulfonate and 1 ml of THF, and the mixture was stirred over night and day at room temperature. Into the reaction mixture was poured water and the mixture was extracted with chloroform, then, the organic layer was washed sequentially with a saturated sodium hydrogen carbonate aqueous solution and water, dried over sodium sulfate, then, concentrated under reduced pressure. The residue was subjected to silica gel preparative thin layer chromatography, to obtain 69 mg of a compound of formula (121):

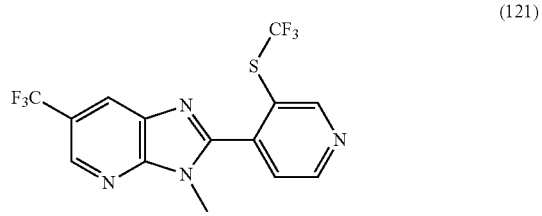

(hereinafter, referred to as present active compound 121).
Present Active Compound 121
$^1$H-NMR (CDCl$_3$) δ: 9.15 (s, 1H), 8.94 (d, J=4.9 Hz, 1H), 8.79 (m, 1H), 8.38 (m, 1H), 7.58 (dd, J=5.0, 0.6 Hz, 1H), 3.82 (s, 3H).

Production Example 122

The present active compound 120 (0.15 g) was suspended in 2 ml of THF, and 0.03 g of 60% sodium hydride (oily) was added, and the mixture was stirred for 15 minutes. To this mixture was added 0.27 g of S-(trifluoromethyl)dibenzothiophenium-3-sulfonate, and the mixture was stirred for 8 hours at room temperature. Into the reaction mixture was poured water and the mixture was extracted with chloroform, then, the organic layer was washed sequentially with a saturated sodium hydrogen carbonate aqueous solution and water, dried over sodium sulfate, then, concentrated under reduced pressure. The residue was subjected to silica gel preparative thin layer chromatography, to obtain 96 mg of a compound of formula (122):

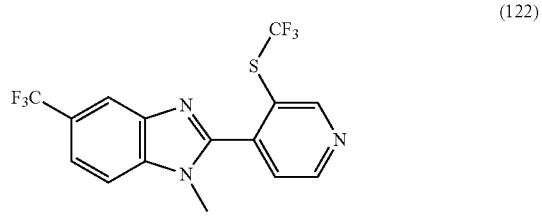

(hereinafter, referred to as present active compound 122).
Present Active Compound 122
$^1$H-NMR (CDCl$_3$) δ: 9.12 (s, 1H), 8.91 (d, J=4.9 Hz, 1H), 8.15-8.14 (m, 1H), 7.67 (dd, J=8.4, 1.3 Hz, 1H), 7.56-7.54 (m, 2H), 3.74 (s, 3H).

Production Example 123

The present active compound 115 (0.15 g) was suspended in 2 ml of DMF, and 0.04 g of 60% sodium hydride (oily) was added, and the mixture was stirred for 5 minutes at about 50° C. To this mixture was added 0.18 g of 1,1-difluoro-2-iodo-ethane, and the mixture was stirred for 3 hours. The reaction mixture was allowed to cool to room temperature, water was poured and the mixture was extracted with t-butyl methyl ether, then, the organic layer was washed sequentially with a saturated sodium hydrogen carbonate aqueous solution and a saturated sodium chloride aqueous solution, dried over sodium sulfate, then, concentrated under reduced pressure. The residue was subjected to silica gel column chromatography, to obtain 0.10 g of a compound of formula (123):

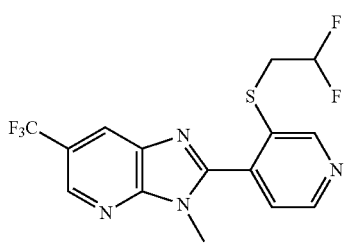

(123)

(hereinafter, referred to as present active compound 123).
Present Active Compound 123
$^1$H-NMR (CDCl$_3$) δ: 8.96 (s, 1H), 8.77-8.76 (m, 2H), 8.37 (d, J=2.0 Hz, 1H), 7.45 (d, J=4.9 Hz, 1H), 5.83 (tt, J=56.0, 4.3 Hz, 1H), 3.80 (s, 3H), 3.19 (td, J=15.1, 4.1 Hz, 2H).

Production Example 124

A compound (0.10 g) of formula (124):

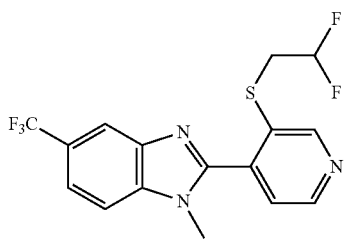

(123)

(hereinafter, referred to as present active compound 124) was obtained according to the method described in Production Example 123, using 0.15 g of the present active compound 120 instead of the present active compound 115.
Present Active Compound 124
$^1$H-NMR (CDCl$_3$) δ: 8.94 (s, 1H), 8.74 (d, J=4.9 Hz, 1H), 8.14 (m, 1H), 7.66 (dd, J=8.5, 1.5 Hz, 1H), 7.55 (d, J=8.5 Hz, 1H), 7.45 (dd, J=4.9, 0.7 Hz, 1H), 5.80 (tt, J=56, 4.2 Hz, 1H), 3.72 (s, 3H), 3.15 (td, J=15.2, 4.2 Hz, 2H).

Production Example 125

The present active compound 118 (0.15 g) was suspended in 2 ml of methanol, and 0.5 ml of a 2N sodium hydroxide aqueous solution and 0.3 ml of a 30% hydrogen peroxide aqueous solution were added, and the mixture was stirred for 1 hour at room temperature. Into the reaction mixture was poured water, and the mixture was extracted with chloroform, then, the organic layer was washed with a saturated sodium thiosulfate aqueous solution, dried over sodium sulfate, then, concentrated under reduced pressure. The residue was subjected to silica gel preparative thin layer chromatography, to obtain 29 mg of a compound of formula (125):

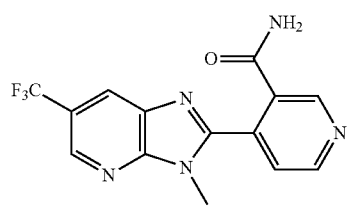

(125)

(hereinafter, referred to as present active compound 125).
Present Active Compound 125
$^1$H-NMR (CDCl$_3$) δ: 9.15 (s, 1H), 8.92 (d, J=5.1 Hz, 1H), 8.76 (m, 1H), 8.31 (m, 1H), 7.46 (dd, J=4.9, 0.7 Hz, 1H), 6.82 (brs, 1H), 5.85 (brs, 1H), 3.81 (s, 3H).

Production Example 126

The present active compound 115 (0.20 g) was suspended in 3 ml of DMF, and 0.05 g of 60% sodium hydride (oily) was added under water cool, and the mixture was stirred for 5 minutes at room temperature. To the mixture was added 0.16 g of 1-bromo-1,1,2,2-tetrafluoroethane, and the mixture was stirred over night and day at room temperature. Into the reaction mixture was poured water under ice cool and the mixture was extracted with t-butyl methyl ether. The organic layer was washed sequentially with water and a saturated sodium chloride aqueous solution, dried over sodium sulfate, then, concentrated under reduced pressure. The resultant solid was washed with t-butyl methyl ether, to obtain 0.16 g of a compound of formula (126):

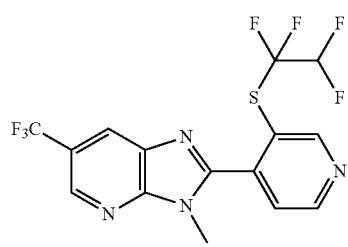

(126)

(hereinafter, referred to as present active compound 126).
Present Active Compound 126
$^1$H-NMR (CDCl$_3$) δ: 9.13 (d, J=0.7 Hz, 1H), 8.93 (d, J=4.9 Hz, 1H), 8.78 (m, 1H), 8.38 (m, 1H), 7.56 (dd, J=4.9, 0.7 Hz, 1H), 5.77 (tt, J=53.5, 2.9 Hz, 1H), 3.80 (s, 3H).

Production Example 127

A compound (0.22 g) of formula (127):

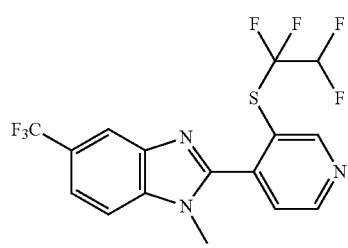

(127)

(hereinafter, referred to as present active compound 127) was obtained according to the method described in Production Example 126, using 0.20 g of the present active compound 120 instead of the present active compound 115.
Present Active Compound 127
¹H-NMR (CDCl₃) δ: 9.10 (s, 1H), 8.90 (d, J=4.9 Hz, 1H), 8.14 (s, 1H), 7.67 (dd, J=8.5, 1.2 Hz, 1H), 7.56-7.54 (m, 2H), 5.76 (tt, J=53.5, 3.2 Hz, 1H), 3.72 (s, 3H).

Production Example 128

A compound (0.21 q) of formula (128):

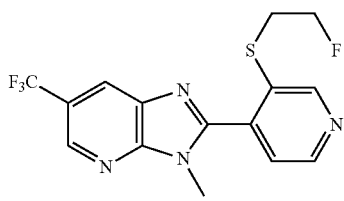

(128)

(hereinafter, referred to as present active compound 128) was obtained according to the method described in Production Example 126, using 0.16 g of 1-bromo-2-fluoroethane instead of 1-bromo-1,1,2,2-tetrafluoroethane.
Present Active Compound 128
¹H-NMR (CDCl₃) δ: 8.90 (s, 1H), 8.76 (d, J=2.0 Hz, 1H), 8.72 (d, J=4.9 Hz, 1H), 8.35 (d, J=2.0 Hz, 1H), 7.43 (d, J=4.9 Hz, 1H), 4.49 (dt, J=46.9, 6.0, 2H), 3.81 (s, 3H), 3.14 (dt, J=20.7, 6.1 Hz, 2H).

Production Example 129 and Production Example 130

The present active compound 120 (0.20 g) was suspended in 3 ml of DMF, and 0.05 g of 60% sodium hydride (oily) was added under water cool and the mixture was stirred for 10 minutes at room temperature To the mixture was added 0.16 g of 1-bromo-2-fluoroethane, and the mixture was stirred for 8 hours at room temperature, and allowed to stand overnight at room temperature. Into the reaction mixture was poured water under ice cool, and the generated crystal was filtrated, then, washed with water and dried under reduced pressure. The resultant crystal was subjected to silica gel preparative thin layer chromatography, to obtain 0.12 g of a compound of formula (129):

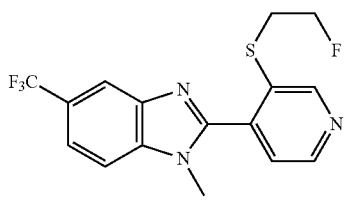

(129)

(hereinafter, referred to as present active compound 129) and 50 mg of a compound of formula (130):

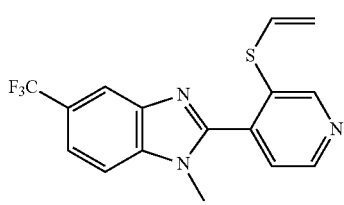

(130)

(hereinafter, referred to as present active compound 130).

Present Active Compound 129
¹H-NMR (CDCl₃) δ: 8.87 (s, 1H), 8.69 (d, J=4.9 Hz, 1H), 8.12 (m, 1H), 7.63 (dd, J=8.5, 1.7, 1H), 7.54 (d, J=8.5 Hz, 1H), 7.44 (d, J=4.9 Hz, 1H), 4.46 (dt, J=46.8, 6.1 Hz, 2H), 3.72 (s, 3H), 3.09 (dt, J=21.0, 6.0 Hz, 2H).
Present Active Compound 130
¹H-NMR (CDCl₃) δ: 8.79 (s, 1H), 8.67 (d, J=4.9 Hz, 1H), 8.13 (m, 1H), 7.63 (dd, J=8.5, 1.2 Hz, 1H), 7.52 (d, J=8.5 Hz, 1H), 7.45 (dd, J=4.9, 0.7 Hz, 1H), 6.41 (dd, J=16.5, 9.4 Hz, 1H), 5.44 (d, J=16.6 Hz, 1H), 5.40 (d, J=9.5 Hz, 1H), 3.74 (s, 3H).

Production Example 131

The present active compound 116 (0.16 g) was suspended in 3 ml of THF, and 0.2 ml of a 50% dimethylamine aqueous solution was added, and the mixture was stirred for 2 hours at room temperature. The reaction mixture was concentrated under reduced pressure, and the resultant residue was subjected to silica gel preparative thin layer chromatography, to obtain 73 mg of a compound of formula (131):

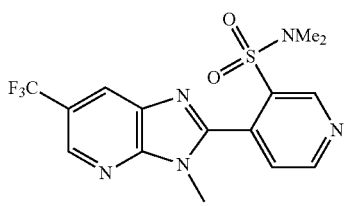

(131)

(hereinafter, referred to as present active compound 131).
Present Active Compound 131
¹H-NMR (CDCl₃) δ: 9.30 (s, 1H), 9.00 (d, J=4.9 Hz, 1H), 8.76 (d, J=1.2 Hz, 1H), 8.29 (d, J=1.5 Hz, 1H), 7.49 (d, J=4.9 Hz, 1H), 3.73 (s, 3H), 2.73 (s, 6H).

Production Example 132

The present active compound 116 (0.18 g) was suspended in 3 ml of THF, and 0.2 ml of 28% ammonia water was added, and the mixture was stirred for 2 hours at room temperature. The reaction mixture was concentrated under reduced pressure, and the resultant residue was subjected to silica gel column chromatography, to obtain 74 mg of a compound of formula (132):

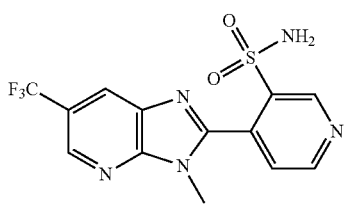

(132)

(hereinafter, referred to as present active compound 132).

Present Active Compound 132

¹H-NMR (CDCl₃) δ: 9.47 (s, 1H), 9.07 (d, J=4.9 Hz, 1H), 8.80 (d, J=1.7 Hz, 1H), 8.33 (d, J=2.0 Hz, 1H), 7.53 (d, J=4.9 Hz, 1H), 6.25 (brs, 2H), 3.89 (s, 3H).

Production Example 133

A compound (0.13 g) of formula (133):

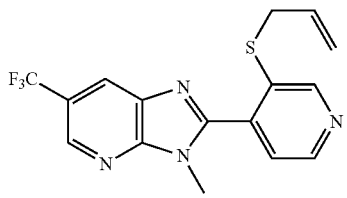
(133)

(hereinafter, referred to as present active compound 133) was obtained according to the method described in Production Example 126, using 0.16 g of 3-bromo-1-propene instead of 1-bromo-1,1,2,2-tetrafluoroethane. Present active compound 133

¹H-NMR (CDCl₃) δ: 8.79 (s, 1H), 8.75 (d, J=1.2 Hz, 1H), 8.66 (d, J=4.9 Hz, 1H), 8.36 (d, J=1.5 Hz, 1H), 7.41 (d, J=4.9 Hz, 1H), 5.79-5.68 (m, 1H), 5.11 (dd, J=12.6, 1.1 Hz, 1H), 5.08 (dd, J=5.5, 1.1 Hz, 1H), 3.81 (s, 3H), 3.48 (dt, J=6.9, 1.1 Hz, 2H).

Production Example 134

A compound (0.12 g) of formula (134):

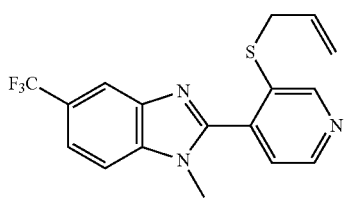
(134)

(hereinafter, referred to as present active compound 134) was obtained according to the method described in Production Example 126, using 0.20 g of the present active compound 120 instead of the present active compound 115 and using 0.16 g of 3-bromo-1-propene instead of 1-bromo-1,1,2,2-tetrafluoroethane.

Present Active Compound 134

¹H-NMR (CDCl₃) δ: 8.77 (d, J=0.7 Hz, 1H), 8.64 (d, J=4.9 Hz, 1H), 8.14 (m, 1H), 7.64 (dd, J=8.5, 1.2 Hz, 1H), 7.53 (d, J=8.5 Hz, 1H), 7.42 (dd, J=4.9, 0.7 Hz, 1H), 5.77-5.67 (m, 1H), 5.12-5.05 (m, 2H), 3.72 (s, 3H), 3.44 (dt, J=7.0, 1.1 Hz, 2H).

Production Example 135

A compound (70 mg) of formula (135):

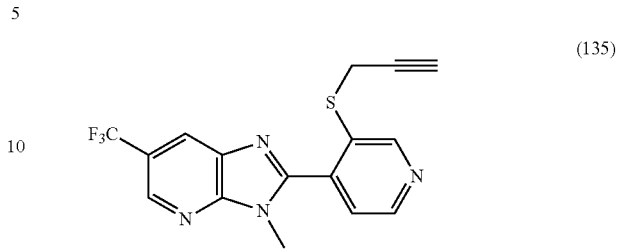
(135)

(hereinafter, referred to as present active compound 135) was obtained according to the method described in Production Example 126, using 0.16 g of 3-bromo-1-propyne instead of 1-bromo-1,1,2,2-tetrafluoroethane.

Present Active Compound 135

¹H-NMR (CDCl₃) δ: 8.98 (d, J=0.5 Hz, 1H), 8.76 (m, 1H), 8.7.4 (d, J=4.9 Hz, 1H), 8.35 (m, 1H), 7.44 (dd, J=5.5, 0.6 Hz, 1H), 3.82 (s, 3H), 3.59 (d, J=2.7 Hz, 2H), 2.23 (t, J=2.6 Hz, 1H).

Production Example 136

A compound (45 mg) of formula (136):

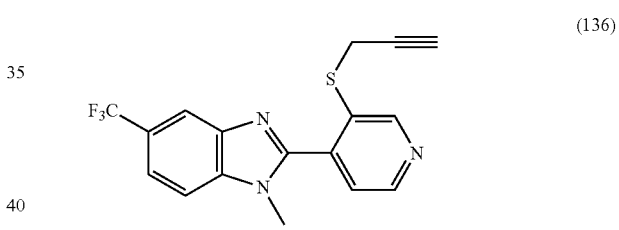
(136)

(hereinafter, referred to as present active compound 136) was obtained according to the method described in Production Example 126, using 0.20 g of the present active compound 120 instead of the present active compound 115 and using 0.16 g of 3-bromo-1-propyne instead of 1-bromo-1,1,2,2-tetrafluoroethane.

Present Active Compound 136

¹H-NMR (CDCl₃) δ: 8.95 (s, 1H), 8.71 (d, J=4.9 Hz, 1H), 8.13 (m, 1H), 7.64 (d, J=8.5 Hz, 1H), 7.53 (d, J=8.5 Hz, 1H), 7.44 (dd, J=4.9, 0.7 Hz, 1H), 3.73 (s, 3H), 3.55 (d, J=2.4 Hz, 2H), 2.21 (t, J=2.6 Hz, 1H).

Production Example 137

The present active compound 119 (0.15 g) was suspended in 3 ml of chloroform, and one drop of DMF and 0.29 g of oxalyl chloride were added under ice cool, and the mixture was stirred for 15 minutes at room temperature. The mixture was concentrated under reduced pressure, the residue was suspended in 3 ml of THF, and 0.2 ml of a 40% methylamine aqueous solution was added under ice cool, and the mixture was stirred for 1 hour at room temperature. The reaction mixture was concentrated under reduced pressure, and the residue was subjected to silica gel preparative thin layer chromatography, to obtain 34 mg of a compound of formula (137):

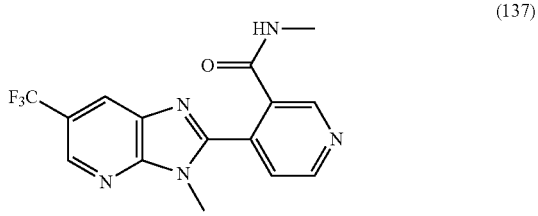

(hereinafter, referred to as present active compound 137).

Present Active Compound 137

$^1$H-NMR (CDCl$_3$) δ: 9.03 (d, J=0.7 Hz, 1H), 8.85 (d, J=4.9 Hz, 1H), 8.76 (d, J=1.2 Hz, 1H), 8.29 (d, J=1.5 Hz, 1H), 7.41 (d, J=5.0, 0.6 Hz, 1H), 7.25 (brs, 1H), 3.80 (s, 3H), 2.86 (d, J=4.9 Hz, 3H).

Production Example 138

The present active compound 119 (0.15 g) was suspended in 3 ml of chloroform, and one drop of DMF and 0.12 g of oxalyl chloride were added under water cool, and the mixture was stirred for 2 hours at room temperature, and concentrated under reduced pressure. The residue was suspended in 2.5 ml of THF, which was then added to a mixture of 0.5 ml of a 70% ethylamine aqueous solution and 2.5 ml of THF, and the mixture was stirred for 1 hour. The reaction mixture was concentrated under reduced pressure, and the residue was subjected to silica gel preparative thin layer chromatography, to obtain 0.10 g of a compound of formula (138):

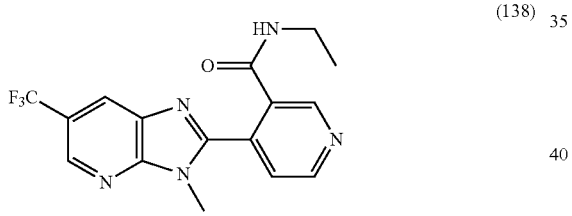

(hereinafter, referred to as present active compound 138).

Present Active Compound 138

$^1$H-NMR (CDCl$_3$) δ: 9.09 (s, 1H), 8.91 (d, J=4.9 Hz, 1H), 8.75 (m, 1H), 8.30 (m, 1H), 7.46 (dd, J=4.9, 0.7 Hz, 1H), 6.47 (brs, 1H), 3.80 (s, 3H), 3.34-3.27 (m, 2H), 1.00 (t, J=7.2 Hz, 3H).

Production Example 139

A compound (93 mg) of formula (139):

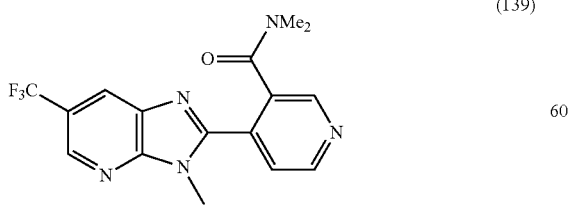

(hereinafter, referred to as present active compound 139) was obtained according to the method described in Production Example 138, using a 50% dimethylamine aqueous solution instead of the 70% ethylamine aqueous solution.

Present Active Compound 139

$^1$H-NMR (CDCl$_3$) δ: 8.87 (d, J=5.1 Hz, 1H), 8.80 (d, J=0.7 Hz, 1H), 8.73 (m, 1H), 8.28 (m, 1H), 7.53 (dd, J=5.1, 0.7 Hz, 1H), 3.89 (s, 3H), 3.01 (s, 3H), 3.00 (s, 6H).

Production Example 140

A compound (83 mg) of formula (140):

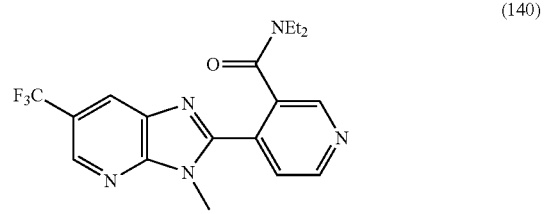

(hereinafter, referred to as present active compound 140) was obtained according to the method described in Production Example 138, using 0.5 ml of diethylamine instead of the 70% ethylamine aqueous solution.

Present Active Compound 140

$^1$H-NMR (CDCl$_3$) δ: 8.86 (d, J=5.1 Hz, 1H), 8.79 (d, J=0.7 Hz, 1H), 8.73 (m, 1H), 8.24 (m, 1H), 7.52 (dd, J=5.1, 0.7 Hz, 1H), 3.89 (s, 3H), 3.42 (q, J=7.0 Hz, 2H), 3.31 (q, J=7.2 Hz, 2H), 1.15 (t, J=7.2 Hz, 3H), 0.96 (t, J=7.1 Hz, 3H).

Production Example 141

To a mixture of 1.0 g of the present active compound 119, 0.30 g of N-methoxymethane amine hydrochloride, 20 mg of 1-hydroxybenzotriazole and 10 ml of pyridine was added 0.71 g of WSC, and the mixture was stirred for 5 hours at room temperature. Into the reaction mixture was poured water, and the mixture was extracted with ethyl acetate, then, the organic layer was washed with water, dried over sodium sulfate, and concentrated under reduced pressure. The resultant solid was washed with hexane, to obtain 0.13 g of a compound of formula (141):

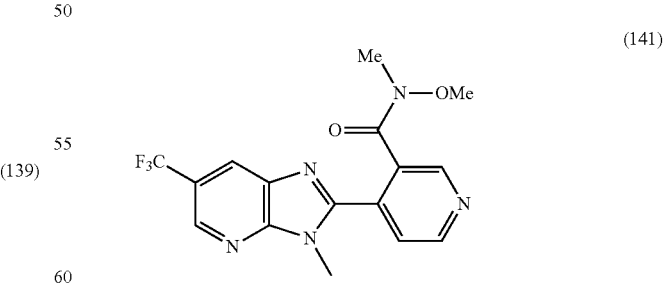

(hereinafter, referred to as present active compound 141).

Present Active Compound 141

$^1$H-NMR (CDCl$_3$) δ: 8.95 (brs, 1H), 8.89 (d, J=5.1 Hz, 1H), 8.73 (m, 1H), 8.30 (m, 1H), 7.54 (dd, J=5.1, 0.7 Hz, 1H), 3.91 (s, 3H), 3.56 (brs, 3H), 3.23 (s, 3H).

Production Example 142

A compound (0.12 g) of formula (142):

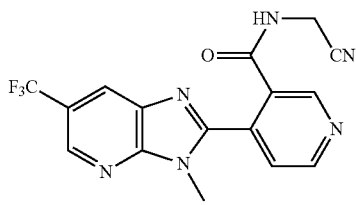

(142)

(hereinafter, referred to as present active compound 142) was obtained according to the method described in Production Example 141, using 0.06 g of 2-aminoacetonitrile hydrochloride instead of N-methoxymethane amine hydrochloride.

Present Active Compound 142

$^1$H-NMR (CDCl$_3$) δ: 9.19 (d, J=0.7 Hz, 2H), 8.96 (d, J=5.1 Hz, 1H), 8.79 (d, J=1.2 Hz, 1H), 8.37 (d, J=1.5 Hz, 1H), 8.14 (brt, J=5.6 Hz, 1H), 7.47 (dd, J=5.0, 0.6 Hz, 1H), 4.23 (d, J=5.9 Hz, 2H), 3.87 (s, 3H).

Production Example 143

The present active compound 119 (0.20 g) was suspended in 10 ml of methanol, and one drop of concentrated sulfuric acid was added, and the mixture was refluxed with heat for 10 hours. The reaction mixture was concentrated under reduced pressure, and to the residue was added a saturated sodium hydrogen carbonate aqueous solution, and the mixture was extracted with ethyl acetate. The organic layer was washed with a saturated sodium hydrogen carbonate aqueous solution, dried over sodium sulfate, then, concentrated under reduced pressure. The residue was subjected to silica gel column chromatography, to obtain 46 mg of a compound of formula (143):

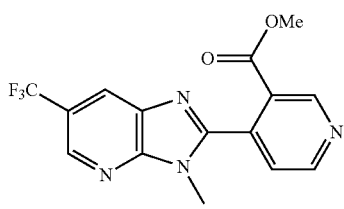

(143)

(hereinafter, referred to as present active compound 143).

Present Active Compound 143

$^1$H-NMR (CDCl$_3$) δ: 9.40 (d, J=0.7 Hz, 1H), 8.99 (d, J=5.1 Hz, 1H), 8.74 (m, 1H), 8.31 (m, 1H), 7.52 (dd, J=5.0, 0.6 Hz, 1H), 3.81 (s, 3H), 3.71 (s, 3H).

Production Example 144

A compound (0.16 g) of formula (144):

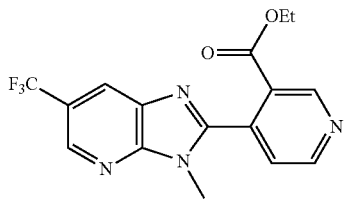

(144)

(hereinafter, referred to as present active compound 144) was obtained according to the method described in Production Example 143, using ethanol instead of methanol.

Present Active Compound 144

$^1$H-NMR (CDCl$_3$) δ: 9.41 (d, J=0.7 Hz, 1H), 8.99 (d, J=4.9 Hz, 1H), 8.74 (m, 1H), 8.31 (m, 1H), 7.52 (dd, J=4.9, 0.7 Hz, 1H), 4.23 (q, J=7.2 Hz, 2H), 3.70 (s, 3H), 1.10 (t, J=7.1 Hz, 3H).

Production Example 145

The present active compound 115 (0.31 g) was suspended in 3 ml of DMF, and 0.07 g of 60% sodium hydride (oily) was added under water cool and the mixture was stirred for 5 minutes at room temperature. To the mixture was added 0.27 g of (bromomethyl)cyclopropane, and the mixture was stirred for 1 hour at room temperature. Into the reaction mixture was poured a saturated sodium chloride aqueous solution, and the mixture was extracted with ethyl acetate. The organic layer was washed with a saturated sodium chloride aqueous solution, dried over magnesium sulfate, then, concentrated under reduced pressure. The residue was subjected to middle pressure preparative liquid chromatography, to obtain 0.17 g of a compound of formula (145):

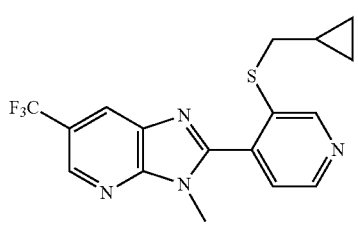

(145)

(hereinafter, referred to as present active compound 145).

Present Active Compound 145

$^1$H-NMR (CDCl$_3$) δ: 8.83 (s, 1H), 8.75 (m, 1H), 8.65 (d, J=5.1 Hz, 1H), 8.35 (m, 1H), 7.40 (dd, J=4.9, 0.6 Hz, 1H), 3.82 (s, 3H), 2.82 (d, J=7.1 Hz, 2H), 0.99-0.89 (m, 1H), 0.56-0.51 (m, 2H), 0.18-0.14 (m, 2H).

Production Example 146

The present active compound 120 (0.31 g) was suspended in 3 ml of DMF, and 0.07 g of 60% sodium hydride (oily) was added under water cool and the mixture was stirred for 5 minutes at room temperature. To the mixture was added 0.27 g of (bromomethyl)cyclopropane, and the mixture was stirred for 1 hour at room temperature. Into the reaction mixture was poured a saturated sodium chloride aqueous solution, and the mixture was extracted with ethyl acetate. The organic layer was washed with a saturated sodium chloride aqueous solution, dried over magnesium sulfate, then, concentrated under reduced pressure. The residue was subjected to middle pressure preparative liquid chromatography, to obtain 0.19 g of a compound of formula (146):

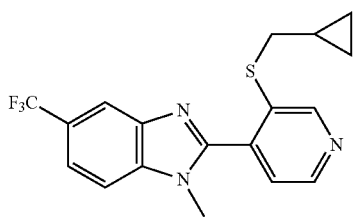

(146)

(hereinafter, referred to as present active compound 146).
Present Active Compound 146
$^1$H-NMR (CDCl$_3$) δ: 8.81 (s, 1H), 8.63 (d, J=4.8 Hz, 1H), 8.13 (s, 1H), 7.64 (dd, J=8.6, 1.3 Hz, 1H), 7.53 (d, J=8.6 Hz, 1H), 7.41 (dd, J=4.9, 0.6 Hz, 1H), 3.73 (s, 3H), 2.77 (d, J=7.1 Hz, 2H), 0.96-0.86 (m, 1H), 0.53-0.49 (m, 2H), 0.16-0.12 (m, 2H).

Production Example 147

A compound (73 mg) of formula (147):

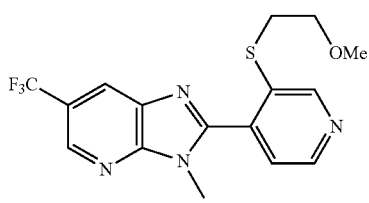

(147)

(hereinafter, referred to as present active compound 147) was obtained according to the method described in Production Example 145, using 0.28 g of 1-bromo-2-methoxyethane instead of (bromomethyl)cyclopropane.
Present Active Compound 147
$^1$H-NMR (CDCl$_3$) δ: 8.87 (d, J=0.5 Hz, 1H), 8.75 (d, J=1.5 Hz, 1H), 8.67 (d, J=4.8 Hz, 1H), 8.35 (d, J=1.5 Hz, 1H), 7.40 (dd, J=4.9, 0.6 Hz, 1H), 3.81 (s, 3H), 3.51 (t, J=6.2 Hz, 2H), 3.28 (s, 3H), 3.07 (t, J=6.2 Hz, 2H).

Production Example 148

A compound (0.17 g) of formula (148):

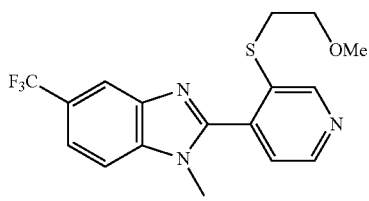

(148)

(hereinafter, referred to as present active compound 148) was obtained according to the method described in Production Example 146, using 0.28 g of 1-bromo-2-methoxyethane instead of (bromomethyl)cyclopropane.
Present Active Compound 148
$^1$H-NMR (CDCl$_3$) δ: 8.85 (s, 1H), 8.65 (d, J=5.1 Hz, 1H), 8.12 (s, 1H), 7.64 (dd, J=8.6, 1.3 Hz, 1H), 7.53 (d, J=8.3 Hz, 1H), 7.42 (dd, J=4.9, 0.6 Hz, 1H), 3.72 (s, 3H), 3.47 (t, J=6.2 Hz, 2H), 3.26 (s, 3H), 3.01 (t, J=6.3 Hz, 2H).

Production Example 149

A compound (82 mg) of formula (149):

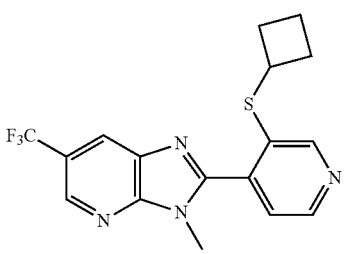

(149)

(hereinafter, referred to as present active compound 149) was obtained according to the method described in Production Example 145, using 0.27 g of bromocyclobutane instead of (bromomethyl)cyclopropane.
Present Active Compound 149
$^1$H-NMR (CDCl$_3$) δ: 8.75 (m, 1H), 8.63 (s, 1H), 8.61 (d, J=4.8 Hz, 1H), 8.36 (m, 1H), 7.37 (dd, J=4.9, 0.6 Hz, 1H), 3.99-3.89 (m, 1H), 3.82 (s, 3H), 2.47-2.42 (m, 2H), 2.05-1.96 (m, 2H).

Production Example 150

A compound (51 mg) of formula (150):

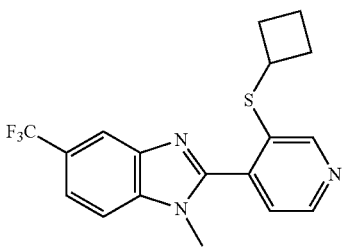

(150)

(hereinafter, referred to as present active compound 150) was obtained according to the method described in Production Example 146, using 0.27 g of bromocyclobutane instead of (bromomethyl)cyclopropane.
Present Active Compound 150
$^1$H-NMR (CDCl$_3$) δ: 8.61 (s, 1H), 8.58 (d, J=5.1 Hz, 1H), 8.14 (m, 1H), 7.64 (d, J=8.6 Hz, 1H), 7.53 (d, J=8.6 Hz, 1H), 7.38 (d, J=4.8 Hz, 1H), 3.93-3.85 (m, 1H), 3.73 (s, 3H), 2.46-2.39 (m, 2H), 2.07-1.92 (m, 4H).

Production Example 151

A compound (0.13 g) of formula (151):

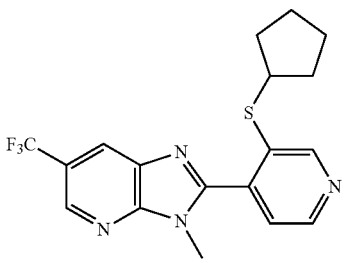

(151)

(hereinafter, referred to as present active compound 151) was obtained according to the method described in Production Example 145, using 0.30 g of bromocyclopentane instead of (bromomethyl)cyclopropane.

Present Active Compound 151

$^1$H-NMR (CDCl$_3$) δ: 8.82 (s, 1H), 8.75 (m, 1H), 8.63 (d, J=5.1 Hz, 1H), 8.35 (m, 1H), 7.38 (d, J=4.8 Hz, 1H), 3.80 (s, 3H), 3.63-3.56 (m, 1H), 2.04-1.98 (m, 2H), 1.72-1.64 (m, 2H), 1.59-1.48 (m, 4H).

Production Example 152

A compound (0.30 g) of formula (152):

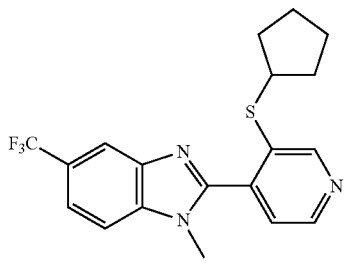
(152)

(hereinafter, referred to as present active compound 152) was obtained according to the method described in Production Example 146, using 0.30 g of bromocyclopentane instead of (bromomethyl)cyclopropane.

Present Active Compound 152

$^1$H-NMR (CDCl$_3$) δ: 8.80 (m, 1H), 8.61 (d, J=4.8 Hz, 1H), 8.13 (m, 1H), 7.63 (dd, J=8.3, 1.3 Hz, 1H), 7.53 (d, J=8.6 Hz, 1H), 7.39 (dd, J=4.8, 0.8 Hz, 1H), 3.71 (s, 3H), 3.58-3.52 (m, 1H), 2.05-1.95 (m, 2H), 1.72-1.62 (m, 2H), 1.60-1.46 (m, 4H).

Production Example 153

A compound (0.23 g) of formula (153):

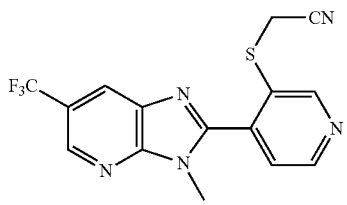
(153)

(hereinafter, referred to as present active compound 153) was obtained according to the method described in Production Example 145, using 0.24 g of bromoacetnitrile instead of (bromomethyl)cyclopropane.

Present Active Compound 153

$^1$H-NMR (CDCl$_3$) δ: 9.09 (s, 1H), 8.89 (d, J=4.8 Hz, 1H), 8.78 (d, J=1.3 Hz, 1H), 8.36 (d, J=1.5 Hz, 1H), 7.51 (d, J=4.8 Hz, 1H), 3.84 (s, 3H), 3.71 (s, 2H).

Production Example 154

A compound (0.24 g) of formula (154):

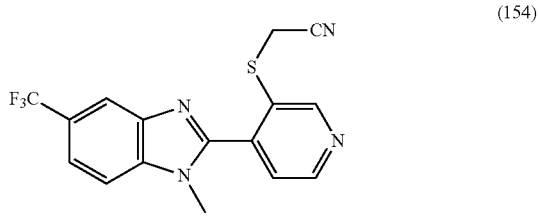
(154)

(hereinafter, referred to as present active compound 154) was obtained according to the method described in Production Example 146, using 0.24 g of bromoacetnitrile instead of (bromomethyl)cyclopropane.

Present Active Compound 154

$^1$H-NMR (CDCl$_3$) δ: 9.06 (m, 1H), 8.86 (d, J=4.8 Hz, 1H), 8.13 (m, 1H), 7.67 (dd, J=8.5, 1.1 Hz, 1H), 7.56 (d, J=8.3 Hz, 1H), 7.49 (dd, J=4.9, 0.6 Hz, 1H), 3.76 (s, 3H), 3.69 (s, 2H).

Production Example 155

A compound (0.19 g) of formula (155):

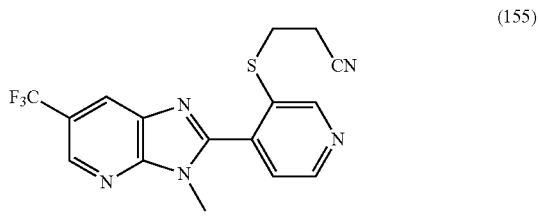
(155)

(hereinafter, referred to as present active compound 155) was obtained according to the method described in Production Example 145, using 0.27 g of 3-bromopropionnitrile instead of (bromomethyl)cyclopropane.

Present Active Compound 155)

$^1$H-NMR (CDCl$_3$) δ: 8.94 (d, J=0.5 Hz, 1H), 8.80 (d, J=4.8 Hz, 1H), 8.78 (d, J=1.3 Hz, 1H), 8.36 (d, J=1.5 Hz, 1H), 7.48 (dd, J=4.8, 0.5 Hz, 1H), 3.81 (s, 3H), 3.04 (t, J=7.1 Hz, 2H), 2.56 (t, J=6.9 Hz, 2H).

Production Example 156

A compound (0.16 g) of formula (156):

(156)

(hereinafter, referred to as present active compound 156) was obtained according to the method described in Production Example 146, using 0.27 g of 3-bromopropionnitrile instead of (bromomethyl)cyclopropane.

Present Active Compound 156

$^1$H-NMR (CDCl$_3$) δ: 8.92 (m, 1H), 8.78 (d, J=4.8 Hz, 1H), 8.12 (m, 1H), 7.66 (dd, J=8.5, 1.4 Hz, 1H), 7.55 (d, J=8.6 Hz, 1H), 7.49 (dd, J=4.8, 0.8 Hz, 1H), 3.73 (s, 3H), 2.98 (t, J=6.9 Hz, 2H), 2.52 (t, J=6.9 Hz, 2H).

Production Example 157

A compound (0.13 g) of formula (157):

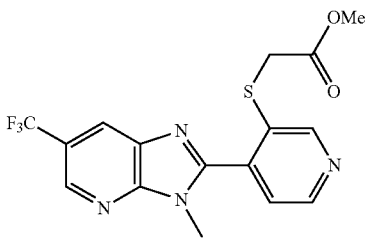
(157)

(hereinafter, referred to as present active compound 157) was obtained according to the method described in Production Example 145, using 0.31 g of methyl 2-bromoacetate instead of (bromomethyl)cyclopropane.

Present Active Compound 157

$^1$H-NMR (CDCl$_3$) δ: 8.90 (d, J=0.5 Hz, 1H), 8.76 (d, J=1.3 Hz, 1H), 8.72 (d, J=5.1 Hz, 1H), 8.36 (d, J=1.5 Hz, 1H), 7.42 (dd, J=4.9, 0.6 Hz, 1H), 3.83 (s, 3H), 3.67 (s, 3H), 3.64 (s, 2H).

Production Example 158

A compound (94 mg) of formula (158):

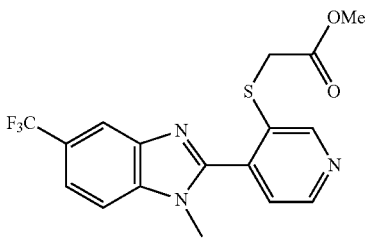
(158)

(hereinafter, referred to as present active compound 158) was obtained according to the method described in Production Example 146, using 0.31 g of methyl 2-bromoacetate instead of (bromomethyl)cyclopropane.

Present Active Compound 158

$^1$H-NMR (CDCl$_3$) δ: 8.87 (m, 1H), 8.70 (d, J=4.8 Hz, 1H), 8.13 (m, 1H), 7.65 (dd, J=8.6, 1.3 Hz, 1H), 7.54 (d, J=8.3 Hz, 1H), 7.43 (d, J=4.8 Hz, 1H), 3.74 (s, 3H), 3.64 (s, 3H), 3.60 (s, 2H).

Production Example 201

A mixture of 0.76 g of N1-sec-butyl-4-trifluoromethylbenzene-1,2-diamine, 0.84 g of sodium hydroxy-pyridin-4-yl-methanesulfonate and 17 ml of DMF was stirred for 1 hour at 120° C. The reaction mixture was cooled down to room temperature. Into the reaction mixture was poured a saturated sodium hydrogen carbonate aqueous solution, and the mixture was extracted three times with ethyl acetate. The organic layer was dried over magnesium sulfate, then, concentrated under reduced pressure. The residue was subjected to silica gel column chromatography, to obtain 0.91 g of 1-sec-butyl-2-pyridin-4-yl-5-trifluoromethyl-1H-benzimidazole (hereinafter, referred to as present active compound 201).

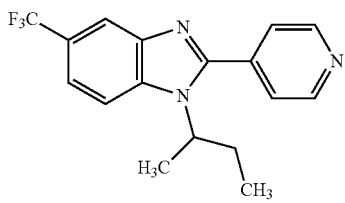

Present active compound 201

$^1$H-NMR (CDCl$_3$) δ: 8.83 (dd, J=4.4, 1.7 Hz, 2H), 8.12 (s, 1H), 7.72 (d, J=8.5 Hz, 1H), 7.58-7.54 (m, 3H), 4.54-4.44 (m, 1H), 2.25-2.12 (m, 1H), 1.99-1.87 (m, 1H), 1.99-1.88 (m, 1H), 1.74 (d, J=6.8 Hz, 3H), 0.66 (t, J=7.3 Hz, 3H)

Production Example 202

1-isobutyl-2-pyridin-4-yl-5-trifluoromethyl-1H-benzimidazole (hereinafter, referred to as present active compound 202) was obtained according to the method described in Production Example 201, using N1-isobutyl-4-trifluoromethyl-benzene-1,2-diamine instead of N1-sec-butyl-4-trifluoromethylbenzene-1,2-diamine.

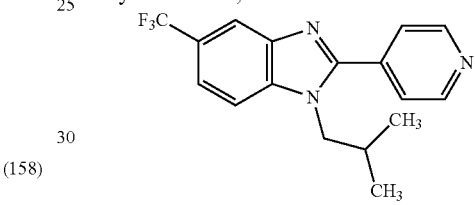

Present active compound 202

$^1$H-NMR (CDCl$_3$) δ: 8.83 (dd, J=4.4, 1.6 Hz, 2H), 8.12 (s, 1H), 7.65 (dd, J=4.4, 1.6 Hz, 2H), 7.60 (d, J=8.7 Hz, 1H), 7.53 (d, J=8.7 Hz, 1H), 4.16 (d, J=7.6 Hz, 2H), 2.17-2.04 (m, 1H), 0.78 (d, J=6.8 Hz, 6H)

Production Example 203

1-propyl-2-pyridin-4-yl-6-trifluoromethyl-1H-benzimidazole (hereinafter, referred to as present active compound 203) was obtained according to the method described in Production Example 201, using N2-propyl-4-trifluoromethyl-benzene-1,2-diamine instead of N1-sec-butyl-4-trifluoromethylbenzene-1,2-diamine.

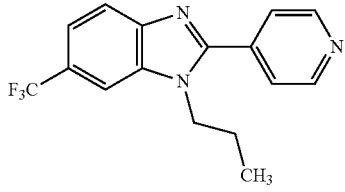

Present active compound 203

$^1$H-NMR (CDCl$_3$) δ: 8.85 (dd, J=4.4, 1.7 Hz, 2H), 7.93 (d, J=8.7 Hz, 1H), 7.73 (s, 1H), 7.67 (dd, J=4.4, 1.7 Hz, 2H), 7.59 (d, J=8.7 Hz, 1H), 4.29 (t, J=7.7 Hz, 2H), 1.94-1.84 (m, 2H), 0.92 (t, J=7.4 Hz, 3H)

Production Example 204

1-ethyl-2-pyridin-4-yl-6-trifluoromethyl-1H-benzimidazole (hereinafter, referred to as present active compound 204)

was obtained according to the method described in Production Example 201, using N2-ethyl-4-trifluoromethylbenzene-1,2-diamine instead of N1-sec-butyl-4-trifluoromethylbenzene-1,2-diamine.

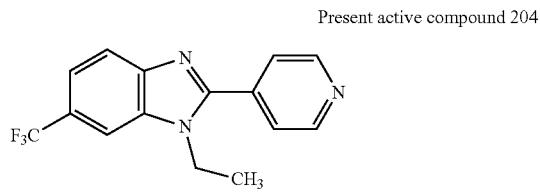

Present active compound 204

$^1$H-NMR (CDCl$_3$) δ: 8.85 (dd, J=4.4, 1.7 Hz, 2H), 7.93 (d, J=8.3 Hz, 1H), 7.75 (s, H), 7.68 (dd, J=4.4, 1.7 Hz, 2H), 7.60 (d, J=8.3 Hz, 1H), 4.39 (q, J=7.3 Hz, 2H), 1.55 (t, J=7.3 Hz, 3H)

Production Example 205

1-sec-butyl-2-pyridin-4-yl-6-trifluoromethyl-1H-benzimidazole (hereinafter, referred to as present active compound 205) was obtained according to the method described in Production Example 201, using N2-sec-butyl-4-trifluoromethylbenzene-1,2-diamine instead of N1-sec-butyl-4-trifluoromethylbenzene-1,2-diamine.

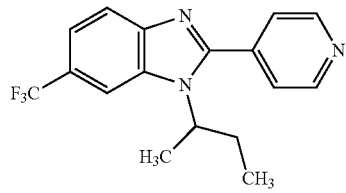

Present active compound 205

$^1$H-NMR (CDCl$_3$) δ: 8.84 (dd, J=4.4, 1.7 Hz, 2H), 7.93 (d, J=8.3 Hz, 1H), 7.88 (s, 1H), 7.60-7.56 (m, 3H), 4.55-4.45 (m, 1H), 2.24-2.13 (m, 1H), 2.00-1.90 (m, 1H), 1.75 (d, J=6.8 Hz, 3H), 0.68 (t, J=7.4 Hz, 3H)

Production Example 206

To a mixture of 0.44 g of 1-butanol and 6 ml of DMF was added 0.24 g of 60% sodium hydride (oily) under ice cool, and the mixture was stirred for 10 minutes. And, 2-(3-fluoro-pyridin-4-yl-)-1-methyl-5-trifluoromethyl-1H-benzimidazole (0.35 g) was added, then, the mixture was stirred for 1.5 hours at room temperature. Into the reaction mixture was poured a saturated ammonium chloride aqueous solution, and the mixture was extracted three times with ethyl acetate. The organic layer was dried over magnesium sulfate, then, concentrated under reduced pressure. The residue was subjected to silica gel column chromatography, to obtain 0.37 g of 2-(3-butoxypyridin-4-yl-)-1-methyl-5-trifluoromethyl-1H-benzimidazole (hereinafter, referred to as present active compound 206).

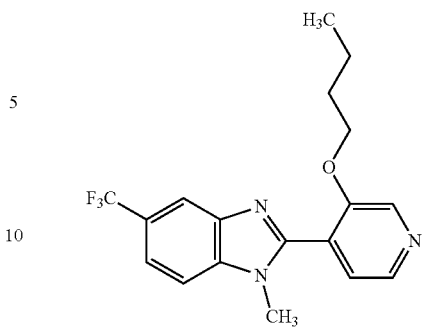

Present active compound 206

$^1$H-NMR (CDCl$_3$) δ: 8.51 (s, 1H), 8.45 (d, J=4.6 Hz, 1H), 8.11 (s, 1H), 7.62 (d, J=8.5 Hz, 1H), 7.54-7.50 (m, 2H), 4.15 (t, J=6.6 Hz, 2H), 3.74 (s, 3H), 1.74-1.66 (m, 2H), 1.39-1.29 (m, 2H), 0.87 (t, J=7.4 Hz, 3H)

Production Example 207

1-methyl-2-[3-(3-methyl-2-buteneoxy)-pyridin-4-yl-]-5-trifluoromethyl-1H-benzimidazole (hereinafter, referred to as present active compound 207) was obtained according to the method described in Production Example 206, using 3-methyl-2-buten-1-ol instead of 1-butanol.

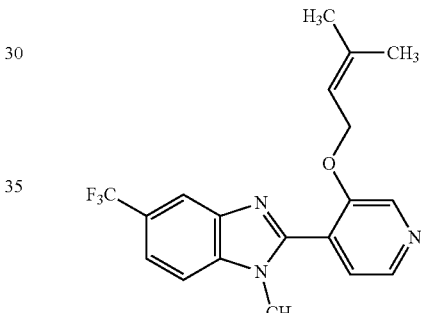

Present active compound 207

$^1$H-NMR (CDCl$_3$) δ: 8.50 (s, 1H), 8.44 (d, J=4.9 Hz, 1H), 8.11 (s, 1H), 7.61 (d, J=8.5 Hz, 1H), 7.55 (d, J=4.9 Hz, 1H), 7.51 (d, J=8.5 Hz, 1H), 5.34 (t, J=6.7 Hz, 1H), 4.68 (d, J=6.7 Hz, 2H), 3.73 (s, 3H), 1.73 (s, 3H), 1.68 (s, 3H)

Production Example 208

1-methyl-2-pyridin-4-yl-6-trifluoromethoxy-1H-benzimidazole (hereinafter, referred to as present active compound 208) was obtained according to the method described in Production Example 201, using N1-methyl-4-trifluoromethoxybenzene-1,2-diamine instead of N1-sec-butyl-4-trifluoromethylbenzene-1,2-diamine.

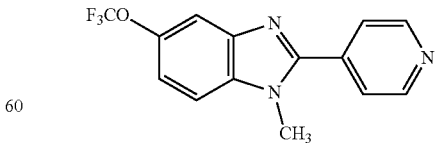

Present active compound 208

$^1$H-NMR (CDCl$_3$) δ: 8.83 (dd, J=4.4, 1.7 Hz, 2H), 7.72 (brs, 1H), 7.71 (dd, J=4.4, 1.7 Hz, 2H), 7.43 (d, J=8.8 Hz, 1H), 7.29 (brs, 1H), 3.95 (s, 3H)

Production Example 209

2-[3-(1-fluoromethyl-vinyloxy)-pyridin-4-yl-]-1-methyl-5-trifluoromethyl-1H-benzimidazole (hereinafter, referred to as present active compound 209) was obtained according to the method described in Production Example 206, using 1,3-difluoroisopropanol instead of 1-butanol.

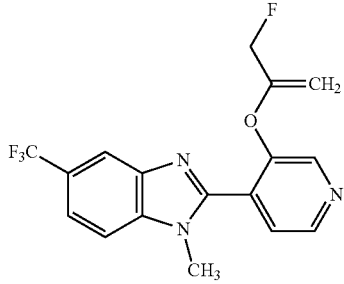

Present active compound 209

$^1$H-NMR (CDCl$_3$) δ: 8.69-8.66 (m, 2H), 8.11 (s, 1H), 7.69 (d, J=5.1 Hz, 1H), 7.63 (d, J=8.1 Hz, 1H), 7.52 (d, J=8.1 Hz, 1H), 4.75 (d, J=47.1 Hz, 2H), 4.50 (t, J=3.5 Hz, 1H), 4.22 (d, J=3.5 Hz, 1H), 3.80 (s, 3H)

Production Example 210

2-(3-cyclobutoxypyridin-4-yl-)-1-methyl-5-trifluoromethyl-1H-benzimidazole (hereinafter, referred to as present active compound 210) was obtained according to the method described in Production Example 206, using cyclobutanol instead of 1-butanol.

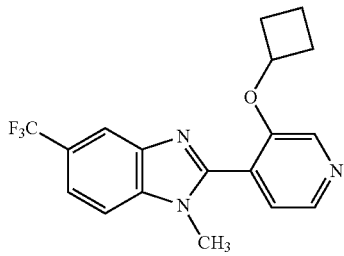

Present active compound 210

$^1$H-NMR (CDCl$_3$) δ: 8.43 (d, J=4.8 Hz, 1H), 8.35 (s, 1H), 8.12 (s, 1H), 7.62 (d, J=8.7 Hz, 1H), 7.55 (d, J=4.8 Hz, 1H), 7.52 (d, J=8.7 Hz, 1H), 4.85-4.77 (m, 1H), 3.76 (s, 3H), 2.52-2.43 (m, 2H), 2.17-2.07 (m, 2H), 1.90-1.80 (m, 1H), 1.77-1.66 (m, 1H)

Production Example 211

A mixture of 0.29 g of N2-methyl-5-trifluoromethylpyridine-2,3-diamine, 0.27 g of 3-ethynylisonicotinic acid, 0.35 g of WSC and 8 ml of pyridine was stirred for 2 hours at 120° C. The reaction mixture was cooled down to room temperature. Into the reaction mixture was poured water, and the mixture was extracted three times with ethyl acetate. The organic layer was dried over magnesium sulfate, then, concentrated under reduced pressure. The residue was subjected to silica gel column chromatography to obtain 0.15 g of 2-(3-ethynylpyridin-4-yl-)-3-methyl-6-trifluoromethyl-3H-imidazo[4,5-b]pyridine (hereinafter, referred to as present active compound 211).

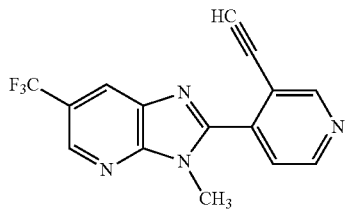

Present active compound 211

$^1$H-NMR (CDCl$_3$) δ: 8.96 (s, 1H), 8.80 (d, J=4.9 Hz, 1H), 8.76 (d, J=1.5 Hz, 1H), 8.37 (d, J=1.5 Hz, 1H), 7.56 (d, J=4.9 Hz, 1H), 3.91 (s, 3H), 3.27 (s, 1H)

Production Example 212

3-methyl-6-trifluoromethyl-2-(3-trifluoromethylpyridin-4-yl-)-3H-imidazo[4,5-b]pyridine (hereinafter, referred to as present active compound 212) was obtained according to the method described in Production Example 211, using 3-trifluoromethylisonicotinic acid instead of 3-ethynylisonicotinic acid.

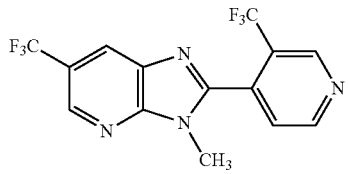

Present active compound 212

$^1$H-NMR (CDCl$_3$) δ: 9.18 (s, 1H), 9.05 (d, J=4.8 Hz, 1H), 8.78 (d, J=1.9 Hz, 1H), 8.37 (d, J=1.9 Hz, 1H), 7.52 (d, J=4.8 Hz, 1H), 3.75 (s, 3H)

Production Example 213

To a mixture of 0.34 g of 2-(3-ethylthiopyridin-4-yl)-3-methyl-6-trifluoromethyl-3H-imidazo[4,5-b]pyridine and 10 ml of chloroform was added 0.75 g of 69% m-chloroperbenzoic acid under ice cool, then, the mixture was stirred at room temperature for 2.5 hours and at 40° C. for 1.5 hours. Into the reaction mixture, a saturated sodium hydrogen carbonate aqueous solution and a saturated sodium thiosulfate aqueous solution were poured, and the mixture was extracted three times with chloroform. The organic layer was dried over magnesium sulfate, then, concentrated under reduced pressure. The residue was subjected to silica gel column chromatography to obtain 0.20 g of 2-(3-ethanesulfonyl-1-oxy-pyridin-4-yl-)-3-methyl-6-trifluoromethyl-3H-imidazo[4,5-b]pyridine (hereinafter, referred to as present active compound 213).

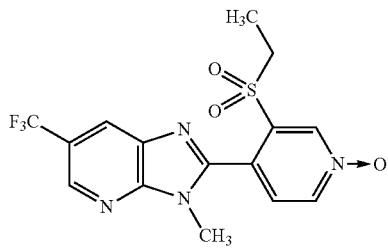

Present active compound 213

$^1$H-NMR (CDCl$_3$) δ: 8.87 (d, J=1.9 Hz, 1H), 8.78 (d, J=1.9 Hz, 1H), 8.49 (ddd, J=6.8, 1.9, 0.5 Hz, 1H), 8.31 (d, J=1.9 Hz, 1H), 7.45 (d, J=6.8 Hz, 1H), 3.80 (d, J=0.5 Hz, 3H), 3.55 (q, J=7.4 Hz, 2H), 1.35 (t, J=7.4 Hz, 3H)

Production Example 214

2-(3-benzyloxypyridin-4-yl-)-3-methyl-6-trifluoromethyl-3H-imidazo[4,5-b]pyridine (hereinafter, referred to as present active compound 214) was obtained according to the method described in Production Example 206, using benzyl alcohol instead of 1-butanol and using 2-(3-fluoropyridin-4-yl)-3-methyl-6-trifluoromethyl-3H-imidazo[4,5-b]pyridine instead of 2-(3-fluoropyridin-4-yl)-1-methyl-5-trifluoromethyl-1H-benzimidazole.

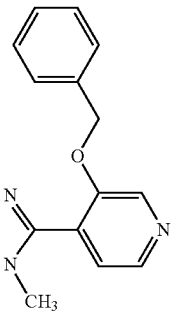

Present active compound 214

¹H-NMR (CDCl₃) δ: 8.72-8.70 (m, 1H), 8.61 (s, 1H), 8.49 (d, J=4.8 Hz, 1H), 8.33 (d, J=1.7 Hz, 1H), 7.55 (d, J=4.8 Hz, 1H), 7.33-7.24 (m, 5H), 5.24 (s, 2H), 3.79 (s, 3H)

Production Example 215

A mixture of 1.16 g of 2-(3-benzyloxypyridin-4-yl-)-3-methyl-6-trifluoromethyl-3H-imidazo[4,5-b]pyridine, 60 ml of ethanol and 0.12 g of 5% palladium charcoal was stirred for 3 hours at room temperature under a hydrogen atmosphere of about 1 atm. The mixture was filtrated through Celite (registered trademark), and the filtrate was concentrated under reduced pressure, to obtain 0.27 g of 4-(3-methyl-6-trifluoromethyl-3H-imidazo[4,5-b]pyridine-2-yl]-pyridin-3-ol (hereinafter, referred to as present active compound 215).

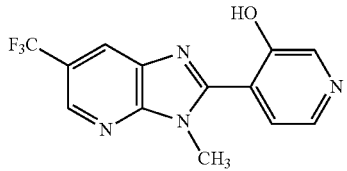

Present active compound 215

¹H-NMR (CDCl₃) δ: 12.67 (brs, 1H), 8.78 (dd, J=2.0, 0.5 Hz, 1H), 8.65 (s, 1H), 8.35 (dd, J=2.0, 0.5 Hz, 1H), 8.33 (d, J=5.2 Hz, 1H), 7.75 (dd, J=5.2, 0.5 Hz, 1H), 4.32 (s, 3H)

Production Example 216

A mixture of 0.40 g of N2-methyl-5-trifluoromethylpyridine-2,3-diamine, 0.32 g of 3-methylisonicotinic acid, 0.44 g of WSC and 10 ml of pyridine was stirred for 5 hours at 120° C. The reaction mixture was cooled down to room temperature. Into the reaction mixture was poured water, and the mixture was extracted three times with ethyl acetate. The organic layer was dried over magnesium sulfate, then, concentrated under reduced pressure. To the residue was added a mixture of 0.60 g of p-toluenesulfonic acid monohydrate and 10 ml of toluene, and the mixture was stirred for 1 hour at 120° C. Toluene was distilled off from this mixture. To the residue was added 10 ml of phenyl bromide, and the mixture was stirred for 4 hours at 150° C. The reaction mixture was cooled down to room temperature. Into the reaction mixture was poured water, and the mixture was extracted three times with ethyl acetate. The organic layer was dried over magnesium sulfate, then, concentrated under reduced pressure. The residue was subjected to silica gel column chromatography to obtain 0.14 g of 3-methyl-2-(3-methylpyridin-4-yl-)-6-trifluoromethyl-3H-imidazo[4,5-b]pyridine (hereinafter, referred to as present active compound 216).

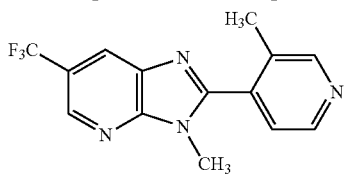

Present active compound 216

¹H-NMR (CDCl₃) δ: 8.76-8.74 (m, 1H), 8.72 (d, J=0.5 Hz, 1H), 8.67 (d, J=4.8 Hz, 1H), 8.35 (d, J=2.2 Hz, 1H), 7.35 (d, J=4.8 Hz, 1H), 3.80 (s, 3H), 2.35 (s, 3H)

Production Example 217

A mixture of 0.40 g of N2-methyl-5-trifluoromethylpyridine-2,3-diamine, 0.41 g of 3-ethylisonicotinic acid, 0.44 g of WSC and 10 ml of pyridine was stirred for 2.5 hours at 120° C. The reaction mixture was cooled down to room temperature. Into the reaction mixture was poured water, and the mixture was extracted three times with ethyl acetate. The organic layer was dried over magnesium sulfate, then, concentrated under reduced pressure. To the residue was added a mixture of 0.60 g of p-toluenesulfonic acid monohydrate and 10 ml of toluene, and the mixture was stirred for 7 hours at 120° C. The reaction mixture was cooled down to room temperature. Into the reaction mixture was poured water, and the mixture was extracted three times with ethyl acetate. The organic layer was dried over magnesium sulfate, then, concentrated under reduced pressure. The residue was subjected to silica gel column chromatography to obtain 0.10 g of 2-(3-ethylpyridin-4-yl-)-3-methyl-6-trifluoromethyl-3H-imidazo[4,5-b]pyridine (hereinafter, referred to as present active compound 217).

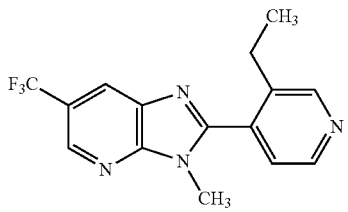

Present active compound 217

¹H-NMR (CDCl₃) δ: 8.76-8.74 (m, 2H), 8.67 (d, J=5.0 Hz, 1H), 8.35 (d, J=1.9 Hz, 1H), 7.31 (d, J=5.0 Hz, 1H), 3.78 (s, 3H), 2.70 (q, J=7.6 Hz, 2H), 1.14 (t, J=7.6 Hz, 3H)

Production Example 218

A mixture of 0.44 g of N1-propyl-4-trifluoromethylbenzene-1,2-diamine, 0.51 g of isonicotinealdehyde-bisulfite adduct and 4 ml of N,N-dimethylformamide was stirred for 1 hour at 150° C. The reaction mixture was allowed to cool to room temperature, and water was poured into this, and the mixture was extracted with ethyl acetate. The organic layer was washed with water, dried over sodium sulfate, then, concentrated under reduced pressure to obtain a solid residue. The residue was washed with hexane, to obtain 0.55 g of 1-propyl-2-(pyridin-4-yl-)-5-trifluoromethyl-1H-benzimidazole (hereinafter, referred to as present active compound 218).

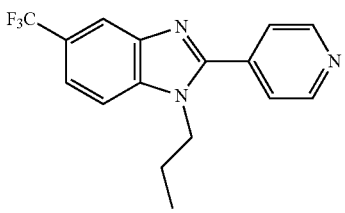

Present active compound 218

$^1$H-NMR (CDCl$_3$) δ: 8.84 (dd, 2H), 8.13 (s, 1H), 7.66 (dd, 2H), 7.61 (dd, 1H), 7.54 (d, 1H), 4.28 (t, 2H), 1.92-1.82 (m, 2H), 0.90 (t, 3H).

Production Example 219

A mixture of 0.44 g of N1-isopropyl-4-trifluoromethylbenzene-1,2-diamine, 0.51 g of isonicotinealdehyde-bisulfite adduct and 4 ml of N,N-dimethylformamide was stirred for 1 hour at 150° C. The reaction mixture was allowed to cool to room temperature, and water was poured into this, and the mixture was extracted with ethyl acetate. The organic layer was washed with water, dried over sodium sulfate, then, concentrated under reduced pressure to obtain a solid residue. The residue was washed with hexane, to obtain 0.50 g of 1-isopropyl-2-(pyridin-4-yl-)-5-trifluoromethyl-1H-benzimidazole (hereinafter, referred to as present active compound 219).

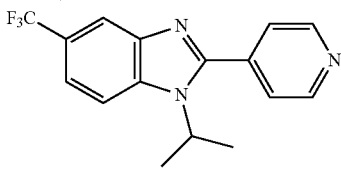

Present active compound 219

$^1$H-NMR (CDCl$_3$) δ: 8.84 (dd, 2H), 8.12 (d, 1H), 7.74 (d, 1H), 7.58-7.55 (m, 3H), 4.88-4.78 (m, 1H), 1.70 (d, 6H).

Production Example 220

A mixture of 0.47 g of N1-tert-butyl-4-trifluoromethylbenzene-1,2-diamine, 0.51 g of isonicotinealdehyde-bisulfite adduct and 5 ml of N,N-dimethylformamide was stirred for 10 minutes at 150° C. The reaction mixture was ice-cooled, then, a 10% sodium hydroxide aqueous solution was poured, and the mixture was extracted with methyl tert-butyl ether. The organic layer was washed with water, dried over sodium sulfate, then, concentrated under reduced pressure to obtain a solid residue. The residue was washed with hexane, to obtain 0.26 g of 1-tert-butyl-2-(pyridin-4-yl)-5-trifluoromethyl-1H-benzimidazole (hereinafter, referred to as present active compound 220).

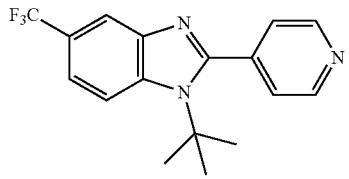

Present active compound 220

$^1$H-NMR (CDCl$_3$) δ: 8.75 (dd, 2H), 8.05 (s, 1H), 7.84 (d, 1H), 7.56 (d, 1H), 7.44 (dd, 2H), 1.67 (s, 9H).

Production Example 221

A mixture of 1.0 g of N1-ethyl-4-trifluoromethylbenzene-1,2-diamine, 1.05 g of isonicotinoyl chloride hydrochloride and 15 ml of pyridine was stirred for 4 hours at 60° C. Then, 0.94 g of WSC was added, and the mixture was stirred for 8 hours at 80° C. The reaction mixture was cooled down to room temperature. Into the reaction mixture was poured water, and the mixture was extracted twice with ethyl acetate. The organic layer was washed with water and saturated saline, then, dried over magnesium sulfate, and concentrated under reduced pressure. The residue was subjected to silica gel column chromatography to obtain 0.65 g of 1-ethyl-2-(pyridin-4-yl)-5-trifluoromethyl-1H-benzimidazole (hereinafter, referred to as present active compound 221).

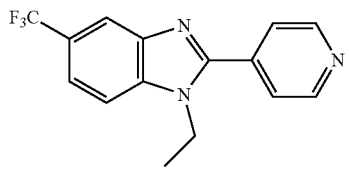

Present active compound 221

$^1$H-NMR (CDCl$_3$) δ: 8.84 (dd, J=4.4, 1.7 Hz, 2H), 8.14-8.13 (m, 1H), 7.68 (dd, J=4.4, 1.7 Hz, 2H), 7.64-7.60 (m, 1H), 7.55 (d, J=8.5 Hz, 1H), 4.37 (q, J=7.2 Hz, 2H), 1.53 (t, J=7.2 Hz, 3H)

Next, reference production examples for production of production intermediates of the above-described present active compounds are shown.

Reference Production Example 1

To a mixture of 2.09 g of 4-fluoro-3-nitrobenzo trifluoride and 20 ml of N-methylpyrrolidone was added 2.33 g of a 40% methylamine aqueous solution under ice cool, and the mixture was heated up to room temperature and stirred for 1 hour. Water was poured, and the deposited precipitate was filtrated, then, washed with water, then, dried under reduced pressure to obtain 2.0 g of N-methyl-2-nitro-4-trifluoromethylaniline.

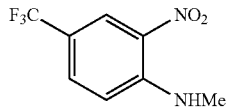

$^1$H-NMR (CDCl$_3$) δ: 8.48 (s, 1H), 8.28 (br s, 1H), 7.65 (dd, J=9.0, 2.1 Hz, 1H), 6.94 (d, J=9.0 Hz, 1H), 3.09 (d, J=5.1 Hz, 3H)

A mixture of 2.0 g of N-methyl-2-nitro-4-trifluoromethylaniline, 18 ml of ethanol and 0.20 g of 5% palladium charcoal was stirred for 3 hours at room temperature under a hydrogen atmosphere of about 1 atm. The mixture was filtrated through Celite (registered trademark), and the filtrate was concentrated under reduced pressure to obtain 1.17 g of N-1-methyl-4-trifluoromethylbenzene-1,2-diamine.

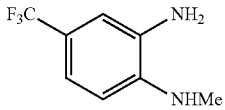

$^1$H-NMR (CDCl$_3$) δ: 7.14-7.10 (m, 1H), 6.92 (d, J=2.0 Hz, 1H), 6.63 (d, J=8.3 Hz, 1H), 3.73 (br s, 1H), 3.34 (br s, 2H), 2.90 (d, J=5.1 Hz, 3H)

Reference Production Example 2

N-methyl-2-nitro-5-trifluoromethylaniline was obtained according to the method described in Reference Production Example 1, using 2-chloro-1-nitro-4-trifluoromethylbenzene instead of 4-fluoro-3-nitrobenzo trifluoride.

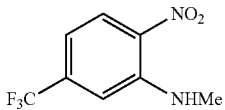

$^1$H-NMR (CDCl$_3$) δ: 8.29 (d, J=8.9 Hz, 1H), 8.09 (br s, 1H), 7.10 (s, 1H), 6.87 (dd, J=8.9, 1.7 Hz, 1H), 3.08 (d, J=5.1 Hz, 3H)

N2-methyl-4-trifluoromethylbenzene-1,2-diamine was obtained according to the method described in Reference Production Example 1, using N-methyl-2-nitro-5-trifluoromethylaniline instead of N-methyl-2-nitro-4-trifluoromethylaniline.

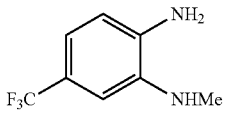

$^1$H-NMR (CDCl$_3$) δ: 6.95 (d, J=7.8 Hz, 1H), 6.83 (s, 1H), 6.72 (d, J=7.8 Hz, 1H), 3.55 (br s, 2H), 3.39 (br s, 1H), 2.89 (d, J=5.6 Hz, 3H)

Reference Production Example 3

N-methyl(1,1,3,3-tetrafluoro-6-nitro-1,3-dihydro-isobenzofuran-5-yl)-amine was obtained according to the method described in Reference Production Example 1, using 5-chloro-1,1,3,3-tetrafluoro-6-nitro-1,3-dihydro-isobenzofuran instead of 4-fluoro-3-nitrobenzo trifluoride.

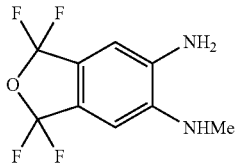

$^1$H-NMR (CDCl$_3$) δ: 8.50 (s, 1H), 8.41 (br s, 1H), 7.07 (s, 1H), 3.13 (d, J=4.9 Hz, 3H)

1,1,3,3-tetrafluoro-N-methyl-1,3-dihydroisobenzofuran-5,6-diamine was obtained according to the method described in Reference Production Example 1, using N-methyl-(1,1,3,3-tetrafluoro-6-nitro-1,3-dihydro-isobenzofuran-5-yl)-amine instead of N-methyl-2-nitro-4-trifluoromethylaniline.

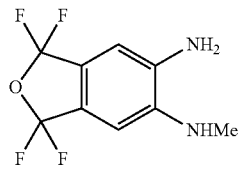

$^1$H-NMR (CDCl$_3$) δ: 6.84 (s, 1H), 6.72 (s, 1H), 3.83 (br s, 1H), 3.65 (br s, 2H), 2.94 (d, J=5.1 Hz, 3H)

Reference Production Example 4

To a mixture of 39.9 ml of diisopropylamine and 257 ml of tetrahydrofuran was added 107 ml of a 2.64 M hexane solution of n-butyllithium under stirring while cooling the mixture in a dry ice-acetone bath, then, the mixture was stirred for 1.5 hours. Then, 25.0 g of 3-fluoropyridine was added, and the mixture was further stirred for 1.5 hours. Crushed dry ice was added to the reaction mixture, then, cooling was stopped, and the mixture was stirred until returning to room temperature. Water was added, and most of hexane and tetrahydrofuran were distilled off under reduced pressure. The residue was washed with tert-butyl methyl ether, and the aqueous layer was recovered. To the resultant aqueous layer was added concentrated hydrochloric acid under ice cool, and pH of the mixture was adjusted to 3 and the mixture was stirred for 1 hour. The deposit was collected by filtration, and dried under reduced pressure to obtain 32.51 g of 3-fluoroisonicotinic acid.

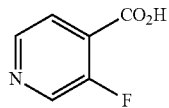

$^1$H-NMR (DMSO-d$_6$) δ: 8.74 (d, J=2.4 Hz, 1H), 8.58 (d, J=4.9 Hz, 1H), 7.80-7.77 (m, 1H)

Reference Production Example 5

A mixture of 0.64 g of 2-fluoro-4-pyridinemethanol, 10 ml of chloroform and 2.54 g of Dess-Martin Periodinane (1,1,1-triacetoxy-1,1-dihydro-1,2-benziodoxol-3(1H)-one) was stirred for 30 minutes at room temperature. A saturated sodium hydrogen carbonate aqueous solution was poured, and the mixture was extracted three times with ethyl acetate. The combined organic layers were dried over magnesium sulfate, then, concentrated under reduced pressure. The residue was subjected to silica gel column chromatography to obtain 0.19 g of 2-fluoropyridine-4-carbaldehyde.

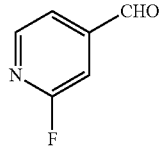

$^1$H-NMR (CDCl$_3$) δ: 10.09 (d, J=1.2 Hz, 1H), 8.49 (d, J=4.9 Hz, 1H), 7.65-7.62 (m, 1H), 7.38-7.36 (m, 1H)

Reference Production Example 6

To a mixture of 18.2 of 2-chloro-5-trifluoromethylpyridine and 100 ml of N-methylpyrrolidone was added 23.3 g of a 40% methylamine aqueous solution, and the mixture was stirred for 3 hours at room temperature. Water was poured, and the mixture was extracted three times with ethyl acetate.

The combined organic layers were dried over magnesium sulfate, then, concentrated under reduced pressure. The residue was subjected to silica gel column chromatography to obtain 17.3 g of N-methyl-(5-trifluoromethylpyridine-2-yl)-amine.

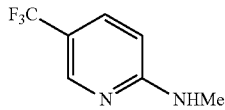

$^1$H-NMR (CDCl$_3$) δ: 8.34 (s, 1H), 7.60 (dd, J=8.8, 2.4 Hz, 1H), 6.40 (d, J=8.8 Hz, 1H), 4.89 (br s, 1H), 2.97 (d, J=5.1 Hz, 3H)

Into a mixture of 17.3 g of N-methyl(5-trifluoromethylpyridin-2-yl)-amine and 100 ml of sulfuric acid was dropped 12.3 g of nitric acid, then, the mixture was stirred for 2 hours while heating at 80° C. After cooling down to room temperature, water was poured into the reaction mixture, and the deposited precipitate was filtrated, then, washed with water, then, dried under reduced pressure to obtain 18.8 g of N-methyl(3-nitro-5-trifluoromethylpyridin-2-yl)-amine.

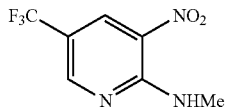

$^1$H-NMR (CDCl$_3$) δ: 8.66-8.64 (m, 2H), 8.43 (br s, 1H), 3.23 (d, J=4.9 Hz, 3H)

N2-methyl-5-trifluoromethylpyridine-2,3-diamine was obtained according to the method described in Reference Production Example 1, using N-methyl(3-nitro-5-trifluoromethylpyridin-2-yl)-amine instead of N-methyl-2-nitro-4-trifluoromethylaniline.

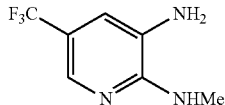

$^1$H-NMR (CDCl$_3$) δ: 8.04 (s, 1H), 6.98 (d, J=1.7 Hz, 1H), 4.56 (br s, 1H), 3.25 (br s, 2H), 3.06 (d, J=4.9 Hz, 3H)

Reference Production Example 201

To a mixture of 1.05 g of 4-fluoro-3-nitro-benzo trifluoride and 10 ml of N-methylpyrrolidone was added 1.10 g of sec-butylamine under ice cool, and the mixture was heated up to room temperature and stirred for 1.5 hours. Into the reaction mixture was poured water, and the deposited solid was collected by filtration. This solid was washed with water, then, dried under reduced pressure to obtain 1.16 g of N-sec-butyl-2-nitro-4-trifluoromethylaniline.

$^1$H-NMR (CDCl$_3$) δ: 8.48-8.46 (m, 1H), 8.25 (brs, 1H), 7.59 (dd, J=9.2, 2.2 Hz, 1H), 6.94 (d, J=9.2 Hz, 1H), 3.72-3.62 (m, 1H), 1.77-1.61 (m, 2H), 1.32 (d, J=6.3 Hz, 3H), 1.01 (t, J=7.6 Hz, 3H)

A mixture of 1.16 g of N-(sec-butyl)-2-nitro-4-trifluoromethylaniline, 9 ml of ethanol and 0.12 g of 5% palladium charcoal was stirred for 5.5 hours at room temperature under a hydrogen atmosphere of about 1 atm. The reaction mixture was filtrated through Celite (registered trademark), and the filtrate was concentrated under reduced pressure. The residue was subjected to silica gel column chromatography to obtain 0.76 g of N1-sec-butyl-4-trifluoromethylbenzene-1,2-diamine.

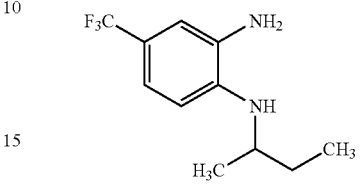

$^1$H-NMR (CDCl$_3$) δ: 7.10-7.06 (m, 1H), 6.93 (d, J=2.0 Hz, 1H), 6.61 (d, J=8.3 Hz, 1H), 3.56 (brs, 1H), 3.47-3.38 (m, 1H), 3.30 (br s, 2H), 1.71-1.59 (m, 1H), 1.58-1.46 (m, 1H), 1.21 (d, J=6.1 Hz, 3H), 0.98 (t, J=7.4 Hz, 3H)

Reference Production Example 202

N-isobutyl-2-nitro-4-trifluoromethylaniline was obtained according to the method described in Reference Production Example 201, using isobutylamine instead of sec-butylamine.

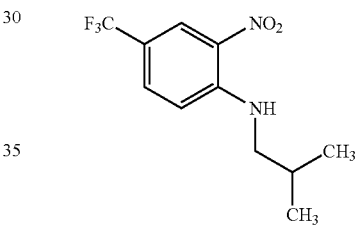

$^1$H-NMR (CDCl$_3$) δ: 8.48-8.46 (m, 1H), 8.39 (brs, 1H), 7.60 (dd, J=9.0, 2.3 Hz, 1H), 6.93 (d, J=9.0 Hz, 1H), 3.17 (dd, J=6.8, 5.4 Hz, 2H), 2.09-1.98 (m, 1H), 1.08 (s, 3H), 1.06 (s, 3H)

N1-isobutyl-4-trifluoromethylbenzene-1,2-diamine was obtained according to the method described in Reference Production Example 201, using N-isobutyl-2-nitro-4-trifluoromethylaniline instead of N-(sec-butyl)-2-nitro-4-trifluoromethylaniline.

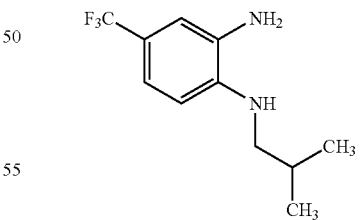

$^1$H-NMR (CDCl$_3$) δ: 7.11-7.06 (m, 1H), 6.93 (d, J=2.0 Hz, 1H), 6.62 (d, J=8.3 Hz, 1H), 3.74 (brs, 1H), 3.32 (br s, 2H), 2.96 (m, 2H), 1.99-1.86 (m, 1H), 1.03 (s, 3H), 1.01 (s, 3H)

Reference Production Example 203

N-propyl-2-nitro-5-trifluoromethylaniline was obtained according to the method described in Reference Production Example 201, using 2-chloro-1-nitro-4-trifluorobenzene instead of 4-fluoro-3-nitro-benzo trifluoride and using propylamine instead of sec-butylamine.

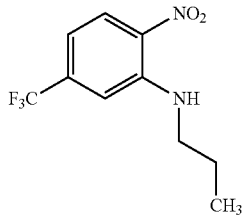

¹H-NMR (CDCl₃) δ: 8.28 (d, J=8.8 Hz, 1H), 8.09 (brs, 1H), 7.09 (s, 1H), 6.84 (dd, J=8.8, 1.7 Hz, 1H), 3.34-3.28 (m, 2H), 1.85-1.74 (m, 2H), 1.08 (t, J=7.5 Hz, 3H)

N2-propyl-4-trifluoromethylbenzene-1,2-diamine was obtained according to the method described in Reference Production Example 201, using N-propyl-2-nitro-5-trifluoromethylaniline instead of N-(sec-butyl)-2-nitro-4-trifluoromethylaniline.

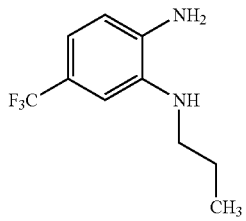

¹H-NMR (CDCl₃) δ: 6.95-6.92 (m, 1H), 6.83 (d, J=1.7 Hz, 1H), 6.72 (d, J=8.0 Hz, 1H), 3.55 (br s, 2H), 3.28 (brs, 1H), 3.09 (t, J=7.1 Hz, 2H), 1.76-1.66 (m, 2H), 1.05 (t, J=7.4 Hz, 3H)

Reference Production Example 204

N-ethyl-2-nitro-5-trifluoromethylaniline was obtained according to the method described in Reference Production Example 201, using 2-chloro-1-nitro-4-trifluorobenzene instead of 4-fluoro-3-nitro-benzo trifluoride and using ethylamine instead of sec-butylamine.

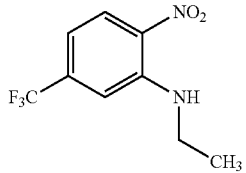

¹H-NMR (CDCl₃) δ: 8.28 (d, J=9.0 Hz, 1H), 8.00 (brs, 1H), 7.09 (s, 1H), 6.85 (dd, J=9.0, 1.7 Hz, 1H), 3.43-3.35 (m, 2H), 1.41 (t, J=7.2 Hz, 3H)

N2-ethyl-4-trifluoromethylbenzene-1,2-diamine was obtained according to the method described in Reference Production Example 201, using N-ethyl-2-nitro-5-trifluoromethylaniline instead of N-(sec-butyl)-2-nitro-4-trifluoromethylaniline.

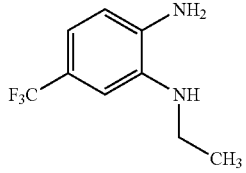

¹H-NMR (CDCl₃) δ: 6.94 (dt, J=8.0, 0.9 Hz, 1H), 6.84 (s, 1H), 6.72 (d, J=8.0 Hz, 1H), 3.56 (br s, 2H), 3.25-3.13 (m, 3H), 1.32 (t, J=7.0 Hz, 3H)

Reference Production Example 205

N-sec-butyl-2-nitro-5-trifluoromethylaniline was obtained according to the method described in Reference Production Example 201, using 2-chloro-1-nitro-4-trifluorobenzene instead of 4-fluoro-3-nitro-benzo trifluoride.

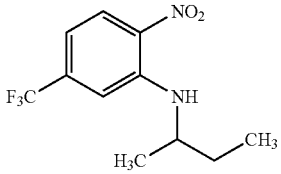

¹H-NMR (CDCl₃) δ: 8.28 (d, J=8.9 Hz, 1H), 8.07 (brs, 1H), 7.09 (s, 1H), 6.81 (dd, J=8.9, 2.0 Hz, 1H), 3.72-3.60 (m, 1H), 1.78-1.61 (m, 2H), 1.31 (d, J=6.3 Hz, 3H), 1.02 (t, J=7.4 Hz, 3H)

N2-sec-butyl-4-trifluoromethylbenzene-1,2-diamine was obtained according to the method described in Reference Production Example 201, using N-sec-butyl-2-nitro-5-trifluoromethylaniline instead of N-(sec-butyl)-2-nitro-4-trifluoromethylaniline.

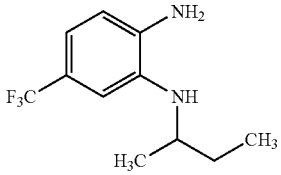

¹H-NMR (CDCl₃) δ: 6.91 (dt, J=8.0, 1.2 Hz, 1H), 6.82 (d, J=1.2 Hz, 1H), 6.72 (d, J=8.0 Hz, 1H), 3.54 (br s, 2H), 3.44-3.34 (m, 1H), 3.17 (brs, 1H), 1.70-1.46 (m, 2H), 0.98 (t, J=7.5 Hz, 3H)

Reference Production Example 206

To a mixture of 2.22 g of 2-nitro-4-trifluoromethoxyaniline and 20 ml of DMF was added 0.44 g of sodium hydride (60% oily), and the mixture was stirred for 10 minutes under ice cool. To this mixture was added 1.42 g of methyl iodide, then, the mixture was stirred for 1 hour at room temperature. Into the reaction mixture, a saturated ammonium chloride aqueous solution was poured, and the mixture was extracted three times with ethyl acetate. The organic layer was dried over magnesium sulfate, then, concentrated under reduced pressure. The residue was subjected to silica gel column chromatography to obtain 1.80 g of N-methyl-2-nitro-4-trifluoromethoxyaniline.

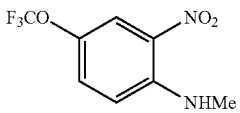

¹H-NMR (CDCl₃) δ: 8.10-8.01 (m, 2H), 7.37 (dtd, J=9.3, 1.8, 1.0 Hz, 1H), 6.87 (d, J=9.3 Hz, 1H), 3.05 (d, J=5.1 Hz, 3H)

N1-methyl-4-trifluoromethoxybenzene-1,2-diamine was obtained according to the method described in Reference Production Example 201, using N-methyl-2-nitro-4-trifluoromethoxyaniline instead of N-(sec-butyl)-2-nitro-4-trifluoromethylaniline.

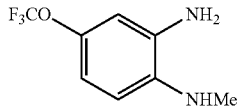

¹H-NMR (CDCl₃) δ: 6.72-6.67 (m, 1H), 6.61-6.56 (m, 2H), 3.42 (br s, 2H), 3.30 (brs, 1H), 2.86 (s, 3H)

Reference Production Example 207

To a mixture of 5.23 g of 4-fluoro-3-nitro-benzo trifluoride and 25 ml of N-methylpyrrolidone was added 3.69 g of n-propylamine under ice cool, and the mixture was stirred for 1 hour at room temperature. The reaction mixture was poured into water, and the deposited solid was collected by filtration. This solid was washed with water, then, dried under reduced pressure to obtain 2.78 g of N-propyl-2-nitro-4-trifluoromethylaniline.

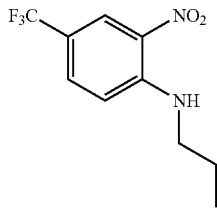

¹H-NMR (CDCl₃) δ: 8.47 (d, 1H), 8.29 (brs, 1H), 7.61 (dd, 1H), 6.94 (d, 1H), 3.36-3.30 (m, 2H), 1.84-1.74 (m, 2H), 1.07 (t, 3H).

A mixture of 2.48 g of N-propyl-2-nitro-4-trifluoromethylaniline, 30 ml of ethyl acetate and 5% palladium charcoal was stirred for 1.5 hours at room temperature under a hydrogen atmosphere of about 1 atm. The reaction mixture was filtrated through Celite (registered trademark). The filtrate was washed with water, dried over sodium sulfate, then, concentrated under reduced pressure, to obtain 1.91 g of N1-propyl-4-trifluoromethylbenzene-1,2-diamine.

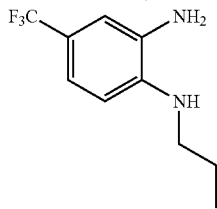

¹H-NMR (CDCl₃) δ: 7.09 (dd, 1H), 6.92 (d, 1H), 6.63 (d, 1H), 3.66 (brs, 1H), 3.32 (br s, 2H), 3.11 (t, 2H), 1.75-1.65 (m, 2H), 1.03 (t, 3H).

Reference Production Example 208

A mixture (150 ml) of 150 g of water and 80 g of sodium bisulfate was cooled with ice, and 17.0 g of isonicotinealdehyde and 20 ml of ethanol were added into this. The deposited solid was collected by filtration. This solid was washed with water, to obtain 24.9 g of an isonicotinealdehyde-bisulfite adduct.

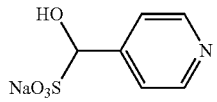

Reference Production Example 209

To a mixture of 5.23 g of 4-fluoro-3-nitro-benzo trifluoride and 25 ml of N-methylpyrrolidone was added 3.69 g of isopropylamine under ice cool, and the mixture was stirred for 1 hour at room temperature. The reaction mixture was poured into water, the deposited solid was collected by filtration. This solid was washed with water, then, dried under reduced pressure to obtain 5.90 g of N-isopropyl-2-nitro-4-trifluoromethylaniline.

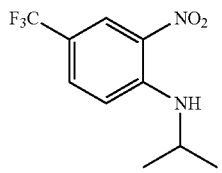

¹H-NMR (CDCl₃) δ: 8.47 (d, 1H), 8.22 (brs, 1H), 7.60 (dd, 1H), 6.95 (d, 1H), 3.94-3.82 (m, 1H), 1.36 (d, 6H).

A mixture of 5.46 g of N-isopropyl-2-nitro-4-trifluoromethylaniline, 30 ml of ethyl acetate and 5% palladium charcoal (catalytic amount) was stirred for 1.5 hours at room temperature under a hydrogen atmosphere of about 1 atm. The reaction mixture was filtrated through Celite (registered trademark). The filtrate was washed with water, dried over sodium sulfate, then, concentrated under reduced pressure, to obtain 4.35 g of N1-isopropyl-4-trifluoromethylbenzene-1,2-diamine.

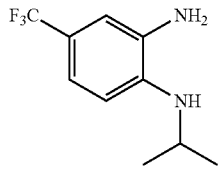

¹H-NMR (CDCl₃) δ: 7.08 (dd, 1H), 6.93 (d, 1H), 6.63 (d, 1H), 3.65 (brs, 1H), 3.54 (brs, 1H), 3.31 (br s, 2H), 1.25 (d, 6H).

Reference Production Example 210

To a mixture of 5.22 g of 4-fluoro-3-nitro-benzo trifluoride and 25 ml of N-methylpyrrolidone was added 3.88 g of tert-butylamine, and the mixture was stirred for 2 hours at room temperature. The reaction mixture was poured into water, the deposited solid was collected by filtration. This solid was washed with water, then, dried under reduced pressure, to obtain 5.35 g of N-tert-butyl-2-nitro-4-trifluoromethylaniline.

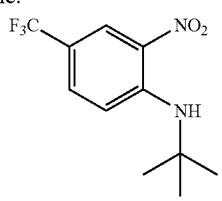

¹H-NMR (CDCl₃) δ: 8.61 (brs, 1H), 8.48 (d, 1H), 7.56 (dd, 1H), 7.18 (d, 1H), 1.53 (s, 9H).

S

A mixture of 5.25 g of N-tert-butyl-2-nitro-4-trifluoromethylaniline, 20 ml of ethyl acetate and 5% palladium charcoal was stirred for 9 hours at room temperature under a hydrogen atmosphere of about 1 atm. The reaction mixture was filtrated through Celite (registered trademark). The filtrate was washed with water, dried over sodium sulfate, then, concentrated under reduced pressure to obtain a residue. The resultant residue was subjected to silica gel chromatography to obtain 4.82 g of N1-tert-butyl-4-trifluoromethylbenzene-1,2-diamine.

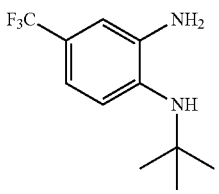

$^1$H-NMR (CDCl$_3$) δ: 7.03 (d, 1H), 6.94 (s, 1H), 6.89 (d, 1H), 3.54 (brs, 1H), 3.40 (br s, 2H), 1.39 (s, 9H).

Next, formulation examples of the present active compounds are shown. Parts are by weight.

Formulation Example 1

Each 10 parts of the present active compounds (1) to (56), (101) to (158) and (201) to (221) were dissolved in a mixture composed of 35 parts of xylene and 35 parts of N,N-dimethylformamide, and 14 parts of polyoxyethylene styryl phenyl ether and 6 parts of calcium dodecylbenzenesulfonate were added and thoroughly stirred and mixed, to obtain 10% emulsifiable concentrates.

Formulation Example 2

Each 20 parts of the present active compounds (1) to (56), (101) to (158) and (201) to (221) were added to a mixture of 4 parts of sodium lauryl sulfate, 2 parts of calcium ligninsulfoate, 20 parts of synthetic hydrated silicon oxide fine powder and 54 parts of diatomaceous earth, and the mixture was thoroughly stirred and mixed, to obtain 20% wettable powders.

Formulation Example 3

To each 2 parts of the present active compounds (1) to (56), (101) to (158) and (201) to (221) were added 1 part of synthetic hydrated silicon oxide fine powder, 2 parts of calcium ligninsulfoate, 30 parts of bentonite and 65 parts of kaolin clay, and the mixtures were stirred and mixed sufficiently. Then, a suitable amount of water was added to the mixtures, and the mixtures were further stirred, and granulated by a granulator, and dried under air to obtain 2% granules.

Formulation Example 4

Each 1 part of the present active compounds (1) to (56), (101) to (158) and (201) to (221) were dissolved in a suitable amount of acetone, and 5 parts of synthetic hydrated silicon oxide fine powder, 0.3 parts of PAP and 93.7 parts of Fubasami clay were added to them, and the mixtures were stirred and mixed sufficiently, and acetone was removed by distillation to obtain 1% granules.

Formulation Example 5

Each 10 parts of the present active compounds (1) to (56), (101) to (158) and (201) to (221), 35 parts of white carbon containing 50 parts of polyoxyethylene alkyl ether sulfate ammonium salt; and 55 parts of water were mixed, and finely ground by a wet grinding method, to obtain 10% flowable formulations.

Formulation Example 6

Each 0.1 part of the present active compounds (1) to (56), (101) to (158) and (201) to (221) were dissolved in 5 parts of xylene and 5 parts of trichloroethane, and these were mixed with 89.9 parts of deodorized kerosene, to obtain 0.1% oil solutions.

Formulation Example 7

Each 10 mg of the present active compounds (1) to (56), (101) to (158) and (201) to (221) were dissolved in 0.5 ml of acetone, and the solutions were treated with 5 g of an animal solid feedstuff powder (breeding-propagation solid feedstuff powder CE-2, manufactured by CLEA Japan Inc.), and mixed uniformly. Then, acetone was dried by distillation, to obtain poison baits.

Formulation Example 8

Each 0.1 part of the present active compounds (1) to (56), (101) to (158) and (201) to (221) and 49.9 parts of Neothiozole (Chuo Kasei Co. Ltd.) were charged in an aerosol can which was then equipped with an aerosol valve, then, 25 parts of dimethyl ether and 25 parts of LPG were filled in and vibration was applied, and an actuator was mounted to obtain an oil solution aerosol.

Formulation Example 9

Each 0.6 parts of the present active compounds (1) to (56), (101) to (158) and (201) to (221), 0.01 part of BHT, 5 parts of xylene, 3.39 parts of deodorized kerosene and 1 part of an emulsifiable concentrate {Atmos 300 (registered trademark of Atmos Chemical)} were mixed and dissolved, and the resultant solutions and 50 parts of distilled water were filled in an aerosol vessel which was then equipped with a valve, then, 40 parts of an injection agent (LPG) was filled under press through the valve, to obtain an aqueous aerosol.

Next, the noxious arthropod controlling effect of the present active compound is shown by test examples.

Test Example 1

The formulations of the present active compounds (1) to (15), (17) to (25), (27) to (56), (101) to (103), (105) to (108), (117), (118), (121) to (130), (133) to (144), (147), (148), (152) to (156), (202), (204) to (206), (208), (209), (211) to (213), and (216) to (221) obtained by Formulation Example 5 were diluted with water so that the active ingredient concentration was 500 ppm, to prepare spray solutions for test.

Separately, a cucumber seedling (second true leaf spreading stage) planted on a plastic cup was inoculated with about 30 *Aphis gossypii*, and left for 1 day. The above-described diluted solutions were sprayed each in an amount of 10 ml on this seedling.

Five days after spraying, the number of insect of living *Aphis gossypii* parasited on the leaves of this cucumber was checked, and the control value was calculated according to the following formula.

Control value (%)={1−(Cb×Tai)/(Cai×Tb)}×100

Letters in the formula represent the following meanings.

Cb: the number of insect before treatment on non-treated district

Cai: the number of insect in observation on non-treated district

Tb: the number of insect before treatment on treated district

Tai: the number of insect in observation on treated district

As a result, 90% or more control value was obtained in all of the treated districts with the spray solutions for test of the present active compounds (1) to (15), (17) to (25), (27) to (56), (101) to (103), (105) to (108), (117), (118), (121) to (130), (133) to (144), (147), (148), (152) to (156), (202), (204) to (206), (208), (209), (211) to (213), and (216) to (221).

Test Example 2

The formulations of the present active compounds (4), (5), (8), (9), (11), (12), (14), (15), (17), (20), (35) to (45), (48) to (51), (54) to (56), (206), (209) and (211) to (213) obtained by Formulation Example 5 were diluted with water so that the active ingredient concentration was 500 ppm, to prepare diluted solutions for test.

Separately, a cucumber seedling (second true leaf spreading stage) planted on a urethane mat was drenched at its foot with each 5 ml of the diluted solutions, and one day after treatment, the cucumber leaf surface was inoculated with 30 *Aphis gossypii* (whole stage). Further seven days after, the number of insect of living *Aphis gossypii* parasited on the leaves of this cucumber was checked, and the control value was calculated according to the following formula.

Control value (%)={1−(Cb×Tai)/(Cai×Tb)}×100

Letters in the formula represent the following meanings.

Cb: the number of insect before treatment on non-treated district

Cai: the number of insect in observation on non-treated district

Tb: the number of insect before treatment on treated district

Tai: the number of insect in observation on treated district

As a result, 90% or more control value was obtained in all of the treated districts with the diluted solutions for test of the present active compounds (4), (5), (8), (9), (11), (12), (14), (15), (17), (20), (35) to (45), (48) to (51), (54) to (56), (206), (209) and (211) to (213).

Test Example 3

The formulations of the present active compounds (18), (19), (21), (22), (24), (25), (28), (31) to (34), (46), (47), (52), (53), (101) to (104), (106) to (108), (112) to (114), (117), (118), (122), (123), (126), (128), (129), (133), (134), (138), (144), (153) to (155) and (157) obtained by Formulation Example 5 were diluted with water so that the active ingredient concentration was 500 ppm, to prepare diluted solutions for test.

A root part of a cucumber seedling (first true leaf spreading stage) from which soil had been washed off was immersed in 5 ml of this diluted solution, and one day after treatment, the cucumber leaf surface was inoculated with 30 *Aphis gossypii* (whole stage). Further seven days after, the number of insect of living *Aphis gossypii* parasited on the leaves of this cucumber was checked, and the control value was calculated according to the following formula.

Control value (%)={1−(Cb×Tai)/(Cai×Tb)}×100

Letters in the formula represent the following meanings.

Cb: the number of insect before treatment on non-treated district

Cai: the number of insect in observation on non-treated district

Tb: the number of insect before treatment on treated district

Tai: the number of insect in observation on treated district

As a result, 90% or more control value was obtained in all of the treated districts with the diluted solutions for test of the present active compounds (18), (19), (21), (22), (24), (25), (28), (31) to (34), (46), (47), (52), (53), (101) to (104), (106) to (108), (112) to (114), (117), (118), (122), (123), (126), (128), (129), (133), (134), (138), (144), (153) to (155) and (157).

Test Example 4

The formulations of the present active compounds (3) to (7), (17), (19), (20), (22), (29) to (31), (35) to (37), (39), (41) to (45), (47) to (56), (101), (106), (121) to (123), (128), (131), (137), (139), (143), (145), (147), (211) to (213), (216) and (217) obtained by Formulation Example 5 were diluted with water so that the active ingredient concentration was 500 ppm, to prepare diluted solutions for test.

Separately, a cucumber seedling (second true leaf spreading stage) planted on a plastic cup was drenched at its foot with each 5 ml of the diluted solutions, and kept in a greenhouse of 25° C. for 7 days. The cucumber leaf surface was inoculated with 30 *Aphis gossypii* (whole stage), and further kept in the greenhouse for 6 days, then, the number of insect of living *Aphis gossypii* parasited on the leaves of this cucumber was checked, and the control value was calculated according to the following formula.

Control value (%)={1−(Cb×Tai)/(Cai×Tb)}×100

Letters in the formula represent the following meanings.

Cb: the number of insect before treatment on non-treated district

Cai: the number of insect in observation on non-treated district

Tb: the number of insect before treatment on treated district

Tai: the number of insect in observation on treated district

As a result, 90% or more control value was obtained in all of the treated districts with the diluted solutions for test of the present active compounds (3) to (7), (17), (19), (20), (22), (29) to (31), (35) to (37), (39), (41) to (45), (47) to (56), (101), (106), (121) to (123), (128), (131), (137), (139), (143), (145), (147), (211) to (213), (216) and (217).

Test Example 5

The formulations of the present active compounds (1) to (5), (7) to (15), (17) to (21), (25), (28) to (45), (48) to (56), (101) to (103), (106), (107), (117), (118), (121) to (145), (147) to (151), (153) to (155), (204), (206), (208), (209), (211) to (213) and (216) to (221) obtained by Formulation Example 5 were diluted with water so that the active ingredient concentration was 500 ppm, to prepare spray solutions for test.

Separately, on a tomato seedling planted on a plastic cup, *Bemisia tabaci* adult insects were released and allowed to lay eggs for about 24 hours. The tomato seedling was kept in a greenhouse of for 8 days, and the above-described spray solutions for test were sprayed at a proportion of 10 ml/cup on the condition of hatching of larvae from the laid eggs, and kept in a greenhouse of 25° C. for 7 days. The number of living larvae on the tomato leaves was checked, and the control value was calculated according to the following formula.

Control value (%)={1−(Cb×Tai)/(Cai×Tb)}×100

Letters in the formula represent the following meanings.
Cb: the number of insect before treatment on non-treated district
Cai: the number of insect in observation on non-treated district
Tb: the number of insect before treatment on treated district
Tai: the number of insect in observation on treated district
As a result, 90% or more control value was obtained in all of the treated districts with the spray solutions for test of the present active compounds (1) to (5), (7) to (15), (17) to (21), (25), (28) to (45), (48) to (56), (101) to (103), (106), (107), (117), (118), (121) to (145), (147) to (151), (153) to (155), (204), (206), (208), (209), (211) to (213) and (216) to (221).

Test Example 6

The formulations of the present active compounds (3) to (5), (8) to (17), (20), (23), (27), (35) to (45), (48), (49), (51), (54) to (56), (206) and (208) to (212) obtained by Formulation Example 5 were diluted with water so that the active ingredient concentration was 500 ppm, to prepare spray solutions for test.
Separately, on a rice seedling (2 weeks after sowing, second leaf spreading stage) planted on a plastic cup, the drug solutions for test prepared as described above were sprayed each in an amount of 10 ml. After drying of the drug solution sprayed on rice, 30 first instar larvae of Nilaparvata lugens were released, and kept in a greenhouse of 25° C. for 6 days. Thereafter, the number of Nilaparvata lugens parasited on rice was checked, and the control value was calculated according to the following formula.

Control value (%)={1−(Cb×Tai)/(Cai×Tb)}×100

Letters in the formula represent the following meanings.
Cb: the number of insect before treatment on non-treated district
Cai: the number of insect in observation on non-treated district
Tb: the number of insect before treatment on treated district
Tai: the number of insect in observation on treated district
As a result, 90% or more control value was obtained in all of the treated districts with the spray solutions for test of the present active compounds (3) to (5), (8) to (17), (20), (23), (27), (35) to (45), (48), (49), (51), (54) to (56), (206) and (208) to (212).

Test Example 7

The formulations of the present active compounds (11), (13) to (15), (17), (23), (26), (35) to (41), (43) to (45), (48) to (51), (54), (55), (209), (211) and (212) obtained by Formulation Example 5 were diluted with water so that the active ingredient concentration was 500 ppm, to prepare diluted solutions for test.
Separately, a rice seedling (2 weeks after sowing, second leaf spreading stage) planted on a plastic cup was drenched at its foot with each 5 ml of the diluted solutions, and kept in a greenhouse of 25° C. for 7 days. Thirty first instar larvae of Nilaparvata lugens were released, and further kept in the greenhouse for 6 days. The number of insect of living Nilaparvata lugens parasited on rice was checked, and the control value was calculated according to the following formula.

Control value (%)={1−(Cb×Tai)/(Cai×Tb)}×100

Letters in the formula represent the following meanings.
Cb: the number of insect before treatment on non-treated district
Cai: the number of insect in observation on non-treated district
Tb: the number of insect before treatment on treated district
Tai: the number of insect in observation on treated district
As a result, 90% or more control value was obtained in all of the treated districts with the diluted solutions for test of the present active compounds (11), (13) to (15), (17), (23), (26), (35) to (41), (43) to (45), (48) to (51), (54), (55), (209), (211) and (212).

Test Example 8

The formulations of the present active compounds (6), (7), (18), (21), (24), (25), (28) to (30), (32), (46), (52), (101) to (103), (105) to (107), (111), (112), (115), (119) to (124), (126) to (130), (133) to (135), (139), (142), (144) to (146), (149) to (151), (153), (154), (216) and (217) obtained by Formulation Example 5 were diluted with water so that the active ingredient concentration was 500 ppm, to prepare spray solutions for test.
Separately, on a rice seedling (2 weeks after sowing, second leaf spreading stage) planted on a plastic cup, the drug solutions for test prepared as described above were sprayed each in an amount of 10 ml. After drying of the drug solution sprayed on rice, 20 first instar larvae of Nilaparvata lugens were released, and kept in a greenhouse of 25° C. for 6 days. Thereafter, the number of Nilaparvata lugens parasited on rice was checked, and the control value was calculated according to the following formula.

Control value (%)={1−(Cb×Tai)/(Cai×Tb)}×100

Letters in the formula represent the following meanings.
Cb: the number of insect before treatment on non-treated district
Cai: the number of insect in observation on non-treated district
Tb: the number of insect before treatment on treated district
Tai: the number of insect in observation on treated district
As a result, 90% or more control value was obtained in all of the treated districts with the spray solutions for test of the present active compounds (6), (7), (18), (21), (24), (25), (28) to (30), (32), (46), (52), (101) to (103), (105) to (107), (111), (112), (115), (119) to (124), (126) to (130), (133) to (135), (139), (142), (144) to (146), (149) to (151), (153), (154), (216) and (217).

Test Example 9

The formulations of the present active compounds (6), (7), (18), (22), (25), (30), (33), (46), (47), (53), (101) to (103), (106), (121) to (124), (126) to (128), (135), (139), (216) and (217) obtained by Formulation Example 5 were diluted with water so that the active ingredient concentration was 500 ppm, to prepare diluted solutions for test.
Separately, a rice seedling (2 weeks after sowing, second leaf spreading stage) planted on a plastic cup was drenched at its foot with each 5 ml of the diluted solutions, and kept in a greenhouse of 25° C. for 7 days. Twenty first instar larvae of *Nilaparvata lugens* were released, and further kept in the greenhouse for 6 days, then, the number of insect of living *Nilaparvata lugens* parasited on rice was checked, and the control value was calculated according to the following formula.

Control value (%)={1−(Cb×Tai)/(Cai×Tb)}×100

Letters in the formula represent the following meanings.

Cb: the number of insect before treatment on non-treated district

Cai: the number of insect in observation on non-treated district

Tb: the number of insect before treatment on treated district

Tai: the number of insect in observation on treated district

As a result, 90% or more control value was obtained in all of the treated districts with the diluted solutions for test of the present active compounds (6), (7), (18), (22), (25), (30), (33), (46), (47), (53), (101) to (103), (106), (121) to (124), (126) to (128), (135), (139), (216) and (217).

Comparative Test Example 1

A compound of the following formula (B) described in Farmaco, Edizione Scientifica (1987), 42(7), 475-90 (hereinafter, referred to as comparative compound (B)) was subjected to the same test as in Test Example 1, as a result, a control value was less than 30% in the treated district with the spray solution for test of the comparative compound (B).

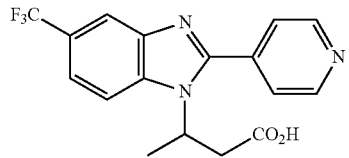
(B)

Comparative Test Example 2

A compound of the following formula (C) described in Heterocycles (1977), 6(7), 911-27 (hereinafter, referred to as comparative compound (C)) was subjected to the same test as in Test Example 1, as a result, a control value was less than 30% in the treated district with the spray solution for test of the comparative compound (C).

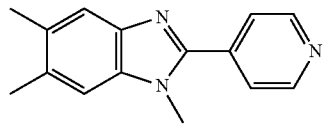
(C)

INDUSTRIAL APPLICABILITY

The composition of the present invention has an excellent controlling effect on noxious arthropods and thus is useful.

The invention claimed is:
1. A fused heterocyclic compound of formula (1):

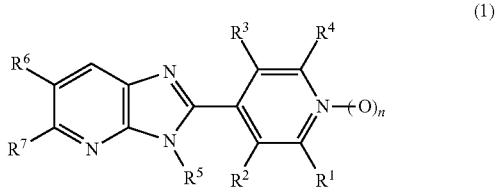
(1)

wherein,
m represents 0, 1 or 2,
$R^1$, $R^2$, $R^3$ and $R^4$ are the same or different and represent a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y, —$OR^8$, —$NR^8R^9$, —$NR^8C(O)R^9$, —$S(O)_mR^8$, —$SO_2Cl$, —$SO_2NR^8R^9$, —$CO_2R^{10}$, —$CONR^8R^9$, —$CONR^{10}NR^{11}R^{12}$, a cyano group, a nitro group, a halogen atom or a hydrogen atom,
$R^5$ represents a C1-C4 chain hydrocarbon group optionally substituted with one or more halogen atoms, a cyclopropyl group optionally substituted with one or more halogen atoms, a cyclopropylmethyl group optionally substituted with one or more halogen atoms, —$OR^{13}$, —$NR^{13}R^{14}$ or a cyano group,
$R^6$ and $R^7$ are the same or different and represent a C1-C4 chain hydrocarbon group substituted with one or more halogen atoms, —$OR^{15}$, —$S(O)_mR^{15}$, a halogen atom or a hydrogen atom (here, either $R^6$ or $R^7$ represents a C1-C4 chain hydrocarbon group substituted with one or more halogen atoms, —$OR^{15}$, —$S(O)_mR^{15}$), alternatively $R^6$ and $R^7$ may be bonded to form a 5-membered ring or 6-membered ring substituted with one or more halogen atoms together with carbon atoms to which $R^6$ and $R^7$ are connected,
$R^8$ and $R^9$ are the same or different and represent a C1-C6 chain hydrocarbon group optionally substituted with one or more members selected from the group X, a C3-C6 alicyclic hydrocarbon group optionally substituted with one or more members selected from the group X, a phenyl group optionally substituted with one or more members selected from the group Y, a benzyl group optionally substituted with one or more members selected from the group Y, a 5-membered heterocyclic group or 6-membered heterocyclic group optionally substituted with one or more members selected from the group Y, or a hydrogen atom (concerning —$S(O)_mR^8$, m represents the same meaning as described above, but when m represents 1 or 2, $R^8$ does not represent a hydrogen atom),
$R^{10}$ represents a C1-C4 alkyl group optionally substituted with one or more halogen atoms, or a hydrogen atom,
$R^{11}$ and $R^{12}$ are the same or different and represents a C1-C4 alkyl group optionally substituted with one or more halogen atoms, a C2-C5 alkoxycarbonyl group or a hydrogen atom,
$R^{13}$ and $R^{14}$ are the same or different and represents a C1-C3 chain hydrocarbon group optionally substituted with one or more halogen atoms, a cyclopropyl group optionally substituted with one or more halogen atoms, or a hydrogen atom, $R^{15}$ represents a C1-C4 chain hydrocarbon group substituted with one or more halogen atoms, and n represents 0 or 1; wherein group X is selected from the group consisting of a C1-C4 alkoxy group optionally substituted with one or more halogen atoms, —$CO_2R^{16}$ (here, $R^{16}$ represents a C1-C4 alkyl group optionally substituted by a halogen), a cyano group and a halogen atom; and wherein group Y is selected from the group consisting of a C1-C4 alkyl group optionally substituted with one or more halogen atoms, a C1-C4 alkoxy group optionally substituted with one or more halogen atoms, a cyano group, a nitro group and a halogen atom.

2. The fused heterocyclic compound according to claim 1, wherein $R^6$ and $R^7$ are the same or different and are a C1-C4 chain hydrocarbon group substituted with one or more halogen atoms, —$OR^{15}$, —$S(O)_mR^{15}$, a halogen atom or a hydrogen atom (here, either $R^6$ or $R^7$ represents a C1-C4 chain hydrocarbon group substituted with one or more halogen atoms, —$OR^{15}$, —$S(O)_mR^{15}$).

3. The fused heterocyclic compound according to claim 1, wherein $R^6$ is a C1-C4 chain hydrocarbon group substituted with one or more halogen atoms.

4. The fused heterocyclic compound according to claim 1, wherein $R^5$ is a methyl group, ethyl group, cyclopropyl group or cyclopropylmethyl group.

5. The fused heterocyclic compound according to claim 1, wherein $R^1$ and $R^4$ are hydrogen atoms.

6. The fused heterocyclic compound according to claim 1, wherein $R^2$ is a hydrogen atom or a halogen atom.

7. The fused heterocyclic compound according to claim 1, wherein $R^3$ is a C3-C6 alicyclic hydrocarbon group optionally substituted with one or more members selected from the group X, a phenyl group optionally substituted with one or more members selected from the group Y, a benzyl group optionally substituted with one or more members selected from the group Y, or a 5-membered heterocyclic group or 6-membered heterocyclic group optionally substituted with one or more members selected from the group Y.

8. The fused heterocyclic compound according to claim 1, wherein $R^3$ is a C1-C6 chain hydrocarbon group optionally substituted with one or more members selected from the group X, —$OR^8$, —$NR^8R^9$, —$NR^8C(O)R^9$, —$S(O)_mR^8$, —$CO_2R^{10}$, —$CONR^8R^9$, —$CONR^{10}NR^{11}R^{12}$, a cyano group, a nitro group, a halogen atom or a hydrogen atom, and $R^8$ and $R^9$ are the same or different and represent a C1-C6 chain hydrocarbon group optionally substituted with one or more members selected from the group X, or a hydrogen atom (here, $R^8$ is not a hydrogen atom when m in —$S(O)_mR^8$ represents 1 or 2).

9. The fused heterocyclic compound according to claim 1, wherein $R^3$ is a C1-C6 chain hydrocarbon group optionally substituted with one or more members selected from the group X, —$OR^8$, —$NR^8R^9$, —$S(O)_mR^8$, a halogen atom or a hydrogen atom, and $R^8$ and $R^9$ are the same or different and represent a C1-C6 chain hydrocarbon group optionally substituted with one or more members selected from the group X, or a hydrogen atom (here, $R^8$ is not a hydrogen atom when m in —$S(O)_mR^8$ represents 1 or 2).

10. A noxious arthropod controlling composition which comprises the fused heterocyclic compound as described in claim 1 and an inert carrier.

11. A method of controlling a noxious arthropod which comprises applying an effective amount of the fused heterocyclic compound as described in claim 1 to a noxious arthropod or to a habitat of a noxious arthropod.

* * * * *